US007803612B2

(12) United States Patent
Audonnet

(10) Patent No.: US 7,803,612 B2
(45) Date of Patent: Sep. 28, 2010

(54) NIPAH VIRUS VACCINES

(75) Inventor: Jean Christophe Francis Audonnet, Lyons (FR)

(73) Assignee: Merial Limited, Duluth, GA (US)

( * ) Notice: Subject to any disclaimer, the term of this patent is extended or adjusted under 35 U.S.C. 154(b) by 1082 days.

(21) Appl. No.: 11/404,534

(22) Filed: Apr. 14, 2006

(65) Prior Publication Data

US 2007/0031455 A1 Feb. 8, 2007

Related U.S. Application Data

(60) Provisional application No. 60/674,583, filed on Apr. 25, 2005.

(51) Int. Cl.
*C12N 15/33* (2006.01)
*C07H 21/04* (2006.01)

(52) U.S. Cl. ................................ 435/320.1; 536/23.72

(58) Field of Classification Search ....................... None
See application file for complete search history.

(56) References Cited

U.S. PATENT DOCUMENTS

| | | | | |
|---|---|---|---|---|
| 5,766,598 A * | 6/1998 | Paoletti et al. | ........... | 424/199.1 |
| 5,843,456 A * | 12/1998 | Paoletti et al. | ........... | 424/199.1 |

OTHER PUBLICATIONS

Tamin, A. et al., "Functional Properties of the Fusion and Attachment Glycoproteins of Nipah Virus", Virology, 2002, vol. 296: pp. 190-200.*

Genbank entry for Accession No. AF238466, Jun. 2000, 3 pages.*

Harcourt, B. et al., "Molecular Characterization of Nipah Virus, a Newly Emergent Parramyxovirus", Virology, 2000, vol. 271: pp. 334-349.*

Harcourt, B. et al., "Molecular Characterization of the Polymerase Gene and Genomic Termini of Nipah Virus", 2001, Virology, vol. 287 pp. 192-201.*

Guillaume V, Contamin H, Loth P, Georges-Courbot MC, Lefeuvre A, Marianneau P, Chua KB, Lam SK, Buckland R, Deubel V, Wild TF. Nipah virus: vaccination and passive protection studies in a hamster model. J Virol. Jan. 2004;78(2):834-40.

Paoletti E, Taylor J, Meignier B, Meric C, Tartaglia J. Highly attenuated poxvirus vectors: NYVAC, ALVAC and TROVAC. Dev Biol Stand. 1995;84:159-63.

Weingartl HM, Berhane Y, Caswell JL, Loosmore S, Audonnet JC, Roth JA, Czub M. Recombinant nipah virus vaccines protect pigs against challenge. J Virol. Aug. 2006;80(16):7929-38.

* cited by examiner

*Primary Examiner*—Michael Burkhart
(74) *Attorney, Agent, or Firm*—Judy Jarecki-Black; Ruoying Chen; Merial Limited

(57) ABSTRACT

The present invention relates to recombinant anti-Nipah virus vaccines and the administration of such vaccines to animals, advantageously pigs. Advantageously, the anti-Nipah virus vaccine may comprise a recombinant avipox virus containing a Nipah virus glycoprotein gene. The invention encompasses methods of vaccinating animals, advantageously pigs, by administration of anti-Nipah virus vaccines that may comprise a recombinant avipox virus that may contain a Nipah virus glycoprotein gene.

2 Claims, 39 Drawing Sheets

Nipah virus, complete genome:

```
   1 accaaacaag ggagaatatg gatacgttaa aatatataac gtatttttaa aacttaggaa
  61 ccaagacaaa cacttttggt cttggtattg gatcctcaag aaatatatca tcatgagtga
 121 tatctttgaa gaggcggcta gttttaggag ttatcaatct aagttaggga gagatgggag
 181 ggctagtgca gcaactgcta ctttgacaac caagataagg atatttgtac cagctactaa
 241 tagtccagag ctcagatggg aactaacatt gtttgcactt gatgtgatta gatctccgag
 301 tgctgccgag tcaatgaaag ttggagctgc tttcacactc atctctatgt attcagagag
 361 acccggggct ctcattagaa gtctcctcaa tgacccagac attgaagctg taataataga
 421 tgttggatca atggtcaacg gaataccagt aatggagagg agaggagaca aggctcagga
 481 ggagatggaa ggcttgatga gaatcctcaa aactgctcga gacagcagca agggaaaaac
 541 accttttgtt gacagccgag cttacggcct acggataaca gacatgagca ccctggtctc
 601 tgcagttatc accatcgagg cccagatctg gatactgatc gctaaagcag ttacagctcc
 661 cgacactgcc gaggaaagtg aaactagaag atgggctaaa tacgtccaac aaaagagagt
 721 caatccgttc tttgctctaa ctcagcaatg gctaacagaa atgaggaatc tgctctccca
 781 gagtctatca gtaaggaagt tcatggttga gatcctcata gaagtcaaga aaggaggatc
 841 tgctaaaggc agagcagtag aaataatctc agacatcgga aactatgtcg aggaaactgg
 901 tatggcagga ttcttcgcaa ccatcagatt cgggttggag acaaggtatc cagcacttgc
 961 actcaacgaa ttccagagtg acctcaacac catcaaaagc ttgatgctac tctacagaga
1021 aattggccca agagcccctt atatggtgct tcttgaagaa tcaattcaga ctaaatttgc
1081 ccctggaggt tacccattat tgtggagctt tgccatgggt gtggctacta ctattgacag
1141 gtctatgggg gcattgaata tcaatcgtgg ttatcttgag cctatgtatt tcagactagg
1201 ccaaaaatca gcacgtcacc atgctggagg aattgatcag aacatggcaa atagactggg
1261 actaagttca gatcaagttg cagaactcgc tgctgcagtt caggaaacat cagcaggaag
1321 gcaagagagt aatgttcagg ctagagaggc aaaatttgct gcaggaggtg tgctcattgg
1381 aggcagtgat caagatatcg atgaagggga agaacctata gaacagagtg gcagacagtc
1441 agttaccttc aaaagggaga tgagtatttc atcccttgct aacagtgtgc cgagcagttc
1501 tgtgagcaca tccggtggga ccagattgac taattcatta ctaaacctca gatcaagact
1561 ggctgcaaaa gcagcaaaag aagccgcctc atccaatgca acagatgatc cagcaatcag
1621 caacagaact caaggggaat cagagaagaa gaataatcaa gacctcaaac ctgctcaaaa
1681 tgaccttgat ttcgtcagag ctgatgtgtg acgtctattt ccaatattct acagtatcca
1741 aaaatctttc tatagtacac tatcataata cgacactaag ggatcaacca tatcaaagtt
1801 acgaatcgtt ttaattatat taatcaaatg atactctttt atgggcaaac cgaagaacca
1861 atgtctacat gtaaattgag ctttggtatt gcaatctaat acttgctcaa aatcttgaac
1921 tattagtgta atttctatca tcatagagtt atcaagattt tattatataa gttggtgcag
1981 atctttggac atgaattaca cactacactc taatgaagac aaaatttaca ttacatattt
2041 aaggactatt tcctatcctt tcaatggtac ttggttatga aggtttctta atttaactaa
2101 gctactgtct ttgcactgga atatacaata cctcttacct catttcttac tttaatatca
2161 tgttattttt ttgataagtc acttaacttg accaaggtct accaggtaat gctcgcacaa
2221 gtgaactgca atctcaactt agattaaaca taatcatgca aaatcactat tttgtactac
2281 taactcatta agaaaaactt aggatccaag agatttactc taggatctcc tattaagctt
2341 agcagtcatt agttgagagt tcaacttgca aaactctaac cttcactcta ataacaattc
2401 atccaatgga taaattggaa ctagtcaatg atggcctcaa tattattgac tttattcaga
2461 agaaccaaaa agaaatacag aagacatacg gacgatcaag tattcaacaa cccagcatca
2521 aagatcaaac aaaagcctgg gaagattttc tgcagtgcac cagtggagaa tctgaacaag
2581 ttgagggggg aatgtctaag gatgatggag atgttgaaag aagaaacttg gaggatctat
2641 ccagtacttc tcccacagat ggaactattg gaaagagagt gtcgaacacc cgtgactggg
2701 cagaaggttc agatgacata caactggacc cagtggttac agacgttgta taccatgatc
2761 atggaggaga atgtaccgga tatggattta cttcaagccc tgagagaggg tggagtgatt
2821 acacatcagg agcaaacaat gggaatgtat gtcttgtatc tgatgcaaag atgctgtcct
2881 atgctcccga aattgcagtt tctaaagaag atcgggaaac tgatctagtt catcttgaga
2941 ataaactatc tactacagga ctgaatccca cagcagtacc gttcactctg agaaacctgt
3001 ctgatcctgc aaaagactct cctgtgattg ctgaacacta ctacggacta ggagttaaag
3061 agcaaaacgt tggccctcag actagcagaa atgtcaattt ggacagcatc aaattgtaca
3121 catcagatga cgaagaggca gatcagcttg aattcgaaga tgagtttgca ggaagctcaa
```

FIG. 1A

```
3181 gtgaagtgat agtcggcatt tctcctgaag atgaagagcc ttcaagtgtt ggcggaaaac
3241 ccaatgaatc cattggacgt acaatcgaag gccaatcaat ccgagacaac cttcaagcca
3301 aggacaacaa atcaacagat gtaccaggag caggaccgaa agattcagca gtgaaggaag
3361 aaccacccca gaagaggcta cctatgttag ctgaagaatt tgagtgctct ggatcggaag
3421 acccaatcat tcgggagctg ctgaaggaga actcactcat aaattgtcag caagggaaag
3481 atgctcagcc tccatatcat tggagcatcg agaggtcaat aagcccggat aaaactgaga
3541 tcgtcaacgg tgctgtgcaa actgctgaca ggcaaagacc aggaactccg atgccaaagt
3601 cccgaggtat tcccattaaa aagggcacag acgcgaaata tccatctgct gggacggaaa
3661 acgtgcctgg gtcgaagagt ggtgcaaccc ggcatgttcg aggatcaccc ccctaccaag
3721 aaggcaagag tgtcaatgcg gagaatgtcc aactgaatgc ttccactgcg gttaaggaaa
3781 ctgataagtc agaagtaaac cccgtagacg acaacgactc acttgatgat aaatacatca
3841 tgccttcaga tgatttctca aacactttct tcccgcacga cactgatcgc ttgaattatc
3901 acgcagatca tttaggtgat tatgaccttg aaaccctgtg tgaagagtcg gttctaatgg
3961 gagtgatcaa ctctataaaa ttaattaatc tggatatgcg cttaaatcac attgaagaac
4021 aagttaaaga gatcccaaag atcatcaata agcttgagtc cattgacaga gttctggcca
4081 agactaacac cgcactctca accattgaag gacacctggt ttccatgatg ataatgatac
4141 cagggaaagg gaaaggagaa agaaagggga aaaataatcc tgagcttaaa ccagtgatag
4201 gaagagacat tctagagcag caatctcttt tttcttttga caatgtcaag aatttcagag
4261 atggatcgtt gacaaacgaa ccgtatgggg cagctgtaca gttgagagaa gatcttattc
4321 ttcctgaact taattttgag gagacaaatg catctcaatt tgttcctatg gcagatgatt
4381 catccagaga tgttatcaag acattgataa ggactcacat taaagataga gagttgagat
4441 cagaactgat tggttacctg aataaagcgg aaaatgatga ggaaattcag gagatagcga
4501 acactgtcaa tgacatcatt gacggtaata tttgatcact gaattgtcag cagaaataca
4561 atgatctaac aacaatctcc cacaagtaga caatggtttc aggtcaataa taacaacctc
4621 aatactaatc tttcacataa gcattactca ttccagccct cagacgataa cacaatactt
4681 gatacatgtt tattgaagtg tatgtagcat gattgaacta ttcaataact gtatttctca
4741 ctcttgctct tagttagtca ttgtgtctaa taattattat tacagtacaa ggtattatga
4801 attcaaagat acgcaataaa tctgatatca gcatagagta gaaaattgtt gtttttgtca
4861 tgatcattcg aagatttaac aatgatgtca actttcatac ctaaacataa taacataaaa
4921 tggtcgattt gtattgtaga tctctcacgc attttagtgt catgaattag tgtttcaaat
4981 cagttgcata tcaattaaga aaaacttagg agacaggtat agaacctctc tttcagataa
5041 ctggtcaatt aaggacagaa attctgtttc tcaaatccgc tagcctttgt caaagaggac
5101 acaagcaatg gagccggaca tcaagagtat ttcaagtgag tcaatggaag gagtatctga
5161 tttcagccct agttcttggg agcatggtgg gtatcttgat aaggttgaac cagaaattga
5221 tgaaaatggc agtatgattc caaaatacaa gatctatacc ccaggagcta acgagaggaa
5281 atacaacaac tacatgtacc ttatatgtta cggctttgtt gaagatgttg agagaacccc
5341 agagacaggg aaacgcaaga agatcaggac aattgctgcc taccctctgg gtgttggtaa
5401 gagtgcctct catccccaag atcttctgga ggaactctgt tccctcaaag ttactgtgag
5461 aagaacagct ggatcaactg agaaaattgt gtttggatca tctggccctc taaatcacct
5521 cgttccgtgg aagaaagtac tgactagtgg ttcaattttt aatgcagtca aggtttgtcg
5581 gaacgttgat cagatacagc ttgacaagca tcaagctctg agaatatttt ttctcagtat
5641 cacaaagctc aatgattctg gaatctacat gattccacga accatgcttg agttcaggag
5701 aaacaatgcc attgccttca atcttctagt gtacttgaag attgatgctg atttatccaa
5761 aatggggatc cagggaagcc tcgataaaga tggcttcaag gttgcctcct tcatgctaca
5821 cttggggaac tttgtccgtc gtgcagggaa gtattactct gttgattatt gtaggaggaa
5881 gattgatagg atgaaattgc agttttcact gggttccata ggcggactaa gtctccacat
5941 taagatcaat ggtgtaatca gcaaacggct gtttgctcaa atgggattcc aaaaaaacct
6001 ttgtttctct ttgatggaca tcaatccttg gctcaacaga ttgacctgga acaacagttg
6061 tgagatcagc cgagtagcag ctgtgttgca gccttctatt ccaagagagt tcatgatcta
6121 tgatgatgtc ttcattgaca atacagggag aattctaaag ggctaaacag aattcttcta
6181 aaatttaatc agtcatgagt ttagtaatca tacctagtca taatacatca cacaggacta
6241 tttacaaaag acagttaaaa aatggaataa tcatgtagta gtaattgaga acattattag
6301 aatagtataa ctaaaatgta gtttttttga gtatttgatt taaaattaga taactattac
6361 aaaaaactta ggagccaagc tcttgcctcg ttcagaaggt taaacaagca ttcttaccat
```

FIG. 1A (Continued)

```
6_1 tggatcaaca aaaggattgg ttttatcgtc taagaaattt attgaaaggc aaagaaattc
6481 ctggttttat gttgaatgag gtgtatcaaa ctaaggagac cttctaacag ccaggtcata
6541 ggaatataaa taaaaataag aataaaattg attccatcgg aagattcatt tcaagaagtg
6601 atcaaatcaa agcggttggc agacctacca atcatatacc acaagactcg acaatggtag
6661 ttatacttga caagagatgt tattgtaatc ttttaatatt gattttgatg atctcggagt
6721 gtagtgttgg gattctacat tatgagaaat tgagtaaaat tggacttgtc aaaggagtaa
6781 caagaaaata caagattaaa agcaatcctc tcacaaaaga cattgttata aaaatgattc
6841 cgaatgtgtc gaacatgtct cagtgcacag ggagtgtcat ggaaaattat aaaacacgat
6901 taaacggtat cttaacacct ataaagggag cgttagagat ctacaaaaac aacactcatg
6961 accttgtcgg tgatgtgaga ttagccggag ttataatggc aggagttgct attgggattg
7021 caaccgcagc tcaaatcact gcaggtgtag cactatatga ggcaatgaag aatgctgaca
7081 acatcaacaa actcaaaagc agcattgaat caactaatga agctgtcgtt aaacttcaag
7141 agactgcaga aaagacagtc tatgtgctga ctgctctaca ggattacatt aatactaatt
7201 tagtaccgac aattgacaag ataagctgca aacagacaga actctcacta gatctggcat
7261 tatcaaagta cctctctgat ttgctttttg tatttggccc caaccttcaa gacccagttt
7321 ctaattcaat gactatacag gctatatctc aggcattcgg tggaaattat gaaacactgc
7381 taagaacatt gggttacgct acagaagact ttgatgatct tctagaaagt gacagcataa
7441 caggtcaaat catctatgtt gatctaagta gctactatat aattgtcagg gtttattttc
7501 ctattctgac tgaaattcaa caggcctata tccaagagtt gttaccagtg agcttcaaca
7561 atgataattc agaatggatc agtattgtcc caaatttcat attggtaagg aatacattaa
7621 tatcaaatat agagattgga ttttgcctaa ttacaaagag gagcgtgatc tgcaaccaag
7681 attatgccac acctatgacc aacaacatga gagaatgttt aacgggatcg actgagaagt
7741 gtcctcgaga gctggttgtt tcatcacatg ttcccagatt tgcactatct aacggggttc
7801 tgtttgccaa ttgcataagt gttacatgtc agtgtcaaac aacaggcagg gcaatctcac
7861 aatcaggaga acaaactctg ctgatgattg acaacaccac ctgtcctaca gccgtactcg
7921 gtaatgtgat tatcagctta gggaaatatc tggggtcagt aaattataat tctgaaggca
7981 ttgctatcgg tcctccagtc tttacagata aagttgatat atcaagtcag atatccagca
8041 tgaatcagtc cttacaacag tctaaggact atatcaaaga ggctcaacga ctccttgata
8101 ctgttaatcc atcattaata agcatgttgt ctatgatcat actgtatgta ttatcgatcg
8161 catcgttgtg tatagggttg attacattta tcagttttat cattgttgag aaaaagagaa
8221 acacctacag cagattagag gataggagag tcagacctac aagcagtggg gatctctact
8281 acattgggac atagtgtatt cagattgatg aaattatgtt agagaaatca gaaaacttct
8341 gactttcaga aatggattgt atacaattag ttagatcatc ctgaataatc gaggtgagaa
8401 cattgcaact ataaaatcag atcatgtaaa tagttgtaaa aaattaaaag cttcttttaa
8461 ttcttttgaa caataattta attaatatat aacatattct ctcacacgag cgctaaccta
8521 tacactctct actaatattt tatactcata attaatgata taatgacaaa taaggattca
8581 aattggatta tgatatagtt tcatactaca atagcatttc gaccaagaaa atatccttac
8641 aattatacaa tgtacttaac cgtgaatatg taattgataa tttccccttta gaaatttaat
8701 aaaaaactta ggacccaggt ccataactca ttggatactt aactgtatct ttctaagcta
8761 tcacatatca aaggagagat tgaatgcttt tttggagatc tagatcatta ctatatgtgt
8821 ctcctataat cacatcatag gagtgaacca taatacacat ctttgggtag gggaaggaaa
8881 gtattgttga cgtactgatt gatctgcttg agtcaaataa tcagtcataa caattcaaga
8941 aaatgccggc agaaaacaag aaagttagat tcgaaaatac tacttcagac aaagggaaaa
9001 ttcctagtaa agttattaag agctactacg gaaccatgga cattaagaaa ataaatgaag
9061 gattattgga cagcaaaata ttaagtgctt tcaacacagt aatagcattg cttggatcta
9121 tcgtgatcat agtgatgaat ataatgatca tccaaaatta cacaagatca acagacaatc
9181 aggccgtgat caaagatgcg ttgcagggta tccaacagca gatcaaaggg cttgctgaca
9241 aaatcggcac agagataggg cccaaagtat cactgattga cacatccagt accattacta
9301 tcccagctaa cattgggctg ttaggttcaa agatcagcca gtcgactgca agtataaatg
9361 agaatgtgaa tgaaaaatgc aaattcacac tgcctccctt gaaaatccac gaatgtaaca
9_1 tttcttgtcc taacccactc ccttttagag agtataggcc acagacagaa ggggtgagca
9481 atctagtagg attacctaat aatatttgcc tgcaaaagac atctaatcag atattgaagc
9541 caaagctgat ttcatacact ttacccgtag tcggtcaaag tggtacctgt atcacagacc
9601 cattgctggc tatggacgag ggctattttg catatagcca cctggaaaga atcggatcat
```

FIG. 1A (Continued)

9661 gttcaagagg ggtctccaaa caaagaataa taggagttgg agaggtacta gacagaggtg
9721 atgaagttcc ttctttattt atgaccaatg tctggacccc accaaatcca aacaccgttt
9781 accactgtag tgctgtatac aacaatgaat tctattatgt actttgtgca gtgtcaactg
9841 ttggagaccc tattctgaat agcacctact ggtccggatc tctaatgatg acccgtctag
9901 ctgtgaaacc caagagtaat ggtggggtt acaatcaaca tcaacttgcc ctacgaagta
9961 tcgagaaagg gaggtatgat aaagttatgc cgtatggacc ttcaggcatc aaacagggtg
10021 acaccctgta ttttcctgct gtaggatttt tggtcaggac agagtttaaa tacaatgatt
10081 caaattgtcc catcacgaag tgtcaataca gtaaacctga aaattgcagg ctatctatgg
10141 ggattagacc aaacagccat tatatccttc gatctggact attaaaatac aatctatcag
10201 atggggagaa ccccaaagtt gtattcattg aaatatctga tcaaagatta tctattggat
10261 ctcctagcaa aatctatgat tctttgggtc aacctgtttt ctaccaagcg tcattttcat
10321 gggatactat gattaaattt ggagatgttc taacagtcaa ccctctggtt gtcaattggc
10381 gtaataacac ggtaatatca agacccgggc aatcacaatg ccctagattc aatacatgtc
10441 cagagatctg ctgggaagga gtttataatg atgcattcct aattgacaga atcaattgga
10501 taagcgcggg tgtattcctt gacagcaatc agaccgcaga aaatcctgtt tttactgtat
10561 tcaaagataa tgaaatactt tatagggcac aactggcttc tgaggacacc aatgcacaaa
10621 aaacaataac taattgtttt ctcttgaaga ataagatttg gtgcatatca ttggttgaga
10681 tatatgacac aggagacaat gtcataagac ccaaactatt cgcggttaag ataccagagc
10741 aatgtacata aaaatcaacc tcataattta atggattgat ctaatataat gataataatc
10801 gtacaaagac atgtgatgta aacaaaattg ttgtaattaa ataagtcctc agctgaatac
10861 tttttaaga ttagcaatag catgtttttc cagttattgg atagttgata atataattct
10921 gaaactgggt taataaataa tcttgatcgg tgatctttga gaacaatgat atcatatagt
10981 tcatcaagtg ataatcaatt ctttatatgt acactttaga gtatattttg agacttagta
11041 ttttcggccc gaatgttaaa tttaatagtt catacataac ctaaactcaa gttctaagca
11101 taatgataac aattaatgcg aacttgtctt gatgtaagga agatttgata ttaactgaga
11161 ctccacttga tatagtagag ctgaatcttg taaataaatt ataatgaata gtttattcaa
11221 agattatcat tcatattagt gtaaattaag aaaaacttag gacccaggtc cttgattatg
11281 ccaattttct cgagaaatca ttcaattgac catagactga aagcgttgtt acctagttct
11341 tcagaagaga tcttattaga attaatttat atgatctaat tcccttaaaa actgaatacc
11401 aaaaaacaaa aatggccgat gaattatcaa tatccgacat catttacccct gaatgtcatt
11461 tggatagtcc tatagtctct ggtaaactaa tatcagctat tgaatatgct caattgagac
11521 acaatcagcc cagtgatgat aaaagactgt ctgagaatat taggttaaac cttcacggga
11581 aaagaaagag tctatacata ttaagacaat ccaaacaggg tgattacatt agaaacaaca
11641 taaaaaacct aaaggaattc atgcatattg cgtaccctga atgcaataac attctattct
11701 ccatcacatc ccaaggcatg actagcaaac ttgataacat catgaaaaag tcattcaaag
11761 catacaatat cattagtaag aaagtaattg ggatgctgca aaatatcact agaaatctca
11821 taactcaaga tagaagagat gaaataatta atatacatga gtgtaggcga ttaggggatt
11881 tagggaagaa tatgagtcaa tctaaatggt atgagtgttt tttgttttgg tttactatca
11941 aaacagagat gcgagcagtg atcaagaatt cgcaaaagcc gaaattccgt tcagattcat
12001 gcataataca catgcgagac aaaagtactg aaataatcct aaatccgaat cttatctgca
12061 ttttcaaatc agacaaaact ggaaagaagt gttattatct tacacccgaa atggttctaa
12121 tgtattgtga tgtcctagag ggaaggatga tgatggagac aacagtcaaa tcggatatca
12181 agtaccaacc tctaatctcg agatccaatg ccctctgggg gctaattgat cccttgttcc
12241 ctgtcatggg aaacagaatt tacaatatag tgtctatgat agagccttta gttcttgcac
12301 tactccaact caaggatgag gctaggatcc tgaggggtgc atttctgcat cactgcataa
12361 aggaaatgca tcaagaattg agtgagtgtg gttttacaga tcagaagatt cggtctatgt
12_1 ttattgatga tcttttatcc attctaaata tcgataatat acatctgttg gcagagttct
12481 tttctttctt tcgtacgttt ggccatccta ttcttgaggc taaagttgct gcagaaaaag
12541 tgagagaaca tatgttggca gataaagttc ttgaatatgc ccctataatg aaagcacatg
12601 ctatattctg cgggactata ataaatgggt atagggatag acacggagga gcctggcctc
12661 ctctttacct ccccgcacat gcatctaaac atataatccg tttgaaaaat tctggggaat
12721 ctttgaccat tgatgactgt gtcaagaatt gggaatcatt ctgtgggatt caatttgatt
12781 gtttcatgga gctgaaattg gacagtgatc tgagtatgta tatgaaagat aaagctttat
12841 ctccaatcaa agacgaatgg gacagtgtat acccacgtga agtgttgagc tatacccccac FIG. 1A (Continued)

12901 cgaagtcaac cgagccaaga agattggttg acgtttttgt aaatgatgaa aactttgatc
12961 catacaacat gctggaatat gtcttatccg gtgcttatct cgaggatgaa caattcaatg
13021 tttcttatag cttgaaggag aaagagacga agcaagctgg acgattgttc gcaaagatga
13081 cctacaaaat gcgtgcatgt caagtcatag cagaggccct gatagcctca ggtgtcggta
13141 aatattttaa ggagaacggg atggttaagg atgagcacga acttttgaag acactcttcc
13201 aattgtctat ttcctcagtt cctcgaggga acagtcaggg taatgatcct caatccatca
13261 ataatataga aagagatttc caatacttta aggggtcac taccaatgtg aaagacaaaa
13321 agaataactc ttttaataag gttaaatctg ctctcaataa tccgtgccaa gctgacggag
13381 tccatcataa catgtcaccc aatacacgaa atcgttataa gtgtagtaat acaagtaagt
13441 cttttctcga ttatcatacc gagtttaatc ctcacaatca ctataaatca gacaatacag
13501 aggcggccgt actgtccagg tatgaggaca acactgggac aaaatttgat acagtaagtg
13561 catttcttac aactgatctt aagaaattct gtctcaattg gagatacgaa tcaatggcta
13621 tatttgctga acgtctggat gagatatacg gtttacctgg atttttaat tggatgcaca
13681 aacgactaga aagatctgtt atctatgttg cagaccctaa ttgcccccct aatattgaca
13741 aacatatgga actagaaaaa actcctgaag atgatatatt cattcattat cctaaaggcg
13801 gtattgaagg atatagccaa aaaacatgga ctatagcaac tatccccttt ttattcttga
13861 gtgcctatga gacaaacacg aggattgctg caattgtcca aggagacaat gaatcaattg
13921 ctatcactca aaaagttcat cctaatcttc cctacaaggt aaagaaagag atctgtgcaa
13981 agcaagctca gctttatttt gaaaggttaa ggatgaactt aagagccctc ggccacaatc
14041 ttaaagctac agaaactatc atcagtacac atctttttat ttattcgaag aaaattcatt
14101 atgatggtgc tgtgctgtct caggcactca aatcaatgtc aagatgttgc ttttggtcag
14161 agactctggt ggatgaaact agatcagctt gtagtaacat cagcactaca atagctaaag
1_21 ctatagaaaa tgggttgtca agaaatgtcg gctattgcat caatatttg aaagtaattc
1_81 agcagcttct catatcaact gagtttagta ttaacgagac attgacactg gatgtgacat
14341 ctcccatttc aaataattta gattggctta taacagctgc attaatcccg gcacctattg
14401 gaggattcaa ttaccttaat ttgtctagaa tttttgttag aaatataggt gatccggtta
14461 cagcatcttt ggctgatctt aagagaatga ttgatcacag tattatgact gaaagcgtat
14521 tacaaaaagt tatgaatcaa gaacctggtg atgcgagttt cttggactgg gccagtgatc
14581 catactcggg caacttgcct gactcacaaa gcatcactaa aacaattaaa aatatcacag
14641 caaggactat actgaggaac tcaccgaacc caatgctaaa aggtttattt catgacaaat
14701 cttttgatga agatcttgaa ctagctagct tcttaatgga caggagggtt atattaccta
14761 gagccgctca tgagatactg gataattcat tgacaggtgc cagagaggaa attgctggtt
14821 tattagatac aactaaaggc ttgatcagat cagggctaag aaagagtgga cttcagccaa
14881 agttagtttc tagattatct catcatgatt ataatcaatt tttaatactg aacaaacttc
14941 tatcaaacag aagacaaaat gacttgatat catcaaatac ttgctcagtt gacttggcac
15001 gagcattgag atctcacatg tggagggaat tagcgttagg tagagtaata tacggtcttg
15061 aggtaccaga tgcacttgag gctatggtgg gaaggtatat aacagggagc ttagagtgcc
15121 aaatttgtga gcagggaaac acgatgtatg ggtggttctt tgtacctagg gattcccaat
15181 tggatcaggt agatagagag cactcatcaa taagagtacc ttatgtagga tcaagtacgg
15241 atgaaagatc ggatatcaaa ctagggaatg tcaaaagacc aactaaggcc ttgcgttctg
15301 ctatcagaat tgcgacagta tatacttggg cctatgggga caatgaagag tgttggtatg
15361 aagcttggta cctagcgtct cagagggtaa acatagactt agatgtattg aaagctataa
15_1 ccccagtttc cacttcaaac aatttatccc atagattgag agataaatcc acacaattta
15481 agtttgcagg gagtgtactc aacagagttt ctagatatgt taacataagc aatgacaatc
15541 tagatttcag aattgaggga gaaaaggtag atacgaatct tatttatcaa caagcaatgc
15601 tattagggtt atcggtattg gaaggtaaat tcagattgag attagaaact gatgattaca
15661 acgggatata tcacttacac gtaaaggata attgttgtgt caaagaagtg gctgatgtag
15721 gccaagtaga cgctgagttg cctatcccag aatatactga agtggataac aatcatctta
15781 tatatgatcc agaccccgtt tcagaaatag attgcagccg tctttctaat caggagtcca
15841 aatcaagaga attagacttt cctttatggt caactgagga acttcatgat gtcctagcta
15901 agactgttgc tcagaccgtt cttgagatta taacaaaggc tgacaaggat gttttaaagc
15961 aacaccttgc aatagactct gacgataaca tcaacagctt aatcacagaa tttctaatag
16021 ttgatcctga actgtttgca ctttatctag gacaatctat atcaataaaa tgggcctttg
16081 aaattcatca taggcgtcct agaggaagac atactatggt cgacctattg tcagatcttg FIG. 1A (Continued)

```
16141 tatcaaatac atcaaagcac acttacaaag tgttgtcaaa tgccttgtca catcctagag
16201 tattcaagag atttgtaaac tgtggcttgc tattgcctac acagggtcct taccttcatc
16261 aacaagattt tgaaaagttg tctcaaaacc ttcttgtaac atcttatatg atttatctaa
16321 tgaactggtg tgacttcaag aaatccccct ttttaatcgc cgaacaggat gaaactgtga
16381 taagtctacg agaggatata ataacatcca aacatctctg tgttataatt gacttatatg
16441 caaatcacca taaacctcct tggataatag atctaaaccc acaagaaaaa atatgtgtac
16501 tgcgtgactt tatttctaaa tctaggcatg tggacacgtc ctccagatca tggaatactt
16561 ctgacctgga ttttgtaata ttctatgcat ctttgactta tttgagaaga ggtataataa
16621 aacaattaag gataagacaa gttactgagg ttatagatac cacaacaatg ttaagggaca
16681 atataattgt agagaatcct cctattaaaa caggagtgtt agacatcaga ggttgtataa
16741 tatacaattt agaggaaatc ctgtctatga acacaaaatc agcatcaaaa aagatcttta
16801 atcttaatag taggccgtca gtggagaatc ataaatatag aaggataggt ctcaactcat
16861 catcttgtta caaggcatta aatctatcac ctctgattca aaggtatttg ccgtcgggag
16921 ctcaaaggtt gtttatagga gaaggttctg ggagcatgat gttattatat cagtctacat
16981 tggggcaatc aatttctttt tacaattcag gtatagatgg agattatata ccaggtcaaa
17041 gagaactgaa actatttccc tctgaatact caattgctga ggaagaccca tctctgacgg
17101 ggaaattgaa aggactagtg gtgcccctat tcaatggaag accagaaaca acatggatcg
17161 ggaatttaga ctcctacgag tatatcataa ataggacagc ggggcgaagt ataggtcttg
17221 tccattctga catggagtct gggattgaca aaaatgtaga ggagatacta gtagaacatt
17281 cccatctaat atctatcgcg ataaatgtta tgatggagga cggactatta gtatccaaga
17341 tagcatacac ccctggattc ccaatctcaa gattatttaa catgtacaga tcatatttcg
17401 gactagtact ggtgtgtttc ccagtatata gtaatccaga ttctactgaa gtatatcttc
17461 tttgcttaca gaagacggtc aagactattg ttcccccgca aaaagtcctt gagcactcta
17521 atttgcacga tgaagtcaat gaccagggaa taacatcagt gatttttaaa atcaagaatt
17581 cacagtctaa gcagttccac gatgatctaa agaagtacta tcagattgac caaccttttt
17641 ttgtaccaac taaaatcact agtgatgaac aagtacttct ccaagcaggg ctgaaactca
17701 atgggccaga aattcttaag agtgaaatca gttatgatat cggttcagat atcaatacat
17761 taagagacac catcataatt atgttaaatg aggctatgaa ttattttgat gacaacagat
17821 caccttcaca ccacctagaa ccctatccag ttttggagag aactagaatt aaaacaataa
17881 tgaattgtgt gactaaaaaa gtgattgtct actcacttat caagttcaag gacaccaaaa
17941 gctcagaact ttatcacatc aaaaataaca tcagaagaaa agttctaatc ttagatttca
18001 gatcgaagct catgacaaag actctaccta aagggatgca agagagaaga gaaaaaaacg
18061 gtttcaaaga agtttggata gtagatttat cgaatcgaga agttaaaatc tggtggaaga
18121 taatcggata catatctatt atctgattta accttccaaa tccaagacca actgataact
18181 tatgttgatc taaggttcag ttattaagaa aaacttaata acgattcttc tttacccttg
18241 ttcggt (SEQ ID NO: 1)
```

FIG. 1A (Continued)

Nucleocapsid protein:

MSDIFEEAASFRSYQSKLGRDGRASAATATLTTKIRIFVPATNSPELRWELTLFALDVIRSPSAAESMKVGAAFTLI
SMYSERPGALIRSLLNDPDIEAVIIDVGSMVNGIPVMERRGDKAQEEMEGLMRILKTARDSSKGKTPFVDSRAYGLR
ITDMSTLVSAVITIEAQIWILIAKAVTAPDTAEESETRRWAKYVQQKRVNPFFALTQQWLTEMRNLLSQSLSVRKFM
VEILIEVKKGGSAKGRAVEIISDIGNYVEETGMAGFFATIRFGLETRYPALALNEFQSDLNTIKSLMLLYREIGPRA
PYMVLLEESIQTKFAPGGYPLLWSFAMGVATTIDRSMGALNINRGYLEPMYFRLGQKSARHHAGGIDQNMANRLGLS
SDQVAELAAAVQETSAGRQESNVQAREAKFAAGGVLIGGSDQDIDEGEEPIEQSGRQSVTFKREMSISSLANSVPSS
SVSTSGGTRLTNSLLNLRSRLAAKAAKEAASSNATDDPAISNRTQGESEKKNNQDLKPAQNDLDFVRADV (SEQ
ID NO: 2)

Phosphoprotein:

MDKLELVNDGLNIIDFIQKNQKEIQKTYGRSSIQQPSIKDQTKAWEDFLQCTSGESEQVEGGMSKDDGDVERRNLED
LSSTSPTDGTIGKRVSNTRDWAEGSDDIQLDPVVTDVVYHDHGGECTGYGFTSSPERGWSDYTSGANNGNVCLVSDA
KMLSYAPEIAVSKEDRETDLVHLENKLSTTGLNPTAVPFTLRNLSDPAKDSPVIAEHYYGLGVKEQNVGPQTSRNVN
LDSIKLYTSDDEEADQLEFEDEFAGSSSEVIVGISPEDEEPSSVGGKPNESIGRTIEGQSIRDNLQAKDNKSTDVPG
AGPKDSAVKEEPPQKRLPMLAEEFECSGSEDPIIRELLKENSLINCQQGKDAQPPYHWSIERSISPDKTEIVNGAVQ
TADRQRPGTPMPKSRGIPIKKGTDAKYPSAGTENVPGSKSGATRHVRGSPPYQEGKSVNAENVQLNASTAVKETDKS
EVNPVDDNDSLDDKYIMPSDDFSNTFFPHDTDRLNYHADHLGDYDLETLCEESVLMGVINSIKLINLDMRLNHIEEQ
VKEIPKIINKLESIDRVLAKTNTALSTIEGHLVSMMIMIPGKGKGERKGKNNPELKPVIGRDILEQQSLFSFDNVKN
FRDGSLTNEPYGAAVQLREDLILPELNFEETNASQFVPMADDSSRDVIKTLIRTHIKDRELRSELIGYLNKAENDEE
IQEIANTVNDIIDGNI (SEQ ID NO: 3)

V protein:

MDKLELVNDGLNIIDFIQKNQKEIQKTYGRSSIQQPSIKDQTKAWEDFLQCTSGESEQVEGGMSKDDGDVERRNLED
LSSTSPTDGTIGKRVSNTRDWAEGSDDIQLDPVVTDVVYHDHGGECTGYGFTSSPERGWSDYTSGANNGNVCLVSDA
KMLSYAPEIAVSKEDRETDLVHLENKLSTTGLNPTAVPFTLRNLSDPAKDSPVIAEHYYGLGVKEQNVGPQTSRNVN
LDSIKLYTSDDEEADQLEFEDEFAGSSSEVIVGISPEDEEPSSVGGKPNESIGRTIEGQSIRDNLQAKDNKSTDVPG
AGPKDSAVKEEPPQKRLPMLAEEFECSGSEDPIIRELLKENSLINCQQGKDAQPPYHWSIERSISPDKTEIVNGAVQ
TADRQRPGTPMPKSRGIPIKKGHRREISICWDGKRAWVEEWCNPACSRITPLPRRQECQCGECPTECFHCG (SEQ
ID NO: 4)

C protein:

MMASILLTLFRRTKKKYRRHTDDQVFNNPASKIKQKPGKIFCSAPVENLNKLRGECLRMMEMLKEETWRIYPVLLPQ
MELLERECRTPVTGQKVQMTYNWTQWLQTLYTMIMEENVPDMDLLQALREGGVITHQEQTMGMYVLYLMQRCCPMLP
KLQFLKKIGKLI (SEQ ID NO: 5)

Matrix protein:

MEPDIKSISSESMEGVSDFSPSSWEHGGYLDKVEPEIDENGSMIPKYKIYTPGANERKYNNYMYLICYGFVEDVERT
PETGKRKKIRTIAAYPLGVGKSASHPQDLLEELCSLKVTVRRTAGSTEKIVFGSSGPLNHLVPWKKVLTSGSIFNAV
KVCRNVDQIQLDKHQALRIFFLSITKLNDSGIYMIPRTMLEFRRNNAIAFNLLVYLKIDADLSKMGIQGSLDKDGFK
VASFMLHLGNFVRRAGKYYSVDYCRRKIDRMKLQFSLGSIGGLSLHIKINGVISKRLFAQMGFQKNLCFSLMDINPW
LNRLTWNNSCEISRVAAVLQPSIPREFMIYDDVFIDNTGRILKG (SEQ ID NO: 6)

Fusion protein:

MVVILDKRCYCNLLILILMISECSVGILHYEKLSKIGLVKGVTRKYKIKSNPLTKDIVIKMIPNVSNMSQCTGSVME
NYKTRLNGILTPIKGALEIYKNNTHDLVGDVRLAGVIMAGVAIGIATAAQITAGVALYEAMKNADNINKLKSSIEST
NEAVVKLQETAEKTVYVLTALQDYINTNLVPTIDKISCKQTELSLDLALSKYLSDLLFVFGPNLQDPVSNSMTIQAI
SQAFGGNYETLLRTLGYATEDFDDLLESDSITGQIIYVDLSSYYIIVRVYFPILTEIQQAYIQELLPVSFNNDNSEW
ISIVPNFILVRNTLISNIEIGFCLITKRSVICNQDYATPMTNNMRECLTGSTEKCPRELVVSSHVPRFALSNGVLFA
NCISVTCQCQTTGRAISQSGEQTLLMIDNTTCPTAVLGNVIISLGKYLGSVNYNSEGIAIGPPVFTDKVDISSQISS
MNQSLQQSKDYIKEAQRLLDTVNPSLISMLSMIILYVLSIASLCIGLITFISFIIVEKKRNTYSRLEDRRVRPTSSG
DLYYIGT (SEQ ID NO: 7)

FIG. 1B

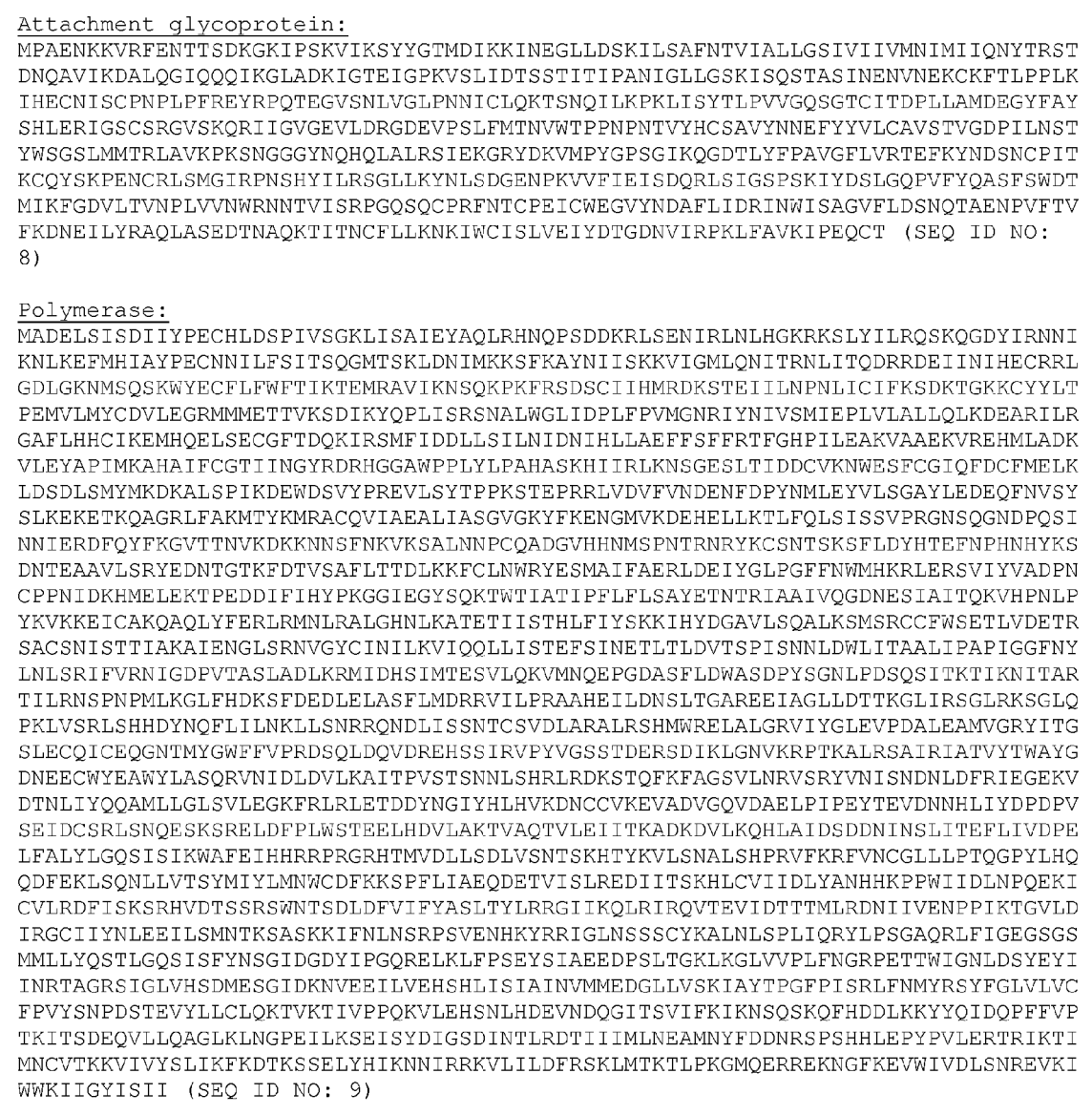

Attachment glycoprotein:

MPAENKKVRFENTTSDKGKIPSKVIKSYYGTMDIKKINEGLLDSKILSAFNTVIALLGSIVIIVMNIMIIQNYTRST
DNQAVIKDALQGIQQQIKGLADKIGTEIGPKVSLIDTSSTITIPANIGLLGSKISQSTASINENVNEKCKFTLPPLK
IHECNISCPNPLPFREYRPQTEGVSNLVGLPNNICLQKTSNQILKPKLISYTLPVVGQSGTCITDPLLAMDEGYFAY
SHLERIGSCSRGVSKQRIIGVGEVLDRGDEVPSLFMTNVWTPPNPNTVYHCSAVYNNEFYYVLCAVSTVGDPILNST
YWSGSLMMTRLAVKPKSNGGGYNQHQLALRSIEKGRYDKVMPYGPSGIKQGDTLYFPAVGFLVRTEFKYNDSNCPIT
KCQYSKPENCRLSMGIRPNSHYILRSGLLKYNLSDGENPKVVFIEISDQRLSIGSPSKIYDSLGQPVFYQASFSWDT
MIKFGDVLTVNPLVVNWRNNTVISRPGQSQCPRFNTCPEICWEGVYNDAFLIDRINWISAGVFLDSNQTAENPVFTV
FKDNEILYRAQLASEDTNAQKTITNCFLLKNKIWCISLVEIYDTGDNVIRPKLFAVKIPEQCT (SEQ ID NO:
8)

Polymerase:

MADELSISDIIYPECHLDSPIVSGKLISAIEYAQLRHNQPSDDKRLSENIRLNLHGKRKSLYILRQSKQGDYIRNNI
KNLKEFMHIAYPECNNILFSITSQGMTSKLDNIMKKSFKAYNIISKKVIGMLQNITRNLITQDRRDEIINIHECRRL
GDLGKNMSQSKWYECFLFWFTIKTEMRAVIKNSQKPKFRSDSCIIHMRDKSTEIILNPNLICIFKSDKTGKKCYYLT
PEMVLMYCDVLEGRMMMETTVKSDIKYQPLISRSNALWGLIDPLFPVMGNRIYNIVSMIEPLVLALLQLKDEARILR
GAFLHHCIKEMHQELSECGFTDQKIRSMFIDDLLSILNIDNIHLLAEFFSFFRTFGHPILEAKVAAEKVREHMLADK
VLEYAPIMKAHAIFCGTIINGYRDRHGGAWPPLYLPAHASKHIIRLKNSGESLTIDDCVKNWESFCGIQFDCFMELK
LDSDLSMYMKDKALSPIKDEWDSVYPREVLSYTPPKSTEPRRLVDVFVNDENFDPYNMLEYVLSGAYLEDEQFNVSY
SLKEKETKQAGRLFAKMTYKMRACQVIAEALIASGVGKYFKENGMVKDEHELLKTLFQLSISSVPRGNSQGNDPQSI
NNIERDFQYFKGVTTNVKDKKNNSFNKVKSALNNPCQADGVHHNMSPNTRNRYKCSNTSKSFLDYHTEFNPHNHYKS
DNTEAAVLSRYEDNTGTKFDTVSAFLTTDLKKFCLNWRYESMAIFAERLDEIYGLPGFFNWMHKRLERSVIYVADPN
CPPNIDKHMELEKTPEDDIFIHYPKGGIEGYSQKTWTIATIPFLFLSAYETNTRIAAIVQGDNESIAITQKVHPNLP
YKVKKEICAKQAQLYFERLRMNLRALGHNLKATETIISTHLFIYSKKIHYDGAVLSQALKSMSRCCFWSETLVDETR
SACSNISTTIAKAIENGLSRNVGYCINILKVIQQLLISTEFSINETLTLDVTSPISNNLDWLITAALIPAPIGGFNY
LNLSRIFVRNIGDPVTASLADLKRMIDHSIMTESVLQKVMNQEPGDASFLDWASDPYSGNLPDSQSITKTIKNITAR
TILRNSPNPMLKGLFHDKSFDEDLELASFLMDRRVILPRAAHEILDNSLTGAREEIAGLLDTTKGLIRSGLRKSGLQ
PKLVSRLSHHDYNQFLILNKLLSNRRQNDLISSNTCSVDLARALRSHMWRELALGRVIYGLEVPDALEAMVGRYITG
SLECQICEQGNTMYGWFFVPRDSQLDQVDREHSSIRVPYVGSSTDERSDIKLGNVKRPTKALRSAIRIATVYTWAYG
DNEECWYEAWYLASQRVNIDLDVLKAITPVSTSNNLSHRLRDKSTQFKFAGSVLNRVSRYVNISNDNLDFRIEGEKV
DTNLIYQQAMLLGLSVLEGKFRLRLETDDYNGIYHLHVKDNCCVKEVADVGQVDAELPIPEYTEVDNNHLIYDPDPV
SEIDCSRLSNQESKSRELDFPLWSTEELHDVLAKTVAQTVLEIITKADKDVLKQHLAIDSDDNINSLITEFLIVDPE
LFALYLGQSISIKWAFEIHHRRPRGRHTMVDLLSDLVSNTSKHTYKVLSNALSHPRVFKRFVNCGLLLPTQGPYLHQ
QDFEKLSQNLLVTSYMIYLMNWCDFKKSPFLIAEQDETVISLREDIITSKHLCVIIDLYANHHKPPWIIDLNPQEKI
CVLRDFISKSRHVDTSSRSWNTSDLDFVIFYASLTYLRRGIIKQLRIRQVTEVIDTTTMLRDNIIVENPPIKTGVLD
IRGCIIYNLEEILSMNTKSASKKIFNLNSRPSVENHKYRRIGLNSSSCYKALNLSPLIQRYLPSGAQRLFIGEGSGS
MMLLYQSTLGQSISFYNSGIDGDYIPGQRELKLFPSEYSIAEEDPSLTGKLKGLVVPLFNGRPETTWIGNLDSYEYI
INRTAGRSIGLVHSDMESGIDKNVEEILVEHSHLISIAINVMMEDGLLVSKIAYTPGFPISRLFNMYRSYFGLVLVC
FPVYSNPDSTEVYLLCLQKTVKTIVPPQKVLEHSNLHDEVNDQGITSVIFKIKNSQSKQFHDDLKKYYQIDQPFFVP
TKITSDEQVLLQAGLKLNGPEILKSEISYDIGSDINTLRDTIIIMLNEAMNYFDDNRSPSHHLEPYPVLERTRIKTI
MNCVTKKVIVYSLIKFKDTKSSELYHIKNNIRRKVLILDFRSKLMTKTLPKGMQERREKNGFKEVWIVDLSNREVKI
WWKIIGYISII (SEQ ID NO: 9)

FIG. 1B (Continued)

```
                 Nru I    H6p                    M   P   A   E   N   K   K   V
11470.SL   5'  ATCGCGATATCCGTTAAGTTTGTATCGTAATGCCGGCAGAAAACAAGAAAGTT

V   K   I   P   E   Q   C   T   *   Xho I (SEQ ID NO: 10)
               GTTAAGATACCAGAGCAATGTACATAACTCGAGCG (SEQ ID NO: 11)
11471.SL   3'  CAATTCTATGGTCTCGTTACATGTATTGAGCTCGC (SEQ ID NO: 13)
```

```
               ⇒ C5R
  1   GCGGCCGCAT TCTGAATGTT AAATGTTATA CTTTGGATGA AGCTATAAAT ATGCATTGGA
      CGCCGGCGTA AGACTTACAA TTTACAATAT GAAACCTACT TCGATATTTA TACGTAACCT

 61   AAAATAATCC ATTTAAAGAA AGGATTCAAA TACTACAAAA CCTAAGCGAT AATATGTTAA
      TTTTATTAGG TAAATTTCTT TCCTAAGTTT ATGATGTTTT GGATTCGCTA TTATACAATT

121   CTAAGCTTAT TCTTAACGAC GCTTTAAATA TACACAAATA AACATAATTT TTGTATAACC
      GATTCGAATA AGAATTGCTG CGAAATTTAT ATGTGTTTAT TTGTATTAAA AACATATTGG

181   TAACAAATAA CTAAAACATA AAAATAATAA AAGGAAATGT AATATCGTAA TTATTTTACT
      ATTGTTTATT GATTTTGTAT TTTTATTATT TTCCTTTACA TTATAGCATT AATAAAATGA

241   CAGGAATGGG GTTAAATATT TATATCACGT GTATATCTAT ACTGTTATCG TATACTCTTT
      GTCCTTACCC CAATTTATAA ATATAGTGCA CATATAGATA TGACAATAGC ATATGAGAAA

301   ACAATTACTA TTACGAATAT GCAAGAGATA ATAAGATTAC GTATTTAAGA GAATCTTGTC
      TGTTAATGAT AATGCTTATA CGTTCTCTAT TATTCTAATG CATAAATTCT CTTAGAACAG
                ← 7927.DC

361   ATGATAATTG GGTACGACAT AGTGATAAAT GCTATTTCGC ATCGTTACAT AAAGTCAGTT
      TACTATTAAC CCATGCTGTA TCACTATTTA CGATAAAGCG TAGCAATGTA TTTCAGTCAA

 _1   GGAAAGATGG ATTTGACAGA TGTAACTTAA TAGGTGCAAA AATGTTAAAT AACAGCATTC
      CCTTTCTACC TAAACTGTCT ACATTGAATT ATCCACGTTT TTACAATTTA TTGTCGTAAG

          7696.CXL →
481   TATCGGAAGA TAGGATACCA GTTATATTAT ACAAAAATCA CTGGTTGGAT AAAACAGATT
      ATAGCCTTCT ATCCTATGGT CAATATAATA TGTTTTTAGT GACCAACCTA TTTTGTCTAA

541   CTGCAATATT CGTAAAAGAT GAAGATTACT GCGAATTTGT AAACTATGAC AATAAAAAGC
      GACGTTATAA GCATTTTCTA CTTCTAATGA CGCTTAAACA TTTGATACTG TTATTTTTCG

601   CATTTATCTC AACGACATCG TGTAATTCTT CCATGTTTTA TGTATGTGTT TCAGATATTA
      GTAAATAGAG TTGCTGTAGC ACATTAAGAA GGTACAAAAT ACATACACAA AGTCTATAAT

661   TGAGATTACT ATAAACTTTT TGTATACTTA TATTCCGTAA ACTATATTAA TCATGAAGAA
      ACTCTAATGA TATTTGAAAA ACATATGAAT ATAAGGCATT TGATATAATT AGTACTTCTT

721   AATGAAAAAG TATAGAAGCT GTTCACGAGC GGTTGTTGAA AACAACAAAA TTATACATTC
      TTACTTTTTC ATATCTTCGA CAAGTGCTCG CCAACAACTT TTGTTGTTTT AATATGTAAG
                          ← 7926.DC

781   AAGATGGCTT ACATATACGT CTGTGAGGCT ATCATGGATA ATGACAATGC ATCTCTAAAT
      TTCTACCGAA TGTATATGCA GACACTCCGA TAGTACCTAT TACTGTTACG TAGAGATTTA

841   AGGTTTTTGG ACAATGGATT CGACCCTAAC ACGGAATATG GTACTCTACA ATCTCCTCTT
      TCCAAAAACC TGTTACCTAA GCTGGGATTG TGCCTTATAC CATGAGATGT TAGAGGAGAA

901   GAAATGGCTG TAATGTTCAA GAATACCGAG GCTATAAAAA TCTTGATGAG GTATGGAGCT
      CTTTACCGAC ATTACAAGTT CTTATGGCTC CGATATTTTT AGAACTACTC CATACCTCGA
```

FIG. 2D

```
                          7697.CXL →
 961   AAACCTGTAG TTACTGAATG CACAACTTCT TGTCTGCATG ATGCGGTGTT GAGAGACGAC
       TTTGGACATC AATGACTTAC GTGTTGAAGA ACAGACGTAC TACGCCACAA CTCTCTGCTG

1021   TACAAAATAG TGAAAGATCT GTTGAAGAAT AACTATGTAA ACAATGTTCT TTACAGCGGA
       ATGTTTTATC ACTTTCTAGA CAACTTCTTA TTGATACATT TGTTACAAGA AATGTCGCCT

1081   GGCTTTACTC CTTTGTGTTT GGCAGCTTAC CTTAACAAAG TTAATTTGGT TAAACTTCTA
       CCGAAATGAG GAAACACAAA CCGTCGAATG GAATTGTTTC AATTAAACCA ATTTGAAGAT

1141   TTGGCTCATT CGGCGGATGT AGATATTTCA AACACGGATC GGTTAACTCC TCTACATATA
       AACCGAGTAA GCCGCCTACA TCTATAAAGT TTGTGCCTAG CCAATTGAGG AGATGTATAT
                                                      ← 7925.DC

1201   GCCGTATCAA ATAAAAATTT AACAATGGTT AAACTTCTAT TGAACAAAGG TGCTGATACT
       CGGCATAGTT TATTTTTAAA TTGTTACCAA TTTGAAGATA ACTTGTTTCC ACGACTATGA

1261   GACTTGCTGG ATAACATGGG ACGTACTCCT TTAATGATCG CTGTACAATC TGGAAATATT
       CTGAACGACC TATTGTACCC TGCATGAGGA AATTACTAGC GACATGTTAG ACCTTTATAA

1321   GAAATATGTA GCACACTACT TAAAAAAAAT AAAATGTCCA GAACTGGGAA AAATTGATCT
       CTTTATACAT CGTGTGATGA ATTTTTTTTA TTTTACAGGT CTTGACCCTT TTTAACTAGA

1381   TGCCAGCTGT AATTCATGGT AGAAAAGAAG TGCTCAGGCT ACTTTTCAAC AAAGGAGCAG
       ACGGTCGACA TTAAGTACCA TCTTTTCTTC ACGAGTCCGA TGAAAAGTTG TTTCCTCGTC

1441   ATGTAAACTA CATCTTTGAA AGAAATGGAA AATCATATAC TGTTTTGGAA TTGATTAAAG
       TACATTTGAT GTAGAAACTT TCTTTACCTT TTAGTATATG ACAAAACCTT AACTAATTTC

7792.SL →
1501   AAAGTTACTC TGAGACACAA AAGAGGTAGC TGAAGTGGTA CTCTCAAAGG TACGTGACTA
       TTTCAATGAG ACTCTGTGTT TTCTCCATCG ACTTCACCAT GAGAGTTTCC ATGCACTGAT

1561   ATTAGCTATA AAAAGGATCC GGGTTAATTA ATTAGTCATC AGGCAGGGCG AGAACGAGAC
       TAATCGATAT TTTTCCTAGG CCCAATTAAT TAATCAGTAG TCCGTCCCGC TCTTGCTCTG

⇒ H6p
1621   TATCTGCTCG TTAATTAATT AGAGCTTCTT TATTCTATAC TTAAAAAGTG AAAATAAATA
       ATAGACGAGC AATTAATTAA TCTCGAAGAA ATAAGATATG AATTTTTCAC TTTTATTTAT

1681   CAAAGGTTCT TGAGGGTTGT GTTAAATTGA AAGCGAGAAA TAATCATAAA TTATTTCATT
       GTTTCCAAGA ACTCCCAACA CAATTTAACT TTCGCTCTTT ATTAGTATTT AATAAAGTAA

⇒ Nipah G
                                   Met ProAlaGlu AsnLysLys ValArgPheGlu·
1741   ATCGCGATAT CCGTTAAGTT TGTATCGTAA TGCCGGCAGA AAACAAGAAA GTTAGATTCG
       TAGCGCTATA GGCAATTCAA ACATAGCATT ACGGCCGTCT TTTGTTCTTT CAATCTAAGC ..AsnThrThr SerAspLys GlyLysIlePro SerLysVal IleLysSer TyrTyrGlyThr·
1801   AAAATACTAC TTCAGACAAA GGGAAAATTC CTAGTAAAGT TATTAAGAGC TACTACGGAA
       TTTTATGATG AAGTCTGTTT CCCTTTTAAG GATCATTTCA ATAATTCTCG ATGATGCCTT
                      ← 11472.SL
```

FIG. 2D (Continued)

```
     ..MetAspIle LysLysIle AsnGluGlyLeu LeuAspSer LysIleLeu SerAlaPheAsn·
1861 CCATGGACAT TAAGAAAATA AATGAAGGAT TATTGGACAG CAAAATATTA AGTGCTTTCA
     GGTACCTGTA ATTCTTTTAT TTACTTCCTA ATAACCTGTC GTTTTATAAT TCACGAAAGT

     ..ThrValIle AlaLeuLeu GlySerIleVal IleIleVal MetAsnIle MetIleIleGln·
1921 ACACAGTAAT AGCATTGCTT GGATCTATCG TGATCATAGT GATGAATATA ATGATCATCC
     TGTGTCATTA TCGTAACGAA CCTAGATAGC ACTAGTATCA CTACTTATAT TACTAGTAGG

     ..AsnTyrThr ArgSerThr AspAsnGlnAla ValIleLys AspAlaLeu GlnGlyIleGln·
1981 AAAATTACAC AAGATCAACA GACAATCAGG CCGTGATCAA AGATGCGTTG CAGGGTATCC
     TTTTAATGTG TTCTAGTTGT CTGTTAGTCC GGCACTAGTT TCTACGCAAC GTCCCATAGG

     ..GlnGlnIle LysGlyLeu AlaAspLysIle GlyThrGlu IleGlyPro LysValSerLeu·
2041 AACAGCAGAT CAAAGGGCTT GCTGACAAAA TCGGCACAGA GATAGGGCCC AAAGTATCAC
     TTGTCGTCTA GTTTCCCGAA CGACTGTTTT AGCCGTGTCT CTATCCCGGG TTTCATAGTG

     ..IleAspThr SerSerThr IleThrIlePro AlaAsnIle GlyLeuLeu GlySerLysIle·
2101 TGATTGACAC ATCCAGTACC ATTACTATCC CAGCTAACAT TGGGCTGTTA GGTTCAAAGA
     ACTAACTGTG TAGGTCATGG TAATGATAGG GTCGATTGTA ACCCGACAAT CCAAGTTTCT

            11473.SL →
     ..SerGlnSer ThrAlaSer IleAsnGluAsn ValAsnGlu LysCysLys PheThrLeuPro·
2161 TCAGCCAGTC GACTGCAAGT ATAAATGAGA ATGTGAATGA AAAATGCAAA TTCACACTGC
     AGTCGGTCAG CTGACGTTCA TATTTACTCT TACACTTACT TTTTACGTTT AAGTGTGACG

     ..ProLeuLys IleHisGlu CysAsnIleSer CysProAsn ProLeuPro PheArgGluTyr·
2221 CTCCCTTGAA AATCCACGAA TGTAACATTT CTTGTCCTAA CCCACTCCCT TTTAGAGAGT
     GAGGGAACTT TTAGGTGCTT ACATTGTAAA GAACAGGATT GGGTGAGGGA AAATCTCTCA
         ← 11474.SL

     ..ArgProGln ThrGluGly ValSerAsnLeu ValGlyLeu ProAsnAsn IleCysLeuGln·
2281 ATAGGCCACA GACAGAAGGG GTGAGCAATC TAGTAGGATT ACCTAATAAT ATTTGCCTGC
     TATCCGGTGT CTGTCTTCCC CACTCGTTAG ATCATCCTAA TGGATTATTA TAAACGGACG

     ..LysThrSer AsnGlnIle LeuLysProLys LeuIleSer TyrThrLeu ProValValGly·
2341 AAAAGACATC TAATCAGATA TTGAAGCCAA AGCTGATTTC ATACACTTTA CCCGTAGTCG
     TTTTCTGTAG ATTAGTCTAT AACTTCGGTT TCGACTAAAG TATGTGAAAT GGGCATCAGC

     ..GlnSerGly ThrCysIle ThrAspProLeu LeuAlaMet AspGluGly TyrPheAlaTyr·
2401 GTCAAAGTGG TACCTGTATC ACAGACCCAT TGCTGGCTAT GGACGAGGGC TATTTTGCAT
     CAGTTTCACC ATGGACATAG TGTCTGGGTA ACGACCGATA CCTGCTCCCG ATAAAACGTA

     ..SerHisLeu GluArgIle GlySerCysSer ArgGlyVal SerLysGln ArgIleIleGly·
2461 ATAGCCACCT GGAAAGAATC GGATCATGTT CAAGAGGGGT CTCCAAACAA AGAATAATAG
     TATCGGTGGA CCTTTCTTAG CCTAGTACAA GTTCTCCCCA GAGGTTTGTT TCTTATTATC

                                                         11475.SL →
     ..ValGlyGlu ValLeuAsp ArgGlyAspGlu ValProSer LeuPheMet ThrAsnValTrp·
2521 GAGTTGGAGA GGTACTAGAC AGAGGTGATG AAGTTCCTTC TTTATTTATG ACCAATGTCT
     CTCAACCTCT CCATGATCTG TCTCCACTAC TTCAAGGAAG AAATAAATAC TGGTTACAGA

     ..ThrProPro AsnProAsn ThrValTyrHis CysSerAla ValTyrAsn AsnGluPheTyr·
2581 GGACCCCACC AAATCCAAAC ACCGTTTACC ACTGTAGTGC TGTATACAAC AATGAATTCT
     CCTGGGGTGG TTTAGGTTTG TGGCAAATGG TGACATCACG ACATATGTTG TTACTTAAGA
```

FIG. 2D (Continued)

```
     ..TyrValLeu CysAlaVal SerThrValGly AspProIle LeuAsnSer ThrTyrTrpSer·
2641 ATTATGTACT TTGTGCAGTG TCAACTGTTG GAGACCCTAT TCTGAATAGC ACCTACTGGT
     TAATACATGA AACACGTCAC AGTTGACAAC CTCTGGGATA AGACTTATCG TGGATGACCA
                        ← 11476.SL
     ..GlySerLeu MetMetThr ArgLeuAlaVal LysProLys SerAsnGly GlyGlyTyrAsn·
2701 CCGGATCTCT AATGATGACC CGTCTAGCTG TGAAACCCAA GAGTAATGGT GGGGGTTACA
     GGCCTAGAGA TTACTACTGG GCAGATCGAC ACTTTGGGTT CTCATTACCA CCCCCAATGT

     ..GlnHisGln LeuAlaLeu ArgSerIleGlu LysGlyArg TyrAspLys ValMetProTyr·
2761 ATCAACATCA ACTTGCCCTA CGAAGTATCG AGAAAGGGAG GTATGATAAA GTTATGCCGT
     TAGTTGTAGT TGAACGGGAT GCTTCATAGC TCTTTCCCTC CATACTATTT CAATACGGCA

     ..GlyProSer GlyIleLys GlnGlyAspThr LeuTyrPhe ProAlaVal GlyPheLeuVal·
2821 ATGGACCTTC AGGCATCAAA CAGGGTGACA CCCTGTATTT TCCTGCTGTA GGATTTTTGG
     TACCTGGAAG TCCGTAGTTT GTCCCACTGT GGGACATAAA AGGACGACAT CCTAAAAACC

     ..ArgThrGlu PheLysTyr AsnAspSerAsn CysProIle ThrLysCys GlnTyrSerLys·
2881 TCAGGACAGA GTTTAAATAC AATGATTCAA ATTGTCCCAT CACGAAGTGT CAATACAGTA
     AGTCCTGTCT CAAATTTATG TTACTAAGTT TAACAGGGTA GTGCTTCACA GTTATGTCAT

                                                    11477.SL →
     ..ProGluAsn CysArgLeu SerMetGlyIle ArgProAsn SerHisTyr IleLeuArgSer·
2941 AACCTGAAAA TTGCAGGCTA TCTATGGGGA TTAGACCAAA CAGCCATTAT ATCCTTCGAT
     TTGGACTTTT AACGTCCGAT AGATACCCCT AATCTGGTTT GTCGGTAATA TAGGAAGCTA

     ..GlyLeuLeu LysTyrAsn LeuSerAspGly GluAsnPro LysValVal PheIleGluIle·
3001 CTGGACTATT AAAATACAAT CTATCAGATG GGAGAACCCC CAAAGTTGTA TTCATTGAAA
     GACCTGATAA TTTTATGTTA GATAGTCTAC CCCTCTTGGG GTTTCAACAT AAGTAACTTT
                           ← 11478.SL

     ..SerAspGln ArgLeuSer IleGlySerPro SerLysIle TyrAspSer LeuGlyGlnPro·
3061 TATCTGATCA AAGATTATCT ATTGGATCTC CTAGCAAAAT CTATGATTCT TTGGGTCAAC
     ATAGACTAGT TTCTAATAGA TAACCTAGAG GATCGTTTTA GATACTAAGA AACCCAGTTG

     ..ValPheTyr GlnAlaSer PheSerTrpAsp ThrMetIle LysPheGly AspValLeuThr·
3121 CTGTTTTCTA CCAAGCGTCA TTTTCATGGG ATACTATGAT TAAATTTGGA GATGTTCTAA
     GACAAAAGAT GGTTCGCAGT AAAAGTACCC TATGATACTA ATTTAAACCT CTACAAGATT

     ..ValAsnPro LeuValVal AsnTrpArgAsn AsnThrVal IleSerArg ProGlyGlnSer·
3181 CAGTCAACCC TCTGGTTGTC AATTGGCGTA ATAACACGGT AATATCAAGA CCCGGGCAAT
     GTCAGTTGGG AGACCAACAG TTAACCGCAT TATTGTGCCA TTATAGTTCT GGGCCCGTTA

     ..GlnCysPro ArgPheAsn ThrCysProGlu IleCysTrp GluGlyVal TyrAsnAspAla·
3241 CACAATGCCC TAGATTCAAT ACATGTCCAG AGATCTGCTG GGAAGGAGTT TATAATGATG
     GTGTTACGGG ATCTAAGTTA TGTACAGGTC TCTAGACGAC CCTTCCTCAA ATATTACTAC

                                           11479.SL →
     ..PheLeuIle AspArgIle AsnTrpIleSer AlaGlyVal PheLeuAsp SerAsnGlnThr·
3301 CATTCCTAAT TGACAGAATC AATTGGATAA GCGCGGGTGT ATTCCTTGAC AGCAATCAGA
     GTAAGGATTA ACTGTCTTAG TTAACCTATT CGCGCCCACA TAAGGAACTG TCGTTAGTCT

     ..AlaGluAsn ProValPhe ThrValPheLys AspAsnGlu IleLeuTyr ArgAlaGlnLeu·
3361 CCGCAGAAAA TCCTGTTTTT ACTGTATTCA AAGATAATGA AATACTTTAT AGGGCACAAC
     GGCGTCTTTT AGGACAAAAA TGACATAAGT TTCTATTACT TTATGAAATA TCCCGTGTTG
```

FIG. 2D (Continued)

```
        ..AlaSerGlu AspThrAsn AlaGlnLysThr IleThrAsn CysPheLeu LeuLysAsnLys·
3_1     TGGCTTCTGA GGACACCAAT GCACAAAAAA CAATAACTAA TTGTTTTCTC TTGAAGAATA
        ACCGAAGACT CCTGTGGTTA CGTGTTTTTT GTTATTGATT AACAAAAGAG AACTTCTTAT
          ← 11480.SL

        ..IleTrpCys IleSerLeu ValGluIleTyr AspThrGly AspAsnVal IleArgProLys·
3481    AGATTTGGTG CATATCATTG GTTGAGATAT ATGACACAGG AGACAATGTC ATAAGACCCA
        TCTAAACCAC GTATAGTAAC CAACTCTATA TACTGTGTCC TCTGTTACAG TATTCTGGGT

        ..LeuPheAla ValLysIle ProGluGlnCys Thr (SEQ ID NO: 14)
3541    AACTATTCGC GGTTAAGATA CCAGAGCAAT GTACATAACT CGAGTCTAGA ATCGATCCCG
        TTGATAAGCG CCAATTCTAT GGTCTCGTTA CATGTATTGA GCTCAGATCT TAGCTAGGGC

                                         ⇒ C5L
3601    GGTTTTTATG ACTAGTTAAT CACGGCCGCT TATAAAGATC TAAAATGCAT AATTTCTAAA
        CCAAAAATAC TGATCAATTA GTGCCGGCGA ATATTTCTAG ATTTTACGTA TTAAAGATTT

                              7928.DC →
3661    TAATGAAAAA AAGTACATCA TGAGCAACGC GTTAGTATAT TTTACAATGG AGATTAACGC
        ATTACTTTTT TTCATGTAGT ACTCGTTGCG CAATCATATA AAATGTTACC TCTAATTGCG

3721    TCTATACCGT TCTATGTTTA TTGATTCAGA TGATGTTTTA GAAAAGAAAG TTATTGAATA
        AGATATGGCA AGATACAAAT AACTAAGTCT ACTACAAAAT CTTTTCTTTC AATAACTTAT
          ← 7793.SL

3781    TGAAAACTTT AATGAAGATG AAGATGACGA CGATGATTAT TGTTGTAAAT CTGTTTTAGA
        ACTTTTGAAA TTACTTCTAC TTCTACTGCT GCTACTAATA ACAACATTTA GACAAAATCT

3841    TGAAGAAGAT GACGCGCTAA AGTATACTAT GGTTACAAAG TATAAGTCTA TACTACTAAT
        ACTTCTTCTA CTGCGCGATT TCATATGATA CCAATGTTTC ATATTCAGAT ATGATGATTA

3901    GGCGACTTGT GCAAGAAGGT ATAGTATAGT GAAAATGTTG TTAGATTATG ATTATGAAAA
        CCGCTGAACA CGTTCTTCCA TATCATATCA CTTTTACAAC AATCTAATAC TAATACTTTT

3961    ACCAAATAAA TCAGATCCAT ATCTAAAGGT ATCTCCTTTG CACATAATTT CATCTATTCC
        TGGTTTATTT AGTCTAGGTA TAGATTTCCA TAGAGGAAAC GTGTATTAAA GTAGATAAGG

4021    TAGTTTAGAA TACCTGCAGC CAAGCTTGGC ACTGGCCGTC GTTTTAC (SEQ ID NO: 15)
        ATCAAATCTT ATGGACGTCG GTTCGAACCG TGACCGGCAG CAAAATG (SEQ ID NO: 16)
                                           ← M13F
```

FIG. 2D (Continued)

```
                  Nru I    H6p                  M  P  A  E  N  K  K  V
11470.SL  5' ATCGCGATATCCGTTAAGTTTGTATCGTAATGCCGGCAGAAAACAAGAAAGTT

V  K  I  P  E  Q  C  T  *  Xho I (SEQ ID NO: 10)
             GTTAAGATACCAGAGCAATGTACATAACTCGAGCG (SEQ ID NO: 11)
11471.SL  3' CAATTCTATGGTCTCGTTACATGTATTGAGCTCGC (SEQ ID NO: 13)
```

M13F → ⇒ F8R
1 GTAAAACGAC GGCCAGTGAA TTGTAATACG ACTCACTATA GGGCGAATTG GGTGACCCTT
CATTTTGCTG CCGGTCACTT AACATTATGC TGAGTGATAT CCCGCTTAAC CCACTGGGAA

61 TACAAGAATA AAAGAAGAAA CAACTGTGAA ATAGTTTATA AATGTAATTC GTATGCAGAA
ATGTTCTTAT TTTCTTCTTT GTTGACACTT TATCAAATAT TTACATTAAG CATACGTCTT

121 AACGATAATA TATTTTGGTA TGAGAAATCT AAAGGAGACA TAGTTTGTAT AGACATGCGC
TTGCTATTAT ATAAAACCAT ACTCTTTAGA TTTCCTCTGT ATCAAACATA TCTGTACGCG

181 TCTTCCGATG AGATATTCGA TGCTTTTCTA ATGTATCATA TAGCTACAAG ATATGCCTAT
AGAAGGCTAC TCTATAAGCT ACGAAAAGAT TACATAGTAT ATCGATGTTC TATACGGATA

241 CATGATGATG ATATATATCT ACAAATAGTG TTATATTATT CTAATAATCA AAATGTTATA
GTACTACTAC TATATATAGA TGTTTATCAC AATATAATAA GATTATTAGT TTTACAATAT

301 TCTTATATTA CGAAAAATAA ATACGTTAAG TATATAAGAA ATAAAACTAG AGACGATATT
AGAATATAAT GCTTTTTATT TATGCAATTC ATATATTCTT TATTTTGATC TCTGCTATAA

361 CATAAAGTAA AAATATTAGC TCTAGAAGAC TTTACAACGG AAGAAATATA TTGTTGGATT
GTATTTCATT TTTATAATCG AGATCTTCTG AAATGTTGCC TTCTTTATAT AACAACCTAA

421 AGTAATATAT AACAGCGTAG CTGCACGGTT TTGATCATTT TCCAACAATA TAAACCAATG
TCATTATATA TTGTCGCATC GACGTGCCAA AACTAGTAAA AGGTTGTTAT ATTTGGTTAC

7864.SL →
481 AAGGAGGACG ACTCATCAAA CATAAATAAC ATTCACGGAA AATATTCAGT ATCAGATTTA
TTCCTCCTGC TGAGTAGTTT GTATTTATTG TAAGTGCCTT TTATAAGTCA TAGTCTAAAT
← 7876.SL

541 TCACAAGATG ATTATGTTAT TGAATGTATA GACGGATCTT TTGATTCGAT CAAGTATAGA
AGTGTTCTAC TAATACAATA ACTTACATAT CTGCCTAGAA AACTAAGCTA GTTCATATCT

601 GATATAAAGG TTATAATAAT GAAGAATAAC GGTTACGTTA ATTGTAGTAA ATTATGTAAA
CTATATTTCC AATATTATTA CTTCTTATTG CCAATGCAAT TAACATCATT TAATACATTT

661 ATGCGGAATA AATACTTTTC TAGATGGTTG CGTCTTTCTA CTTCTAAAGC ATTATTAGAC
TACGCCTTAT TTATGAAAAG ATCTACCAAC GCAGAAAGAT GAAGATTTCG TAATAATCTG

721 ATTTACAATA ATAAGTCAGT AGATAATGCT ATTGTTAAAG TCTATGGTAA AGGTAAGAAA
TAAATGTTAT TATTCAGTCA TCTATTACGA TAACAATTTC AGATACCATT TCCATTCTTT

781 CTTATTATAA CAGGATTTTA TCTCAAACAA AATATGATAC GTTATGTTAT TGAGTGGATA
GAATAATATT GTCCTAAAAT AGAGTTTGTT TTATACTATG CAATACAATA ACTCACCTAT

841 GGGGATGATT TTACAAACGA TATATACAAA ATGATTAATT TCTATAATGC GTTATTCGGT
CCCCTACTAA AATGTTTGCT ATATATGTTT TACTAATTAA AGATATTACG CAATAAGCCA

7865.SL →
901 AACGATGAAT TAAAAATAGT ATCCTGTGAA AACACTCTAT GCCCGTTTAT AGAACTTGGT
TTGCTACTTA ATTTTTATCA TAGGACACTT TTGTGAGATA CGGGCAAATA TCTTGAACCA
← 7875.SL

961 AGATGCTATT ATGGTAAAAA ATGTAAGTAT ATACACGGAG ATCAATGTGA TATCTGTGGT
TCTACGATAA TACCATTTTT TACATTCATA TATGTGCCTC TAGTTACACT ATAGACACCA

FIG. 3C

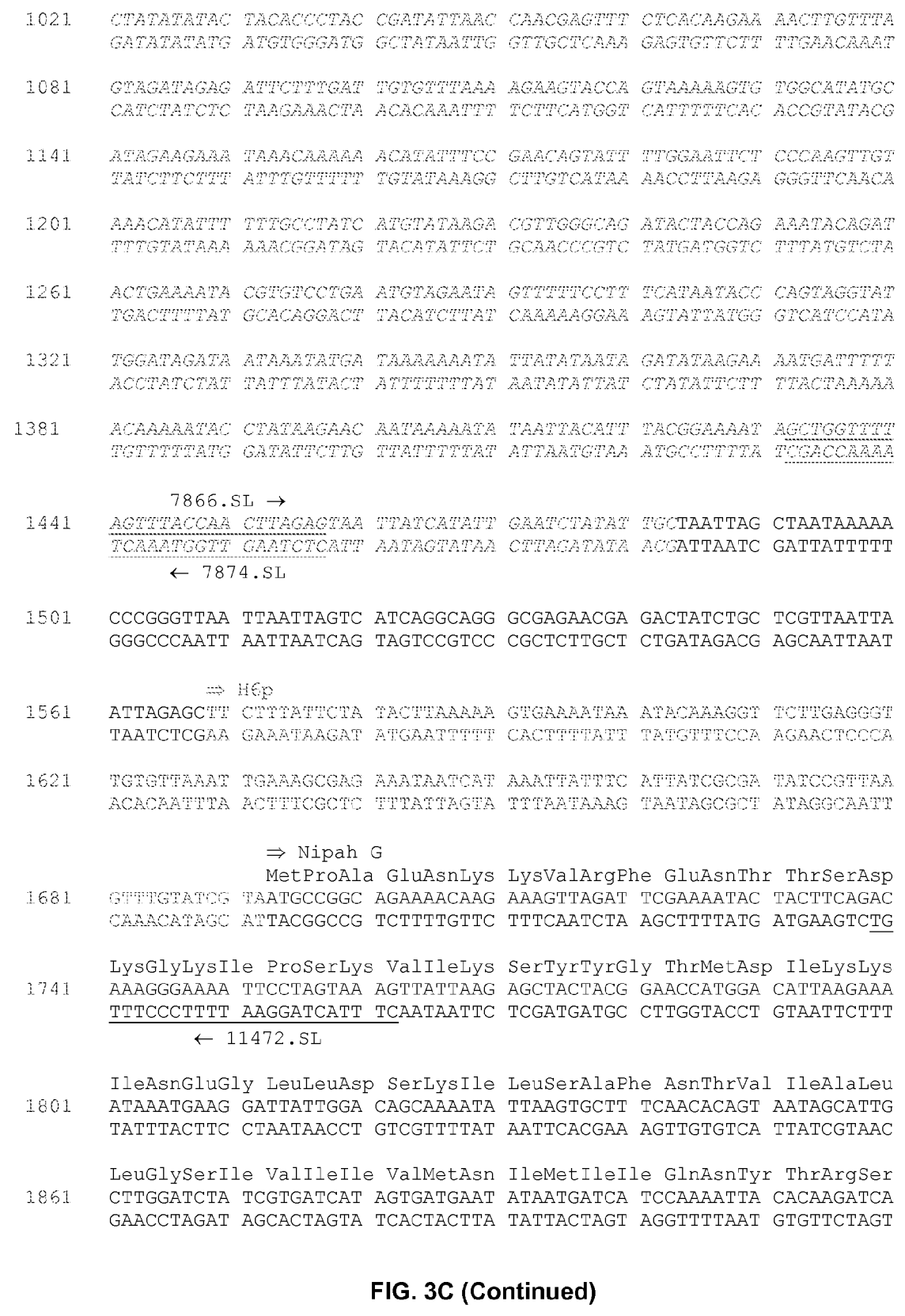

1021 CTATATATAC TACACCCTAC CGATATTAAC CAACGAGTTT CTCACAAGAA AACTTGTTTA
GATATATATG ATGTGGGATG GCTATAATTG GTTGCTCAAA GAGTGTTCTT TTGAACAAAT

1081 GTAGATAGAG ATTCTTTGAT TGTGTTTAAA AGAAGTACCA GTAAAAAGTG TGGCATATGC
CATCTATCTC TAAGAAACTA ACACAAATTT TCTTCATGGT CATTTTTCAC ACCGTATACG

1141 ATAGAAGAAA TAAACAAAAA ACATATTTCC GAACAGTATT TTGGAATTCT CCCAAGTTGT
TATCTTCTTT ATTTGTTTTT TGTATAAAGG CTTGTCATAA AACCTTAAGA GGGTTCAACA

1201 AAACATATTT TTTGCCTATC ATGTATAAGA CGTTGGGCAG ATACTACCAG AAATACAGAT
TTTGTATAAA AAACGGATAG TACATATTCT GCAACCCGTC TATGATGGTC TTTATGTCTA

1261 ACTGAAAATA CGTGTCCTGA ATGTAGAATA GTTTTTCCTT TCATAATACC CAGTAGGTAT
TGACTTTTAT GCACAGGACT TACATCTTAT CAAAAAGGAA AGTATTATGG GTCATCCATA

1321 TGGATAGATA ATAAATATGA TAAAAAAATA TTATATAATA GATATAAGAA AATGATTTTT
ACCTATCTAT TATTTATACT ATTTTTTTAT AATATATTAT CTATATTCTT TTACTAAAAA

1381 ACAAAAATAC CTATAAGAAC AATAAAAATA TAATTACATT TACGGAAAAT AGCTGGTTTT
TGTTTTTATG GATATTCTTG TTATTTTTAT ATTAATGTAA ATGCCTTTTA TCGACCAAAA

7866.SL →
1441 AGTTTACCAA CTTAGAGTAA TTATCATATT GAATCTATAT TGCTAATTAG CTAATAAAAA
TCAAATGGTT GAATCTCATT AATAGTATAA CTTAGATATA ACGATTAATC GATTATTTTT
← 7874.SL

1501 CCCGGGTTAA TTAATTAGTC ATCAGGCAGG GCGAGAACGA GACTATCTGC TCGTTAATTA
GGGCCCAATT AATTAATCAG TAGTCCGTCC CGCTCTTGCT CTGATAGACG AGCAATTAAT

⇒ H6p
1561 ATTAGAGCTT CTTTATTCTA TACTTAAAAA GTGAAAATAA ATACAAAGGT TCTTGAGGGT
TAATCTCGAA GAAATAAGAT ATGAATTTTT CACTTTTATT TATGTTTCCA AGAACTCCCA

1621 TGTGTTAAAT TGAAAGCGAG AAATAATCAT AAATTATTTC ATTATCGCGA TATCCGTTAA
ACACAATTTA ACTTTCGCTC TTTATTAGTA TTTAATAAAG TAATAGCGCT ATAGGCAATT

⇒ Nipah G
MetProAla GluAsnLys LysValArgPhe GluAsnThr ThrSerAsp
1681 GTTTGTATCG TAATGCCGGC AGAAAAACAAG AAAGTTAGAT TCGAAAATAC TACTTCAGAC
CAAACATAGC ATTACGGCCG TCTTTTGTTC TTTCAATCTA AGCTTTTATG ATGAAGTCTG LysGlyLysIle ProSerLys ValIleLys SerTyrTyrGly ThrMetAsp IleLysLys
1741 AAAGGGAAAA TTCCTAGTAA AGTTATTAAG AGCTACTACG GAACCATGGA CATTAAGAAA
TTTCCCTTTT AAGGATCATT TCAATAATTC TCGATGATGC CTTGGTACCT GTAATTCTTT
← 11472.SL IleAsnGluGly LeuLeuAsp SerLysIle LeuSerAlaPhe AsnThrVal IleAlaLeu
1801 ATAAATGAAG GATTATTGGA CAGCAAAATA TTAAGTGCTT TCAACACAGT AATAGCATTG
TATTTACTTC CTAATAACCT GTCGTTTTAT AATTCACGAA AGTTGTGTCA TTATCGTAAC LeuGlySerIle ValIleIle ValMetAsn IleMetIleIle GlnAsnTyr ThrArgSer
1861 CTTGGATCTA TCGTGATCAT AGTGATGAAT ATAATGATCA TCCAAAATTA CACAAGATCA
GAACCTAGAT AGCACTAGTA TCACTACTTA TATTACTAGT AGGTTTTAAT GTGTTCTAGT

FIG. 3C (Continued)

```
     ThrAspAsnGln AlaValIle LysAspAla LeuGlnGlyIle GlnGlnGln IleLysGly
1921 ACAGACAATC AGGCCGTGAT CAAAGATGCG TTGCAGGGTA TCCAACAGCA GATCAAAGGG
     TGTCTGTTAG TCCGGCACTA GTTTCTACGC AACGTCCCAT AGGTTGTCGT CTAGTTTCCC

     LeuAlaAspLys IleGlyThr GluIleGly ProLysValSer LeuIleAsp ThrSerSer
1981 CTTGCTGACA AAATCGGCAC AGAGATAGGG CCCAAAGTAT CACTGATTGA CACATCCAGT
     GAACGACTGT TTTAGCCGTG TCTCTATCCC GGGTTTCATA GTGACTAACT GTGTAGGTCA

                                                   11473.SL →
     ThrIleThrIle ProAlaAsn IleGlyLeu LeuGlySerLys IleSerGln SerThrAla
2041 ACCATTACTA TCCCAGCTAA CATTGGGCTG TTAGGTTCAA AGATCAGCCA GTCGACTGCA
     TGGTAATGAT AGGGTCGATT GTAACCCGAC AATCCAAGTT TCTAGTCGGT CAGCTGACGT

     SerIleAsnGlu AsnValAsn GluLysCys LysPheThrLeu ProProLeu LysIleHis
2101 AGTATAAATG AGAATGTGAA TGAAAAATGC AAATTCACAC TGCCTCCCTT GAAAATCCAC
     TCATATTTAC TCTTACACTT ACTTTTTACG TTTAAGTGTG ACGGAGGGAA CTTTTAGGTG
                                                  ← 11474.SL

     GluCysAsnIle SerCysPro AsnProLeu ProPheArgGlu TyrArgPro GlnThrGlu
2161 GAATGTAACA TTTCTTGTCC TAACCCACTC CCTTTTAGAG AGTATAGGCC ACAGACAGAA
     CTTACATTGT AAAGAACAGG ATTGGGTGAG GGAAAATCTC TCATATCCGG TGTCTGTCTT

     GlyValSerAsn LeuValGly LeuProAsn AsnIleCysLeu GlnLysThr SerAsnGln
2221 GGGGTGAGCA ATCTAGTAGG ATTACCTAAT AATATTTGCC TGCAAAAGAC ATCTAATCAG
     CCCCACTCGT TAGATCATCC TAATGGATTA TTATAAACGG ACGTTTTCTG TAGATTAGTC

     IleLeuLysPro LysLeuIle SerTyrThr LeuProValVal GlyGlnSer GlyThrCys
2281 ATATTGAAGC CAAAGCTGAT TTCATACACT TTACCCGTAG TCGGTCAAAG TGGTACCTGT
     TATAACTTCG GTTTCGACTA AAGTATGTGA AATGGGCATC AGCCAGTTTC ACCATGGACA

     IleThrAspPro LeuLeuAla MetAspGlu GlyTyrPheAla TyrSerHis LeuGluArg
2341 ATCACAGACC CATTGCTGGC TATGGACGAG GGCTATTTTG CATATAGCCA CCTGGAAAGA
     TAGTGTCTGG GTAACGACCG ATACCTGCTC CCGATAAAAC GTATATCGGT GGACCTTTCT

     IleGlySerCys SerArgGly ValSerLys GlnArgIleIle GlyValGly GluValLeu
2401 ATCGGATCAT GTTCAAGAGG GGTCTCCAAA CAAAGAATAA TAGGAGTTGG AGAGGTACTA
     TAGCCTAGTA CAAGTTCTCC CCAGAGGTTT GTTTCTTATT ATCCTCAACC TCTCCATGAT

                                          11475.SL →
     AspArgGlyAsp GluValPro SerLeuPhe MetThrAsnVal TrpThrPro ProAsnPro
2461 GACAGAGGTG ATGAAGTTCC TTCTTTATTT ATGACCAATG TCTGGACCCC ACCAAATCCA
     CTGTCTCCAC TACTTCAAGG AAGAAATAAA TACTGGTTAC AGACCTGGGG TGGTTTAGGT

     AsnThrValTyr HisCysSer AlaValTyr AsnAsnGluPhe TyrTyrVal LeuCysAla
2521 AACACCGTTT ACCACTGTAG TGCTGTATAC AACAATGAAT TCTATTATGT ACTTTGTGCA
     TTGTGGCAAA TGGTGACATC ACGACATATG TTGTTACTTA AGATAATACA TGAAACACGT

     ValSerThrVal GlyAspPro IleLeuAsn SerThrTyrTrp SerGlySer LeuMetMet
2581 GTGTCAACTG TTGGAGACCC TATTCTGAAT AGCACCTACT GGTCCGGATC TCTAATGATG
     CACAGTTGAC AACCTCTGGG ATAAGACTTA TCGTGGATGA CCAGGCCTAG AGATTACTAC
         ← 11476.SL
```

FIG. 3C (Continued)

```
     ThrArgLeuAla ValLysPro LysSerAsn GlyGlyGlyTyr AsnGlnHis GlnLeuAla
2641 ACCCGTCTAG CTGTGAAACC CAAGAGTAAT GGTGGGGGTT ACAATCAACA TCAACTTGCC
     TGGGCAGATC GACACTTTGG GTTCTCATTA CCACCCCCAA TGTTAGTTGT AGTTGAACGG

     LeuArgSerIle GluLysGly ArgTyrAsp LysValMetPro TyrGlyPro SerGlyIle
2701 CTACGAAGTA TCGAGAAAGG GAGGTATGAT AAAGTTATGC CGTATGGACC TTCAGGCATC
     GATGCTTCAT AGCTCTTTCC CTCCATACTA TTTCAATACG GCATACCTGG AAGTCCGTAG

     LysGlnGlyAsp ThrLeuTyr PheProAla ValGlyPheLeu ValArgThr GluPheLys
2761 AAACAGGGTG ACACCCTGTA TTTTCCTGCT GTAGGATTTT TGGTCAGGAC AGAGTTTAAA
     TTTGTCCCAC TGTGGGACAT AAAAGGACGA CATCCTAAAA ACCAGTCCTG TCTCAAATTT

     TyrAsnAspSer AsnCysPro IleThrLys CysGlnTyrSer LysProGlu AsnCysArg
2821 TACAATGATT CAAATTGTCC CATCACGAAG TGTCAATACA GTAAACCTGA AAATTGCAGG
     ATGTTACTAA GTTTAACAGG GTAGTGCTTC ACAGTTATGT CATTTGGACT TTTAACGTCC

                                     11477.SL →
     LeuSerMetGly IleArgPro AsnSerHis TyrIleLeuArg SerGlyLeu LeuLysTyr
2881 CTATCTATGG GGATTAGACC AAACAGCCAT TATATCCTTC GATCTGGACT ATTAAAATAC
     GATAGATACC CCTAATCTGG TTTGTCGGTA ATATAGGAAG CTAGACCTGA TAATTTTATG

     AsnLeuSerAsp GlyGluAsn ProLysVal ValPheIleGlu IleSerAsp GlnArgLeu
2941 AATCTATCAG ATGGGGAGAA CCCCAAAGTT GTATTCATTG AAATATCTGA TCAAAGATTA
     TTAGATAGTC TACCCCTCTT GGGGTTTCAA CATAAGTAAC TTTATAGACT AGTTTCTAAT
          ← 11478.SL

     SerIleGlySer ProSerLys IleTyrAsp SerLeuGlyGln ProValPhe TyrGlnAla
3001 TCTATTGGAT CTCCTAGCAA AATCTATGAT TCTTTGGGTC AACCTGTTTT CTACCAAGCG
     AGATAACCTA GAGGATCGTT TTAGATACTA AGAAACCCAG TTGGACAAAA GATGGTTCGC

     SerPheSerTrp AspThrMet IleLysPhe GlyAspValLeu ThrValAsn ProLeuVal
3061 TCATTTTCAT GGGATACTAT GATTAAATTT GGAGATGTTC TAACAGTCAA CCCTCTGGTT
     AGTAAAAGTA CCCTATGATA CTAATTTAAA CCTCTACAAG ATTGTCAGTT GGGAGACCAA

     ValAsnTrpArg AsnAsnThr ValIleSer ArgProGlyGln SerGlnCys ProArgPhe
3121 GTCAATTGGC GTAATAACAC GGTAATATCA AGACCCGGGC AATCACAATG CCCTAGATTC
     CAGTTAACCG CATTATTGTG CCATTATAGT TCTGGGCCCG TTAGTGTTAC GGGATCTAAG

     AsnThrCysPro GluIleCys TrpGluGly ValTyrAsnAsp AlaPheLeu IleAspArg
3181 AATACATGTC CAGAGATCTG CTGGGAAGGA GTTTATAATG ATGCATTCCT AATTGACAGA
     TTATGTACAG GTCTCTAGAC GACCCTTCCT CAAATATTAC TACGTAAGGA TTAACTGTCT

                          11479.SL →
     IleAsnTrpIle SerAlaGly ValPheLeu AspSerAsnGln ThrAlaGlu AsnProVal
3241 ATCAATTGGA TAAGCGCGGG TGTATTCCTT GACAGCAATC AGACCGCAGA AAATCCTGTT
     TAGTTAACCT ATTCGCGCCC ACATAAGGAA CTGTCGTTAG TCTGGCGTCT TTTAGGACAA

     PheThrValPhe LysAspAsn GluIleLeu TyrArgAlaGln LeuAlaSer GluAspThr
3301 TTTACTGTAT TCAAAGATAA TGAAATACTT TATAGGGCAC AACTGGCTTC TGAGGACACC
     AAATGACATA AGTTTCTATT ACTTTATGAA ATATCCCGTG TTGACCGAAG ACTCCTGTGG
                                                ← 11480.SL
```

FIG. 3C (Continued)

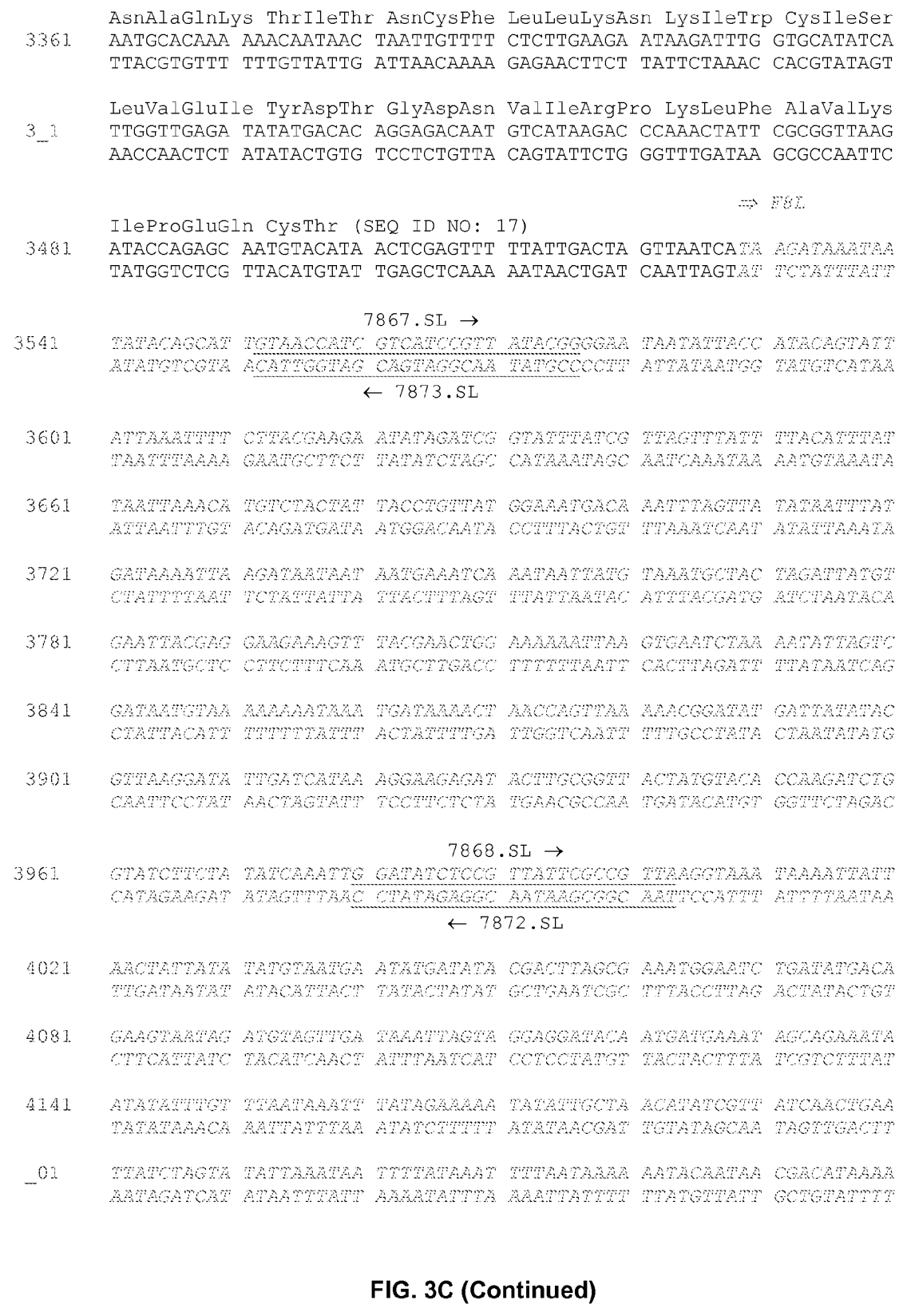

AsnAlaGlnLys ThrIleThr AsnCysPhe LeuLeuLysAsn LysIleTrp CysIleSer
3361 AATGCACAAA AAACAATAAC TAATTGTTTT CTCTTGAAGA ATAAGATTTG GTGCATATCA
TTACGTGTTT TTTGTTATTG ATTAACAAAA GAGAACTTCT TATTCTAAAC CACGTATAGT

LeuValGluIle TyrAspThr GlyAspAsn ValIleArgPro LysLeuPhe AlaValLys
3_1 TTGGTTGAGA TATATGACAC AGGAGACAAT GTCATAAGAC CCAAACTATT CGCGGTTAAG
AACCAACTCT ATATACTGTG TCCTCTGTTA CAGTATTCTG GGTTTGATAA GCGCCAATTC

⇒ F8L
IleProGluGln CysThr (SEQ ID NO: 17)
3481 ATACCAGAGC AATGTACATA ACTCGAGTTT TTATTGACTA GTTAATCATA AGATAAATAA
TATGGTCTCG TTACATGTAT TGAGCTCAAA AATAACTGAT CAATTAGTAT TCTATTTATT

7867.SL →
3541 TATACAGCAT TGTAACCATC GTCATCCGTT ATACGGGGAA TAATATTACC ATACAGTATT
ATATGTCGTA ACATTGGTAG CAGTAGGCAA TATGCCCCTT ATTATAATGG TATGTCATAA
← 7873.SL

3601 ATTAAATTTT CTTACGAAGA ATATAGATCG GTATTTATCG TTAGTTTATT TTACATTTAT
TAATTTAAAA GAATGCTTCT TATATCTAGC CATAAATAGC AATCAAATAA AATGTAAATA

3661 TAATTAAACA TGTCTACTAT TACCTGTTAT GGAAATGACA AATTTAGTTA TATAATTTAT
ATTAATTTGT ACAGATGATA ATGGACAATA CCTTTACTGT TTAAATCAAT ATATTAAATA

3721 GATAAAATTA AGATAATAAT AATGAAATCA AATAATTATG TAAATGCTAC TAGATTATGT
CTATTTTAAT TCTATTATTA TTACTTTAGT TTATTAATAC ATTTACGATG ATCTAATACA

3781 GAATTACGAG GAAGAAAGTT TACGAACTGG AAAAAATTAA GTGAATCTAA AATATTAGTC
CTTAATGCTC CTTCTTTCAA ATGCTTGACC TTTTTTAATT CACTTAGATT TTATAATCAG

3841 GATAATGTAA AAAAAATAAA TGATAAAACT AACCAGTTAA AAACGGATAT GATTATATAC
CTATTACATT TTTTTTATTT ACTATTTTGA TTGGTCAATT TTTGCCTATA CTAATATATG

3901 GTTAAGGATA TTGATCATAA AGGAAGAGAT ACTTGCGGTT ACTATGTACA CCAAGATCTG
CAATTCCTAT AACTAGTATT TCCTTCTCTA TGAACGCCAA TGATACATGT GGTTCTAGAC

7868.SL →
3961 GTATCTTCTA TATCAAATTG GATATCTCCG TTATTCGCCG TTAAGGTAAA TAAAATTATT
CATAGAAGAT ATAGTTTAAC CTATAGAGGC AATAAGCGGC AATTCCATTT ATTTTAATAA
← 7872.SL

4021 AACTATTATA TATGTAATGA ATATGATATA CGACTTAGCG AAATGGAATC TGATATGACA
TTGATAATAT ATACATTACT TATACTATAT GCTGAATCGC TTTACCTTAG ACTATACTGT

4081 GAAGTAATAG ATGTAGTTGA TAAATTAGTA GGAGGATACA ATGATGAAAT AGCAGAAATA
CTTCATTATC TACATCAACT ATTTAATCAT CCTCCTATGT TACTACTTTA TCGTCTTTAT

4141 ATATATTTGT TTAATAAATT TATAGAAAAA TATATTGCTA ACATATCGTT ATCAACTGAA
TATATAAACA AATTATTTAA ATATCTTTTT ATATAACGAT TGTATAGCAA TAGTTGACTT

_01 TTATCTAGTA TATTAAATAA TTTTATAAAT TTTAATAAAA AATACAATAA CGACATAAAA
AATAGATCAT ATAATTTATT AAAATATTTA AAATTATTTT TTATGTTATT GCTGTATTTT

FIG. 3C (Continued)

```
_61   GATATTAAAT CTTTAATTCT TGATCTGAAA AACACATCTA TAAAACTAGA TAAAAAGTTA
      CTATAATTTA GAAATTAAGA ACTAGACTTT TTGTGTAGAT ATTTTGATCT ATTTTTCAAT

4321  TTCGATAAAG ATAATAATGA ATCGAACGAT GAAAAATTGG AAACAGAAGT TGATAAGCTA
      AAGCTATTTC TATTATTACT TAGCTTGCTA CTTTTTAACC TTTGTCTTCA ACTATTCGAT

4381  ATTTTTTTCA TCTAAATAGT ATTATTTTAT TGAAGTACGA AGTTTTACGT TAGATAAATA
      TAAAAAAAGT AGATTTATCA TAATAAAATA ACTTCATGCT TCAAAATGCA ATCTATTTAT

4441  ATAAAGGTCG ATTTTTATTT TGTTAAATAT CAAATATGTC ATTATCTGAT AAAGATACAA
      TATTTCCAGC TAAAAATAAA ACAATTTATA GTTTATACAG TAATAGACTA TTTCTATGTT

                 7869.SL →
4501  AAACACACGG TGATTATCAA CCATCTAACG AACAGATATT ACAAAAAATA CGTCGGACTA
      TTTGTGTGCC ACTAATAGTT GGTAGATTGC TTGTCTATAA TGTTTTTTAT GCAGCCTGAT
                 ← 7871.SL

4561  TGGAAAACGA AGCTGATAGC CTCAATAGAA GAAGCATTAA AGAAATTGTT GTAGATGTTA
      ACCTTTTGCT TCGACTATCG GAGTTATCTT CTTCGTAATT TCTTTAACAA CATCTACAAT

4621  TGAAGAATTG GGATCATCCT CTCAACGAAG AAATAGATAA AGTTCTAAAC TGGAAAAATG
      ACTTCTTAAC CCTAGTAGGA GAGTTGCTTC TTTATCTATT TCAAGATTTG ACCTTTTTAC

4681  ATACATTAAA CGATTTAGAT CATCTAAATA CAGATGATAA TATTAAGGAA ATCATACAAT
      TATGTAATTT GCTAAATCTA GTAGATTTAT GTCTACTATT ATAATTCCTT TAGTATGTTA

4741  GTCTGATTAG AGAATTTGCG TTTAAAAAGA TCAATTCTAT TATGTATAGT TATGCTATGG
      CAGACTAATC TCTTAAACGC AAATTTTTCT AGTTAAGATA ATACATATCA ATACGATACC

4801  TAAAACTCAA TTCAGATAAC GAAACATTGA AAGATAAAAT TAAGGATTAT TTTATAGAAA
      ATTTTGAGTT AAGTCTATTG CTTTGTAACT TTCTATTTTA ATTCCTAATA AAATATCTTT

4861  CTATTCTTAA AGACAAACGT GGTTATAAAC AAAAGCCATT ACCCTAGAGC GGCCGCCACC
      GATAAGAATT TCTGTTTGCA CCAATATTTG TTTTCGGTAA TGGGATCTCG CCGGCGGTGG

4921  GCGGTGGAGC TCCAGCTTTT GTTCCCTTTA GTGAGGGTTA ATTTCGAGCT TGGCGTAATC
      CGCCACCTCG AGGTCGAAAA CAAGGGAAAT CACTCCCAAT TAAAGCTCGA ACCGCATTAG

4981  ATGGTCATAG CTGTTTCC (SEQ ID NO: 18)
      TACCAGTATC GACAAAGG (SEQ ID NO: 19)
             ← M13R
```

FIG. 3C (Continued)

```
                 Nru I  H6p                        M   V   V   I   L   D   K   R
11458.SL    5'  TATCGCGATATCCGTTAAGTTTGTATCGTAATGGTAGTTATACTTGACAAGAGA

D   L   L   F   V   F   G   P   N   L
                GATTTGCTTTTTGTATTTGGCCCCAACCTT
                          ↓
11456.SL    5'  GATTTGCTATTCGTATTTGGGCCCAACCTT
11457.SL    3'  CTAAACGATAAGCATAAACCCGGGTTGGAA
                                    Apa I

G   D   L   Y   Y   I   G   T   *  (SEQ ID NO: 20)
                GGGGATCTCTACTACATTGGGACATAG (SEQ ID NO: 21)
11459.SL    3'  CCCCTAGAGATGATGTAACCCTGTATCGGGCCCTAGGCG (SEQ ID NO: 22)
                                           XmaI BamH I
```

```
            M13F→                                                           ⇒F8R
1      GTAAAACGAC GGCCAGTGAA TTGTAATACG ACTCACTATA GGGCGAATTG GGTGACCCTT
       CATTTTGCTG CCGGTCACTT AACATTATGC TGAGTGATAT CCCGCTTAAC CCACTGGGAA

61     TACAAGAATA AAAGAAGAAA CAACTGTGAA ATAGTTTATA AATGTAATTC GTATGCAGAA
       ATGTTCTTAT TTTCTTCTTT GTTGACACTT TATCAAATAT TTACATTAAG CATACGTCTT

121    AACGATAATA TATTTTGGTA TGAGAAATCT AAAGGAGACA TAGTTTGTAT AGACATGCGC
       TTGCTATTAT ATAAAACCAT ACTCTTTAGA TTTCCTCTGT ATCAAACATA TCTGTACGCG

181    TCTTCCGATG AGATATTCGA TGCTTTTCTA ATGTATCATA TAGCTACAAG ATATGCCTAT
       AGAAGGCTAC TCTATAAGCT ACGAAAAGAT TACATAGTAT ATCGATGTTC TATACGGATA

241    CATGATGATG ATATATATCT ACAAATAGTG TTATATTATT CTAATAATCA AAATGTTATA
       GTACTACTAC TATATATAGA TGTTTATCAC AATATAATAA GATTATTAGT TTTACAATAT

301    TCTTATATTA CGAAAAATAA ATACGTTAAG TATATAAGAA ATAAAACTAG AGACGATATT
       AGAATATAAT GCTTTTTATT TATGCAATTC ATATATTCTT TATTTTGATC TCTGCTATAA

361    CATAAAGTAA AAATATTAGC TCTAGAAGAC TTTACAACGG AAGAAATATA TTGTTGGATT
       GTATTTCATT TTTATAATCG AGATCTTCTG AAATGTTGCC TTCTTTATAT AACAACCTAA

_1     AGTAATATAT AACAGCGTAG CTGCACGGTT TTGATCATTT TCCAACAATA TAAACCAATG
       TCATTATATA TTGTCGCATC GACGTGCCAA AACTAGTAAA AGGTTGTTAT ATTTGGTTAC

           7864.SL →
481    AAGGAGGACG ACTCATCAAA CATAAATAAC ATTCACGGAA AATATTCAGT ATCAGATTTA
       TTCCTCCTGC TGAGTAGTTT GTATTTATTG TAAGTGCCTT TTATAAGTCA TAGTCTAAAT
           ← 7876.SL

541    TCACAAGATG ATTATGTTAT TGAATGTATA GACGGATCTT TTGATTCGAT CAAGTATAGA
       AGTGTTCTAC TAATACAATA ACTTACATAT CTGCCTAGAA AACTAAGCTA GTTCATATCT

601    GATATAAAGG TTATAATAAT GAAGAATAAC GGTTACGTTA ATTGTAGTAA ATTATGTAAA
       CTATATTTCC AATATTATTA CTTCTTATTG CCAATGCAAT TAACATCATT TAATACATTT

661    ATGCGGAATA AATACTTTTC TAGATGGTTG CGTCTTTCTA CTTCTAAAGC ATTATTAGAC
       TACGCCTTAT TTATGAAAAG ATCTACCAAC GCAGAAAGAT GAAGATTTCG TAATAATCTG

721    ATTTACAATA ATAAGTCAGT AGATAATGCT ATTGTTAAAG TCTATGGTAA AGGTAAGAAA
       TAAATGTTAT TATTCAGTCA TCTATTACGA TAACAATTTC AGATACCATT TCCATTCTTT

781    CTTATTATAA CAGGATTTTA TCTCAAACAA AATATGATAC GTTATGTTAT TGAGTGGATA
       GAATAATATT GTCCTAAAAT AGAGTTTGTT TTATACTATG CAATACAATA ACTCACCTAT

841    GGGGATGATT TTACAAACGA TATATACAAA ATGATTAATT TCTATAATGC GTTATTCGGT
       CCCCTACTAA AATGTTTGCT ATATATGTTT TACTAATTAA AGATATTACG CAATAAGCCA

                                     7865.SL →
901    AACGATGAAT TAAAAATAGT ATCCTGTGAA AACACTCTAT GCCCGTTTAT AGAACTTGGT
       TTGCTACTTA ATTTTTATCA TAGGACACTT TTGTGAGATA CGGGCAAATA TCTTGAACCA
                                     ←7875.SL
```

FIG. 4D

```
 961  AGATGCTATT ATGGTAAAAA ATGTAAGTAT ATACACGGAG ATCAATGTGA TATCTGTGGT
      TCTACGATAA TACCATTTTT TACATTCATA TATGTGCCTC TAGTTACACT ATAGACACCA

1021  CTATATATAC TACACCCTAC CGATATTAAC CAACGAGTTT CTCACAAGAA AACTTGTTTA
      GATATATATG ATGTGGGATG GCTATAATTG GTTGCTCAAA GAGTGTTCTT TTGAACAAAT

1081  GTAGATAGAG ATTCTTTGAT TGTGTTTAAA AGAAGTACCA GTAAAAAGTG TGGCATATGC
      CATCTATCTC TAAGAAACTA ACACAAATTT TCTTCATGGT CATTTTTCAC ACCGTATACG

1141  ATAGAAGAAA TAAACAAAAA ACATATTTCC GAACAGTATT TTGGAATTCT CCCAAGTTGT
      TATCTTCTTT ATTTGTTTTT TGTATAAAGG CTTGTCATAA AACCTTAAGA GGGTTCAACA

1201  AAACATATTT TTTGCCTATC ATGTATAAGA CGTTGGGCAG ATACTACCAG AAATACAGAT
      TTTGTATAAA AAACGGATAG TACATATTCT GCAACCCGTC TATGATGGTC TTTATGTCTA

1261  ACTGAAAATA CGTGTCCTGA ATGTAGAATA GTTTTTCCTT TCATAATACC CAGTAGGTAT
      TGACTTTTAT GCACAGGACT TACATCTTAT CAAAAAGGAA AGTATTATGG GTCATCCATA

1321  TGGATAGATA ATAAATATGA TAAAAAAATA TTATATAATA GATATAAGAA AATGATTTTT
      ACCTATCTAT TATTTATACT ATTTTTTTAT AATATATTAT CTATATTCTT TTACTAAAAA

1381  ACAAAAATAC CTATAAGAAC AATAAAAATA TAATTACATT TACGGAAAAT AGCTGGTTTT
      TGTTTTTATG GATATTCTTG TTATTTTTAT ATTAATGTAA ATGCCTTTTA TCGACCAAAA

          7866.SL →
1441  AGTTTACCAA CTTAGAGTAA TTATCATATT GAATCTATAT TGCTAATTAG CTAATAAAAA
      TCAAATGGTT GAATCTCATT AATAGTATAA CTTAGATATA ACGATTAATC GATTATTTTT
          ← 7874.SL

1501  CCCGGGTTAA TTAATTAGTC ATCAGGCAGG GCGAGAACGA GACTATCTGC TCGTTAATTA
      GGGCCCAATT AATTAATCAG TAGTCCGTCC CGCTCTTGCT CTGATAGACG AGCAATTAAT

              ⇒ H6p
1561  ATTAGAGCTT CTTTATTCTA TACTTAAAAA GTGAAAATAA ATACAAAGGT TCTTGAGGGT
      TAATCTCGAA GAAATAAGAT ATGAATTTTT CACTTTTATT TATGTTTCCA AGAACTCCCA

                                                  NruI
1621  TGTGTTAAAT TGAAAGCGAG AAATAATCAT AAATTATTTC ATTATCGCGA TATCCGTTAA
      ACACAATTTA ACTTTCGCTC TTTATTAGTA TTTAATAAAG TAATAGCGCT ATAGGCAATT

                 ⇒Nipah F
                 MetValVal IleLeuAsp LysArgCysTyr CysAsnLeu LeuIleLeu
1681  GTTTGTATCG TAATGGTAGT TATACTTGAC AAGAGATGTT ATTGTAATCT TTTAATATTG
      CAAACATAGC ATTACCATCA ATATGAACTG TTCTCTACAA TAACATTAGA AAATTATAAC

      IleLeuMetIle SerGluCys SerValGly IleLeuHisTyr GluLysLeu SerLysIle
1741  ATTTTGATGA TCTCGGAGTG TAGTGTTGGG ATTCTACATT ATGAGAAATT GAGTAAAATT
      TAAAACTACT AGAGCCTCAC ATCACAACCC TAAGATGTAA TACTCTTTAA CTCATTTTAA
                 ← 11468.SL

      GlyLeuValLys GlyValThr ArgLysTyr LysIleLysSer AsnProLeu ThrLysAsp
1801  GGACTTGTCA AAGGAGTAAC AAGAAAATAC AAGATTAAAA GCAATCCTCT CACAAAAGAC
      CCTGAACAGT TTCCTCATTG TTCTTTTATG TTCTAATTTT CGTTAGGAGA GTGTTTTCTG
```

FIG. 4D (Continued)

```
        IleValIleLys MetIlePro AsnValSer AsnMetSerGln CysThrGly SerValMet
1861    ATTGTTATAA AAATGATTCC GAATGTGTCG AACATGTCTC AGTGCACAGG GAGTGTCATG
        TAACAATATT TTTACTAAGG CTTACACAGC TTGTACAGAG TCACGTGTCC CTCACAGTAC

        GluAsnTyrLys ThrArgLeu AsnGlyIle LeuThrProIle LysGlyAla LeuGluIle
1921    GAAAATTATA AAACACGATT AAACGGTATC TTAACACCTA TAAAGGGAGC GTTAGAGATC
        CTTTTAATAT TTTGTGCTAA TTTGCCATAG AATTGTGGAT ATTTCCCTCG CAATCTCTAG

        TyrLysAsnAsn ThrHisAsp LeuValGly AspValArgLeu AlaGlyVal IleMetAla
1981    TACAAAAACA ACACTCATGA CCTTGTCGGT GATGTGAGAT TAGCCGGAGT TATAATGGCA
        ATGTTTTTGT TGTGAGTACT GGAACAGCCA CTACACTCTA ATCGGCCTCA ATATTACCGT

                                                     11460.SL →
        GlyValAlaIle GlyIleAla ThrAlaAla GlnIleThrAla GlyValAla LeuTyrGlu
2041    GGAGTTGCTA TTGGGATTGC AACCGCAGCT CAAATCACTG CAGGTGTAGC ACTATATGAG
        CCTCAACGAT AACCCTAACG TTGGCGTCGA GTTTAGTGAC GTCCACATCG TGATATACTC

        AlaMetLysAsn AlaAspAsn IleAsnLys LeuLysSerSer IleGluSer ThrAsnGlu
2101    GCAATGAAGA ATGCTGACAA CATCAACAAA CTCAAAAGCA GCATTGAATC AACTAATGAA
        CGTTACTTCT TACGACTGTT GTAGTTGTTT GAGTTTTCGT CGTAACTTAG TTGATTACTT
                                                          ← 11465.SL

        AlaValValLys LeuGlnGlu ThrAlaGlu LysThrValTyr ValLeuThr AlaLeuGln
2161    GCTGTCGTTA AACTTCAAGA GACTGCAGAA AAGACAGTCT ATGTGCTGAC TGCTCTACAG
        CGACAGCAAT TTGAAGTTCT CTGACGTCTT TTCTGTCAGA TACACGACTG ACGAGATGTC

        AspTyrIleAsn ThrAsnLeu ValProThr IleAspLysIle SerCysLys GlnThrGlu
2221    GATTACATTA ATACTAATTT AGTACCGACA ATTGACAAGA TAAGCTGCAA ACAGACAGAA
        CTAATGTAAT TATGATTAAA TCATGGCTGT TAACTGTTCT ATTCGACGTT TGTCTGTCTT

                                                   11456.SL →      ApaI
        LeuSerLeuAsp LeuAlaLeu SerLysTyr LeuSerAspLeu LeuPheVal PheGlyPro
2281    CTCTCACTAG ATCTGGCATT ATCAAAGTAC CTCTCTGATT TGCTATTCGT ATTTGGGCCC
        GAGAGTGATC TAGACCGTAA TAGTTTCATG GAGAGACTAA ACGATAAGCA TAAACCCGGG
                                                     ← 11457.SL

        AsnLeuGlnAsp ProValSer AsnSerMet ThrIleGlnAla IleSerGln AlaPheGly
2341    AACCTTCAAG ACCCAGTTTC TAATTCAATG ACTATACAGG CTATATCTCA GGCATTCGGT
        TTGGAAGTTC TGGGTCAAAG ATTAAGTTAC TGATATGTCC GATATAGAGT CCGTAAGCCA

        GlyAsnTyrGlu ThrLeuLeu ArgThrLeu GlyTyrAlaThr GluAspPhe AspAspLeu
2401    GGAAATTATG AAACACTGCT AAGAACATTG GGTTACGCTA CAGAAGACTT TGATGATCTT
        CCTTTAATAC TTTGTGACGA TTCTTGTAAC CCAATGCGAT GTCTTCTGAA ACTACTAGAA

                     11461.SL →
        LeuGluSerAsp SerIleThr GlyGlnIle IleTyrValAsp LeuSerSer TyrTyrIle
2461    CTAGAAAGTG ACAGCATAAC AGGTCAAATC ATCTATGTTG ATCTAAGTAG CTACTATATA
        GATCTTTCAC TGTCGTATTG TCCAGTTTAG TAGATACAAC TAGATTCATC GATGATATAT

        IleValArgVal TyrPhePro IleLeuThr GluIleGlnGln AlaTyrIle GlnGluLeu
2521    ATTGTCAGGG TTTATTTTCC TATTCTGACT GAAATTCAAC AGGCCTATAT CCAAGAGTTG
        TAACAGTCCC AAATAAAAGG ATAAGACTGA CTTTAAGTTG TCCGGATATA GGTTCTCAAC
                                        ← 11464.SL
```

FIG. 4D (Continued)

```
     LeuProValSer PheAsnAsn AspAsnSer GluTrpIleSer IleValPro AsnPheIle
2581 TTACCAGTGA GCTTCAACAA TGATAATTCA GAATGGATCA GTATTGTCCC AAATTTCATA
     AATGGTCACT CGAAGTTGTT ACTATTAAGT CTTACCTAGT CATAACAGGG TTTAAAGTAT

     LeuValArgAsn ThrLeuIle SerAsnIle GluIleGlyPhe CysLeuIle ThrLysArg
2641 TTGGTAAGGA ATACATTAAT ATCAAATATA GAGATTGGAT TTTGCCTAAT TACAAAGAGG
     AACCATTCCT TATGTAATTA TAGTTTATAT CTCTAACCTA AAACGGATTA ATGTTTCTCC

     SerValIleCys AsnGlnAsp TyrAlaThr ProMetThrAsn AsnMetArg GluCysLeu
2701 AGCGTGATCT GCAACCAAGA TTATGCCACA CCTATGACCA ACAACATGAG AGAATGTTTA
     TCGCACTAGA CGTTGGTTCT AATACGGTGT GGATACTGGT TGTTGTACTC TCTTACAAAT

     ThrGlySerThr GluLysCys ProArgGlu LeuValValSer SerHisVal ProArgPhe
2761 ACGGGATCGA CTGAGAAGTG TCCTCGAGAG CTGGTTGTTT CATCACATGT TCCCAGATTT
     TGCCCTAGCT GACTCTTCAC AGGAGCTCTC GACCAACAAA GTAGTGTACA AGGGTCTAAA

     AlaLeuSerAsn GlyValLeu PheAlaAsn CysIleSerVal ThrCysGln CysGlnThr
2821 GCACTATCTA ACGGGGTTCT GTTTGCCAAT TGCATAAGTG TTACATGTCA GTGTCAAACA
     CGTGATAGAT TGCCCCAAGA CAAACGGTTA ACGTATTCAC AATGTACAGT CACAGTTTGT

                  11462.SL →
     ThrGlyArgAla IleSerGln SerGlyGlu GlnThrLeuLeu MetIleAsp AsnThrThr
2881 ACAGGCAGGG CAATCTCACA ATCAGGAGAA CAAACTCTGC TGATGATTGA CAACACCACC
     TGTCCGTCCC GTTAGAGTGT TAGTCCTCTT GTTTGAGACG ACTACTAACT GTTGTGGTGG

     CysProThrAla ValLeuGly AsnValIle IleSerLeuGly LysTyrLeu GlySerVal
2941 TGTCCTACAG CCGTACTCGG TAATGTGATT ATCAGCTTAG GGAAATATCT GGGGTCAGTA
     ACAGGATGTC GGCATGAGCC ATTACACTAA TAGTCGAATC CCTTTATAGA CCCCAGTCAT
         ← 11463.SL

     AsnTyrAsnSer GluGlyIle AlaIleGly ProProValPhe ThrAspLys ValAspIle
3001 AATTATAATT CTGAAGGCAT TGCTATCGGT CCTCCAGTCT TTACAGATAA AGTTGATATA
     TTAATATTAA GACTTCCGTA ACGATAGCCA GGAGGTCAGA AATGTCTATT TCAACTATAT

     SerSerGlnIle SerSerMet AsnGlnSer LeuGlnGlnSer LysAspTyr IleLysGlu
3061 TCAAGTCAGA TATCCAGCAT GAATCAGTCC TTACAACAGT CTAAGGACTA TATCAAAGAG
     AGTTCAGTCT ATAGGTCGTA CTTAGTCAGG AATGTTGTCA GATTCCTGAT ATAGTTTCTC

     AlaGlnArgLeu LeuAspThr ValAsnPro SerLeuIleSer MetLeuSer MetIleIle
3121 GCTCAACGAC TCCTTGATAC TGTTAATCCA TCATTAATAA GCATGTTGTC TATGATCATA
     CGAGTTGCTG AGGAACTATG ACAATTAGGT AGTAATTATT CGTACAACAG ATACTAGTAT

     LeuTyrValLeu SerIleAla SerLeuCys IleGlyLeuIle ThrPheIle SerPheIle
3181 CTGTATGTAT TATCGATCGC ATCGTTGTGT ATAGGGTTGA TTACATTTAT CAGTTTTATC
     GACATACATA ATAGCTAGCG TAGCAACACA TATCCCAACT AATGTAAATA GTCAAAATAG

     IleValGluLys LysArgAsn ThrTyrSer ArgLeuGluAsp ArgArgVal ArgProThr
3241 ATTGTTGAGA AAAAGAGAAA CACCTACAGC AGATTAGAGG ATAGGAGAGT CAGACCTACA
     TAACAACTCT TTTTCTCTTT GTGGATGTCG TCTAATCTCC TATCCTCTCA GTCTGGATGT

     SerSerGlyAsp LeuTyrTyr IleGlyThr         BamHI (SEQ ID NO: 23)
3301 AGCAGTGGGG ATCTCTACTA CATTGGGACA TAGCCCGGGA TCCCTCGAGT TTTTATTGAC
     TCGTCACCCC TAGAGATGAT GTAACCCTGT ATCGGGCCCT AGGGAGCTCA AAAATAACTG
```

FIG. 4D (Continued)

Figure 4D:
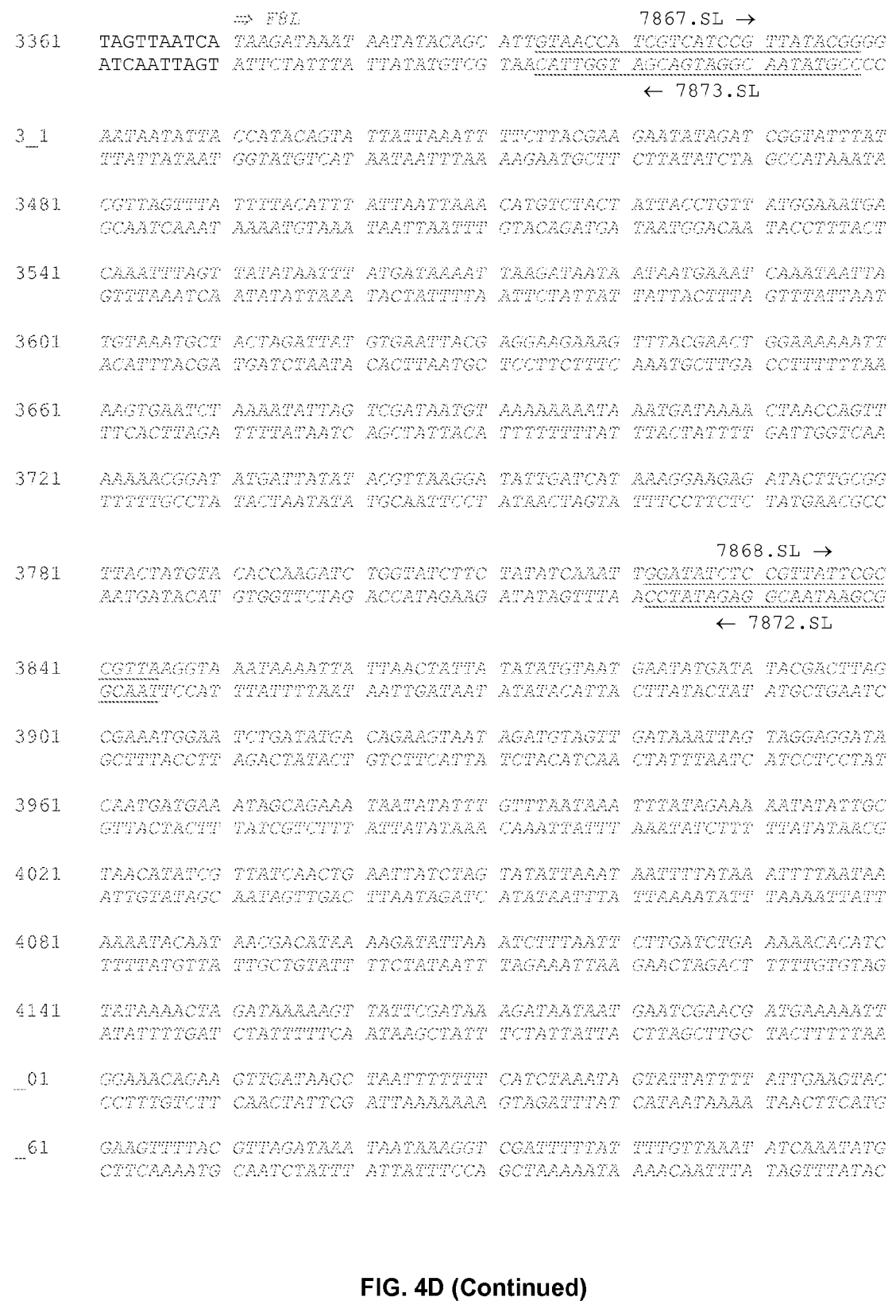

```
                      ⇒ F8L                                                7867.SL →
3361    TAGTTAATCA  TAAGATAAAT  AATATACAGC  ATTGTAACCA  TCGTCATCCG  TTATACGGGG
        ATCAATTAGT  ATTCTATTTA  TTATATGTCG  TAACATTGGT  AGCAGTAGGC  AATATGCCCC
                                                                   ← 7873.SL

3_1     AATAATATTA  CCATACAGTA  TTATTAAATT  TTCTTACGAA  GAATATAGAT  CGGTATTTAT
        TTATTATAAT  GGTATGTCAT  AATAATTTAA  AAGAATGCTT  CTTATATCTA  GCCATAAATA

3481    CGTTAGTTTA  TTTTACATTT  ATTAATTAAA  CATGTCTACT  ATTACCTGTT  ATGGAAATGA
        GCAATCAAAT  AAAATGTAAA  TAATTAATTT  GTACAGATGA  TAATGGACAA  TACCTTTACT

3541    CAAATTTAGT  TATATAATTT  ATGATAAAAT  TAAGATAATA  ATAATGAAAT  CAAATAATTA
        GTTTAAATCA  ATATATTAAA  TACTATTTTA  ATTCTATTAT  TATTACTTTA  GTTTATTAAT

3601    TGTAAATGCT  ACTAGATTAT  GTGAATTACG  AGGAAGAAAG  TTTACGAACT  GGAAAAAATT
        ACATTTACGA  TGATCTAATA  CACTTAATGC  TCCTTCTTTC  AAATGCTTGA  CCTTTTTTAA

3661    AAGTGAATCT  AAAATATTAG  TCGATAATGT  AAAAAAAATA  AATGATAAAA  CTAACCAGTT
        TTCACTTAGA  TTTTATAATC  AGCTATTACA  TTTTTTTTAT  TTACTATTTT  GATTGGTCAA

3721    AAAAACGGAT  ATGATTATAT  ACGTTAAGGA  TATTGATCAT  AAAGGAAGAG  ATACTTGCGG
        TTTTTGCCTA  TACTAATATA  TGCAATTCCT  ATAACTAGTA  TTTCCTTCTC  TATGAACGCC

                                                                7868.SL →
3781    TTACTATGTA  CACCAAGATC  TGGTATCTTC  TATATCAAAT  TGGATATCTC  CGTTATTCGC
        AATGATACAT  GTGGTTCTAG  ACCATAGAAG  ATATAGTTTA  ACCTATAGAG  GCAATAAGCG
                                                                ← 7872.SL

3841    CGTTAAGGTA  AATAAAATTA  TTAACTATTA  TATATGTAAT  GAATATGATA  TACGACTTAG
        GCAATTCCAT  TTATTTTAAT  AATTGATAAT  ATATACATTA  CTTATACTAT  ATGCTGAATC

3901    CGAAATGGAA  TCTGATATGA  CAGAAGTAAT  AGATGTAGTT  GATAAATTAG  TAGGAGGATA
        GCTTTACCTT  AGACTATACT  GTCTTCATTA  TCTACATCAA  CTATTTAATC  ATCCTCCTAT

3961    CAATGATGAA  ATAGCAGAAA  TAATATATTT  GTTTAATAAA  TTTATAGAAA  AATATATTGC
        GTTACTACTT  TATCGTCTTT  ATTATATAAA  CAAATTATTT  AAATATCTTT  TTATATAACG

4021    TAACATATCG  TTATCAACTG  AATTATCTAG  TATATTAAAT  AATTTTATAA  ATTTTAATAA
        ATTGTATAGC  AATAGTTGAC  TTAATAGATC  ATATAATTTA  TTAAAATATT  TAAAATTATT

4081    AAAATACAAT  AACGACATAA  AAGATATTAA  ATCTTTAATT  CTTGATCTGA  AAAACACATC
        TTTTATGTTA  TTGCTGTATT  TTCTATAATT  TAGAAATTAA  GAACTAGACT  TTTTGTGTAG

4141    TATAAAACTA  GATAAAAAGT  TATTCGATAA  AGATAATAAT  GAATCGAACG  ATGAAAAATT
        ATATTTTGAT  CTATTTTTCA  ATAAGCTATT  TCTATTATTA  CTTAGCTTGC  TACTTTTTAA

_01     GGAAACAGAA  GTTGATAAGC  TAATTTTTTT  CATCTAAATA  GTATTATTTT  ATTGAAGTAC
        CCTTTGTCTT  CAACTATTCG  ATTAAAAAAA  GTAGATTTAT  CATAATAAAA  TAACTTCATG

_61     GAAGTTTTAC  GTTAGATAAA  TAATAAAGGT  CGATTTTTAT  TTTGTTAAAT  ATCAAATATG
        CTTCAAAATG  CAATCTATTT  ATTATTTCCA  GCTAAAAATA  AAACAATTTA  TAGTTTATAC
```

4321 TCATTATCTG ATAAAGATAC AAAAACACAC GGTGATTATC AACCATCTAA CGAACAGATA
AGTAATAGAC TATTTCTATG TTTTTGTGTG CCACTAATAG TTGGTAGATT GCTTGTCTAT

← 7871.SL

4381 TTACAAAAAA TACGTCGGAC TATGGAAAAC GAAGCTGATA GCCTCAATAG AAGAAGCATT
AATGTTTTTT ATGCAGCCTG ATACCTTTTG CTTCGACTAT CGGAGTTATC TTCTTCGTAA

4441 AAAGAAATTG TTGTAGATGT TATCAAGAAT TGGGATCATC CTCTCAACGA AGAAATAGAT
TTTCTTTAAC AACATCTACA ATACTTCTTA ACCCTAGTAG GAGAGTTGCT TCTTTATCTA

4501 AAAGTTCTAA ACTGGAAAAA TGATACATTA AACGATTTAG ATCATCTAAA TACAGATGAT
TTTCAAGATT TGACCTTTTT ACTATGTAAT TTGCTAAATC TAGTAGATTT ATGTCTACTA

4561 AATATTAAGG AAATCATACA ATGTCTGATT AGAGAATTTG CGTTTAAAAA GATCAATTCT
TTATAATTCC TTTAGTATGT TACAGACTAA TCTCTTAAAC GCAAATTTTT CTAGTTAAGA

4621 ATTATGTATA GTTATGCTAT GGTAAAACTC AATTCAGATA ACGAAACATT GAAAGATAAA
TAATACATAT CAATACGATA CCATTTTGAG TTAAGTCTAT TGCTTTGTAA CTTTCTATTT

4681 ATTAAGGATT ATTTTATAGA AACTATTCTT AAAGACAAAC GTGGTTATAA ACAAAAGCCA
TAATTCCTAA TAAAATATCT TTGATAAGAA TTTCTGTTTG CACCAATATT TGTTTTCGGT

4741 TTACCCTAGA GCGGCCGCCA CCGCGGTGGA GCTCCAGCTT TTGTTCCCTT TAGTGAGGGT
AATGGGATCT CGCCGGCGGT GGCGCCACCT CGAGGTCGAA AACAAGGGAA ATCACTCCCA

4801 TAATTTCGAG CTTGGCGTAA TCATGGTCAT AGCTGTTTCC (SEQ ID NO: 24)
ATTAAAGCTC GAACCGCATT AGTACCAGTA TCGACAAAGG (SEQ ID NO: 25)

```
                 Nru I  H6p                       M   V   V   I   L   D   K   R
11458.SL    5'  TATCGCGATATCCGTTAAGTTTGTATCGTAATGGTAGTTATACTTGACAAGAGA

D   L   L   F   V   F   G   P   N   L
                GATTTGCTTTTTGTATTTGGCCCCAACCTT
                          ↓
11456.SL    5'  GATTTGCTATTCGTATTTGGGCCCAACCTT
11457.SL    3'  CTAAACGATAAGCATAAACCCGGGTTGGAA
                                  Apa I

G   D   L   Y   Y   I   G   T   *  (SEQ ID NO: 20)
                GGGGATCTCTACTACATTGGGACATAG  (SEQ ID NO: 21)
11459.SL    3'  CCCCTAGAGATGATGTAACCCTGTATCGGGCCCTAGGCG  (SEQ ID NO: 22)
                                           XmaI  BamH I
```

FIG. 5A

```
     M13R →                                      ⇒ C5R
  1  GGAAACAGCT ATGACCATGA TTACGAATTG CGGCCGCAAT TCTGAATGTT AAATGTTATA
     CCTTTGTCGA TACTGGTACT AATGCTTAAC GCCGGCGTTA AGACTTACAA TTTACAATAT

 61  CTTTGGATGA AGCTATAAAT ATGCATTGGA AAAATAATCC ATTTAAAGAA AGGATTCAAA
     GAAACCTACT TCGATATTTA TACGTAACCT TTTTATTAGG TAAATTTCTT TCCTAAGTTT

121  TACTACAAAA CCTAAGCGAT AATATGTTAA CTAAGCTTAT TCTTAACGAC GCTTTAAATA
     ATGATGTTTT GGATTCGCTA TTATACAATT GATTCGAATA AGAATTGCTG CGAAATTTAT

181  TACACAAATA AACATAATTT TTGTATAACC TAACAAATAA CTAAAACATA AAAATAATAA
     ATGTGTTTAT TTGTATTAAA AACATATTGG ATTGTTTATT GATTTTGTAT TTTTATTATT

241  AAGGAAATGT AATATCGTAA TTATTTTACT CAGGAATGGG GTTAAATATT TATATCACGT
     TTCCTTTACA TTATAGCATT AATAAAATGA GTCCTTACCC CAATTTATAA ATATAGTGCA

301  GTATATCTAT ACTGTTATCG TATACTCTTT ACAATTACTA TTACGAATAT GCAAGAGATA
     CATATAGATA TGACAATAGC ATATGAGAAA TGTTAATGAT AATGCTTATA CGTTCTCTAT
                                                   ← 7927.DC

361  ATAAGATTAC GTATTTAAGA GAATCTTGTC ATGATAATTG GGTACGACAT AGTGATAAAT
     TATTCTAATG CATAAATTCT CTTAGAACAG TACTATTAAC CCATGCTGTA TCACTATTTA

_1   GCTATTTCGC ATCGTTACAT AAAGTCAGTT GGAAAGATGG ATTTGACAGA TGTAACTTAA
     CGATAAAGCG TAGCAATGTA TTTCAGTCAA CCTTTCTACC TAAACTGTCT ACATTGAATT

                                           7696.CXL →
481  TAGGTGCAAA AATGTTAAAT AACAGCATTC TATCGGAAGA TAGGATACCA GTTATATTAT
     ATCCACGTTT TTACAATTTA TTGTCGTAAG ATAGCCTTCT ATCCTATGGT CAATATAATA

541  ACAAAAATCA CTGGTTGGAT AAAACAGATT CTGCAATATT CGTAAAAGAT GAAGATTACT
     TGTTTTTAGT GACCAACCTA TTTTGTCTAA GACGTTATAA GCATTTTCTA CTTCTAATGA

601  GCGAATTTGT AAACTATGAC AATAAAAAGC CATTTATCTC AACGACATCG TGTAATTCTT
     CGCTTAAACA TTTGATACTG TTATTTTTCG GTAAATAGAG TTGCTGTAGC ACATTAAGAA

661  CCATGTTTTA TGTATGTGTT TCAGATATTA TGAGATTACT ATAAACTTTT TGTATACTTA
     GGTACAAAAT ACATACACAA AGTCTATAAT ACTCTAATGA TATTTGAAAA ACATATGAAT

721  TATTCCGTAA ACTATATTAA TCATGAAGAA AATGAAAAAG TATAGAAGCT GTTCACGAGC
     ATAAGGCATT TGATATAATT AGTACTTCTT TTACTTTTTC ATATCTTCGA CAAGTGCTCG
                                                        ← 7926.DC

781  GGTTGTTGAA AACAACAAAA TTATACATTC AAGATGGCTT ACATATACGT CTGTGAGGCT
     CCAACAACTT TTGTTGTTTT AATATGTAAG TTCTACCGAA TGTATATGCA GACACTCCGA

841  ATCATGGATA ATGACAATGC ATCTCTAAAT AGGTTTTTGG ACAATGGATT CGACCCTAAC
     TAGTACCTAT TACTGTTACG TAGAGATTTA TCCAAAAACC TGTTACCTAA GCTGGGATTG

901  ACGGAATATG GTACTCTACA ATCTCCTCTT GAAATGGCTG TAATGTTCAA GAATACCGAG
     TGCCTTATAC CATGAGATGT TAGAGGAGAA CTTTACCGAC ATTACAAGTT CTTATGGCTC
```

FIG. 5C

```
                                                                  7697.CXL →
 961  GCTATAAAAA TCTTGATGAG GTATGGAGCT AAACCTGTAG TTACTGAATG CACAACTTCT
      CGATATTTTT AGAACTACTC CATACCTCGA TTTGGACATC AATGACTTAC GTGTTGAAGA

1021  TGTCTGCATG ATGCGGTGTT GAGAGACGAC TACAAAATAG TGAAAGATCT GTTGAAGAAT
      ACAGACGTAC TACGCCACAA CTCTCTGCTG ATGTTTTATC ACTTTCTAGA CAACTTCTTA

1081  AACTATGTAA ACAATGTTCT TTACAGCGGA GGCTTTACTC CTTTGTGTTT GGCAGCTTAC
      TTGATACATT TGTTACAAGA AATGTCGCCT CCGAAATGAG GAAACACAAA CCGTCGAATG

1141  CTTAACAAAG TTAATTTGGT TAAACTTCTA TTGGCTCATT CGGCGGATGT AGATATTTCA
      GAATTGTTTC AATTAAACCA ATTTGAAGAT AACCGAGTAA GCCGCCTACA TCTATAAAGT

1201  AACACGGATC GGTTAACTCC TCTACATATA GCCGTATCAA ATAAAAATTT AACAATGGTT
      TTGTGCCTAG CCAATTGAGG AGATGTATAT CGGCATAGTT TATTTTTAAA TTGTTACCAA
                      ← 7925.DC

1261  AAACTTCTAT TGAACAAAGG TGCTGATACT GACTTGCTGG ATAACATGGG ACGTACTCCT
      TTTGAAGATA ACTTGTTTCC ACGACTATGA CTGAACGACC TATTGTACCC TGCATGAGGA

1321  TTAATGATCG CTGTACAATC TGGAAATATT GAAATATGTA GCACACTACT TAAAAAAAAT
      AATTACTAGC GACATGTTAG ACCTTTATAA CTTTATACAT CGTGTGATGA ATTTTTTTTA

1381  AAAATGTCCA GAACTGGGAA AAATTGATCT TGCCAGCTGT AATTCATGGT AGAAAAGAAG
      TTTTACAGGT CTTGACCCTT TTTAACTAGA ACGGTCGACA TTAAGTACCA TCTTTTCTTC

1441  TGCTCAGGCT ACTTTTCAAC AAAGGAGCAG ATGTAAACTA CATCTTTGAA AGAAATGGAA
      ACGAGTCCGA TGAAAAGTTG TTTCCTCGTC TACATTTGAT GTAGAAACTT TCTTTACCTT

                                                        7792.SL →
1501  AATCATATAC TGTTTTGGAA TTGATTAAAG AAAGTTACTC TGAGACACAA AAGAGGTAGC
      TTAGTATATG ACAAAACCTT AACTAATTTC TTTCAATGAG ACTCTGTGTT TTCTCCATCG

1561  TGAAGTGGTA CTCTCAAAGG TACGTGACTA ATTAGCTATA AAAAGGATCC GGGTTAATTA
      ACTTCACCAT GAGAGTTTCC ATGCACTGAT TAATCGATAT TTTTCCTAGG CCCAATTAAT

                                                                   ⇒ H6p
1621  ATTAGTCATC AGGCAGGGCG AGAACGAGAC TATCTGCTCG TTAATTAATT AGAGCTTCTT
      TAATCAGTAG TCCGTCCCGC TCTTGCTCTG ATAGACGAGC AATTAATTAA TCTCGAAGAA

1681  TATTCTATAC TTAAAAAGTG AAAATAAATA CAAAGGTTCT TGAGGGTTGT GTTAAATTGA
      ATAAGATATG AATTTTTCAC TTTTATTTAT GTTTCCAAGA ACTCCCAACA CAATTTAACT

                                                                Nipah F ⇒
                                                                      Met·
1741  AAGCGAGAAA TAATCATAAA TTATTTCATT ATCGCGATAT CCGTTAAGTT TGTATCGTAA
      TTCGCTCTTT ATTAGTATTT AATAAAGTAA TAGCGCTATA GGCAATTCAA ACATAGCATT

      ..ValValIle LeuAspLys ArgCysTyrCys AsnLeuLeu IleLeuIle LeuMetIleSer·
1801  TGGTAGTTAT ACTTGACAAG AGATGTTATT GTAATCTTTT AATATTGATT TTGATGATCT
      ACCATCAATA TGAACTGTTC TCTACAATAA CATTAGAAAA TTATAACTAA AACTACTAGA
```

FIG. 5C (Continued)

```
      ..GluCysSer ValGlyIle LeuHisTyrGlu LysLeuSer LysIleGly LeuValLysGly·
1861  CGGAGTGTAG TGTTGGGATT CTACATTATG AGAAATTGAG TAAAATTGGA CTTGTCAAAG
      GCCTCACATC ACAACCCTAA GATGTAATAC TCTTTAACTC ATTTTAACCT GAACAGTTTC
        ← 11468.SL

      ..ValThrArg LysTyrLys IleLysSerAsn ProLeuThr LysAspIle ValIleLysMet·
1921  GAGTAACAAG AAAATACAAG ATTAAAAGCA ATCCTCTCAC AAAAGACATT GTTATAAAAA
      CTCATTGTTC TTTTATGTTC TAATTTTCGT TAGGAGAGTG TTTTCTGTAA CAATATTTTT

      ..IleProAsn ValSerAsn MetSerGlnCys ThrGlySer ValMetGlu AsnTyrLysThr·
1981  TGATTCCGAA TGTGTCGAAC ATGTCTCAGT GCACAGGGAG TGTCATGGAA AATTATAAAA
      ACTAAGGCTT ACACAGCTTG TACAGAGTCA CGTGTCCCTC ACAGTACCTT TTAATATTTT

      ..ArgLeuAsn GlyIleLeu ThrProIleLys GlyAlaLeu GluIleTyr LysAsnAsnThr·
2041  CACGATTAAA CGGTATCTTA ACACCTATAA AGGGAGCGTT AGAGATCTAC AAAAACAACA
      GTGCTAATTT GCCATAGAAT TGTGGATATT TCCCTCGCAA TCTCTAGATG TTTTTGTTGT

      ..HisAspLeu ValGlyAsp ValArgLeuAla GlyValIle MetAlaGly ValAlaIleGly·
2101  CTCATGACCT TGTCGGTGAT GTGAGATTAG CCGGAGTTAT AATGGCAGGA GTTGCTATTG
      GAGTACTGGA ACAGCCACTA CACTCTAATC GGCCTCAATA TTACCGTCCT CAACGATAAC

                                 11460.SL →
      ..IleAlaThr AlaAlaGln IleThrAlaGly ValAlaLeu TyrGluAla MetLysAsnAla·
2161  GGATTGCAAC CGCAGCTCAA ATCACTGCAG GTGTAGCACT ATATGAGGCA ATGAAGAATG
      CCTAACGTTG GCGTCGAGTT TAGTGACGTC CACATCGTGA TATACTCCGT TACTTCTTAC

      ..AspAsnIle AsnLysLeu LysSerSerIle GluSerThr AsnGluAla ValValLysLeu·
2221  CTGACAACAT CAACAAACTC AAAAGCAGCA TTGAATCAAC TAATGAAGCT GTCGTTAAAC
      GACTGTTGTA GTTGTTTGAG TTTTCGTCGT AACTTAGTTG ATTACTTCGA CAGCAATTTG
                                        ← 11465.SL

      ..GlnGluThr AlaGluLys ThrValTyrVal LeuThrAla LeuGlnAsp TyrIleAsnThr·
2281  TTCAAGAGAC TGCAGAAAAG ACAGTCTATG TGCTGACTGC TCTACAGGAT TACATTAATA
      AAGTTCTCTG ACGTCTTTTC TGTCAGATAC ACGACTGACG AGATGTCCTA ATGTAATTAT

      ..AsnLeuVal ProThrIle AspLysIleSer CysLysGln ThrGluLeu SerLeuAspLeu·
2341  CTAATTTAGT ACCGACAATT GACAAGATAA GCTGCAAACA GACAGAACTC TCACTAGATC
      GATTAAATCA TGGCTGTTAA CTGTTCTATT CGACGTTTGT CTGTCTTGAG AGTGATCTAG

                               11456.SL →      ApaI
      ..AlaLeuSer LysTyrLeu SerAspLeuLeu PheValPhe GlyProAsn LeuGlnAspPro·
2401  TGGCATTATC AAAGTACCTC TCTGATTTGC TATTCGTATT TGGGCCCAAC CTTCAAGACC
      ACCGTAATAG TTTCATGGAG AGACTAAACG ATAAGCATAA ACCCGGGTTG GAAGTTCTGG
                               ← 11457.SL

      ..ValSerAsn SerMetThr IleGlnAlaIle SerGlnAla PheGlyGly AsnTyrGluThr·
2461  CAGTTTCTAA TTCAATGACT ATACAGGCTA TATCTCAGGC ATTCGGTGGA AATTATGAAA
      GTCAAAGATT AAGTTACTGA TATGTCCGAT ATAGAGTCCG TAAGCCACCT TTAATACTTT

      ..LeuLeuArg ThrLeuGly TyrAlaThrGlu AspPheAsp AspLeuLeu GluSerAspSer·
2521  CACTGCTAAG AACATTGGGT TACGCTACAG AAGACTTTGA TGATCTTCTA GAAAGTGACA
      GTGACGATTC TTGTAACCCA ATGCGATGTC TTCTGAAACT ACTAGAAGAT CTTTCACTGT
```

FIG. 5C (Continued)

```
         11461.SL →
       ..IleThrGly GlnIleIle TyrValAspLeu SerSerTyr TyrIleIle ValArgValTyr·
2581   GCATAACAGG TCAAATCATC TATGTTGATC TAAGTAGCTA CTATATAATT GTCAGGGTTT
       CGTATTGTCC AGTTTAGTAG ATACAACTAG ATTCATCGAT GATATATTAA CAGTCCCAAA

       ..PheProIle LeuThrGlu IleGlnGlnAla TyrIleGln GluLeuLeu ProValSerPhe·
2641   ATTTTCCTAT TCTGACTGAA ATTCAACAGG CCTATATCCA AGAGTTGTTA CCAGTGAGCT
       TAAAAGGATA AGACTGACTT TAAGTTGTCC GGATATAGGT TCTCAACAAT GGTCACTCGA
                           ← 11464.SL

       ..AsnAsnAsp AsnSerGlu TrpIleSerIle ValProAsn PheIleLeu ValArgAsnThr·
2701   TCAACAATGA TAATTCAGAA TGGATCAGTA TTGTCCCAAA TTTCATATTG GTAAGGAATA
       AGTTGTTACT ATTAAGTCTT ACCTAGTCAT AACAGGGTTT AAAGTATAAC CATTCCTTAT

       ..LeuIleSer AsnIleGlu IleGlyPheCys LeuIleThr LysArgSer ValIleCysAsn·
2761   CATTAATATC AAATATAGAG ATTGGATTTT GCCTAATTAC AAAGAGGAGC GTGATCTGCA
       GTAATTATAG TTTATATCTC TAACCTAAAA CGGATTAATG TTTCTCCTCG CACTAGACGT

       ..GlnAspTyr AlaThrPro MetThrAsnAsn MetArgGlu CysLeuThr GlySerThrGlu·
2821   ACCAAGATTA TGCCACACCT ATGACCAACA ACATGAGAGA ATGTTTAACG GGATCGACTG
       TGGTTCTAAT ACGGTGTGGA TACTGGTTGT TGTACTCTCT TACAAATTGC CCTAGCTGAC

       ..LysCysPro ArgGluLeu ValValSerSer HisValPro ArgPheAla LeuSerAsnGly·
2881   AGAAGTGTCC TCGAGAGCTG GTTGTTTCAT CACATGTTCC CAGATTTGCA CTATCTAACG
       TCTTCACAGG AGCTCTCGAC CAACAAAGTA GTGTACAAGG GTCTAAACGT GATAGATTGC

       ..ValLeuPhe AlaAsnCys IleSerValThr CysGlnCys GlnThrThr GlyArgAlaIle·
2941   GGGTTCTGTT TGCCAATTGC ATAAGTGTTA CATGTCAGTG TCAAACAACA GGCAGGGCAA
       CCCAAGACAA ACGGTTAACG TATTCACAAT GTACAGTCAC AGTTTGTTGT CCGTCCCGTT

      11462.SL →
       ..SerGlnSer GlyGluGln ThrLeuLeuMet IleAspAsn ThrThrCys ProThrAlaVal·
3001   TCTCACAATC AGGAGAACAA ACTCTGCTGA TGATTGACAA CACCACCTGT CCTACAGCCG
       AGAGTGTTAG TCCTCTTGTT TGAGACGACT ACTAACTGTT GTGGTGGACA GGATGTCGGC
                                                          ← 11463.SL

       ..LeuGlyAsn ValIleIle SerLeuGlyLys TyrLeuGly SerValAsn TyrAsnSerGlu·
3061   TACTCGGTAA TGTGATTATC AGCTTAGGGA AATATCTGGG GTCAGTAAAT TATAATTCTG
       ATGAGCCATT ACACTAATAG TCGAATCCCT TTATAGACCC CAGTCATTTA ATATTAAGAC

       ..GlyIleAla IleGlyPro ProValPheThr AspLysVal AspIleSer SerGlnIleSer·
3121   AAGGCATTGC TATCGGTCCT CCAGTCTTTA CAGATAAAGT TGATATATCA AGTCAGATAT
       TTCCGTAACG ATAGCCAGGA GGTCAGAAAT GTCTATTTCA ACTATATAGT TCAGTCTATA

       ..SerMetAsn GlnSerLeu GlnGlnSerLys AspTyrIle LysGluAla GlnArgLeuLeu·
3181   CCAGCATGAA TCAGTCCTTA CAACAGTCTA AGGACTATAT CAAAGAGGCT CAACGACTCC
       GGTCGTACTT AGTCAGGAAT GTTGTCAGAT TCCTGATATA GTTTCTCCGA GTTGCTGAGG

       ..AspThrVal AsnProSer LeuIleSerMet LeuSerMet IleIleLeu TyrValLeuSer·
3241   TTGATACTGT TAATCCATCA TTAATAAGCA TGTTGTCTAT GATCATACTG TATGTATTAT
       AACTATGACA ATTAGGTAGT AATTATTCGT ACAACAGATA CTAGTATGAC ATACATAATA
```

FIG. 5C (Continued)

```
      ..IleAlaSer LeuCysIle GlyLeuIleThr PheIleSer PheIleIle ValGluLysLys·
3301  CGATCGCATC GTTGTGTATA GGGTTGATTA CATTTATCAG TTTTATCATT GTTGAGAAAA
      GCTAGCGTAG CAACACATAT CCCAACTAAT GTAAATAGTC AAAATAGTAA CAACTCTTTT

      ..ArgAsnThr TyrSerArg LeuGluAspArg ArgValArg ProThrSer SerGlyAspLeu·
3361  AGAGAAACAC CTACAGCAGA TTAGAGGATA GGAGAGTCAG ACCTACAAGC AGTGGGGATC
      TCTCTTTGTG GATGTCGTCT AATCTCCTAT CCTCTCAGTC TGGATGTTCG TCACCCCTAG

                                                                ⇒ C5L
      ..TyrTyrIle GlyThr (SEQ ID NO: 26)
3_1   TCTACTACAT TGGGACATAG CCCGGGTTTT TATGACTAGT TAATCACGGC CGCTTATAAA
      AGATGATGTA ACCCTGTATC GGGCCCAAAA ATACTGATCA ATTAGTGCCG GCGAATATTT

                                                        7928.DC →
3481  GATCTAAAAT GCATAATTTC TAAATAATGA AAAAAAGTAC ATCATGAGCA ACGCGTTAGT
      CTAGATTTTA CGTATTAAAG ATTTATTACT TTTTTTCATG TAGTACTCGT TGCGCAATCA

3541  ATATTTTACA ATGGAGATTA ACGCTCTATA CCGTTCTATG TTTATTCATT CAGATGATGT
      TATAAAATGT TACCTCTAAT TGCGAGATAT GGCAAGATAC AAATAAGTAA GTCTACTACA
                      ← 7793.SL

3601  TTTAGAAAAG AAAGTTATTG AATATGAAAA CTTTAATGAA GATGAAGATG ACGACGATGA
      AAATCTTTTC TTTCAATAAC TTATACTTTT GAAATTACTT CTACTTCTAC TGCTGCTACT

3661  TTATTGTTGT AAATCTGTTT TAGATGAAGA AGATGACGCG CTAAAGTATA CTATGGTTAC
      AATAACAACA TTTAGACAAA ATCTACTTCT TCTACTGCGC GATTTCATAT GATACCAATG

3721  AAAGTATAAG TCTATACTAC TAATGGCGAC TTGTGCAAGA AGGTATAGTA TAGTGAAAAT
      TTTCATATTC AGATATGATG ATTACCGCTG AACACGTTCT TCCATATCAT ATCACTTTTA

3781  GTTGTTAGAT TATGATTATG AAAAACCAAA TAAATCAGAT CCATATCTAA AGGTATCTCC
      CAACAATCTA ATACTAATAC TTTTTGGTTT ATTTAGTCTA GGTATAGATT TCCATAGAGG

3841  TTTGCACATA ATTTCATCTA TTCCTAGTTT AGAATACCTG CAGCCAAGCT TGGCACTGGC
      AAACGTGTAT TAAAGTAGAT AAGGATCAAA TCTTATGGAC GTCGGTTCGA ACCGTGACCG

3901  CGTCGTTTTA C (SEQ ID NO: 27)
      GCAGCAAAAT G (SEQ ID NO: 28)
        ← M13F
```

FIG. 5C (Continued)

SEQUENCE LISTING

```
<160> NUMBER OF SEQ ID NOS: 31

<210> SEQ ID NO 1
<211> LENGTH: 18246
<212> TYPE: DNA
<213> ORGANISM: Nipah virus

<400> SEQUENCE: 1

accaaacaag ggagaatatg gatacgttaa aatatataac gtatttttaa aacttaggaa      60

ccaagacaaa cacttttggt cttggtattg gatcctcaag aaatatatca tcatgagtga     120

tatctttgaa gaggcggcta gttttaggag ttatcaatct aagttaggga gagatgggag     180

ggctagtgca gcaactgcta ctttgacaac caagataagg atatttgtac cagctactaa     240

tagtccagag ctcagatggg aactaacatt gtttgcactt gatgtgatta gatctccgag     300

tgctgccgag tcaatgaaag ttggagctgc tttcacactc atctctatgt attcagagag     360

acccggggct ctcattagaa gtctcctcaa tgacccagac attgaagctg taataataga     420

tgttggatca atggtcaacg gaataccagt aatggagagg agaggagaca aggctcagga     480

ggagatggaa ggcttgatga gaatcctcaa aactgctcga gacagcagca agggaaaaac     540

accttttgtt gacagccgag cttacggcct acggataaca gacatgagca ccctggtctc     600

tgcagttatc accatcgagg cccagatctg gatactgatc gctaaagcag ttacagctcc     660

cgacactgcc gaggaaagtg aaactagaag atgggctaaa tacgtccaac aaaagagagt     720

caatccgttc tttgctctaa ctcagcaatg gctaacagaa atgaggaatc tgctctccca     780

gagtctatca gtaaggaagt tcatggttga gatcctcata gaagtcaaga aaggaggatc     840

tgctaaaggc agagcagtag aaataatctc agacatcgga aactatgtcg aggaaactgg     900

tatggcagga ttcttcgcaa ccatcagatt cgggttggag acaaggtatc cagcacttgc     960

actcaacgaa ttccagagtg acctcaacac catcaaaagc ttgatgctac tctacagaga    1020

aattggccca agagcccctt atatggtgct tcttgaagaa tcaattcaga ctaaatttgc    1080

ccctggaggt tacccattat tgtggagctt tgccatgggt gtggctacta ctattgacag    1140

gtctatgggg gcattgaata tcaatcgtgg ttatcttgag cctatgtatt tcagactagg    1200

ccaaaaatca gcacgtcacc atgctggagg aattgatcag aacatggcaa atagactggg    1260

actaagttca gatcaagttg cagaactcgc tgctgcagtt caggaaacat cagcaggaag    1320

gcaagagagt aatgttcagg ctagagaggc aaaatttgct gcaggaggtg tgctcattgg    1380

aggcagtgat caagatatcg atgaagggga agaacctata gaacagagtg gcagacagtc    1440
```

-continued

```
agttaccttc aaaagggaga tgagtatttc atcccttgct aacagtgtgc cgagcagttc   1500
tgtgagcaca tccggtggga ccagattgac taattcatta ctaaacctca gatcaagact   1560
ggctgcaaaa gcagcaaaag aagccgcctc atccaatgca acagatgatc cagcaatcag   1620
caacagaact caaggggaat cagagaagaa gaataatcaa gacctcaaac ctgctcaaaa   1680
tgaccttgat ttcgtcagag ctgatgtgtg acgtctattt ccaatattct acagtatcca   1740
aaaatctttc tatagtacac tatcataata cgacactaag ggatcaacca tatcaaagtt   1800
acgaatcgtt ttaattatat taatcaaatg atactctttt atgggcaaac cgaagaacca   1860
atgtctacat gtaaattgag ctttggtatt gcaatctaat acttgctcaa aatcttgaac   1920
tattagtgta atttctatca tcatagagtt atcaagattt tattatataa gttggtgcag   1980
atctttggac atgaattaca cactacactc taatgaagac aaaatttaca ttacatattt   2040
aaggactatt tcctatcctt tcaatggtac ttggttatga aggtttctta atttaactaa   2100
gctactgtct ttgcactgga atatacaata cctcttacct catttcttac tttaatatca   2160
tgttattttt ttgataagtc acttaacttg accaaggtct accaggtaat gctcgcacaa   2220
gtgaactgca atctcaactt agattaaaca taatcatgca aaatcactat tttgtactac   2280
taactcatta agaaaaactt aggatccaag agatttactc taggatctcc tattaagctt   2340
agcagtcatt agttgagagt tcaacttgca aaactctaac cttcactcta ataacaattc   2400
atccaatgga taaattggaa ctagtcaatg atggcctcaa tattattgac tttattcaga   2460
agaaccaaaa agaaatacag aagacatacg gacgatcaag tattcaacaa cccagcatca   2520
aagatcaaac aaaagcctgg gaagattttc tgcagtgcac cagtggagaa tctgaacaag   2580
ttgagggggg aatgtctaag gatgatggag atgttgaaag aagaaacttg gaggatctat   2640
ccagtacttc tcccacagat ggaactattg gaaagagagt gtcgaacacc cgtgactggg   2700
cagaaggttc agatgacata caactggacc cagtggttac agacgttgta taccatgatc   2760
atggaggaga atgtaccgga tatggattta cttcaagccc tgagagaggg tggagtgatt   2820
acacatcagg agcaaacaat gggaatgtat gtcttgtatc tgatgcaaag atgctgtcct   2880
atgctcccga aattgcagtt tctaaagaag atcgggaaac tgatctagtt catcttgaga   2940
ataaactatc tactacagga ctgaatccca cagcagtacc gttcactctg agaaacctgt   3000
ctgatcctgc aaaagactct cctgtgattg ctgaacacta ctacggacta ggagttaaag   3060
agcaaaacgt tggccctcag actagcagaa atgtcaattt ggacagcatc aaattgtaca   3120
catcagatga cgaagaggca gatcagcttg aattcgaaga tgagtttgca ggaagctcaa   3180
gtgaagtgat agtcggcatt tctcctgaag atgaagagcc ttcaagtgtt ggcggaaaac   3240
ccaatgaatc cattggacgt acaatcgaag gccaatcaat ccgagacaac cttcaagcca   3300
aggacaacaa atcaacagat gtaccaggag caggaccgaa agattcagca gtgaaggaag   3360
aaccaccccca gaagaggcta cctatgttag ctgaagaatt tgagtgctct ggatcggaag   3420
acccaatcat tcgggagctg ctgaaggaga actcactcat aaattgtcag caagggaaag   3480
atgctcagcc tccatatcat tggagcatcg agaggtcaat aagcccggat aaaactgaga   3540
tcgtcaacgg tgctgtgcaa actgctgaca ggcaaagacc aggaactccg atgccaaagt   3600
cccgaggtat tcccattaaa aagggcacag acgcgaaata tccatctgct gggacggaaa   3660
acgtgcctgg gtcgaagagt ggtgcaaccc ggcatgttcg aggatcaccc ccctaccaag   3720
aaggcaagag tgtcaatgcg gagaatgtcc aactgaatgc ttccactgcg gttaaggaaa   3780
ctgataagtc agaagtaaac cccgtagacg acaacgactc acttgatgat aaatacatca   3840
```

-continued

```
tgccttcaga tgatttctca aacactttct tcccgcacga cactgatcgc ttgaattatc   3900
acgcagatca tttaggtgat tatgaccttg aaaccctgtg tgaagagtcg gttctaatgg   3960
gagtgatcaa ctctataaaa ttaattaatc tggatatgcg cttaaatcac attgaagaac   4020
aagttaaaga gatcccaaag atcatcaata agcttgagtc cattgacaga gttctggcca   4080
agactaacac cgcactctca accattgaag gacacctggt ttccatgatg ataatgatac   4140
cagggaaagg gaaaggagaa agaaagggga aaaataatcc tgagcttaaa ccagtgatag   4200
gaagagacat tctagagcag caatctcttt tttcttttga caatgtcaag aatttcagag   4260
atggatcgtt gacaaacgaa ccgtatgggg cagctgtaca gttgagagaa gatcttattc   4320
ttcctgaact taattttgag gagacaaatg catctcaatt tgttcctatg gcagatgatt   4380
catccagaga tgttatcaag acattgataa ggactcacat taaagataga gagttgagat   4440
cagaactgat tggttacctg aataaagcgg aaaatgatga ggaaattcag gagatagcga   4500
acactgtcaa tgacatcatt gacggtaata tttgatcact gaattgtcag cagaaataca   4560
atgatctaac aacaatctcc cacaagtaga caatggtttc aggtcaataa taacaacctc   4620
aatactaatc tttcacataa gcattactca ttccagccct cagacgataa cacaatactt   4680
gatacatgtt tattgaagtg tatgtagcat gattgaacta ttcaataact gtatttctca   4740
ctcttgctct tagttagtca ttgtgtctaa taattattat tacagtacaa ggtattatga   4800
attcaaagat acgcaataaa tctgatatca gcatagagta gaaaattgtt gtttttgtca   4860
tgatcattcg aagatttaac aatgatgtca actttcatac ctaaacataa taacataaaa   4920
tggtcgattt gtattgtaga tctctcacgc attttagtgt catgaattag tgtttcaaat   4980
cagttgcata tcaattaaga aaaacttagg agacaggtat agaacctctc tttcagataa   5040
ctggtcaatt aaggacagaa attctgtttc tcaaatccgc tagcctttgt caaagaggac   5100
acaagcaatg gagccggaca tcaagagtat ttcaagtgag tcaatggaag gagtatctga   5160
tttcagccct agttcttggg agcatggtgg gtatcttgat aaggttgaac cagaaattga   5220
tgaaaatggc agtatgattc caaaatacaa gatctatacc ccaggagcta acgagaggaa   5280
atacaacaac tacatgtacc ttatatgtta cggctttgtt gaagatgttg agagaacccc   5340
agagacaggg aaacgcaaga agatcaggac aattgctgcc taccctctgg gtgttggtaa   5400
gagtgcctct catccccaag atcttctgga ggaactctgt tccctcaaag ttactgtgag   5460
aagaacagct ggatcaactg agaaaattgt gtttggatca tctggccctc taaatcacct   5520
cgttccgtgg aagaaagtac tgactagtgg ttcaattttt aatgcagtca aggtttgtcg   5580
gaacgttgat cagatacagc ttgacaagca tcaagctctg agaatatttt ttctcagtat   5640
cacaaagctc aatgattctg gaatctacat gattccacga accatgcttg agttcaggag   5700
aaacaatgcc attgccttca atcttctagt gtacttgaag attgatgctg atttatccaa   5760
aatggggatc cagggaagcc tcgataaaga tggcttcaag gttgcctcct tcatgctaca   5820
cttggggaac tttgtccgtc gtgcagggaa gtattactct gttgattatt gtaggaggaa   5880
gattgatagg atgaaattgc agttttcact gggttccata ggcggactaa gtctccacat   5940
taagatcaat ggtgtaatca gcaaacggct gtttgctcaa atgggattcc aaaaaaacct   6000
ttgtttctct ttgatggaca tcaatccttg gctcaacaga ttgacctgga acaacagttg   6060
tgagatcagc cgagtagcag ctgtgttgca gccttctatt ccaagagagt tcatgatcta   6120
tgatgatgtc ttcattgaca atacagggag aattctaaag ggctaaacag aattcttcta   6180
```

-continued

```
aaatttaatc agtcatgagt ttagtaatca tacctagtca taatacatca cacaggacta   6240
tttacaaaag acagttaaaa aatggaataa tcatgtagta gtaattgaga acattattag   6300
aatagtataa ctaaaatgta gtttttttga gtatttgatt taaaattaga taactattac   6360
aaaaaactta ggagccaagc tcttgcctcg ttcagaaggt taaacaagca ttcttaccat   6420
tggatcaaca aaaggattgg ttttatcgtc taagaaattt attgaaaggc aaagaaattc   6480
ctggttttat gttgaatgag gtgtatcaaa ctaaggagac cttctaacag ccaggtcata   6540
ggaatataaa taaaaataag aataaaaattg attccatcgg aagattcatt tcaagaagtg   6600
atcaaatcaa agcggttggc agacctacca atcatatacc acaagactcg acaatggtag   6660
ttatacttga caagagatgt tattgtaatc ttttaatatt gattttgatg atctcggagt   6720
gtagtgttgg gattctacat tatgagaaat tgagtaaaat tggacttgtc aaaggagtaa   6780
caagaaaata caagattaaa agcaatcctc tcacaaaaga cattgttata aaaatgattc   6840
cgaatgtgtc gaacatgtct cagtgcacag ggagtgtcat ggaaaattat aaaacacgat   6900
taaacggtat cttaacacct ataaagggag cgttagagat ctacaaaaac aacactcatg   6960
accttgtcgg tgatgtgaga ttagccggag ttataatggc aggagttgct attgggattg   7020
caaccgcagc tcaaatcact gcaggtgtag cactatatga ggcaatgaag aatgctgaca   7080
acatcaacaa actcaaaagc agcattgaat caactaatga agctgtcgtt aaacttcaag   7140
agactgcaga aaagacagtc tatgtgctga ctgctctaca ggattacatt aatactaatt   7200
tagtaccgac aattgacaag ataagctgca aacagacaga actctcacta gatctggcat   7260
tatcaaagta cctctctgat ttgctttttg tatttggccc caaccttcaa gacccagttt   7320
ctaattcaat gactatacag gctatatctc aggcattcgg tggaaattat gaaacactgc   7380
taagaacatt gggttacgct acagaagact ttgatgatct tctagaaagt gacagcataa   7440
caggtcaaat catctatgtt gatctaagta gctactatat aattgtcagg gtttattttc   7500
ctattctgac tgaaattcaa caggcctata tccaagagtt gttaccagtg agcttcaaca   7560
atgataattc agaatggatc agtattgtcc caaatttcat attggtaagg aatacattaa   7620
tatcaaatat agagattgga ttttgcctaa ttacaaagag gagcgtgatc tgcaaccaag   7680
attatgccac acctatgacc aacaacatga gagaatgttt aacgggatcg actgagaagt   7740
gtcctcgaga gctggttgtt tcatcacatg ttcccagatt tgcactatct aacggggttc   7800
tgtttgccaa ttgcataagt gttacatgtc agtgtcaaac aacaggcagg gcaatctcac   7860
aatcaggaga acaaactctg ctgatgattg acaacaccac ctgtcctaca gccgtactcg   7920
gtaatgtgat tatcagctta gggaaatatc tggggtcagt aaattataat tctgaaggca   7980
ttgctatcgg tcctccagtc tttacagata aagttgatat atcaagtcag atatccagca   8040
tgaatcagtc cttacaacag tctaaggact atatcaaaga ggctcaacga ctccttgata   8100
ctgttaatcc atcattaata agcatgttgt ctatgatcat actgtatgta ttatcgatcg   8160
catcgttgtg tatagggttg attacattta tcagttttat cattgttgag aaaaagagaa   8220
acacctacag cagattagag gataggagag tcagacctac aagcagtggg gatctctact   8280
acattgggac atagtgtatt cagattgatg aaattatgtt agagaaatca gaaaacttct   8340
gactttcaga aatggattgt atacaattag ttagatcatc ctgaataatc gaggtgagaa   8400
cattgcaact ataaaatcag atcatgtaaa tagttgtaaa aaattaaaag cttcttttaa   8460
ttcttttgaa caataattta attaatatat aacatattct ctcacacgag cgctaaccta   8520
tacactctct actaatattt tatactcata attaatgata taatgacaaa taaggattca   8580
```

-continued aattggatta tgatatagtt tcatactaca atagcatttc gaccaagaaa atatccttac 8640
aattatacaa tgtacttaac cgtgaatatg taattgataa tttcccttta gaaatttaat 8700
aaaaaactta ggacccaggt ccataactca ttggatactt aactgtatct ttctaagcta 8760
tcacatatca aaggagagat tgaatgcttt tttggagatc tagatcatta ctatatgtgt 8820
ctcctataat cacatcatag gagtgaacca taatacacat ctttgggtag gggaaggaaa 8880
gtattgttga cgtactgatt gatctgcttg agtcaaataa tcagtcataa caattcaaga 8940
aaatgccggc agaaaacaag aaagttagat tcgaaaatac tacttcagac aaagggaaaa 9000
ttcctagtaa agttattaag agctactacg gaaccatgga cattaagaaa ataaatgaag 9060
gattattgga cagcaaaata ttaagtgctt tcaacacagt aatagcattg cttggatcta 9120
tcgtgatcat agtgatgaat ataatgatca tccaaaatta cacaagatca acagacaatc 9180
aggccgtgat caaagatgcg ttgcagggta tccaacagca gatcaaaggg cttgctgaca 9240
aaatcggcac agagataggg cccaaagtat cactgattga cacatccagt accattacta 9300
tcccagctaa cattgggctg ttaggttcaa agatcagcca gtcgactgca agtataaatg 9360
agaatgtgaa tgaaaaatgc aaattcacac tgcctccctt gaaaatccac gaatgtaaca 9420
tttcttgtcc taacccactc ccttttagag agtataggcc acagacagaa ggggtgagca 9480
atctagtagg attacctaat aatatttgcc tgcaaaagac atctaatcag atattgaagc 9540
caaagctgat ttcatacact ttacccgtag tcggtcaaag tggtacctgt atcacagacc 9600
cattgctggc tatggacgag ggctattttg catatagcca cctggaaaga atcggatcat 9660
gttcaagagg ggtctccaaa caaagaataa taggagttgg agaggtacta gacagaggtg 9720
atgaagttcc ttctttattt atgaccaatg tctggacccc accaaatcca aacaccgttt 9780
accactgtag tgctgtatac aacaatgaat tctattatgt actttgtgca gtgtcaactg 9840
ttggagaccc tattctgaat agcacctact ggtccggatc tctaatgatg acccgtctag 9900
ctgtgaaacc caagagtaat ggtgggggtt acaatcaaca tcaacttgcc ctacgaagta 9960
tcgagaaagg gaggtatgat aaagttatgc cgtatggacc ttcaggcatc aaacagggtg 10020
acaccctgta ttttcctgct gtaggatttt tggtcaggac agagtttaaa tacaatgatt 10080
caaattgtcc catcacgaag tgtcaataca gtaaacctga aaattgcagg ctatctatgg 10140
ggattagacc aaacagccat tatatccttc gatctggact attaaaatac aatctatcag 10200
atggggagaa ccccaaagtt gtattcattg aaatatctga tcaaagatta tctattggat 10260
ctcctagcaa aatctatgat tctttgggtc aacctgtttt ctaccaagcg tcattttcat 10320
gggatactat gattaaattt ggagatgttc taacagtcaa ccctctggtt gtcaattggc 10380
gtaataacac ggtaatatca agacccgggc aatcacaatg ccctagattc aatacatgtc 10440
cagagatctg ctgggaagga gtttataatg atgcattcct aattgacaga atcaattgga 10500
taagcgcggg tgtattcctt gacagcaatc agaccgcaga aaatcctgtt tttactgtat 10560
tcaaagataa tgaaatactt tatagggcac aactggcttc tgaggacacc aatgcacaaa 10620
aaacaataac taattgtttt ctcttgaaga ataagatttg gtgcatatca ttggttgaga 10680
tatatgacac aggagacaat gtcataagac ccaaactatt cgcggttaag ataccagagc 10740
aatgtacata aaaatcaacc tcataattta atggattgat ctaatataat gataataatc 10800
gtacaaagac atgtgatgta aacaaaattg ttgtaattaa ataagtcctc agctgaatac 10860
ttttttaaga ttagcaatag catgtttttc cagttattgg atagttgata atataattct 10920

-continued

```
gaaactgggt taataaataa tcttgatcgg tgatctttga gaacaatgat atcatatagt  10980
tcatcaagtg ataatcaatt ctttatatgt acactttaga gtatattttg agacttagta  11040
ttttcggccc gaatgttaaa tttaatagtt catacataac ctaaactcaa gttctaagca  11100
taatgataac aattaatgcg aacttgtctt gatgtaagga agatttgata ttaactgaga  11160
ctccacttga tatagtagag ctgaatcttg taaataaatt ataatgaata gtttattcaa  11220
agattatcat tcatattagt gtaaattaag aaaaacttag gacccaggtc cttgattatg  11280
ccaattttct cgagaaatca ttcaattgac catagactga aagcgttgtt acctagttct  11340
tcagaagaga tcttattaga attaatttat atgatctaat tcccttaaaa actgaatacc  11400
aaaaaacaaa aatggccgat gaattatcaa tatccgacat catttaccct gaatgtcatt  11460
tggatagtcc tatagtctct ggtaaactaa tatcagctat tgaatatgct caattgagac  11520
acaatcagcc cagtgatgat aaaagactgt ctgagaatat taggttaaac cttcacggga  11580
aaagaaagag tctatacata ttaagacaat ccaaacaggg tgattacatt agaaacaaca  11640
taaaaaacct aaaggaattc atgcatattg cgtaccctga atgcaataac attctattct  11700
ccatcacatc ccaaggcatg actagcaaac ttgataacat catgaaaaag tcattcaaag  11760
catacaatat cattagtaag aaagtaattg ggatgctgca aaatatcact agaaatctca  11820
taactcaaga tagaagagat gaaataatta atatacatga gtgtaggcga ttaggggatt  11880
tagggaagaa tatgagtcaa tctaaatggt atgagtgttt tttgttttgg tttactatca  11940
aaacagagat gcgagcagtg atcaagaatt cgcaaaagcc gaaattccgt tcagattcat  12000
gcataataca catgcgagac aaaagtactg aaataatcct aaatccgaat cttatctgca  12060
ttttcaaatc agacaaaact ggaaagaagt gttattatct tacacccgaa atggttctaa  12120
tgtattgtga tgtcctagag ggaaggatga tgatggagac aacagtcaaa tcggatatca  12180
agtaccaacc tctaatctcg agatccaatg ccctctgggg gctaattgat cccttgttcc  12240
ctgtcatggg aaacagaatt tacaatatag tgtctatgat agagccttta gttcttgcac  12300
tactccaact caaggatgag gctaggatcc tgaggggtgc atttctgcat cactgcataa  12360
aggaaatgca tcaagaattg agtgagtgtg gttttacaga tcagaagatt cggtctatgt  12420
ttattgatga tcttttatcc attctaaata tcgataaata acatctgttg gcagagttct  12480
tttctttctt tcgtacgttt ggccatccta ttcttgaggc taaagttgct gcagaaaaag  12540
tgagagaaca tatgttggca gataaagttc ttgaatatgc cctataatg  aaagcacatg  12600
ctatattctg cgggactata ataaatgggt atagggatag acacggagga gcctggcctc  12660
ctctttacct ccccgcacat gcatctaaac atataatccg tttgaaaaat tctggggaat  12720
ctttgaccat tgatgactgt gtcaagaatt gggaatcatt ctgtgggatt caatttgatt  12780
gtttcatgga gctgaaattg gacagtgatc tgagtatgta tatgaaagat aaagctttat  12840
ctccaatcaa agacgaatgg gacagtgtat acccacgtga agtgttgagc tataccccac  12900
cgaagtcaac cgagccaaga agattggttg acgtttttgt aaatgatgaa aactttgatc  12960
catacaacat gctggaatat gtcttatccg gtgcttatct cgaggatgaa caattcaatg  13020
tttcttatag cttgaaggag aaagagacga agcaagctgg acgattgttc gcaaagatga  13080
cctacaaaat gcgtgcatgt caagtcatag cagaggccct gatagcctca ggtgtcggta  13140
aatattttaa ggagaacggg atggttaagg atgagcacga acttttgaag acactcttcc  13200
aattgtctat ttcctcagtt cctcgaggga acagtcaggg taatgatcct caatccatca  13260
ataatataga aagagatttc caatacttta aaggggtcac taccaatgtg aaagacaaaa  13320
```

-continued agaataactc ttttaataag gttaaatctg ctctcaataa tccgtgccaa gctgacggag 13380
tccatcataa catgtcaccc aatacacgaa atcgttataa gtgtagtaat acaagtaagt 13440
cttttctcga ttatcatacc gagtttaatc ctcacaatca ctataaatca gacaatacag 13500
aggcggccgt actgtccagg tatgaggaca acactgggac aaaatttgat acagtaagtg 13560
catttcttac aactgatctt aagaaattct gtctcaattg gagatacgaa tcaatggcta 13620
tatttgctga acgtctggat gagatatacg gtttacctgg attttttaat tggatgcaca 13680
aacgactaga aagatctgtt atctatgttg cagaccctaa ttgcccccct aatattgaca 13740
aacatatgga actagaaaaa actcctgaag atgatatatt cattcattat cctaaaggcg 13800
gtattgaagg atatagccaa aaaacatgga ctatagcaac tatccccttt ttattcttga 13860
gtgcctatga gacaaacacg aggattgctg caattgtcca aggagacaat gaatcaattg 13920
ctatcactca aaaagttcat cctaatcttc cctacaaggt aaagaaagag atctgtgcaa 13980
agcaagctca gctttatttt gaaaggttaa ggatgaactt aagagccctc ggccacaatc 14040
ttaaagctac agaaactatc atcagtacac atctttttat ttattcgaag aaaattcatt 14100
atgatggtgc tgtgctgtct caggcactca aatcaatgtc aagatgttgc ttttggtcag 14160
agactctggt ggatgaaact agatcagctt gtagtaacat cagcactaca atagctaaag 14220
ctatagaaaa tgggttgtca agaaatgtcg gctattgcat caatattttg aaagtaattc 14280
agcagcttct catatcaact gagtttagta ttaacgagac attgacactg gatgtgacat 14340
ctcccatttc aaataattta gattggctta taacagctgc attaatcccg gcacctattg 14400
gaggattcaa ttaccttaat ttgtctagaa tttttgttag aaatataggt gatccggtta 14460
cagcatcttt ggctgatctt aagagaatga ttgatcacag tattatgact gaaagcgtat 14520
tacaaaaagt tatgaatcaa gaacctggtg atgcgagttt cttggactgg gccagtgatc 14580
catactcggg caacttgcct gactcacaaa gcatcactaa aacaattaaa aatatcacag 14640
caaggactat actgaggaac tcaccgaacc caatgctaaa aggtttattt catgacaaat 14700
cttttgatga agatcttgaa ctagctagct tcttaatgga caggagggtt atattaccta 14760
gagccgctca tgagatactg gataattcat tgacaggtgc cagagaggaa attgctggtt 14820
tattagatac aactaaaggc ttgatcagat cagggctaag aaagagtgga cttcagccaa 14880
agttagtttc tagattatct catcatgatt ataatcaatt tttaatactg aacaaacttc 14940
tatcaaacag aagacaaaat gacttgatat catcaaatac ttgctcagtt gacttggcac 15000
gagcattgag atctcacatg tggagggaat tagcgttagg tagagtaata tacggtcttg 15060
aggtaccaga tgcacttgag gctatggtgg gaaggtatat aacagggagc ttagagtgcc 15120
aaatttgtga gcagggaaac acgatgtatg ggtggttctt tgtacctagg gattcccaat 15180
tggatcaggt agatagagag cactcatcaa taagagtacc ttatgtagga tcaagtacgg 15240
atgaaagatc ggatatcaaa ctagggaatg tcaaaagacc aactaaggcc ttgcgttctg 15300
ctatcagaat tgcgacagta tatacttggg cctatgggga caatgaagag tgttggtatg 15360
aagcttggta cctagcgtct cagagggtaa acatagactt agatgtattg aaagctataa 15420
ccccagtttc cacttcaaac aatttatccc atagattgag agataaatcc acacaattta 15480
agtttgcagg gagtgtactc aacagagttt ctagatatgt taacataagc aatgacaatc 15540
tagatttcag aattgaggga gaaaaggtag atacgaatct tatttatcaa caagcaatgc 15600
tattagggtt atcggtattg gaaggtaaat tcagattgag attagaaact gatgattaca 15660

-continued acgggatata tcacttacac gtaaaggata attgttgtgt caaagaagtg gctgatgtag 15720
gccaagtaga cgctgagttg cctatcccag aatatactga agtggataac aatcatctta 15780
tatatgatcc agaccccgtt tcagaaatag attgcagccg tctttctaat caggagtcca 15840
aatcaagaga attagacttt cctttatggt caactgagga acttcatgat gtcctagcta 15900
agactgttgc tcagaccgtt cttgagatta taacaaaggc tgacaaggat gttttaaagc 15960
aacaccttgc aatagactct gacgataaca tcaacagctt aatcacagaa tttctaatag 16020
ttgatcctga actgtttgca ctttatctag gacaatctat atcaataaaa tgggcctttg 16080
aaattcatca taggcgtcct agaggaagac atactatggt cgacctattg tcagatcttg 16140
tatcaaatac atcaaagcac acttacaaag tgttgtcaaa tgccttgtca catcctagag 16200
tattcaagag atttgtaaac tgtggcttgc tattgcctac acagggtcct taccttcatc 16260
aacaagattt tgaaaagttg tctcaaaacc ttcttgtaac atcttatatg atttatctaa 16320
tgaactggtg tgacttcaag aaatccccct ttttaatcgc cgaacaggat gaaactgtga 16380
taagtctacg agaggatata ataacatcca aacatctctg tgttataatt gacttatatg 16440
caaatcacca taaacctcct tggataatag atctaaaccc acaagaaaaa atatgtgtac 16500
tgcgtgactt tatttctaaa tctaggcatg tggacacgtc ctccagatca tggaatactt 16560
ctgacctgga ttttgtaata ttctatgcat ctttgactta tttgagaaga ggtataataa 16620
aacaattaag gataagacaa gttactgagg ttatagatac cacaacaatg ttaagggaca 16680
atataattgt agagaatcct cctattaaaa caggagtgtt agacatcaga ggttgtataa 16740
tatacaattt agaggaaatc ctgtctatga acacaaaatc agcatcaaaa aagatcttta 16800
atcttaatag taggccgtca gtggagaatc ataaatatag aaggataggt ctcaactcat 16860
catcttgtta caaggcatta aatctatcac ctctgattca aaggtatttg ccgtcgggag 16920
ctcaaaggtt gtttatagga gaaggttctg ggagcatgat gttattatat cagtctacat 16980
tggggcaatc aatttctttt tacaattcag gtatagatgg agattatata ccaggtcaaa 17040
gagaactgaa actatttccc tctgaatact caattgctga ggaagaccca tctctgacgg 17100
ggaaattgaa aggactagtg gtgcccctat tcaatggaag accagaaaca acatggatcg 17160
ggaatttaga ctcctacgag tatatcataa ataggacagc ggggcgaagt ataggtcttg 17220
tccattctga catggagtct gggattgaca aaaatgtaga ggagatacta gtagaacatt 17280
cccatctaat atctatcgcg ataaatgtta tgatggagga cggactatta gtatccaaga 17340
tagcatacac ccctggattc ccaatctcaa gattatttaa catgtacaga tcatatttcg 17400
gactagtact ggtgtgtttc ccagtatata gtaatccaga ttctactgaa gtatatcttc 17460
tttgcttaca gaagacggtc aagactattg ttcccccgca aaaagtcctt gagcactcta 17520
atttgcacga tgaagtcaat gaccagggaa taacatcagt gatttttaaa atcaagaatt 17580
cacagtctaa gcagttccac gatgatctaa agaagtacta tcagattgac caaccttttt 17640
ttgtaccaac taaaatcact agtgatgaac aagtacttct ccaagcaggg ctgaaactca 17700
atgggccaga aattcttaag agtgaaatca gttatgatat cggttcagat atcaatacat 17760
taagagacac catcataatt atgttaaatg aggctatgaa ttattttgat gacaacagat 17820
caccttcaca ccacctagaa ccctatccag ttttggagag aactagaatt aaaacaataa 17880
tgaattgtgt gactaaaaaa gtgattgtct actcacttat caagttcaag gacaccaaaa 17940
gctcagaact ttatcacatc aaaaataaca tcagaagaaa agttctaatc ttagatttca 18000
gatcgaagct catgacaaag actctaccta aagggatgca agagagaaga gaaaaaaacg 18060

-continued gtttcaaaga agtttggata gtagatttat cgaatcgaga agttaaaatc tggtggaaga 18120
taatcggata catatctatt atctgattta accttccaaa tccaagacca actgataact 18180
tatgttgatc taaggttcag ttattaagaa aaacttaata acgattcttc tttacccttg 18240
ttcggt 18246

<210> SEQ ID NO 2
<211> LENGTH: 532
<212> TYPE: PRT
<213> ORGANISM: Nipah virus

<400> SEQUENCE: 2

Met Ser Asp Ile Phe Glu Glu Ala Ala Ser Phe Arg Ser Tyr Gln Ser
1 5 10 15

Lys Leu Gly Arg Asp Gly Arg Ala Ser Ala Ala Thr Ala Thr Leu Thr
20 25 30

Thr Lys Ile Arg Ile Phe Val Pro Ala Thr Asn Ser Pro Glu Leu Arg
35 40 45

Trp Glu Leu Thr Leu Phe Ala Leu Asp Val Ile Arg Ser Pro Ser Ala
50 55 60

Ala Glu Ser Met Lys Val Gly Ala Ala Phe Thr Leu Ile Ser Met Tyr
65 70 75 80

Ser Glu Arg Pro Gly Ala Leu Ile Arg Ser Leu Leu Asn Asp Pro Asp
85 90 95

Ile Glu Ala Val Ile Ile Asp Val Gly Ser Met Val Asn Gly Ile Pro
100 105 110

Val Met Glu Arg Arg Gly Asp Lys Ala Gln Glu Glu Met Glu Gly Leu
115 120 125

Met Arg Ile Leu Lys Thr Ala Arg Asp Ser Ser Lys Gly Lys Thr Pro
130 135 140

Phe Val Asp Ser Arg Ala Tyr Gly Leu Arg Ile Thr Asp Met Ser Thr
145 150 155 160

Leu Val Ser Ala Val Ile Thr Ile Glu Ala Gln Ile Trp Ile Leu Ile
165 170 175

Ala Lys Ala Val Thr Ala Pro Asp Thr Ala Glu Glu Ser Glu Thr Arg
180 185 190

Arg Trp Ala Lys Tyr Val Gln Gln Lys Arg Val Asn Pro Phe Phe Ala
195 200 205

Leu Thr Gln Gln Trp Leu Thr Glu Met Arg Asn Leu Leu Ser Gln Ser
210 215 220

Leu Ser Val Arg Lys Phe Met Val Glu Ile Leu Ile Glu Val Lys Lys
225 230 235 240

Gly Gly Ser Ala Lys Gly Arg Ala Val Glu Ile Ile Ser Asp Ile Gly
245 250 255

Asn Tyr Val Glu Glu Thr Gly Met Ala Gly Phe Phe Ala Thr Ile Arg
260 265 270

Phe Gly Leu Glu Thr Arg Tyr Pro Ala Leu Ala Leu Asn Glu Phe Gln
275 280 285

Ser Asp Leu Asn Thr Ile Lys Ser Leu Met Leu Leu Tyr Arg Glu Ile
290 295 300

Gly Pro Arg Ala Pro Tyr Met Val Leu Leu Glu Glu Ser Ile Gln Thr
305 310 315 320

Lys Phe Ala Pro Gly Gly Tyr Pro Leu Leu Trp Ser Phe Ala Met Gly
325 330 335

-continued

```
Val Ala Thr Thr Ile Asp Arg Ser Met Gly Ala Leu Asn Ile Asn Arg
            340                 345                 350

Gly Tyr Leu Glu Pro Met Tyr Phe Arg Leu Gly Gln Lys Ser Ala Arg
        355                 360                 365

His His Ala Gly Gly Ile Asp Gln Asn Met Ala Asn Arg Leu Gly Leu
    370                 375                 380

Ser Ser Asp Gln Val Ala Glu Leu Ala Ala Ala Val Gln Glu Thr Ser
385                 390                 395                 400

Ala Gly Arg Gln Glu Ser Asn Val Gln Ala Arg Glu Ala Lys Phe Ala
                405                 410                 415

Ala Gly Gly Val Leu Ile Gly Gly Ser Asp Gln Asp Ile Asp Glu Gly
            420                 425                 430

Glu Glu Pro Ile Glu Gln Ser Gly Arg Gln Ser Val Thr Phe Lys Arg
        435                 440                 445

Glu Met Ser Ile Ser Ser Leu Ala Asn Ser Val Pro Ser Ser Ser Val
    450                 455                 460

Ser Thr Ser Gly Gly Thr Arg Leu Thr Asn Ser Leu Leu Asn Leu Arg
465                 470                 475                 480

Ser Arg Leu Ala Ala Lys Ala Ala Lys Glu Ala Ala Ser Ser Asn Ala
                485                 490                 495

Thr Asp Asp Pro Ala Ile Ser Asn Arg Thr Gln Gly Glu Ser Glu Lys
            500                 505                 510

Lys Asn Asn Gln Asp Leu Lys Pro Ala Gln Asn Asp Leu Asp Phe Val
        515                 520                 525

Arg Ala Asp Val
    530


<210> SEQ ID NO 3
<211> LENGTH: 709
<212> TYPE: PRT
<213> ORGANISM: Nipah virus

<400> SEQUENCE: 3

Met Asp Lys Leu Glu Leu Val Asn Asp Gly Leu Asn Ile Ile Asp Phe
  1               5                  10                  15

Ile Gln Lys Asn Gln Lys Glu Ile Gln Lys Thr Tyr Gly Arg Ser Ser
             20                  25                  30

Ile Gln Gln Pro Ser Ile Lys Asp Gln Thr Lys Ala Trp Glu Asp Phe
         35                  40                  45

Leu Gln Cys Thr Ser Gly Glu Ser Glu Gln Val Glu Gly Gly Met Ser
     50                  55                  60

Lys Asp Asp Gly Asp Val Glu Arg Arg Asn Leu Glu Asp Leu Ser Ser
 65                  70                  75                  80

Thr Ser Pro Thr Asp Gly Thr Ile Gly Lys Arg Val Ser Asn Thr Arg
                 85                  90                  95

Asp Trp Ala Glu Gly Ser Asp Asp Ile Gln Leu Asp Pro Val Val Thr
            100                 105                 110

Asp Val Val Tyr His Asp His Gly Gly Glu Cys Thr Gly Tyr Gly Phe
        115                 120                 125

Thr Ser Ser Pro Glu Arg Gly Trp Ser Asp Tyr Thr Ser Gly Ala Asn
    130                 135                 140

Asn Gly Asn Val Cys Leu Val Ser Asp Ala Lys Met Leu Ser Tyr Ala
145                 150                 155                 160

Pro Glu Ile Ala Val Ser Lys Glu Asp Arg Glu Thr Asp Leu Val His
```

-continued

```
                165                 170                 175

Leu Glu Asn Lys Leu Ser Thr Thr Gly Leu Asn Pro Thr Ala Val Pro
            180                 185                 190

Phe Thr Leu Arg Asn Leu Ser Asp Pro Ala Lys Asp Ser Pro Val Ile
        195                 200                 205

Ala Glu His Tyr Tyr Gly Leu Gly Val Lys Glu Gln Asn Val Gly Pro
    210                 215                 220

Gln Thr Ser Arg Asn Val Asn Leu Asp Ser Ile Lys Leu Tyr Thr Ser
225                 230                 235                 240

Asp Asp Glu Glu Ala Asp Gln Leu Glu Phe Glu Asp Glu Phe Ala Gly
                245                 250                 255

Ser Ser Ser Glu Val Ile Val Gly Ile Ser Pro Glu Asp Glu Glu Pro
            260                 265                 270

Ser Ser Val Gly Gly Lys Pro Asn Glu Ser Ile Gly Arg Thr Ile Glu
        275                 280                 285

Gly Gln Ser Ile Arg Asp Asn Leu Gln Ala Lys Asp Asn Lys Ser Thr
    290                 295                 300

Asp Val Pro Gly Ala Gly Pro Lys Asp Ser Ala Val Lys Glu Glu Pro
305                 310                 315                 320

Pro Gln Lys Arg Leu Pro Met Leu Ala Glu Glu Phe Glu Cys Ser Gly
                325                 330                 335

Ser Glu Asp Pro Ile Ile Arg Glu Leu Leu Lys Glu Asn Ser Leu Ile
            340                 345                 350

Asn Cys Gln Gln Gly Lys Asp Ala Gln Pro Pro Tyr His Trp Ser Ile
        355                 360                 365

Glu Arg Ser Ile Ser Pro Asp Lys Thr Glu Ile Val Asn Gly Ala Val
    370                 375                 380

Gln Thr Ala Asp Arg Gln Arg Pro Gly Thr Pro Met Pro Lys Ser Arg
385                 390                 395                 400

Gly Ile Pro Ile Lys Lys Gly Thr Asp Ala Lys Tyr Pro Ser Ala Gly
                405                 410                 415

Thr Glu Asn Val Pro Gly Ser Lys Ser Gly Ala Thr Arg His Val Arg
            420                 425                 430

Gly Ser Pro Pro Tyr Gln Glu Gly Lys Ser Val Asn Ala Glu Asn Val
        435                 440                 445

Gln Leu Asn Ala Ser Thr Ala Val Lys Glu Thr Asp Lys Ser Glu Val
    450                 455                 460

Asn Pro Val Asp Asp Asn Asp Ser Leu Asp Asp Lys Tyr Ile Met Pro
465                 470                 475                 480

Ser Asp Asp Phe Ser Asn Thr Phe Phe Pro His Asp Thr Asp Arg Leu
                485                 490                 495

Asn Tyr His Ala Asp His Leu Gly Asp Tyr Asp Leu Glu Thr Leu Cys
            500                 505                 510

Glu Glu Ser Val Leu Met Gly Val Ile Asn Ser Ile Lys Leu Ile Asn
        515                 520                 525

Leu Asp Met Arg Leu Asn His Ile Glu Glu Gln Val Lys Glu Ile Pro
    530                 535                 540

Lys Ile Ile Asn Lys Leu Glu Ser Ile Asp Arg Val Leu Ala Lys Thr
545                 550                 555                 560

Asn Thr Ala Leu Ser Thr Ile Glu Gly His Leu Val Ser Met Met Ile
                565                 570                 575

Met Ile Pro Gly Lys Gly Lys Gly Glu Arg Lys Gly Lys Asn Asn Pro
            580                 585                 590
```

-continued

Glu Leu Lys Pro Val Ile Gly Arg Asp Ile Leu Glu Gln Gln Ser Leu
595 600 605

Phe Ser Phe Asp Asn Val Lys Asn Phe Arg Asp Gly Ser Leu Thr Asn
610 615 620

Glu Pro Tyr Gly Ala Ala Val Gln Leu Arg Glu Asp Leu Ile Leu Pro
625 630 635 640

Glu Leu Asn Phe Glu Glu Thr Asn Ala Ser Gln Phe Val Pro Met Ala
645 650 655

Asp Asp Ser Ser Arg Asp Val Ile Lys Thr Leu Ile Arg Thr His Ile
660 665 670

Lys Asp Arg Glu Leu Arg Ser Glu Leu Ile Gly Tyr Leu Asn Lys Ala
675 680 685

Glu Asn Asp Glu Glu Ile Gln Glu Ile Ala Asn Thr Val Asn Asp Ile
690 695 700

Ile Asp Gly Asn Ile
705

<210> SEQ ID NO 4
<211> LENGTH: 456
<212> TYPE: PRT
<213> ORGANISM: Nipah virus

<400> SEQUENCE: 4

Met Asp Lys Leu Glu Leu Val Asn Asp Gly Leu Asn Ile Ile Asp Phe
1 5 10 15

Ile Gln Lys Asn Gln Lys Glu Ile Gln Lys Thr Tyr Gly Arg Ser Ser
20 25 30

Ile Gln Gln Pro Ser Ile Lys Asp Gln Thr Lys Ala Trp Glu Asp Phe
35 40 45

Leu Gln Cys Thr Ser Gly Glu Ser Glu Gln Val Glu Gly Gly Met Ser
50 55 60

Lys Asp Asp Gly Asp Val Glu Arg Arg Asn Leu Glu Asp Leu Ser Ser
65 70 75 80

Thr Ser Pro Thr Asp Gly Thr Ile Gly Lys Arg Val Ser Asn Thr Arg
85 90 95

Asp Trp Ala Glu Gly Ser Asp Asp Ile Gln Leu Asp Pro Val Val Thr
100 105 110

Asp Val Val Tyr His Asp His Gly Gly Glu Cys Thr Gly Tyr Gly Phe
115 120 125

Thr Ser Ser Pro Glu Arg Gly Trp Ser Asp Tyr Thr Ser Gly Ala Asn
130 135 140

Asn Gly Asn Val Cys Leu Val Ser Asp Ala Lys Met Leu Ser Tyr Ala
145 150 155 160

Pro Glu Ile Ala Val Ser Lys Glu Asp Arg Glu Thr Asp Leu Val His
165 170 175

Leu Glu Asn Lys Leu Ser Thr Thr Gly Leu Asn Pro Thr Ala Val Pro
180 185 190

Phe Thr Leu Arg Asn Leu Ser Asp Pro Ala Lys Asp Ser Pro Val Ile
195 200 205

Ala Glu His Tyr Tyr Gly Leu Gly Val Lys Glu Gln Asn Val Gly Pro
210 215 220

Gln Thr Ser Arg Asn Val Asn Leu Asp Ser Ile Lys Leu Tyr Thr Ser
225 230 235 240

Asp Asp Glu Glu Ala Asp Gln Leu Glu Phe Glu Asp Glu Phe Ala Gly

-continued

```
                245                 250                 255

Ser Ser Ser Glu Val Ile Val Gly Ile Ser Pro Glu Asp Glu Glu Pro
            260                 265                 270

Ser Ser Val Gly Gly Lys Pro Asn Glu Ser Ile Gly Arg Thr Ile Glu
        275                 280                 285

Gly Gln Ser Ile Arg Asp Asn Leu Gln Ala Lys Asp Asn Lys Ser Thr
    290                 295                 300

Asp Val Pro Gly Ala Gly Pro Lys Asp Ser Ala Val Lys Glu Glu Pro
305                 310                 315                 320

Pro Gln Lys Arg Leu Pro Met Leu Ala Glu Glu Phe Glu Cys Ser Gly
                325                 330                 335

Ser Glu Asp Pro Ile Ile Arg Glu Leu Leu Lys Glu Asn Ser Leu Ile
            340                 345                 350

Asn Cys Gln Gln Gly Lys Asp Ala Gln Pro Pro Tyr His Trp Ser Ile
        355                 360                 365

Glu Arg Ser Ile Ser Pro Asp Lys Thr Glu Ile Val Asn Gly Ala Val
    370                 375                 380

Gln Thr Ala Asp Arg Gln Arg Pro Gly Thr Pro Met Pro Lys Ser Arg
385                 390                 395                 400

Gly Ile Pro Ile Lys Lys Gly His Arg Arg Glu Ile Ser Ile Cys Trp
                405                 410                 415

Asp Gly Lys Arg Ala Trp Val Glu Glu Trp Cys Asn Pro Ala Cys Ser
            420                 425                 430

Arg Ile Thr Pro Leu Pro Arg Arg Gln Glu Cys Gln Cys Gly Glu Cys
        435                 440                 445

Pro Thr Glu Cys Phe His Cys Gly
    450                 455


<210> SEQ ID NO 5
<211> LENGTH: 166
<212> TYPE: PRT
<213> ORGANISM: Nipah virus

<400> SEQUENCE: 5

Met Met Ala Ser Ile Leu Leu Thr Leu Phe Arg Arg Thr Lys Lys Lys
  1               5                  10                  15

Tyr Arg Arg His Thr Asp Asp Gln Val Phe Asn Asn Pro Ala Ser Lys
             20                  25                  30

Ile Lys Gln Lys Pro Gly Lys Ile Phe Cys Ser Ala Pro Val Glu Asn
         35                  40                  45

Leu Asn Lys Leu Arg Gly Glu Cys Leu Arg Met Met Glu Met Leu Lys
     50                  55                  60

Glu Glu Thr Trp Arg Ile Tyr Pro Val Leu Leu Pro Gln Met Glu Leu
 65                  70                  75                  80

Leu Glu Arg Glu Cys Arg Thr Pro Val Thr Gly Gln Lys Val Gln Met
                 85                  90                  95

Thr Tyr Asn Trp Thr Gln Trp Leu Gln Thr Leu Tyr Thr Met Ile Met
            100                 105                 110

Glu Glu Asn Val Pro Asp Met Asp Leu Leu Gln Ala Leu Arg Glu Gly
        115                 120                 125

Gly Val Ile Thr His Gln Glu Gln Thr Met Gly Met Tyr Val Leu Tyr
    130                 135                 140

Leu Met Gln Arg Cys Cys Pro Met Leu Pro Lys Leu Gln Phe Leu Lys
145                 150                 155                 160
```

-continued

```
Lys Ile Gly Lys Leu Ile
                165


<210> SEQ ID NO 6
<211> LENGTH: 352
<212> TYPE: PRT
<213> ORGANISM: Nipah virus

<400> SEQUENCE: 6

Met Glu Pro Asp Ile Lys Ser Ile Ser Ser Glu Ser Met Glu Gly Val
  1               5                  10                  15

Ser Asp Phe Ser Pro Ser Ser Trp Glu His Gly Gly Tyr Leu Asp Lys
             20                  25                  30

Val Glu Pro Glu Ile Asp Glu Asn Gly Ser Met Ile Pro Lys Tyr Lys
         35                  40                  45

Ile Tyr Thr Pro Gly Ala Asn Glu Arg Lys Tyr Asn Asn Tyr Met Tyr
     50                  55                  60

Leu Ile Cys Tyr Gly Phe Val Glu Asp Val Glu Arg Thr Pro Glu Thr
 65                  70                  75                  80

Gly Lys Arg Lys Lys Ile Arg Thr Ile Ala Ala Tyr Pro Leu Gly Val
                 85                  90                  95

Gly Lys Ser Ala Ser His Pro Gln Asp Leu Leu Glu Glu Leu Cys Ser
            100                 105                 110

Leu Lys Val Thr Val Arg Arg Thr Ala Gly Ser Thr Glu Lys Ile Val
        115                 120                 125

Phe Gly Ser Ser Gly Pro Leu Asn His Leu Val Pro Trp Lys Lys Val
    130                 135                 140

Leu Thr Ser Gly Ser Ile Phe Asn Ala Val Lys Val Cys Arg Asn Val
145                 150                 155                 160

Asp Gln Ile Gln Leu Asp Lys His Gln Ala Leu Arg Ile Phe Phe Leu
                165                 170                 175

Ser Ile Thr Lys Leu Asn Asp Ser Gly Ile Tyr Met Ile Pro Arg Thr
            180                 185                 190

Met Leu Glu Phe Arg Arg Asn Asn Ala Ile Ala Phe Asn Leu Leu Val
        195                 200                 205

Tyr Leu Lys Ile Asp Ala Asp Leu Ser Lys Met Gly Ile Gln Gly Ser
    210                 215                 220

Leu Asp Lys Asp Gly Phe Lys Val Ala Ser Phe Met Leu His Leu Gly
225                 230                 235                 240

Asn Phe Val Arg Arg Ala Gly Lys Tyr Tyr Ser Val Asp Tyr Cys Arg
                245                 250                 255

Arg Lys Ile Asp Arg Met Lys Leu Gln Phe Ser Leu Gly Ser Ile Gly
            260                 265                 270

Gly Leu Ser Leu His Ile Lys Ile Asn Gly Val Ile Ser Lys Arg Leu
        275                 280                 285

Phe Ala Gln Met Gly Phe Gln Lys Asn Leu Cys Phe Ser Leu Met Asp
    290                 295                 300

Ile Asn Pro Trp Leu Asn Arg Leu Thr Trp Asn Asn Ser Cys Glu Ile
305                 310                 315                 320

Ser Arg Val Ala Ala Val Leu Gln Pro Ser Ile Pro Arg Glu Phe Met
                325                 330                 335

Ile Tyr Asp Asp Val Phe Ile Asp Asn Thr Gly Arg Ile Leu Lys Gly
            340                 345                 350


<210> SEQ ID NO 7
```

-continued

<211> LENGTH: 546
<212> TYPE: PRT
<213> ORGANISM: Nipah virus

<400> SEQUENCE: 7

```
Met Val Val Ile Leu Asp Lys Arg Cys Tyr Cys Asn Leu Leu Ile Leu
  1               5                  10                  15

Ile Leu Met Ile Ser Glu Cys Ser Val Gly Ile Leu His Tyr Glu Lys
             20                  25                  30

Leu Ser Lys Ile Gly Leu Val Lys Gly Val Thr Arg Lys Tyr Lys Ile
         35                  40                  45

Lys Ser Asn Pro Leu Thr Lys Asp Ile Val Ile Lys Met Ile Pro Asn
     50                  55                  60

Val Ser Asn Met Ser Gln Cys Thr Gly Ser Val Met Glu Asn Tyr Lys
 65                  70                  75                  80

Thr Arg Leu Asn Gly Ile Leu Thr Pro Ile Lys Gly Ala Leu Glu Ile
                 85                  90                  95

Tyr Lys Asn Asn Thr His Asp Leu Val Gly Asp Val Arg Leu Ala Gly
            100                 105                 110

Val Ile Met Ala Gly Val Ala Ile Gly Ile Ala Thr Ala Ala Gln Ile
        115                 120                 125

Thr Ala Gly Val Ala Leu Tyr Glu Ala Met Lys Asn Ala Asp Asn Ile
    130                 135                 140

Asn Lys Leu Lys Ser Ser Ile Glu Ser Thr Asn Glu Ala Val Val Lys
145                 150                 155                 160

Leu Gln Glu Thr Ala Glu Lys Thr Val Tyr Val Leu Thr Ala Leu Gln
                165                 170                 175

Asp Tyr Ile Asn Thr Asn Leu Val Pro Thr Ile Asp Lys Ile Ser Cys
            180                 185                 190

Lys Gln Thr Glu Leu Ser Leu Asp Leu Ala Leu Ser Lys Tyr Leu Ser
        195                 200                 205

Asp Leu Leu Phe Val Phe Gly Pro Asn Leu Gln Asp Pro Val Ser Asn
    210                 215                 220

Ser Met Thr Ile Gln Ala Ile Ser Gln Ala Phe Gly Gly Asn Tyr Glu
225                 230                 235                 240

Thr Leu Leu Arg Thr Leu Gly Tyr Ala Thr Glu Asp Phe Asp Asp Leu
                245                 250                 255

Leu Glu Ser Asp Ser Ile Thr Gly Gln Ile Ile Tyr Val Asp Leu Ser
            260                 265                 270

Ser Tyr Tyr Ile Ile Val Arg Val Tyr Phe Pro Ile Leu Thr Glu Ile
        275                 280                 285

Gln Gln Ala Tyr Ile Gln Glu Leu Leu Pro Val Ser Phe Asn Asn Asp
    290                 295                 300

Asn Ser Glu Trp Ile Ser Ile Val Pro Asn Phe Ile Leu Val Arg Asn
305                 310                 315                 320

Thr Leu Ile Ser Asn Ile Glu Ile Gly Phe Cys Leu Ile Thr Lys Arg
                325                 330                 335

Ser Val Ile Cys Asn Gln Asp Tyr Ala Thr Pro Met Thr Asn Asn Met
            340                 345                 350

Arg Glu Cys Leu Thr Gly Ser Thr Glu Lys Cys Pro Arg Glu Leu Val
        355                 360                 365

Val Ser Ser His Val Pro Arg Phe Ala Leu Ser Asn Gly Val Leu Phe
    370                 375                 380

Ala Asn Cys Ile Ser Val Thr Cys Gln Cys Gln Thr Thr Gly Arg Ala
```

-continued

```
385                 390                 395                 400

Ile Ser Gln Ser Gly Glu Gln Thr Leu Leu Met Ile Asp Asn Thr Thr
                405                 410                 415

Cys Pro Thr Ala Val Leu Gly Asn Val Ile Ile Ser Leu Gly Lys Tyr
            420                 425                 430

Leu Gly Ser Val Asn Tyr Asn Ser Glu Gly Ile Ala Ile Gly Pro Pro
        435                 440                 445

Val Phe Thr Asp Lys Val Asp Ile Ser Ser Gln Ile Ser Ser Met Asn
    450                 455                 460

Gln Ser Leu Gln Gln Ser Lys Asp Tyr Ile Lys Glu Ala Gln Arg Leu
465                 470                 475                 480

Leu Asp Thr Val Asn Pro Ser Leu Ile Ser Met Leu Ser Met Ile Ile
                485                 490                 495

Leu Tyr Val Leu Ser Ile Ala Ser Leu Cys Ile Gly Leu Ile Thr Phe
            500                 505                 510

Ile Ser Phe Ile Ile Val Glu Lys Lys Arg Asn Thr Tyr Ser Arg Leu
        515                 520                 525

Glu Asp Arg Arg Val Arg Pro Thr Ser Ser Gly Asp Leu Tyr Tyr Ile
    530                 535                 540

Gly Thr
545


<210> SEQ ID NO 8
<211> LENGTH: 602
<212> TYPE: PRT
<213> ORGANISM: Nipah virus

<400> SEQUENCE: 8

Met Pro Ala Glu Asn Lys Lys Val Arg Phe Glu Asn Thr Thr Ser Asp
  1               5                  10                  15

Lys Gly Lys Ile Pro Ser Lys Val Ile Lys Ser Tyr Tyr Gly Thr Met
             20                  25                  30

Asp Ile Lys Lys Ile Asn Glu Gly Leu Leu Asp Ser Lys Ile Leu Ser
         35                  40                  45

Ala Phe Asn Thr Val Ile Ala Leu Leu Gly Ser Ile Val Ile Ile Val
     50                  55                  60

Met Asn Ile Met Ile Ile Gln Asn Tyr Thr Arg Ser Thr Asp Asn Gln
 65                  70                  75                  80

Ala Val Ile Lys Asp Ala Leu Gln Gly Ile Gln Gln Gln Ile Lys Gly
                 85                  90                  95

Leu Ala Asp Lys Ile Gly Thr Glu Ile Gly Pro Lys Val Ser Leu Ile
            100                 105                 110

Asp Thr Ser Ser Thr Ile Thr Ile Pro Ala Asn Ile Gly Leu Leu Gly
        115                 120                 125

Ser Lys Ile Ser Gln Ser Thr Ala Ser Ile Asn Glu Asn Val Asn Glu
    130                 135                 140

Lys Cys Lys Phe Thr Leu Pro Pro Leu Lys Ile His Glu Cys Asn Ile
145                 150                 155                 160

Ser Cys Pro Asn Pro Leu Pro Phe Arg Glu Tyr Arg Pro Gln Thr Glu
                165                 170                 175

Gly Val Ser Asn Leu Val Gly Leu Pro Asn Asn Ile Cys Leu Gln Lys
            180                 185                 190

Thr Ser Asn Gln Ile Leu Lys Pro Lys Leu Ile Ser Tyr Thr Leu Pro
        195                 200                 205
```

-continued

```
Val Val Gly Gln Ser Gly Thr Cys Ile Thr Asp Pro Leu Leu Ala Met
    210                 215                 220

Asp Glu Gly Tyr Phe Ala Tyr Ser His Leu Glu Arg Ile Gly Ser Cys
225                 230                 235                 240

Ser Arg Gly Val Ser Lys Gln Arg Ile Ile Gly Val Gly Glu Val Leu
                245                 250                 255

Asp Arg Gly Asp Glu Val Pro Ser Leu Phe Met Thr Asn Val Trp Thr
            260                 265                 270

Pro Pro Asn Pro Asn Thr Val Tyr His Cys Ser Ala Val Tyr Asn Asn
        275                 280                 285

Glu Phe Tyr Tyr Val Leu Cys Ala Val Ser Thr Val Gly Asp Pro Ile
    290                 295                 300

Leu Asn Ser Thr Tyr Trp Ser Gly Ser Leu Met Met Thr Arg Leu Ala
305                 310                 315                 320

Val Lys Pro Lys Ser Asn Gly Gly Gly Tyr Asn Gln His Gln Leu Ala
                325                 330                 335

Leu Arg Ser Ile Glu Lys Gly Arg Tyr Asp Lys Val Met Pro Tyr Gly
            340                 345                 350

Pro Ser Gly Ile Lys Gln Gly Asp Thr Leu Tyr Phe Pro Ala Val Gly
        355                 360                 365

Phe Leu Val Arg Thr Glu Phe Lys Tyr Asn Asp Ser Asn Cys Pro Ile
    370                 375                 380

Thr Lys Cys Gln Tyr Ser Lys Pro Glu Asn Cys Arg Leu Ser Met Gly
385                 390                 395                 400

Ile Arg Pro Asn Ser His Tyr Ile Leu Arg Ser Gly Leu Leu Lys Tyr
                405                 410                 415

Asn Leu Ser Asp Gly Glu Asn Pro Lys Val Val Phe Ile Glu Ile Ser
            420                 425                 430

Asp Gln Arg Leu Ser Ile Gly Ser Pro Ser Lys Ile Tyr Asp Ser Leu
        435                 440                 445

Gly Gln Pro Val Phe Tyr Gln Ala Ser Phe Ser Trp Asp Thr Met Ile
    450                 455                 460

Lys Phe Gly Asp Val Leu Thr Val Asn Pro Leu Val Val Asn Trp Arg
465                 470                 475                 480

Asn Asn Thr Val Ile Ser Arg Pro Gly Gln Ser Gln Cys Pro Arg Phe
                485                 490                 495

Asn Thr Cys Pro Glu Ile Cys Trp Glu Gly Val Tyr Asn Asp Ala Phe
            500                 505                 510

Leu Ile Asp Arg Ile Asn Trp Ile Ser Ala Gly Val Phe Leu Asp Ser
        515                 520                 525

Asn Gln Thr Ala Glu Asn Pro Val Phe Thr Val Phe Lys Asp Asn Glu
    530                 535                 540

Ile Leu Tyr Arg Ala Gln Leu Ala Ser Glu Asp Thr Asn Ala Gln Lys
545                 550                 555                 560

Thr Ile Thr Asn Cys Phe Leu Leu Lys Asn Lys Ile Trp Cys Ile Ser
                565                 570                 575

Leu Val Glu Ile Tyr Asp Thr Gly Asp Asn Val Ile Arg Pro Lys Leu
            580                 585                 590

Phe Ala Val Lys Ile Pro Glu Gln Cys Thr
        595                 600
```

<210> SEQ ID NO 9
<211> LENGTH: 2244
<212> TYPE: PRT

-continued

<213> ORGANISM: Nipah virus

<400> SEQUENCE: 9

```
Met Ala Asp Glu Leu Ser Ile Ser Asp Ile Ile Tyr Pro Glu Cys His
  1               5                  10                  15

Leu Asp Ser Pro Ile Val Ser Gly Lys Leu Ile Ser Ala Ile Glu Tyr
             20                  25                  30

Ala Gln Leu Arg His Asn Gln Pro Ser Asp Asp Lys Arg Leu Ser Glu
         35                  40                  45

Asn Ile Arg Leu Asn Leu His Gly Lys Arg Lys Ser Leu Tyr Ile Leu
     50                  55                  60

Arg Gln Ser Lys Gln Gly Asp Tyr Ile Arg Asn Asn Ile Lys Asn Leu
 65                  70                  75                  80

Lys Glu Phe Met His Ile Ala Tyr Pro Glu Cys Asn Asn Ile Leu Phe
                 85                  90                  95

Ser Ile Thr Ser Gln Gly Met Thr Ser Lys Leu Asp Asn Ile Met Lys
            100                 105                 110

Lys Ser Phe Lys Ala Tyr Asn Ile Ile Ser Lys Lys Val Ile Gly Met
        115                 120                 125

Leu Gln Asn Ile Thr Arg Asn Leu Ile Thr Gln Asp Arg Arg Asp Glu
    130                 135                 140

Ile Ile Asn Ile His Glu Cys Arg Arg Leu Gly Asp Leu Gly Lys Asn
145                 150                 155                 160

Met Ser Gln Ser Lys Trp Tyr Glu Cys Phe Leu Phe Trp Phe Thr Ile
                165                 170                 175

Lys Thr Glu Met Arg Ala Val Ile Lys Asn Ser Gln Lys Pro Lys Phe
            180                 185                 190

Arg Ser Asp Ser Cys Ile Ile His Met Arg Asp Lys Ser Thr Glu Ile
        195                 200                 205

Ile Leu Asn Pro Asn Leu Ile Cys Ile Phe Lys Ser Asp Lys Thr Gly
    210                 215                 220

Lys Lys Cys Tyr Tyr Leu Thr Pro Glu Met Val Leu Met Tyr Cys Asp
225                 230                 235                 240

Val Leu Glu Gly Arg Met Met Met Glu Thr Thr Val Lys Ser Asp Ile
                245                 250                 255

Lys Tyr Gln Pro Leu Ile Ser Arg Ser Asn Ala Leu Trp Gly Leu Ile
            260                 265                 270

Asp Pro Leu Phe Pro Val Met Gly Asn Arg Ile Tyr Asn Ile Val Ser
        275                 280                 285

Met Ile Glu Pro Leu Val Leu Ala Leu Leu Gln Leu Lys Asp Glu Ala
    290                 295                 300

Arg Ile Leu Arg Gly Ala Phe Leu His His Cys Ile Lys Glu Met His
305                 310                 315                 320

Gln Glu Leu Ser Glu Cys Gly Phe Thr Asp Gln Lys Ile Arg Ser Met
                325                 330                 335

Phe Ile Asp Asp Leu Leu Ser Ile Leu Asn Ile Asp Asn Ile His Leu
            340                 345                 350

Leu Ala Glu Phe Phe Ser Phe Phe Arg Thr Phe Gly His Pro Ile Leu
        355                 360                 365

Glu Ala Lys Val Ala Ala Glu Lys Val Arg Glu His Met Leu Ala Asp
    370                 375                 380

Lys Val Leu Glu Tyr Ala Pro Ile Met Lys Ala His Ala Ile Phe Cys
385                 390                 395                 400
```

-continued

```
Gly Thr Ile Ile Asn Gly Tyr Arg Asp Arg His Gly Gly Ala Trp Pro
                405                 410                 415

Pro Leu Tyr Leu Pro Ala His Ala Ser Lys His Ile Ile Arg Leu Lys
            420                 425                 430

Asn Ser Gly Glu Ser Leu Thr Ile Asp Asp Cys Val Lys Asn Trp Glu
        435                 440                 445

Ser Phe Cys Gly Ile Gln Phe Asp Cys Phe Met Glu Leu Lys Leu Asp
    450                 455                 460

Ser Asp Leu Ser Met Tyr Met Lys Asp Lys Ala Leu Ser Pro Ile Lys
465                 470                 475                 480

Asp Glu Trp Asp Ser Val Tyr Pro Arg Glu Val Leu Ser Tyr Thr Pro
                485                 490                 495

Pro Lys Ser Thr Glu Pro Arg Arg Leu Val Asp Val Phe Val Asn Asp
            500                 505                 510

Glu Asn Phe Asp Pro Tyr Asn Met Leu Glu Tyr Val Leu Ser Gly Ala
        515                 520                 525

Tyr Leu Glu Asp Glu Gln Phe Asn Val Ser Tyr Ser Leu Lys Glu Lys
    530                 535                 540

Glu Thr Lys Gln Ala Gly Arg Leu Phe Ala Lys Met Thr Tyr Lys Met
545                 550                 555                 560

Arg Ala Cys Gln Val Ile Ala Glu Ala Leu Ile Ala Ser Gly Val Gly
                565                 570                 575

Lys Tyr Phe Lys Glu Asn Gly Met Val Lys Asp Glu His Glu Leu Leu
            580                 585                 590

Lys Thr Leu Phe Gln Leu Ser Ile Ser Ser Val Pro Arg Gly Asn Ser
        595                 600                 605

Gln Gly Asn Asp Pro Gln Ser Ile Asn Asn Ile Glu Arg Asp Phe Gln
    610                 615                 620

Tyr Phe Lys Gly Val Thr Thr Asn Val Lys Asp Lys Lys Asn Asn Ser
625                 630                 635                 640

Phe Asn Lys Val Lys Ser Ala Leu Asn Asn Pro Cys Gln Ala Asp Gly
                645                 650                 655

Val His His Asn Met Ser Pro Asn Thr Arg Asn Arg Tyr Lys Cys Ser
            660                 665                 670

Asn Thr Ser Lys Ser Phe Leu Asp Tyr His Thr Glu Phe Asn Pro His
        675                 680                 685

Asn His Tyr Lys Ser Asp Asn Thr Glu Ala Ala Val Leu Ser Arg Tyr
    690                 695                 700

Glu Asp Asn Thr Gly Thr Lys Phe Asp Thr Val Ser Ala Phe Leu Thr
705                 710                 715                 720

Thr Asp Leu Lys Lys Phe Cys Leu Asn Trp Arg Tyr Glu Ser Met Ala
                725                 730                 735

Ile Phe Ala Glu Arg Leu Asp Glu Ile Tyr Gly Leu Pro Gly Phe Phe
            740                 745                 750

Asn Trp Met His Lys Arg Leu Glu Arg Ser Val Ile Tyr Val Ala Asp
        755                 760                 765

Pro Asn Cys Pro Pro Asn Ile Asp Lys His Met Glu Leu Glu Lys Thr
    770                 775                 780

Pro Glu Asp Asp Ile Phe Ile His Tyr Pro Lys Gly Gly Ile Glu Gly
785                 790                 795                 800

Tyr Ser Gln Lys Thr Trp Thr Ile Ala Thr Ile Pro Phe Leu Phe Leu
                805                 810                 815

Ser Ala Tyr Glu Thr Asn Thr Arg Ile Ala Ala Ile Val Gln Gly Asp
```

-continued

```
            820                 825                 830

Asn Glu Ser Ile Ala Ile Thr Gln Lys Val His Pro Asn Leu Pro Tyr
        835                 840                 845

Lys Val Lys Lys Glu Ile Cys Ala Lys Gln Ala Gln Leu Tyr Phe Glu
    850                 855                 860

Arg Leu Arg Met Asn Leu Arg Ala Leu Gly His Asn Leu Lys Ala Thr
865                 870                 875                 880

Glu Thr Ile Ile Ser Thr His Leu Phe Ile Tyr Ser Lys Lys Ile His
                885                 890                 895

Tyr Asp Gly Ala Val Leu Ser Gln Ala Leu Lys Ser Met Ser Arg Cys
            900                 905                 910

Cys Phe Trp Ser Glu Thr Leu Val Asp Glu Thr Arg Ser Ala Cys Ser
        915                 920                 925

Asn Ile Ser Thr Thr Ile Ala Lys Ala Ile Glu Asn Gly Leu Ser Arg
    930                 935                 940

Asn Val Gly Tyr Cys Ile Asn Ile Leu Lys Val Ile Gln Gln Leu Leu
945                 950                 955                 960

Ile Ser Thr Glu Phe Ser Ile Asn Glu Thr Leu Thr Leu Asp Val Thr
                965                 970                 975

Ser Pro Ile Ser Asn Asn Leu Asp Trp Leu Ile Thr Ala Ala Leu Ile
            980                 985                 990

Pro Ala Pro Ile Gly Gly Phe Asn Tyr Leu Asn Leu Ser Arg Ile Phe
        995                1000                1005

Val Arg Asn Ile Gly Asp Pro Val Thr Ala Ser Leu Ala Asp Leu Lys
   1010                1015                1020

Arg Met Ile Asp His Ser Ile Met Thr Glu Ser Val Leu Gln Lys Val
1025                1030                1035                1040

Met Asn Gln Glu Pro Gly Asp Ala Ser Phe Leu Asp Trp Ala Ser Asp
               1045                1050                1055

Pro Tyr Ser Gly Asn Leu Pro Asp Ser Gln Ser Ile Thr Lys Thr Ile
           1060                1065                1070

Lys Asn Ile Thr Ala Arg Thr Ile Leu Arg Asn Ser Pro Asn Pro Met
       1075                1080                1085

Leu Lys Gly Leu Phe His Asp Lys Ser Phe Asp Glu Asp Leu Glu Leu
   1090                1095                1100

Ala Ser Phe Leu Met Asp Arg Arg Val Ile Leu Pro Arg Ala Ala His
1105                1110                1115                1120

Glu Ile Leu Asp Asn Ser Leu Thr Gly Ala Arg Glu Glu Ile Ala Gly
               1125                1130                1135

Leu Leu Asp Thr Thr Lys Gly Leu Ile Arg Ser Gly Leu Arg Lys Ser
           1140                1145                1150

Gly Leu Gln Pro Lys Leu Val Ser Arg Leu Ser His His Asp Tyr Asn
       1155                1160                1165

Gln Phe Leu Ile Leu Asn Lys Leu Leu Ser Asn Arg Arg Gln Asn Asp
   1170                1175                1180

Leu Ile Ser Ser Asn Thr Cys Ser Val Asp Leu Ala Arg Ala Leu Arg
1185                1190                1195                1200

Ser His Met Trp Arg Glu Leu Ala Leu Gly Arg Val Ile Tyr Gly Leu
               1205                1210                1215

Glu Val Pro Asp Ala Leu Glu Ala Met Val Gly Arg Tyr Ile Thr Gly
           1220                1225                1230

Ser Leu Glu Cys Gln Ile Cys Glu Gln Gly Asn Thr Met Tyr Gly Trp
       1235                1240                1245
```

-continued

```
Phe Phe Val Pro Arg Asp Ser Gln Leu Asp Gln Val Asp Arg Glu His
    1250                1255                1260

Ser Ser Ile Arg Val Pro Tyr Val Gly Ser Ser Thr Asp Glu Arg Ser
1265                1270                1275                1280

Asp Ile Lys Leu Gly Asn Val Lys Arg Pro Thr Lys Ala Leu Arg Ser
                1285                1290                1295

Ala Ile Arg Ile Ala Thr Val Tyr Thr Trp Ala Tyr Gly Asp Asn Glu
            1300                1305                1310

Glu Cys Trp Tyr Glu Ala Trp Tyr Leu Ala Ser Gln Arg Val Asn Ile
        1315                1320                1325

Asp Leu Asp Val Leu Lys Ala Ile Thr Pro Val Ser Thr Ser Asn Asn
    1330                1335                1340

Leu Ser His Arg Leu Arg Asp Lys Ser Thr Gln Phe Lys Phe Ala Gly
1345                1350                1355                1360

Ser Val Leu Asn Arg Val Ser Arg Tyr Val Asn Ile Ser Asn Asp Asn
                1365                1370                1375

Leu Asp Phe Arg Ile Glu Gly Glu Lys Val Asp Thr Asn Leu Ile Tyr
            1380                1385                1390

Gln Gln Ala Met Leu Leu Gly Leu Ser Val Leu Glu Gly Lys Phe Arg
        1395                1400                1405

Leu Arg Leu Glu Thr Asp Asp Tyr Asn Gly Ile Tyr His Leu His Val
    1410                1415                1420

Lys Asp Asn Cys Cys Val Lys Glu Val Ala Asp Val Gly Gln Val Asp
1425                1430                1435                1440

Ala Glu Leu Pro Ile Pro Glu Tyr Thr Glu Val Asp Asn Asn His Leu
                1445                1450                1455

Ile Tyr Asp Pro Asp Pro Val Ser Glu Ile Asp Cys Ser Arg Leu Ser
            1460                1465                1470

Asn Gln Glu Ser Lys Ser Arg Glu Leu Asp Phe Pro Leu Trp Ser Thr
        1475                1480                1485

Glu Glu Leu His Asp Val Leu Ala Lys Thr Val Ala Gln Thr Val Leu
    1490                1495                1500

Glu Ile Ile Thr Lys Ala Asp Lys Asp Val Leu Lys Gln His Leu Ala
1505                1510                1515                1520

Ile Asp Ser Asp Asp Asn Ile Asn Ser Leu Ile Thr Glu Phe Leu Ile
                1525                1530                1535

Val Asp Pro Glu Leu Phe Ala Leu Tyr Leu Gly Gln Ser Ile Ser Ile
            1540                1545                1550

Lys Trp Ala Phe Glu Ile His His Arg Arg Pro Arg Gly Arg His Thr
        1555                1560                1565

Met Val Asp Leu Leu Ser Asp Leu Val Ser Asn Thr Ser Lys His Thr
    1570                1575                1580

Tyr Lys Val Leu Ser Asn Ala Leu Ser His Pro Arg Val Phe Lys Arg
1585                1590                1595                1600

Phe Val Asn Cys Gly Leu Leu Leu Pro Thr Gln Gly Pro Tyr Leu His
                1605                1610                1615

Gln Gln Asp Phe Glu Lys Leu Ser Gln Asn Leu Leu Val Thr Ser Tyr
            1620                1625                1630

Met Ile Tyr Leu Met Asn Trp Cys Asp Phe Lys Lys Ser Pro Phe Leu
        1635                1640                1645

Ile Ala Glu Gln Asp Glu Thr Val Ile Ser Leu Arg Glu Asp Ile Ile
    1650                1655                1660
```

-continued

```
Thr Ser Lys His Leu Cys Val Ile Ile Asp Leu Tyr Ala Asn His His
1665                1670                1675                1680

Lys Pro Pro Trp Ile Ile Asp Leu Asn Pro Gln Glu Lys Ile Cys Val
                1685                1690                1695

Leu Arg Asp Phe Ile Ser Lys Ser Arg His Val Asp Thr Ser Ser Arg
            1700                1705                1710

Ser Trp Asn Thr Ser Asp Leu Asp Phe Val Ile Phe Tyr Ala Ser Leu
        1715                1720                1725

Thr Tyr Leu Arg Arg Gly Ile Ile Lys Gln Leu Arg Ile Arg Gln Val
    1730                1735                1740

Thr Glu Val Ile Asp Thr Thr Thr Met Leu Arg Asp Asn Ile Ile Val
1745                1750                1755                1760

Glu Asn Pro Pro Ile Lys Thr Gly Val Leu Asp Ile Arg Gly Cys Ile
                1765                1770                1775

Ile Tyr Asn Leu Glu Glu Ile Leu Ser Met Asn Thr Lys Ser Ala Ser
            1780                1785                1790

Lys Lys Ile Phe Asn Leu Asn Ser Arg Pro Ser Val Glu Asn His Lys
        1795                1800                1805

Tyr Arg Arg Ile Gly Leu Asn Ser Ser Ser Cys Tyr Lys Ala Leu Asn
    1810                1815                1820

Leu Ser Pro Leu Ile Gln Arg Tyr Leu Pro Ser Gly Ala Gln Arg Leu
1825                1830                1835                1840

Phe Ile Gly Glu Gly Ser Gly Ser Met Met Leu Leu Tyr Gln Ser Thr
                1845                1850                1855

Leu Gly Gln Ser Ile Ser Phe Tyr Asn Ser Gly Ile Asp Gly Asp Tyr
            1860                1865                1870

Ile Pro Gly Gln Arg Glu Leu Lys Leu Phe Pro Ser Glu Tyr Ser Ile
        1875                1880                1885

Ala Glu Glu Asp Pro Ser Leu Thr Gly Lys Leu Lys Gly Leu Val Val
    1890                1895                1900

Pro Leu Phe Asn Gly Arg Pro Glu Thr Thr Trp Ile Gly Asn Leu Asp
1905                1910                1915                1920

Ser Tyr Glu Tyr Ile Ile Asn Arg Thr Ala Gly Arg Ser Ile Gly Leu
                1925                1930                1935

Val His Ser Asp Met Glu Ser Gly Ile Asp Lys Asn Val Glu Glu Ile
            1940                1945                1950

Leu Val Glu His Ser His Leu Ile Ser Ile Ala Ile Asn Val Met Met
        1955                1960                1965

Glu Asp Gly Leu Leu Val Ser Lys Ile Ala Tyr Thr Pro Gly Phe Pro
    1970                1975                1980

Ile Ser Arg Leu Phe Asn Met Tyr Arg Ser Tyr Phe Gly Leu Val Leu
1985                1990                1995                2000

Val Cys Phe Pro Val Tyr Ser Asn Pro Asp Ser Thr Glu Val Tyr Leu
                2005                2010                2015

Leu Cys Leu Gln Lys Thr Val Lys Thr Ile Val Pro Pro Gln Lys Val
            2020                2025                2030

Leu Glu His Ser Asn Leu His Asp Glu Val Asn Asp Gln Gly Ile Thr
        2035                2040                2045

Ser Val Ile Phe Lys Ile Lys Asn Ser Gln Ser Lys Gln Phe His Asp
    2050                2055                2060

Asp Leu Lys Lys Tyr Tyr Gln Ile Asp Gln Pro Phe Phe Val Pro Thr
2065                2070                2075                2080

Lys Ile Thr Ser Asp Glu Gln Val Leu Leu Gln Ala Gly Leu Lys Leu
```

-continued

```
            2085                2090                2095

Asn Gly Pro Glu Ile Leu Lys Ser Glu Ile Ser Tyr Asp Ile Gly Ser
        2100                2105                2110

Asp Ile Asn Thr Leu Arg Asp Thr Ile Ile Ile Met Leu Asn Glu Ala
    2115                2120                2125

Met Asn Tyr Phe Asp Asp Asn Arg Ser Pro Ser His His Leu Glu Pro
    2130                2135                2140

Tyr Pro Val Leu Glu Arg Thr Arg Ile Lys Thr Ile Met Asn Cys Val
2145                2150                2155                2160

Thr Lys Lys Val Ile Val Tyr Ser Leu Ile Lys Phe Lys Asp Thr Lys
            2165                2170                2175

Ser Ser Glu Leu Tyr His Ile Lys Asn Asn Ile Arg Arg Lys Val Leu
        2180                2185                2190

Ile Leu Asp Phe Arg Ser Lys Leu Met Thr Lys Thr Leu Pro Lys Gly
    2195                2200                2205

Met Gln Glu Arg Arg Glu Lys Asn Gly Phe Lys Glu Val Trp Ile Val
    2210                2215                2220

Asp Leu Ser Asn Arg Glu Val Lys Ile Trp Trp Lys Ile Ile Gly Tyr
2225                2230                2235                2240

Ile Ser Ile Ile


<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Pro Ala Glu Asn Lys Lys Val Val Lys Ile Pro Glu Gln Cys Thr
  1               5                  10                  15


<210> SEQ ID NO 11
<211> LENGTH: 88
<212> TYPE: DNA
<213> ORGANISM: Artificial Sequence
<220> FEATURE:
<221> NAME/KEY: CDS
<222> LOCATION: (30)..(77)
<220> FEATURE:
<223> OTHER INFORMATION: Description of Artificial Sequence: Synthetic
      oligonucleotide

<400> SEQUENCE: 11

atcgcgatat ccgttaagtt tgtatcgta atg ccg gca gaa aac aag aaa gtt       53
                                Met Pro Ala Glu Asn Lys Lys Val
                                  1               5

gtt aag ata cca gag caa tgt aca taactcgagc g                          88
Val Lys Ile Pro Glu Gln Cys Thr
     10                  15


<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

ggcagtgtcg ggagctgtaa                                                 20
```

-continued

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 13
cgctcgagtt atgtacattg ctctggtatc ttaac 35

<210> SEQ ID NO 14
<211> LENGTH: 602
<212> TYPE: PRT
<213> ORGANISM: Artificial Sequence
<220> FEATURE:
<223> OTHER INFORMATION: Description of Artificial Sequence: Synthetic
plasmid pSL-6802-1-4

<400> SEQUENCE: 14

```
Met Pro Ala Glu Asn Lys Lys Val Arg Phe Glu Asn Thr Thr Ser Asp
  1               5                  10                  15

Lys Gly Lys Ile Pro Ser Lys Val Ile Lys Ser Tyr Tyr Gly Thr Met
             20                  25                  30

Asp Ile Lys Lys Ile Asn Glu Gly Leu Leu Asp Ser Lys Ile Leu Ser
         35                  40                  45

Ala Phe Asn Thr Val Ile Ala Leu Leu Gly Ser Ile Val Ile Ile Val
     50                  55                  60

Met Asn Ile Met Ile Ile Gln Asn Tyr Thr Arg Ser Thr Asp Asn Gln
 65                  70                  75                  80

Ala Val Ile Lys Asp Ala Leu Gln Gly Ile Gln Gln Gln Ile Lys Gly
                 85                  90                  95

Leu Ala Asp Lys Ile Gly Thr Glu Ile Gly Pro Lys Val Ser Leu Ile
            100                 105                 110

Asp Thr Ser Ser Thr Ile Thr Ile Pro Ala Asn Ile Gly Leu Leu Gly
        115                 120                 125

Ser Lys Ile Ser Gln Ser Thr Ala Ser Ile Asn Glu Asn Val Asn Glu
    130                 135                 140

Lys Cys Lys Phe Thr Leu Pro Pro Leu Lys Ile His Glu Cys Asn Ile
145                 150                 155                 160

Ser Cys Pro Asn Pro Leu Pro Phe Arg Glu Tyr Arg Pro Gln Thr Glu
                165                 170                 175

Gly Val Ser Asn Leu Val Gly Leu Pro Asn Asn Ile Cys Leu Gln Lys
            180                 185                 190

Thr Ser Asn Gln Ile Leu Lys Pro Lys Leu Ile Ser Tyr Thr Leu Pro
        195                 200                 205

Val Val Gly Gln Ser Gly Thr Cys Ile Thr Asp Pro Leu Leu Ala Met
    210                 215                 220

Asp Glu Gly Tyr Phe Ala Tyr Ser His Leu Glu Arg Ile Gly Ser Cys
225                 230                 235                 240

Ser Arg Gly Val Ser Lys Gln Arg Ile Ile Gly Val Gly Glu Val Leu
                245                 250                 255

Asp Arg Gly Asp Glu Val Pro Ser Leu Phe Met Thr Asn Val Trp Thr
            260                 265                 270

Pro Pro Asn Pro Asn Thr Val Tyr His Cys Ser Ala Val Tyr Asn Asn
        275                 280                 285
```

-continued

```
Glu Phe Tyr Tyr Val Leu Cys Ala Val Ser Thr Val Gly Asp Pro Ile
    290                 295                 300

Leu Asn Ser Thr Tyr Trp Ser Gly Ser Leu Met Met Thr Arg Leu Ala
305                 310                 315                 320

Val Lys Pro Lys Ser Asn Gly Gly Gly Tyr Asn Gln His Gln Leu Ala
                325                 330                 335

Leu Arg Ser Ile Glu Lys Gly Arg Tyr Asp Lys Val Met Pro Tyr Gly
            340                 345                 350

Pro Ser Gly Ile Lys Gln Gly Asp Thr Leu Tyr Phe Pro Ala Val Gly
        355                 360                 365

Phe Leu Val Arg Thr Glu Phe Lys Tyr Asn Asp Ser Asn Cys Pro Ile
    370                 375                 380

Thr Lys Cys Gln Tyr Ser Lys Pro Glu Asn Cys Arg Leu Ser Met Gly
385                 390                 395                 400

Ile Arg Pro Asn Ser His Tyr Ile Leu Arg Ser Gly Leu Leu Lys Tyr
                405                 410                 415

Asn Leu Ser Asp Gly Glu Asn Pro Lys Val Val Phe Ile Glu Ile Ser
            420                 425                 430

Asp Gln Arg Leu Ser Ile Gly Ser Pro Ser Lys Ile Tyr Asp Ser Leu
        435                 440                 445

Gly Gln Pro Val Phe Tyr Gln Ala Ser Phe Ser Trp Asp Thr Met Ile
    450                 455                 460

Lys Phe Gly Asp Val Leu Thr Val Asn Pro Leu Val Val Asn Trp Arg
465                 470                 475                 480

Asn Asn Thr Val Ile Ser Arg Pro Gly Gln Ser Gln Cys Pro Arg Phe
                485                 490                 495

Asn Thr Cys Pro Glu Ile Cys Trp Glu Gly Val Tyr Asn Asp Ala Phe
            500                 505                 510

Leu Ile Asp Arg Ile Asn Trp Ile Ser Ala Gly Val Phe Leu Asp Ser
        515                 520                 525

Asn Gln Thr Ala Glu Asn Pro Val Phe Thr Val Phe Lys Asp Asn Glu
    530                 535                 540

Ile Leu Tyr Arg Ala Gln Leu Ala Ser Glu Asp Thr Asn Ala Gln Lys
545                 550                 555                 560

Thr Ile Thr Asn Cys Phe Leu Leu Lys Asn Lys Ile Trp Cys Ile Ser
                565                 570                 575

Leu Val Glu Ile Tyr Asp Thr Gly Asp Asn Val Ile Arg Pro Lys Leu
            580                 585                 590

Phe Ala Val Lys Ile Pro Glu Gln Cys Thr
        595                 600
```

<210> SEQ ID NO 15
<211> LENGTH: 4067
<212> TYPE: DNA
<213> ORGANISM: Artificial Sequence
<220> FEATURE:
<221> NAME/KEY: CDS
<222> LOCATION: (1770)..(3575)
<220> FEATURE:
<223> OTHER INFORMATION: Description of Artificial Sequence: Synthetic
      plasmid pSL-6802-1-4

<400> SEQUENCE: 15

```
gcggccgcat tctgaatgtt aaatgttata ctttggatga agctataaat atgcattgga      60

aaaataatcc atttaaagaa aggattcaaa tactacaaaa cctaagcgat aatatgttaa     120

ctaagcttat tcttaacgac gctttaaata tacacaaata aacataattt ttgtataacc     180
```

-continued

```
taacaaataa ctaaaacata aaaataataa aaggaaatgt aatatcgtaa ttattttact    240

caggaatggg gttaaatatt tatatcacgt gtatatctat actgttatcg tatactcttt    300

acaattacta ttacgaatat gcaagagata ataagattac gtatttaaga gaatcttgtc    360

atgataattg ggtacgacat agtgataaat gctatttcgc atcgttacat aaagtcagtt    420

ggaaagatgg atttgacaga tgtaacttaa taggtgcaaa aatgttaaat aacagcattc    480

tatcggaaga taggatacca gttatattat acaaaaatca ctggttggat aaaacagatt    540

ctgcaatatt cgtaaaagat gaagattact gcgaatttgt aaactatgac aataaaaagc    600

catttatctc aacgacatcg tgtaattctt ccatgtttta tgtatgtgtt tcagatatta    660

tgagattact ataaactttt tgtatactta tattccgtaa actatattaa tcatgaagaa    720

aatgaaaaag tatagaagct gttcacgagc ggttgttgaa aacaacaaaa ttatacattc    780

aagatggctt acatatacgt ctgtgaggct atcatggata atgacaatgc atctctaaat    840

aggtttttgg acaatggatt cgaccctaac acggaatatg gtactctaca atctcctctt    900

gaaatggctg taatgttcaa gaataccgag gctataaaaa tcttgatgag gtatggagct    960

aaacctgtag ttactgaatg cacaacttct tgtctgcatg atgcggtgtt gagagacgac   1020

tacaaaatag tgaaagatct gttgaagaat aactatgtaa acaatgttct ttacagcgga   1080

ggctttactc ctttgtgttt ggcagcttac cttaacaaag ttaatttggt taaacttcta   1140

ttggctcatt cggcggatgt agatatttca aacacggatc ggttaactcc tctacatata   1200

gccgtatcaa ataaaaattt aacaatggtt aaacttctat tgaacaaagg tgctgatact   1260

gacttgctgg ataacatggg acgtactcct ttaatgatcg ctgtacaatc tggaaatatt   1320

gaaatatgta gcacactact taaaaaaaat aaaatgtcca gaactgggaa aaattgatct   1380

tgccagctgt aattcatggt agaaaagaag tgctcaggct acttttcaac aaaggagcag   1440

atgtaaacta catctttgaa agaaatggaa aatcatatac tgttttggaa ttgattaaag   1500

aaagttactc tgagacacaa aagaggtagc tgaagtggta ctctcaaagg tacgtgacta   1560

attagctata aaaaggatcc gggttaatta attagtcatc aggcagggcg agaacgagac   1620

tatctgctcg ttaattaatt agagcttctt tattctatac ttaaaaagtg aaaataaata   1680

caaaggttct tgagggttgt gttaaattga aagcgagaaa taatcataaa ttatttcatt   1740

atcgcgatat ccgttaagtt tgtatcgta atg ccg gca gaa aac aag aaa gtt     1793
                                Met Pro Ala Glu Asn Lys Lys Val
                                 1               5

aga ttc gaa aat act act tca gac aaa ggg aaa att cct agt aaa gtt     1841
Arg Phe Glu Asn Thr Thr Ser Asp Lys Gly Lys Ile Pro Ser Lys Val
     10                  15                  20

att aag agc tac tac gga acc atg gac att aag aaa ata aat gaa gga     1889
Ile Lys Ser Tyr Tyr Gly Thr Met Asp Ile Lys Lys Ile Asn Glu Gly
 25                  30                  35                  40

tta ttg gac agc aaa ata tta agt gct ttc aac aca gta ata gca ttg     1937
Leu Leu Asp Ser Lys Ile Leu Ser Ala Phe Asn Thr Val Ile Ala Leu
                 45                  50                  55

ctt gga tct atc gtg atc ata gtg atg aat ata atg atc atc caa aat     1985
Leu Gly Ser Ile Val Ile Ile Val Met Asn Ile Met Ile Ile Gln Asn
             60                  65                  70

tac aca aga tca aca gac aat cag gcc gtg atc aaa gat gcg ttg cag     2033
Tyr Thr Arg Ser Thr Asp Asn Gln Ala Val Ile Lys Asp Ala Leu Gln
         75                  80                  85

ggt atc caa cag cag atc aaa ggg ctt gct gac aaa atc ggc aca gag     2081
Gly Ile Gln Gln Gln Ile Lys Gly Leu Ala Asp Lys Ile Gly Thr Glu
```

-continued

```
    90                  95                  100

ata ggg ccc aaa gta tca ctg att gac aca tcc agt acc att act atc      2129
Ile Gly Pro Lys Val Ser Leu Ile Asp Thr Ser Ser Thr Ile Thr Ile
105                 110                 115                 120

cca gct aac att ggg ctg tta ggt tca aag atc agc cag tcg act gca      2177
Pro Ala Asn Ile Gly Leu Leu Gly Ser Lys Ile Ser Gln Ser Thr Ala
                125                 130                 135

agt ata aat gag aat gtg aat gaa aaa tgc aaa ttc aca ctg cct ccc      2225
Ser Ile Asn Glu Asn Val Asn Glu Lys Cys Lys Phe Thr Leu Pro Pro
            140                 145                 150

ttg aaa atc cac gaa tgt aac att tct tgt cct aac cca ctc cct ttt      2273
Leu Lys Ile His Glu Cys Asn Ile Ser Cys Pro Asn Pro Leu Pro Phe
        155                 160                 165

aga gag tat agg cca cag aca gaa ggg gtg agc aat cta gta gga tta      2321
Arg Glu Tyr Arg Pro Gln Thr Glu Gly Val Ser Asn Leu Val Gly Leu
    170                 175                 180

cct aat aat att tgc ctg caa aag aca tct aat cag ata ttg aag cca      2369
Pro Asn Asn Ile Cys Leu Gln Lys Thr Ser Asn Gln Ile Leu Lys Pro
185                 190                 195                 200

aag ctg att tca tac act tta ccc gta gtc ggt caa agt ggt acc tgt      2417
Lys Leu Ile Ser Tyr Thr Leu Pro Val Val Gly Gln Ser Gly Thr Cys
                205                 210                 215

atc aca gac cca ttg ctg gct atg gac gag ggc tat ttt gca tat agc      2465
Ile Thr Asp Pro Leu Leu Ala Met Asp Glu Gly Tyr Phe Ala Tyr Ser
            220                 225                 230

cac ctg gaa aga atc gga tca tgt tca aga ggg gtc tcc aaa caa aga      2513
His Leu Glu Arg Ile Gly Ser Cys Ser Arg Gly Val Ser Lys Gln Arg
        235                 240                 245

ata ata gga gtt gga gag gta cta gac aga ggt gat gaa gtt cct tct      2561
Ile Ile Gly Val Gly Glu Val Leu Asp Arg Gly Asp Glu Val Pro Ser
    250                 255                 260

tta ttt atg acc aat gtc tgg acc cca cca aat cca aac acc gtt tac      2609
Leu Phe Met Thr Asn Val Trp Thr Pro Pro Asn Pro Asn Thr Val Tyr
265                 270                 275                 280

cac tgt agt gct gta tac aac aat gaa ttc tat tat gta ctt tgt gca      2657
His Cys Ser Ala Val Tyr Asn Asn Glu Phe Tyr Tyr Val Leu Cys Ala
                285                 290                 295

gtg tca act gtt gga gac cct att ctg aat agc acc tac tgg tcc gga      2705
Val Ser Thr Val Gly Asp Pro Ile Leu Asn Ser Thr Tyr Trp Ser Gly
            300                 305                 310

tct cta atg atg acc cgt cta gct gtg aaa ccc aag agt aat ggt ggg      2753
Ser Leu Met Met Thr Arg Leu Ala Val Lys Pro Lys Ser Asn Gly Gly
        315                 320                 325

ggt tac aat caa cat caa ctt gcc cta cga agt atc gag aaa ggg agg      2801
Gly Tyr Asn Gln His Gln Leu Ala Leu Arg Ser Ile Glu Lys Gly Arg
    330                 335                 340

tat gat aaa gtt atg ccg tat gga cct tca ggc atc aaa cag ggt gac      2849
Tyr Asp Lys Val Met Pro Tyr Gly Pro Ser Gly Ile Lys Gln Gly Asp
345                 350                 355                 360

acc ctg tat ttt cct gct gta gga ttt ttg gtc agg aca gag ttt aaa      2897
Thr Leu Tyr Phe Pro Ala Val Gly Phe Leu Val Arg Thr Glu Phe Lys
                365                 370                 375

tac aat gat tca aat tgt ccc atc acg aag tgt caa tac agt aaa cct      2945
Tyr Asn Asp Ser Asn Cys Pro Ile Thr Lys Cys Gln Tyr Ser Lys Pro
            380                 385                 390

gaa aat tgc agg cta tct atg ggg att aga cca aac agc cat tat atc      2993
Glu Asn Cys Arg Leu Ser Met Gly Ile Arg Pro Asn Ser His Tyr Ile
        395                 400                 405

ctt cga tct gga cta tta aaa tac aat cta tca gat ggg gag aac ccc      3041
```

-continued

```
Leu Arg Ser Gly Leu Leu Lys Tyr Asn Leu Ser Asp Gly Glu Asn Pro
    410                 415                 420

aaa gtt gta ttc att gaa ata tct gat caa aga tta tct att gga tct     3089
Lys Val Val Phe Ile Glu Ile Ser Asp Gln Arg Leu Ser Ile Gly Ser
425                 430                 435                 440

cct agc aaa atc tat gat tct ttg ggt caa cct gtt ttc tac caa gcg     3137
Pro Ser Lys Ile Tyr Asp Ser Leu Gly Gln Pro Val Phe Tyr Gln Ala
                445                 450                 455

tca ttt tca tgg gat act atg att aaa ttt gga gat gtt cta aca gtc     3185
Ser Phe Ser Trp Asp Thr Met Ile Lys Phe Gly Asp Val Leu Thr Val
            460                 465                 470

aac cct ctg gtt gtc aat tgg cgt aat aac acg gta ata tca aga ccc     3233
Asn Pro Leu Val Val Asn Trp Arg Asn Asn Thr Val Ile Ser Arg Pro
        475                 480                 485

ggg caa tca caa tgc cct aga ttc aat aca tgt cca gag atc tgc tgg     3281
Gly Gln Ser Gln Cys Pro Arg Phe Asn Thr Cys Pro Glu Ile Cys Trp
    490                 495                 500

gaa gga gtt tat aat gat gca ttc cta att gac aga atc aat tgg ata     3329
Glu Gly Val Tyr Asn Asp Ala Phe Leu Ile Asp Arg Ile Asn Trp Ile
505                 510                 515                 520

agc gcg ggt gta ttc ctt gac agc aat cag acc gca gaa aat cct gtt     3377
Ser Ala Gly Val Phe Leu Asp Ser Asn Gln Thr Ala Glu Asn Pro Val
                525                 530                 535

ttt act gta ttc aaa gat aat gaa ata ctt tat agg gca caa ctg gct     3425
Phe Thr Val Phe Lys Asp Asn Glu Ile Leu Tyr Arg Ala Gln Leu Ala
            540                 545                 550

tct gag gac acc aat gca caa aaa aca ata act aat tgt ttt ctc ttg     3473
Ser Glu Asp Thr Asn Ala Gln Lys Thr Ile Thr Asn Cys Phe Leu Leu
        555                 560                 565

aag aat aag att tgg tgc ata tca ttg gtt gag ata tat gac aca gga     3521
Lys Asn Lys Ile Trp Cys Ile Ser Leu Val Glu Ile Tyr Asp Thr Gly
    570                 575                 580

gac aat gtc ata aga ccc aaa cta ttc gcg gtt aag ata cca gag caa     3569
Asp Asn Val Ile Arg Pro Lys Leu Phe Ala Val Lys Ile Pro Glu Gln
585                 590                 595                 600

tgt aca taactcgagt ctagaatcga tcccgggttt ttatgactag ttaatcacgg      3625
Cys Thr

ccgcttataa agatctaaaa tgcataattt ctaaataatg aaaaaaagta catcatgagc   3685

aacgcgttag tatattttac aatggagatt aacgctctat accgttctat gtttattgat   3745

tcagatgatg ttttagaaaa gaaagttatt gaatatgaaa actttaatga agatgaagat   3805

gacgacgatg attattgttg taaatctgtt ttagatgaag aagatgacgc gctaaagtat   3865

actatggtta caaagtataa gtctatacta ctaatggcga cttgtgcaag aaggtatagt   3925

atagtgaaaa tgttgttaga ttatgattat gaaaaaccaa ataaatcaga tccatatcta   3985

aaggtatctc ctttgcacat aatttcatct attcctagtt tagaatacct gcagccaagc   4045

ttggcactgg ccgtcgtttt ac                                            4067


<210> SEQ ID NO 16
<211> LENGTH: 4067
<212> TYPE: DNA
<213> ORGANISM: Artificial Sequence
<220> FEATURE:
<223> OTHER INFORMATION: Description of Artificial Sequence: Synthetic
      plasmid pSL-6802-1-4

<400> SEQUENCE: 16

gtaaaacgac ggccagtgcc aagcttggct gcaggtattc taaactagga atagatgaaa     60
```

-continued

```
ttatgtgcaa aggagatacc tttagatatg gatctgattt atttggtttt tcataatcat    120
aatctaacaa cattttcact atactatacc ttcttgcaca agtcgccatt agtagtatag    180
acttatactt tgtaaccata gtatacttta gcgcgtcatc ttcttcatct aaaacagatt    240
tacaacaata atcatcgtcg tcatcttcat cttcattaaa gttttcatat tcaataactt    300
tcttttctaa aacatcatct gaatcaataa acatagaacg gtatagagcg ttaatctcca    360
ttgtaaaata tactaacgcg ttgctcatga tgtacttttt ttcattattt agaaattatg    420
cattttagat ctttataagc ggccgtgatt aactagtcat aaaaacccgg gatcgattct    480
agactcgagt tatgtacatt gctctggtat cttaaccgcg aatagtttgg gtcttatgac    540
attgtctcct gtgtcatata tctcaaccaa tgatatgcac caaatcttat tcttcaagag    600
aaaacaatta gttattgttt tttgtgcatt ggtgtcctca gaagccagtt gtgccctata    660
aagtatttca ttatctttga atacagtaaa aacaggattt tctgcggtct gattgctgtc    720
aaggaataca cccgcgctta tccaattgat tctgtcaatt aggaatgcat cattataaac    780
tccttcccag cagatctctg gacatgtatt gaatctaggg cattgtgatt gcccgggtct    840
tgatattacc gtgttattac gccaattgac aaccagaggg ttgactgtta gaacatctcc    900
aaatttaatc atagtatccc atgaaaatga cgcttggtag aaaacaggtt gacccaaaga    960
atcatagatt ttgctaggag atccaataga taatctttga tcagatattt caatgaatac   1020
aactttgggg ttctccccat ctgatagatt gtattttaat agtccagatc gaaggatata   1080
atggctgttt ggtctaatcc ccatagatag cctgcaattt tcaggtttac tgtattgaca   1140
cttcgtgatg ggacaatttg aatcattgta tttaaactct gtcctgacca aaaatcctac   1200
agcaggaaaa tacagggtgt caccctgttt gatgcctgaa ggtccatacg gcataacttt   1260
atcatacctc cctttctcga tacttcgtag ggcaagttga tgttgattgt aacccccacc   1320
attactcttg ggtttcacag ctagacgggt catcattaga gatccggacc agtaggtgct   1380
attcagaata gggtctccaa cagttgacac tgcacaaagt acataataga attcattgtt   1440
gtatacagca ctacagtggt aaacggtgtt tggatttggt ggggtccaga cattggtcat   1500
aaataaagaa ggaacttcat cacctctgtc tagtacctct ccaactccta ttattctttg   1560
tttggagacc cctcttgaac atgatccgat tctttccagg tggctatatg caaaatagcc   1620
ctcgtccata gccagcaatg ggtctgtgat acaggtacca ctttgaccga ctacgggtaa   1680
agtgtatgaa atcagctttg gcttcaatat ctgattagat gtcttttgca ggcaaatatt   1740
attaggtaat cctactagat tgctcacccc ttctgtctgt ggcctatact ctctaaaagg   1800
gagtgggtta ggacaagaaa tgttacattc gtggattttc aagggaggca gtgtgaattt   1860
gcatttttca ttcacattct catttatact tgcagtcgac tggctgatct ttgaacctaa   1920
cagcccaatg ttagctggga tagtaatggt actggatgtg tcaatcagtg atactttggg   1980
ccctatctct gtgccgattt tgtcagcaag ccctttgatc tgctgttgga taccctgcaa   2040
cgcatctttg atcacggcct gattgtctgt tgatcttgtg taattttgga tgatcattat   2100
attcatcact atgatcacga tagatccaag caatgctatt actgtgttga aagcacttaa   2160
tattttgctg tccaataatc cttcatttat tttcttaatg tccatggttc cgtagtagct   2220
cttaataact ttactaggaa ttttcccttt gtctgaagta gtattttcga atctaacttt   2280
cttgttttct gccggcatta cgatacaaac ttaacggata tcgcgataat gaaataattt   2340
atgattattt ctcgctttca atttaacaca accctcaaga acctttgtat ttattttcac   2400
tttttaagta tagaataaag aagctctaat taattaacga gcagatagtc tcgttctcgc   2460
```

-continued

```
cctgcctgat gactaattaa ttaacccgga tcctttttat agctaattag tcacgtacct   2520

ttgagagtac cacttcagct acctcttttg tgtctcagag taactttctt taatcaattc   2580

caaaacagta tatgattttc catttctttc aaagatgtag tttacatctg ctcctttgtt   2640

gaaaagtagc ctgagcactt cttttctacc atgaattaca gctggcaaga tcaatttttc   2700

ccagttctgg acattttatt ttttttaagt agtgtgctac atatttcaat atttccagat   2760

tgtacagcga tcattaaagg agtacgtccc atgttatcca gcaagtcagt atcagcacct   2820

ttgttcaata gaagtttaac cattgttaaa tttttatttg atacggctat atgtagagga   2880

gttaaccgat ccgtgtttga aatatctaca tccgccgaat gagccaatag aagtttaacc   2940

aaattaactt tgttaaggta agctgccaaa cacaaaggag taaagcctcc gctgtaaaga   3000

acattgttta catagttatt cttcaacaga tctttcacta ttttgtagtc gtctctcaac   3060

accgcatcat gcagacaaga agttgtgcat tcagtaacta caggtttagc tccatacctc   3120

atcaagattt ttatagcctc ggtattcttg aacattacag ccatttcaag aggagattgt   3180

agagtaccat attccgtgtt agggtcgaat ccattgtcca aaaacctatt tagagatgca   3240

ttgtcattat ccatgatagc ctcacagacg tatatgtaag ccatcttgaa tgtataattt   3300

tgttgttttc aacaaccgct cgtgaacagc ttctatactt tttcattttc ttcatgatta   3360

atatagttta cggaatataa gtatacaaaa agtttatagt aatctcataa tatctgaaac   3420

acatacataa aacatggaag aattacacga tgtcgttgag ataaatggct ttttattgtc   3480

atagtttaca aattcgcagt aatcttcatc ttttacgaat attgcagaat ctgttttatc   3540

caaccagtga tttttgtata atataactgg tatcctatct tccgatagaa tgctgttatt   3600

taacattttt gcacctatta agttacatct gtcaaatcca tctttccaac tgactttatg   3660

taacgatgcg aaatagcatt tatcactatg tcgtacccaa ttatcatgac aagattctct   3720

taaatacgta atcttattat ctcttgcata ttcgtaatag taattgtaaa gagtatacga   3780

taacagtata gatatacacg tgatataaat atttaacccc attcctgagt aaaataatta   3840

cgatattaca tttcctttta ttatttttat gttttagtta tttgttaggt tatacaaaaa   3900

ttatgtttat ttgtgtatat ttaaagcgtc gttaagaata agcttagtta acatattatc   3960

gcttaggttt tgtagtattt gaatcctttc tttaaatgga ttatttttcc aatgcatatt   4020

tatagcttca tccaaagtat aacatttaac attcagaatg cggccgc                 4067
```

<210> SEQ ID NO 17
<211> LENGTH: 602
<212> TYPE: PRT
<213> ORGANISM: Artificial Sequence
<220> FEATURE:
<223> OTHER INFORMATION: Description of Artificial Sequence: Synthetic
      plasmid pSL-6802-2-5

<400> SEQUENCE: 17

```
Met Pro Ala Glu Asn Lys Lys Val Arg Phe Glu Asn Thr Thr Ser Asp
  1               5                  10                  15

Lys Gly Lys Ile Pro Ser Lys Val Ile Lys Ser Tyr Tyr Gly Thr Met
             20                  25                  30

Asp Ile Lys Lys Ile Asn Glu Gly Leu Leu Asp Ser Lys Ile Leu Ser
         35                  40                  45

Ala Phe Asn Thr Val Ile Ala Leu Leu Gly Ser Ile Val Ile Ile Val
     50                  55                  60

Met Asn Ile Met Ile Ile Gln Asn Tyr Thr Arg Ser Thr Asp Asn Gln
```

-continued

```
 65                  70                  75                  80

Ala Val Ile Lys Asp Ala Leu Gln Gly Ile Gln Gln Gln Ile Lys Gly
                 85                  90                  95

Leu Ala Asp Lys Ile Gly Thr Glu Ile Gly Pro Lys Val Ser Leu Ile
            100                 105                 110

Asp Thr Ser Ser Thr Ile Thr Ile Pro Ala Asn Ile Gly Leu Leu Gly
        115                 120                 125

Ser Lys Ile Ser Gln Ser Thr Ala Ser Ile Asn Glu Asn Val Asn Glu
    130                 135                 140

Lys Cys Lys Phe Thr Leu Pro Pro Leu Lys Ile His Glu Cys Asn Ile
145                 150                 155                 160

Ser Cys Pro Asn Pro Leu Pro Phe Arg Glu Tyr Arg Pro Gln Thr Glu
                165                 170                 175

Gly Val Ser Asn Leu Val Gly Leu Pro Asn Asn Ile Cys Leu Gln Lys
            180                 185                 190

Thr Ser Asn Gln Ile Leu Lys Pro Lys Leu Ile Ser Tyr Thr Leu Pro
        195                 200                 205

Val Val Gly Gln Ser Gly Thr Cys Ile Thr Asp Pro Leu Leu Ala Met
    210                 215                 220

Asp Glu Gly Tyr Phe Ala Tyr Ser His Leu Glu Arg Ile Gly Ser Cys
225                 230                 235                 240

Ser Arg Gly Val Ser Lys Gln Arg Ile Ile Gly Val Gly Glu Val Leu
                245                 250                 255

Asp Arg Gly Asp Glu Val Pro Ser Leu Phe Met Thr Asn Val Trp Thr
            260                 265                 270

Pro Pro Asn Pro Asn Thr Val Tyr His Cys Ser Ala Val Tyr Asn Asn
        275                 280                 285

Glu Phe Tyr Tyr Val Leu Cys Ala Val Ser Thr Val Gly Asp Pro Ile
    290                 295                 300

Leu Asn Ser Thr Tyr Trp Ser Gly Ser Leu Met Met Thr Arg Leu Ala
305                 310                 315                 320

Val Lys Pro Lys Ser Asn Gly Gly Gly Tyr Asn Gln His Gln Leu Ala
                325                 330                 335

Leu Arg Ser Ile Glu Lys Gly Arg Tyr Asp Lys Val Met Pro Tyr Gly
            340                 345                 350

Pro Ser Gly Ile Lys Gln Gly Asp Thr Leu Tyr Phe Pro Ala Val Gly
        355                 360                 365

Phe Leu Val Arg Thr Glu Phe Lys Tyr Asn Asp Ser Asn Cys Pro Ile
    370                 375                 380

Thr Lys Cys Gln Tyr Ser Lys Pro Glu Asn Cys Arg Leu Ser Met Gly
385                 390                 395                 400

Ile Arg Pro Asn Ser His Tyr Ile Leu Arg Ser Gly Leu Leu Lys Tyr
                405                 410                 415

Asn Leu Ser Asp Gly Glu Asn Pro Lys Val Val Phe Ile Glu Ile Ser
            420                 425                 430

Asp Gln Arg Leu Ser Ile Gly Ser Pro Ser Lys Ile Tyr Asp Ser Leu
        435                 440                 445

Gly Gln Pro Val Phe Tyr Gln Ala Ser Phe Ser Trp Asp Thr Met Ile
    450                 455                 460

Lys Phe Gly Asp Val Leu Thr Val Asn Pro Leu Val Val Asn Trp Arg
465                 470                 475                 480

Asn Asn Thr Val Ile Ser Arg Pro Gly Gln Ser Gln Cys Pro Arg Phe
                485                 490                 495
```

```
Asn Thr Cys Pro Glu Ile Cys Trp Glu Gly Val Tyr Asn Asp Ala Phe
            500                 505                 510

Leu Ile Asp Arg Ile Asn Trp Ile Ser Ala Gly Val Phe Leu Asp Ser
        515                 520                 525

Asn Gln Thr Ala Glu Asn Pro Val Phe Thr Val Phe Lys Asp Asn Glu
    530                 535                 540

Ile Leu Tyr Arg Ala Gln Leu Ala Ser Glu Asp Thr Asn Ala Gln Lys
545                 550                 555                 560

Thr Ile Thr Asn Cys Phe Leu Leu Lys Asn Lys Ile Trp Cys Ile Ser
                565                 570                 575

Leu Val Glu Ile Tyr Asp Thr Gly Asp Asn Val Ile Arg Pro Lys Leu
            580                 585                 590

Phe Ala Val Lys Ile Pro Glu Gln Cys Thr
        595                 600


<210> SEQ ID NO 18
<211> LENGTH: 4998
<212> TYPE: DNA
<213> ORGANISM: Artificial Sequence
<220> FEATURE:
<221> NAME/KEY: CDS
<222> LOCATION: (1693)..(3498)
<220> FEATURE:
<223> OTHER INFORMATION: Description of Artificial Sequence: Synthetic
      plasmid pSL-6802-2-5

<400> SEQUENCE: 18

gtaaaacgac ggccagtgaa ttgtaatacg actcactata gggcgaattg ggtgaccctt     60

tacaagaata aaagaagaaa caactgtgaa atagtttata aatgtaattc gtatgcagaa    120

aacgataata tattttggta tgagaaatct aaaggagaca tagtttgtat agacatgcgc    180

tcttccgatg agatattcga tgcttttcta atgtatcata tagctacaag atatgcctat    240

catgatgatg atatatatct acaaatagtg ttatattatt ctaataatca aaatgttata    300

tcttatatta cgaaaaataa atacgttaag tatataagaa ataaaactag agacgatatt    360

cataaagtaa aaatattagc tctagaagac tttacaacgg aagaaatata ttgttggatt    420

agtaatatat aacagcgtag ctgcacggtt ttgatcattt tccaacaata taaaccaatg    480

aaggaggacg actcatcaaa cataaataac attcacggaa aatattcagt atcagattta    540

tcacaagatg attatgttat tgaatgtata gacggatctt ttgattcgat caagtataga    600

gatataaagg ttataataat gaagaataac ggttacgtta attgtagtaa attatgtaaa    660

atgcggaata aatacttttc tagatggttg cgtctttcta cttctaaagc attattagac    720

atttacaata ataagtcagt agataatgct attgttaaag tctatggtaa aggtaagaaa    780

cttattataa caggatttta tctcaaacaa aatatgatac gttatgttat tgagtggata    840

ggggatgatt ttacaaacga tatatacaaa atgattaatt tctataatgc gttattcggt    900

aacgatgaat taaaaatagt atcctgtgaa aacactctat gcccgtttat agaacttggt    960

agatgctatt atggtaaaaa atgtaagtat atacacggag atcaatgtga tatctgtggt   1020

ctatatatac tacaccctac cgatattaac caacgagttt ctcacaagaa aacttgttta   1080

gtagatagag attctttgat tgtgtttaaa agaagtacca gtaaaaagtg tggcatatgc   1140

atagaagaaa taaacaaaaa acatatttcc gaacagtatt ttggaattct cccaagttgt   1200

aaacatattt tttgcctatc atgtataaga cgttgggcag atactaccag aaatacagat   1260

actgaaaata cgtgtcctga atgtagaata gtttttcctt tcataatacc cagtaggtat   1320
```

-continued

```
tggatagata ataaatatga taaaaaaata ttatataata gatataagaa aatgatttt   1380

acaaaaatac ctataagaac aataaaaata taattacatt tacggaaaat agctggtttt   1440

agtttaccaa cttagagtaa ttatcatatt gaatctatat tgctaattag ctaataaaaa   1500

cccgggttaa ttaattagtc atcaggcagg gcgagaacga gactatctgc tcgttaatta   1560

attagagctt ctttattcta tacttaaaaa gtgaaaataa atacaaaggt tcttgagggt   1620

tgtgttaaat tgaaagcgag aaataatcat aaattatttc attatcgcga tatccgttaa   1680

gtttgtatcg ta atg ccg gca gaa aac aag aaa gtt aga ttc gaa aat act   1731
              Met Pro Ala Glu Asn Lys Lys Val Arg Phe Glu Asn Thr
              1               5                   10

act tca gac aaa ggg aaa att cct agt aaa gtt att aag agc tac tac     1779
Thr Ser Asp Lys Gly Lys Ile Pro Ser Lys Val Ile Lys Ser Tyr Tyr
    15                  20                  25

gga acc atg gac att aag aaa ata aat gaa gga tta ttg gac agc aaa     1827
Gly Thr Met Asp Ile Lys Lys Ile Asn Glu Gly Leu Leu Asp Ser Lys
30                  35                  40                  45

ata tta agt gct ttc aac aca gta ata gca ttg ctt gga tct atc gtg     1875
Ile Leu Ser Ala Phe Asn Thr Val Ile Ala Leu Leu Gly Ser Ile Val
                50                  55                  60

atc ata gtg atg aat ata atg atc atc caa aat tac aca aga tca aca     1923
Ile Ile Val Met Asn Ile Met Ile Ile Gln Asn Tyr Thr Arg Ser Thr
            65                  70                  75

gac aat cag gcc gtg atc aaa gat gcg ttg cag ggt atc caa cag cag     1971
Asp Asn Gln Ala Val Ile Lys Asp Ala Leu Gln Gly Ile Gln Gln Gln
        80                  85                  90

atc aaa ggg ctt gct gac aaa atc ggc aca gag ata ggg ccc aaa gta     2019
Ile Lys Gly Leu Ala Asp Lys Ile Gly Thr Glu Ile Gly Pro Lys Val
    95                  100                 105

tca ctg att gac aca tcc agt acc att act atc cca gct aac att ggg     2067
Ser Leu Ile Asp Thr Ser Ser Thr Ile Thr Ile Pro Ala Asn Ile Gly
110                 115                 120                 125

ctg tta ggt tca aag atc agc cag tcg act gca agt ata aat gag aat     2115
Leu Leu Gly Ser Lys Ile Ser Gln Ser Thr Ala Ser Ile Asn Glu Asn
                130                 135                 140

gtg aat gaa aaa tgc aaa ttc aca ctg cct ccc ttg aaa atc cac gaa     2163
Val Asn Glu Lys Cys Lys Phe Thr Leu Pro Pro Leu Lys Ile His Glu
            145                 150                 155

tgt aac att tct tgt cct aac cca ctc cct ttt aga gag tat agg cca     2211
Cys Asn Ile Ser Cys Pro Asn Pro Leu Pro Phe Arg Glu Tyr Arg Pro
        160                 165                 170

cag aca gaa ggg gtg agc aat cta gta gga tta cct aat aat att tgc     2259
Gln Thr Glu Gly Val Ser Asn Leu Val Gly Leu Pro Asn Asn Ile Cys
    175                 180                 185

ctg caa aag aca tct aat cag ata ttg aag cca aag ctg att tca tac     2307
Leu Gln Lys Thr Ser Asn Gln Ile Leu Lys Pro Lys Leu Ile Ser Tyr
190                 195                 200                 205

act tta ccc gta gtc ggt caa agt ggt acc tgt atc aca gac cca ttg     2355
Thr Leu Pro Val Val Gly Gln Ser Gly Thr Cys Ile Thr Asp Pro Leu
                210                 215                 220

ctg gct atg gac gag ggc tat ttt gca tat agc cac ctg gaa aga atc     2403
Leu Ala Met Asp Glu Gly Tyr Phe Ala Tyr Ser His Leu Glu Arg Ile
            225                 230                 235

gga tca tgt tca aga ggg gtc tcc aaa caa aga ata ata gga gtt gga     2451
Gly Ser Cys Ser Arg Gly Val Ser Lys Gln Arg Ile Ile Gly Val Gly
        240                 245                 250

gag gta cta gac aga ggt gat gaa gtt cct tct tta ttt atg acc aat     2499
Glu Val Leu Asp Arg Gly Asp Glu Val Pro Ser Leu Phe Met Thr Asn
```

-continued

```
    255                 260                 265

gtc tgg acc cca cca aat cca aac acc gtt tac cac tgt agt gct gta     2547
Val Trp Thr Pro Pro Asn Pro Asn Thr Val Tyr His Cys Ser Ala Val
270                 275                 280                 285

tac aac aat gaa ttc tat tat gta ctt tgt gca gtg tca act gtt gga     2595
Tyr Asn Asn Glu Phe Tyr Tyr Val Leu Cys Ala Val Ser Thr Val Gly
                290                 295                 300

gac cct att ctg aat agc acc tac tgg tcc gga tct cta atg atg acc     2643
Asp Pro Ile Leu Asn Ser Thr Tyr Trp Ser Gly Ser Leu Met Met Thr
            305                 310                 315

cgt cta gct gtg aaa ccc aag agt aat ggt ggg ggt tac aat caa cat     2691
Arg Leu Ala Val Lys Pro Lys Ser Asn Gly Gly Gly Tyr Asn Gln His
        320                 325                 330

caa ctt gcc cta cga agt atc gag aaa ggg agg tat gat aaa gtt atg     2739
Gln Leu Ala Leu Arg Ser Ile Glu Lys Gly Arg Tyr Asp Lys Val Met
    335                 340                 345

ccg tat gga cct tca ggc atc aaa cag ggt gac acc ctg tat ttt cct     2787
Pro Tyr Gly Pro Ser Gly Ile Lys Gln Gly Asp Thr Leu Tyr Phe Pro
350                 355                 360                 365

gct gta gga ttt ttg gtc agg aca gag ttt aaa tac aat gat tca aat     2835
Ala Val Gly Phe Leu Val Arg Thr Glu Phe Lys Tyr Asn Asp Ser Asn
                370                 375                 380

tgt ccc atc acg aag tgt caa tac agt aaa cct gaa aat tgc agg cta     2883
Cys Pro Ile Thr Lys Cys Gln Tyr Ser Lys Pro Glu Asn Cys Arg Leu
            385                 390                 395

tct atg ggg att aga cca aac agc cat tat atc ctt cga tct gga cta     2931
Ser Met Gly Ile Arg Pro Asn Ser His Tyr Ile Leu Arg Ser Gly Leu
        400                 405                 410

tta aaa tac aat cta tca gat ggg gag aac ccc aaa gtt gta ttc att     2979
Leu Lys Tyr Asn Leu Ser Asp Gly Glu Asn Pro Lys Val Val Phe Ile
    415                 420                 425

gaa ata tct gat caa aga tta tct att gga tct cct agc aaa atc tat     3027
Glu Ile Ser Asp Gln Arg Leu Ser Ile Gly Ser Pro Ser Lys Ile Tyr
430                 435                 440                 445

gat tct ttg ggt caa cct gtt ttc tac caa gcg tca ttt tca tgg gat     3075
Asp Ser Leu Gly Gln Pro Val Phe Tyr Gln Ala Ser Phe Ser Trp Asp
                450                 455                 460

act atg att aaa ttt gga gat gtt cta aca gtc aac cct ctg gtt gtc     3123
Thr Met Ile Lys Phe Gly Asp Val Leu Thr Val Asn Pro Leu Val Val
            465                 470                 475

aat tgg cgt aat aac acg gta ata tca aga ccc ggg caa tca caa tgc     3171
Asn Trp Arg Asn Asn Thr Val Ile Ser Arg Pro Gly Gln Ser Gln Cys
        480                 485                 490

cct aga ttc aat aca tgt cca gag atc tgc tgg gaa gga gtt tat aat     3219
Pro Arg Phe Asn Thr Cys Pro Glu Ile Cys Trp Glu Gly Val Tyr Asn
    495                 500                 505

gat gca ttc cta att gac aga atc aat tgg ata agc gcg ggt gta ttc     3267
Asp Ala Phe Leu Ile Asp Arg Ile Asn Trp Ile Ser Ala Gly Val Phe
510                 515                 520                 525

ctt gac agc aat cag acc gca gaa aat cct gtt ttt act gta ttc aaa     3315
Leu Asp Ser Asn Gln Thr Ala Glu Asn Pro Val Phe Thr Val Phe Lys
                530                 535                 540

gat aat gaa ata ctt tat agg gca caa ctg gct tct gag gac acc aat     3363
Asp Asn Glu Ile Leu Tyr Arg Ala Gln Leu Ala Ser Glu Asp Thr Asn
            545                 550                 555

gca caa aaa aca ata act aat tgt ttt ctc ttg aag aat aag att tgg     3411
Ala Gln Lys Thr Ile Thr Asn Cys Phe Leu Leu Lys Asn Lys Ile Trp
        560                 565                 570

tgc ata tca ttg gtt gag ata tat gac aca gga gac aat gtc ata aga     3459
```

-continued

```
Cys Ile Ser Leu Val Glu Ile Tyr Asp Thr Gly Asp Asn Val Ile Arg
    575                 580                 585

ccc aaa cta ttc gcg gtt aag ata cca gag caa tgt aca taactcgagt      3508
Pro Lys Leu Phe Ala Val Lys Ile Pro Glu Gln Cys Thr
590                 595                 600

ttttattgac tagttaatca taagataaat aatatacagc attgtaacca tcgtcatccg   3568

ttatacgggg aataatatta ccatacagta ttattaaatt ttcttacgaa gaatatagat   3628

cggtatttat cgttagttta ttttacattt attaattaaa catgtctact attacctgtt   3688

atggaaatga caaatttagt tatataattt atgataaaat taagataata ataatgaaat   3748

caaataatta tgtaaatgct actagattat gtgaattacg aggaagaaag tttacgaact   3808

ggaaaaaatt aagtgaatct aaaatattag tcgataatgt aaaaaaaata aatgataaaa   3868

ctaaccagtt aaaaacggat atgattatat acgttaagga tattgatcat aaaggaagag   3928

atacttgcgg ttactatgta caccaagatc tggtatcttc tatatcaaat tggatatctc   3988

cgttattcgc cgttaaggta aataaaatta ttaactatta tatatgtaat gaatatgata   4048

tacgacttag cgaaatggaa tctgatatga cagaagtaat agatgtagtt gataaattag   4108

taggaggata caatgatgaa atagcagaaa taatatattt gtttaataaa tttatagaaa   4168

aatatattgc taacatatcg ttatcaactg aattatctag tatattaaat aattttataa   4228

attttaataa aaaatacaat aacgacataa aagatattaa atctttaatt cttgatctga   4288

aaaacacatc tataaaacta gataaaaagt tattcgataa agataataat gaatcgaacg   4348

atgaaaaatt ggaaacagaa gttgataagc taattttttt catctaaata gtattatttt   4408

attgaagtac gaagttttac gttagataaa taataaaggt cgatttttat tttgttaaat   4468

atcaaatatg tcattatctg ataaagatac aaaaacacac ggtgattatc aaccatctaa   4528

cgaacagata ttacaaaaaa tacgtcggac tatggaaaac gaagctgata gcctcaatag   4588

aagaagcatt aaagaaattg ttgtagatgt tatgaagaat tgggatcatc ctctcaacga   4648

agaaatagat aaagttctaa actggaaaaa tgatacatta aacgatttag atcatctaaa   4708

tacagatgat aatattaagg aaatcataca atgtctgatt agagaatttg cgtttaaaaa   4768

gatcaattct attatgtata gttatgctat ggtaaaactc aattcagata acgaaacatt   4828

gaaagataaa attaaggatt attttataga aactattctt aaagacaaac gtggttataa   4888

acaaaagcca ttaccctaga gcggccgcca ccgcggtgga gctccagctt ttgttccctt   4948

tagtgagggt taatttcgag cttggcgtaa tcatggtcat agctgtttcc              4998


<210> SEQ ID NO 19
<211> LENGTH: 4998
<212> TYPE: DNA
<213> ORGANISM: Artificial Sequence
<220> FEATURE:
<223> OTHER INFORMATION: Description of Artificial Sequence: Synthetic
      plasmid pSL-6802-2-5

<400> SEQUENCE: 19

ggaaacagct atgaccatga ttacgccaag ctcgaaatta accctcacta aagggaacaa     60

aagctggagc tccaccgcgg tggcggccgc tctagggtaa tggcttttgt ttataaccac    120

gtttgtcttt aagaatagtt tctataaaat aatccttaat tttatctttc aatgtttcgt    180

tatctgaatt gagttttacc atagcataac tatacataat agaattgatc tttttaaacg    240

caaattctct aatcagacat tgtatgattt ccttaatatt atcatctgta tttagatgat    300

ctaaatcgtt taatgtatca tttttccagt ttagaacttt atctatttct tcgttgagag    360
```

-continued

```
gatgatccca attcttcata acatctacaa caatttcttt aatgcttctt ctattgaggc    420
tatcagcttc gttttccata gtccgacgta ttttttgtaa tatctgttcg ttagatggtt    480
gataatcacc gtgtgttttt gtatctttat cagataatga catatttgat atttaacaaa    540
ataaaaatcg acctttatta tttatctaac gtaaaacttc gtacttcaat aaaataatac    600
tatttagatg aaaaaaatta gcttatcaac ttctgtttcc aatttttcat cgttcgattc    660
attattatct ttatcgaata actttttatc tagttttata gatgtgtttt tcagatcaag    720
aattaaagat ttaatatctt ttatgtcgtt attgtatttt ttattaaaat ttataaaatt    780
atttaatata ctagataatt cagttgataa cgatatgtta gcaatatatt tttctataaa    840
tttattaaac aaatatatta tttctgctat ttcatcattg tatcctccta ctaatttatc    900
aactacatct attacttctg tcatatcaga ttccatttcg ctaagtcgta tatcatattc    960
attacatata taatagttaa taattttatt taccttaacg gcgaataacg gagatatcca   1020
atttgatata gaagatacca gatcttggtg tacatagtaa ccgcaagtat ctcttccttt   1080
atgatcaata tccttaacgt atataatcat atccgttttt aactggttag ttttatcatt   1140
tattttttt acattatcga ctaatatttt agattcactt aatttttcc agttcgtaaa     1200
ctttcttcct cgtaattcac ataatctagt agcatttaca taattatttg atttcattat   1260
tattatctta attttatcat aaattatata actaaatttg tcatttccat aacaggtaat   1320
agtagacatg tttaattaat aaatgtaaaa taaactaacg ataaataccg atctatattc   1380
ttcgtaagaa aatttaataa tactgtatgg taatattatt ccccgtataa cggatgacga   1440
tggttacaat gctgtatatt atttatctta tgattaacta gtcaataaaa actcgagtta   1500
tgtacattgc tctggtatct taaccgcgaa tagtttgggt cttatgacat tgtctcctgt   1560
gtcatatatc tcaaccaatg atatgcacca aatcttattc ttcaagagaa aacaattagt   1620
tattgttttt tgtgcattgg tgtcctcaga agccagttgt gccctataaa gtatttcatt   1680
atctttgaat acagtaaaaa caggattttc tgcggtctga ttgctgtcaa ggaatacacc   1740
cgcgcttatc caattgattc tgtcaattag gaatgcatca ttataaactc cttcccagca   1800
gatctctgga catgtattga atctagggca ttgtgattgc ccgggtcttg atattaccgt   1860
gttattacgc caattgacaa ccagagggtt gactgttaga acatctccaa atttaatcat   1920
agtatcccat gaaaatgacg cttggtagaa aacaggttga cccaaagaat catagatttt   1980
gctaggagat ccaatagata atctttgatc agatatttca atgaatacaa ctttggggtt   2040
ctccccatct gatagattgt attttaatag tccagatcga aggatataat ggctgtttgg   2100
tctaatcccc atagatagcc tgcaattttc aggtttactg tattgacact tcgtgatggg   2160
acaatttgaa tcattgtatt taaactctgt cctgaccaaa aatcctacag caggaaaata   2220
cagggtgtca ccctgtttga tgcctgaagg tccatacggc ataactttat catacctccc   2280
tttctcgata cttcgtaggg caagttgatg ttgattgtaa cccccaccat tactcttggg   2340
tttcacagct agacgggtca tcattagaga tccggaccag taggtgctat tcagaatagg   2400
gtctccaaca gttgacactg cacaaagtac ataatagaat tcattgttgt atacagcact   2460
acagtggtaa acggtgtttg gatttggtgg ggtccagaca ttggtcataa ataaagaagg   2520
aacttcatca cctctgtcta gtacctctcc aactcctatt attctttgtt tggagacccc   2580
tcttgaacat gatccgattc tttccaggtg gctatatgca aaatagccct cgtccatagc   2640
cagcaatggg tctgtgatac aggtaccact ttgaccgact acgggtaaag tgtatgaaat   2700
```

-continued

```
cagctttggc ttcaatatct gattagatgt cttttgcagg caaatattat taggtaatcc   2760
tactagattg ctcacccctt ctgtctgtgg cctatactct ctaaaaggga gtgggttagg   2820
acaagaaatg ttacattcgt ggattttcaa gggaggcagt gtgaatttgc atttttcatt   2880
cacattctca tttatacttg cagtcgactg gctgatcttt gaacctaaca gcccaatgtt   2940
agctgggata gtaatggtac tggatgtgtc aatcagtgat actttgggcc ctatctctgt   3000
gccgattttg tcagcaagcc ctttgatctg ctgttggata ccctgcaacg catctttgat   3060
cacggcctga ttgtctgttg atcttgtgta attttggatg atcattatat tcatcactat   3120
gatcacgata gatccaagca atgctattac tgtgttgaaa gcacttaata ttttgctgtc   3180
caataatcct tcatttattt tcttaatgtc catggttccg tagtagctct taataacttt   3240
actaggaatt ttccctttgt ctgaagtagt attttcgaat ctaactttct tgttttctgc   3300
cggcattacg atacaaactt aacggatatc gcgataatga aataatttat gattatttct   3360
cgctttcaat ttaacacaac cctcaagaac ctttgtattt attttcactt tttaagtata   3420
gaataaagaa gctctaatta attaacgagc agatagtctc gttctcgccc tgcctgatga   3480
ctaattaatt aacccgggtt tttattagct aattagcaat atagattcaa tatgataatt   3540
actctaagtt ggtaaactaa aaccagctat tttccgtaaa tgtaattata tttttattgt   3600
tcttataggt atttttgtaa aaatcatttt cttatatcta ttatataata ttttttttatc   3660
atatttatta tctatccaat acctactggg tattatgaaa ggaaaaacta ttctacattc   3720
aggacacgta ttttcagtat ctgtatttct ggtagtatct gcccaacgtc ttatacatga   3780
taggcaaaaa atatgtttac aacttgggag aattccaaaa tactgttcgg aaatatgttt   3840
tttgtttatt tcttctatgc atatgccaca ctttttactg gtacttcttt taaacacaat   3900
caaagaatct ctatctacta aacaagtttt cttgtgagaa actcgttggt taatatcggt   3960
agggtgtagt atatatagac cacagatatc acattgatct ccgtgtatat acttacattt   4020
tttaccataa tagcatctac caagttctat aaacgggcat agagtgtttt cacaggatac   4080
tatttttaat tcatcgttac cgaataacgc attatagaaa ttaatcattt tgtatatatc   4140
gtttgtaaaa tcatccccta tccactcaat aacataacgt atcatatttt gtttgagata   4200
aaatcctgtt ataataagtt tcttaccttt accatagact ttaacaatag cattatctac   4260
tgacttatta ttgtaaatgt ctaataatgc tttagaagta gaaagacgca accatctaga   4320
aaagtattta ttccgcattt tacataattt actacaatta acgtaaccgt tattcttcat   4380
tattataacc tttatatctc tatacttgat cgaatcaaaa gatccgtcta tacattcaat   4440
aacataatca tcttgtgata aatctgatac tgaatatttt ccgtgaatgt tatttatgtt   4500
tgatgagtcg tcctccttca ttggtttata ttgttggaaa atgatcaaaa ccgtgcagct   4560
acgctgttat atattactaa tccaacaata tatttcttcc gttgtaaagt cttctagagc   4620
taatattttt actttatgaa tatcgtctct agttttattt cttatatact taacgtattt   4680
atttttcgta atataagata taacattttg attattagaa taatataaca ctatttgtag   4740
atatatatca tcatcatgat aggcatatct tgtagctata tgatacatta gaaaagcatc   4800
gaatatctca tcggaagagc gcatgtctat acaaactatg tctcctttag atttctcata   4860
ccaaaatata ttatcgtttt ctgcatacga attacattta taaactattt cacagttgtt   4920
tcttctttta ttcttgtaaa gggtcaccca attcgcccta tagtgagtcg tattacaatt   4980
cactggccgt cgttttac                                                 4998
```

-continued

<210> SEQ ID NO 20
<211> LENGTH: 26
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

```
Met Val Val Ile Leu Asp Lys Arg Asp Leu Leu Phe Val Phe Gly Pro
  1               5                  10                  15

Asn Leu Gly Asp Leu Tyr Tyr Ile Gly Thr
             20                  25
```

<210> SEQ ID NO 21
<211> LENGTH: 111
<212> TYPE: DNA
<213> ORGANISM: Artificial Sequence
<220> FEATURE:
<221> NAME/KEY: CDS
<222> LOCATION: (31)..(108)
<220> FEATURE:
<223> OTHER INFORMATION: Description of Artificial Sequence: Synthetic
oligonucleotide

<400> SEQUENCE: 21

```
tatcgcgata tccgttaagt ttgtatcgta atg gta gtt ata ctt gac aag aga      54
                                 Met Val Val Ile Leu Asp Lys Arg
                                   1               5

gat ttg ctt ttt gta ttt ggc ccc aac ctt ggg gat ctc tac tac att      102
Asp Leu Leu Phe Val Phe Gly Pro Asn Leu Gly Asp Leu Tyr Tyr Ile
     10                  15                  20

ggg aca tag                                                          111
Gly Thr
 25
```

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22

```
gcggatcccg ggctatgtcc caatgtagta gagatcccc                            39
```

<210> SEQ ID NO 23
<211> LENGTH: 546
<212> TYPE: PRT
<213> ORGANISM: Artificial Sequence
<220> FEATURE:
<223> OTHER INFORMATION: Description of Artificial Sequence: Synthetic
plasmid pSL-6839-1

<400> SEQUENCE: 23

```
Met Val Val Ile Leu Asp Lys Arg Cys Tyr Cys Asn Leu Leu Ile Leu
  1               5                  10                  15

Ile Leu Met Ile Ser Glu Cys Ser Val Gly Ile Leu His Tyr Glu Lys
             20                  25                  30

Leu Ser Lys Ile Gly Leu Val Lys Gly Val Thr Arg Lys Tyr Lys Ile
         35                  40                  45

Lys Ser Asn Pro Leu Thr Lys Asp Ile Val Ile Lys Met Ile Pro Asn
     50                  55                  60

Val Ser Asn Met Ser Gln Cys Thr Gly Ser Val Met Glu Asn Tyr Lys
```

-continued

```
65                  70                  75                  80

Thr Arg Leu Asn Gly Ile Leu Thr Pro Ile Lys Gly Ala Leu Glu Ile
                85                  90                  95

Tyr Lys Asn Asn Thr His Asp Leu Val Gly Asp Val Arg Leu Ala Gly
            100                 105                 110

Val Ile Met Ala Gly Val Ala Ile Gly Ile Ala Thr Ala Ala Gln Ile
        115                 120                 125

Thr Ala Gly Val Ala Leu Tyr Glu Ala Met Lys Asn Ala Asp Asn Ile
    130                 135                 140

Asn Lys Leu Lys Ser Ser Ile Glu Ser Thr Asn Glu Ala Val Val Lys
145                 150                 155                 160

Leu Gln Glu Thr Ala Glu Lys Thr Val Tyr Val Leu Thr Ala Leu Gln
                165                 170                 175

Asp Tyr Ile Asn Thr Asn Leu Val Pro Thr Ile Asp Lys Ile Ser Cys
            180                 185                 190

Lys Gln Thr Glu Leu Ser Leu Asp Leu Ala Leu Ser Lys Tyr Leu Ser
        195                 200                 205

Asp Leu Leu Phe Val Phe Gly Pro Asn Leu Gln Asp Pro Val Ser Asn
    210                 215                 220

Ser Met Thr Ile Gln Ala Ile Ser Gln Ala Phe Gly Gly Asn Tyr Glu
225                 230                 235                 240

Thr Leu Leu Arg Thr Leu Gly Tyr Ala Thr Glu Asp Phe Asp Asp Leu
                245                 250                 255

Leu Glu Ser Asp Ser Ile Thr Gly Gln Ile Ile Tyr Val Asp Leu Ser
            260                 265                 270

Ser Tyr Tyr Ile Ile Val Arg Val Tyr Phe Pro Ile Leu Thr Glu Ile
        275                 280                 285

Gln Gln Ala Tyr Ile Gln Glu Leu Leu Pro Val Ser Phe Asn Asn Asp
    290                 295                 300

Asn Ser Glu Trp Ile Ser Ile Val Pro Asn Phe Ile Leu Val Arg Asn
305                 310                 315                 320

Thr Leu Ile Ser Asn Ile Glu Ile Gly Phe Cys Leu Ile Thr Lys Arg
                325                 330                 335

Ser Val Ile Cys Asn Gln Asp Tyr Ala Thr Pro Met Thr Asn Asn Met
            340                 345                 350

Arg Glu Cys Leu Thr Gly Ser Thr Glu Lys Cys Pro Arg Glu Leu Val
        355                 360                 365

Val Ser Ser His Val Pro Arg Phe Ala Leu Ser Asn Gly Val Leu Phe
    370                 375                 380

Ala Asn Cys Ile Ser Val Thr Cys Gln Cys Gln Thr Thr Gly Arg Ala
385                 390                 395                 400

Ile Ser Gln Ser Gly Glu Gln Thr Leu Leu Met Ile Asp Asn Thr Thr
                405                 410                 415

Cys Pro Thr Ala Val Leu Gly Asn Val Ile Ile Ser Leu Gly Lys Tyr
            420                 425                 430

Leu Gly Ser Val Asn Tyr Asn Ser Glu Gly Ile Ala Ile Gly Pro Pro
        435                 440                 445

Val Phe Thr Asp Lys Val Asp Ile Ser Ser Gln Ile Ser Ser Met Asn
    450                 455                 460

Gln Ser Leu Gln Gln Ser Lys Asp Tyr Ile Lys Glu Ala Gln Arg Leu
465                 470                 475                 480

Leu Asp Thr Val Asn Pro Ser Leu Ile Ser Met Leu Ser Met Ile Ile
                485                 490                 495
```

-continued

Leu Tyr Val Leu Ser Ile Ala Ser Leu Cys Ile Gly Leu Ile Thr Phe
500 505 510

Ile Ser Phe Ile Ile Val Glu Lys Lys Arg Asn Thr Tyr Ser Arg Leu
515 520 525

Glu Asp Arg Arg Val Arg Pro Thr Ser Ser Gly Asp Leu Tyr Tyr Ile
530 535 540

Gly Thr
545

<210> SEQ ID NO 24
<211> LENGTH: 4840
<212> TYPE: DNA
<213> ORGANISM: Artificial Sequence
<220> FEATURE:
<221> NAME/KEY: CDS
<222> LOCATION: (1693)..(3330)
<220> FEATURE:
<223> OTHER INFORMATION: Description of Artificial Sequence: Synthetic plasmid pSL-6839-1

<400> SEQUENCE: 24
gtaaaacgac ggccagtgaa ttgtaatacg actcactata gggcgaattg ggtgaccctt 60
tacaagaata aaagaagaaa caactgtgaa atagtttata aatgtaattc gtatgcagaa 120
aacgataata tattttggta tgagaaatct aaaggagaca tagtttgtat agacatgcgc 180
tcttccgatg agatattcga tgcttttcta atgtatcata tagctacaag atatgcctat 240
catgatgatg atatatatct acaaatagtg ttatattatt ctaataatca aaatgttata 300
tcttatatta cgaaaaataa atacgttaag tatataagaa ataaaactag agacgatatt 360
cataaagtaa aaatattagc tctagaagac tttacaacgg aagaaatata ttgttggatt 420
agtaatatat aacagcgtag ctgcacggtt ttgatcattt tccaacaata taaaccaatg 480
aaggaggacg actcatcaaa cataaataac attcacggaa aatattcagt atcagattta 540
tcacaagatg attatgttat tgaatgtata gacggatctt ttgattcgat caagtataga 600
gatataaagg ttataataat gaagaataac ggttacgtta attgtagtaa attatgtaaa 660
atgcggaata aatacttttc tagatggttg cgtctttcta cttctaaagc attattagac 720
atttacaata ataagtcagt agataatgct attgttaaag tctatggtaa aggtaagaaa 780
cttattataa caggatttta tctcaaacaa aatatgatac gttatgttat tgagtggata 840
ggggatgatt ttacaaacga tatatacaaa atgattaatt tctataatgc gttattcggt 900
aacgatgaat taaaaatagt atcctgtgaa aacactctat gcccgtttat agaacttggt 960
agatgctatt atggtaaaaa atgtaagtat atacacggag atcaatgtga tatctgtggt 1020
ctatatatac tacaccctac cgatattaac caacgagttt ctcacaagaa aacttgttta 1080
gtagatagag attctttgat tgtgtttaaa agaagtacca gtaaaaagtg tggcatatgc 1140
atagaagaaa taaacaaaaa acatatttcc gaacagtatt ttggaattct cccaagttgt 1200
aaacatattt tttgcctatc atgtataaga cgttgggcag atactaccag aaatacagat 1260
actgaaaata cgtgtcctga atgtagaata gtttttcctt tcataatacc cagtaggtat 1320
tggatagata ataaatatga taaaaaaata ttatataata gatataagaa aatgattttt 1380
acaaaaatac ctataagaac aataaaaata taattacatt tacggaaaat agctggtttt 1440
agtttaccaa cttagagtaa ttatcatatt gaatctatat tgctaattag ctaataaaaa 1500
cccgggttaa ttaattagtc atcaggcagg gcgagaacga gactatctgc tcgttaatta 1560

-continued

```
attagagctt ctttattcta tacttaaaaa gtgaaaataa atacaaaggt tcttgagggt   1620

tgtgttaaat tgaaagcgag aaataatcat aaattatttc attatcgcga tatccgttaa   1680

gtttgtatcg ta atg gta gtt ata ctt gac aag aga tgt tat tgt aat ctt   1731
              Met Val Val Ile Leu Asp Lys Arg Cys Tyr Cys Asn Leu
              1               5                   10

tta ata ttg att ttg atg atc tcg gag tgt agt gtt ggg att cta cat     1779
Leu Ile Leu Ile Leu Met Ile Ser Glu Cys Ser Val Gly Ile Leu His
    15                  20                  25

tat gag aaa ttg agt aaa att gga ctt gtc aaa gga gta aca aga aaa     1827
Tyr Glu Lys Leu Ser Lys Ile Gly Leu Val Lys Gly Val Thr Arg Lys
30                  35                  40                  45

tac aag att aaa agc aat cct ctc aca aaa gac att gtt ata aaa atg     1875
Tyr Lys Ile Lys Ser Asn Pro Leu Thr Lys Asp Ile Val Ile Lys Met
                50                  55                  60

att ccg aat gtg tcg aac atg tct cag tgc aca ggg agt gtc atg gaa     1923
Ile Pro Asn Val Ser Asn Met Ser Gln Cys Thr Gly Ser Val Met Glu
            65                  70                  75

aat tat aaa aca cga tta aac ggt atc tta aca cct ata aag gga gcg     1971
Asn Tyr Lys Thr Arg Leu Asn Gly Ile Leu Thr Pro Ile Lys Gly Ala
        80                  85                  90

tta gag atc tac aaa aac aac act cat gac ctt gtc ggt gat gtg aga     2019
Leu Glu Ile Tyr Lys Asn Asn Thr His Asp Leu Val Gly Asp Val Arg
    95                  100                 105

tta gcc gga gtt ata atg gca gga gtt gct att ggg att gca acc gca     2067
Leu Ala Gly Val Ile Met Ala Gly Val Ala Ile Gly Ile Ala Thr Ala
110                 115                 120                 125

gct caa atc act gca ggt gta gca cta tat gag gca atg aag aat gct     2115
Ala Gln Ile Thr Ala Gly Val Ala Leu Tyr Glu Ala Met Lys Asn Ala
                130                 135                 140

gac aac atc aac aaa ctc aaa agc agc att gaa tca act aat gaa gct     2163
Asp Asn Ile Asn Lys Leu Lys Ser Ser Ile Glu Ser Thr Asn Glu Ala
            145                 150                 155

gtc gtt aaa ctt caa gag act gca gaa aag aca gtc tat gtg ctg act     2211
Val Val Lys Leu Gln Glu Thr Ala Glu Lys Thr Val Tyr Val Leu Thr
        160                 165                 170

gct cta cag gat tac att aat act aat tta gta ccg aca att gac aag     2259
Ala Leu Gln Asp Tyr Ile Asn Thr Asn Leu Val Pro Thr Ile Asp Lys
    175                 180                 185

ata agc tgc aaa cag aca gaa ctc tca cta gat ctg gca tta tca aag     2307
Ile Ser Cys Lys Gln Thr Glu Leu Ser Leu Asp Leu Ala Leu Ser Lys
190                 195                 200                 205

tac ctc tct gat ttg cta ttc gta ttt ggg ccc aac ctt caa gac cca     2355
Tyr Leu Ser Asp Leu Leu Phe Val Phe Gly Pro Asn Leu Gln Asp Pro
                210                 215                 220

gtt tct aat tca atg act ata cag gct ata tct cag gca ttc ggt gga     2403
Val Ser Asn Ser Met Thr Ile Gln Ala Ile Ser Gln Ala Phe Gly Gly
            225                 230                 235

aat tat gaa aca ctg cta aga aca ttg ggt tac gct aca gaa gac ttt     2451
Asn Tyr Glu Thr Leu Leu Arg Thr Leu Gly Tyr Ala Thr Glu Asp Phe
        240                 245                 250

gat gat ctt cta gaa agt gac agc ata aca ggt caa atc atc tat gtt     2499
Asp Asp Leu Leu Glu Ser Asp Ser Ile Thr Gly Gln Ile Ile Tyr Val
    255                 260                 265

gat cta agt agc tac tat ata att gtc agg gtt tat ttt cct att ctg     2547
Asp Leu Ser Ser Tyr Tyr Ile Ile Val Arg Val Tyr Phe Pro Ile Leu
270                 275                 280                 285

act gaa att caa cag gcc tat atc caa gag ttg tta cca gtg agc ttc     2595
Thr Glu Ile Gln Gln Ala Tyr Ile Gln Glu Leu Leu Pro Val Ser Phe
                290                 295                 300
```

-continued

```
aac aat gat aat tca gaa tgg atc agt att gtc cca aat ttc ata ttg     2643
Asn Asn Asp Asn Ser Glu Trp Ile Ser Ile Val Pro Asn Phe Ile Leu
            305                 310                 315

gta agg aat aca tta ata tca aat ata gag att gga ttt tgc cta att     2691
Val Arg Asn Thr Leu Ile Ser Asn Ile Glu Ile Gly Phe Cys Leu Ile
        320                 325                 330

aca aag agg agc gtg atc tgc aac caa gat tat gcc aca cct atg acc     2739
Thr Lys Arg Ser Val Ile Cys Asn Gln Asp Tyr Ala Thr Pro Met Thr
    335                 340                 345

aac aac atg aga gaa tgt tta acg gga tcg act gag aag tgt cct cga     2787
Asn Asn Met Arg Glu Cys Leu Thr Gly Ser Thr Glu Lys Cys Pro Arg
350                 355                 360                 365

gag ctg gtt gtt tca tca cat gtt ccc aga ttt gca cta tct aac ggg     2835
Glu Leu Val Val Ser Ser His Val Pro Arg Phe Ala Leu Ser Asn Gly
                370                 375                 380

gtt ctg ttt gcc aat tgc ata agt gtt aca tgt cag tgt caa aca aca     2883
Val Leu Phe Ala Asn Cys Ile Ser Val Thr Cys Gln Cys Gln Thr Thr
            385                 390                 395

ggc agg gca atc tca caa tca gga gaa caa act ctg ctg atg att gac     2931
Gly Arg Ala Ile Ser Gln Ser Gly Glu Gln Thr Leu Leu Met Ile Asp
        400                 405                 410

aac acc acc tgt cct aca gcc gta ctc ggt aat gtg att atc agc tta     2979
Asn Thr Thr Cys Pro Thr Ala Val Leu Gly Asn Val Ile Ile Ser Leu
    415                 420                 425

ggg aaa tat ctg ggg tca gta aat tat aat tct gaa ggc att gct atc     3027
Gly Lys Tyr Leu Gly Ser Val Asn Tyr Asn Ser Glu Gly Ile Ala Ile
430                 435                 440                 445

ggt cct cca gtc ttt aca gat aaa gtt gat ata tca agt cag ata tcc     3075
Gly Pro Pro Val Phe Thr Asp Lys Val Asp Ile Ser Ser Gln Ile Ser
                450                 455                 460

agc atg aat cag tcc tta caa cag tct aag gac tat atc aaa gag gct     3123
Ser Met Asn Gln Ser Leu Gln Gln Ser Lys Asp Tyr Ile Lys Glu Ala
            465                 470                 475

caa cga ctc ctt gat act gtt aat cca tca tta ata agc atg ttg tct     3171
Gln Arg Leu Leu Asp Thr Val Asn Pro Ser Leu Ile Ser Met Leu Ser
        480                 485                 490

atg atc ata ctg tat gta tta tcg atc gca tcg ttg tgt ata ggg ttg     3219
Met Ile Ile Leu Tyr Val Leu Ser Ile Ala Ser Leu Cys Ile Gly Leu
    495                 500                 505

att aca ttt atc agt ttt atc att gtt gag aaa aag aga aac acc tac     3267
Ile Thr Phe Ile Ser Phe Ile Ile Val Glu Lys Lys Arg Asn Thr Tyr
510                 515                 520                 525

agc aga tta gag gat agg aga gtc aga cct aca agc agt ggg gat ctc     3315
Ser Arg Leu Glu Asp Arg Arg Val Arg Pro Thr Ser Ser Gly Asp Leu
                530                 535                 540

tac tac att ggg aca tagcccggga tccctcgagt tttattgac tagttaatca     3370
Tyr Tyr Ile Gly Thr
            545

taagataaat aatatacagc attgtaacca tcgtcatccg ttatacgggg aataatatta   3430

ccatacagta ttattaaatt ttcttacgaa gaatatagat cggtatttat cgttagttta   3490

ttttacattt attaattaaa catgtctact attacctgtt atggaaatga caaatttagt   3550

tatataattt atgataaaat taagataata ataatgaaat caaataatta tgtaaatgct   3610

actagattat gtgaattacg aggaagaaag tttacgaact ggaaaaaatt aagtgaatct   3670

aaaatattag tcgataatgt aaaaaaaata aatgataaaa ctaaccagtt aaaaacggat   3730

atgattatat acgttaagga tattgatcat aaaggaagag atacttgcgg ttactatgta   3790
```

-continued

```
caccaagatc tggtatcttc tatatcaaat tggatatctc cgttattcgc cgttaaggta   3850

aataaaatta ttaactatta tatatgtaat gaatatgata tacgacttag cgaaatggaa   3910

tctgatatga cagaagtaat agatgtagtt gataaattag taggaggata caatgatgaa   3970

atagcagaaa taatatattt gtttaataaa tttatagaaa aatatattgc taacatatcg   4030

ttatcaactg aattatctag tatattaaat aattttataa attttaataa aaaatacaat   4090

aacgacataa aagatattaa atctttaatt cttgatctga aaaacacatc tataaaacta   4150

gataaaaagt tattcgataa agataataat gaatcgaacg atgaaaaatt ggaaacagaa   4210

gttgataagc taattttttt catctaaata gtattatttt attgaagtac gaagttttac   4270

gttagataaa taataaaggt cgatttttat tttgttaaat atcaaatatg tcattatctg   4330

ataaagatac aaaaacacac ggtgattatc aaccatctaa cgaacagata ttacaaaaaa   4390

tacgtcggac tatggaaaac gaagctgata gcctcaatag aagaagcatt aaagaaattg   4450

ttgtagatgt tatgaagaat tgggatcatc ctctcaacga agaaatagat aaagttctaa   4510

actggaaaaa tgatacatta aacgatttag atcatctaaa tacagatgat aatattaagg   4570

aaatcataca atgtctgatt agagaatttg cgtttaaaaa gatcaattct attatgtata   4630

gttatgctat ggtaaaactc aattcagata acgaaacatt gaaagataaa attaaggatt   4690

attttataga aactattctt aaagacaaac gtggttataa acaaaagcca ttaccctaga   4750

gcggccgcca ccgcggtgga gctccagctt ttgttccctt tagtgagggt taatttcgag   4810

cttggcgtaa tcatggtcat agctgtttcc                                    4840
```

<210> SEQ ID NO 25
<211> LENGTH: 4840
<212> TYPE: DNA
<213> ORGANISM: Artificial Sequence
<220> FEATURE:
<223> OTHER INFORMATION: Description of Artificial Sequence: Synthetic
plasmid pSL-6839-1

<400> SEQUENCE: 25

```
ggaaacagct atgaccatga ttacgccaag ctcgaaatta accctcacta aagggaacaa     60

aagctggagc tccaccgcgg tggcggccgc tctagggtaa tggcttttgt ttataaccac    120

gtttgtcttt aagaatagtt tctataaaat aatccttaat tttatctttc aatgtttcgt    180

tatctgaatt gagttttacc atagcataac tatacataat agaattgatc tttttaaacg    240

caaattctct aatcagacat tgtatgattt ccttaatatt atcatctgta tttagatgat    300

ctaaatcgtt taatgtatca tttttccagt ttagaacttt atctatttct tcgttgagag    360

gatgatccca attcttcata acatctacaa caatttcttt aatgcttctt ctattgaggc    420

tatcagcttc gttttccata gtccgacgta ttttttgtaa tatctgttcg ttagatggtt    480

gataatcacc gtgtgttttt gtatctttat cagataatga catatttgat atttaacaaa    540

ataaaaatcg acctttatta tttatctaac gtaaaacttc gtacttcaat aaaataatac    600

tatttagatg aaaaaaatta gcttatcaac ttctgtttcc aatttttcat cgttcgattc    660

attattatct ttatcgaata actttttatc tagttttata gatgtgtttt tcagatcaag    720

aattaaagat ttaatatctt ttatgtcgtt attgtatttt ttattaaaat ttataaaatt    780

atttaatata ctagataatt cagttgataa cgatatgtta gcaatatatt tttctataaa    840

tttattaaac aaatatatta tttctgctat ttcatcattg tatcctccta ctaatttatc    900

aactacatct attacttctg tcatatcaga ttccatttcg ctaagtcgta tatcatattc    960
```

-continued

```
attacatata taatagttaa taattttatt taccttaacg gcgaataacg gagatatcca   1020
atttgatata gaagatacca gatcttggtg tacatagtaa ccgcaagtat ctcttccttt   1080
atgatcaata tccttaacgt atataatcat atccgttttt aactggttag ttttatcatt   1140
tatttttttt acattatcga ctaatatttt agattcactt aatttttttcc agttcgtaaa   1200
ctttcttcct cgtaattcac ataatctagt agcatttaca taattatttg atttcattat   1260
tattatctta attttatcat aaattatata actaaatttg tcatttccat aacaggtaat   1320
agtagacatg tttaattaat aaatgtaaaa taaactaacg ataaataccg atctatattc   1380
ttcgtaagaa aatttaataa tactgtatgg taatattatt ccccgtataa cggatgacga   1440
tggttacaat gctgtatatt atttatctta tgattaacta gtcaataaaa actcgaggga   1500
tcccgggcta tgtcccaatg tagtagagat ccccactgct tgtaggtctg actctcctat   1560
cctctaatct gctgtaggtg tttctctttt tctcaacaat gataaaactg ataaatgtaa   1620
tcaaccctat acacaacgat gcgatcgata atacatacag tatgatcata gacaacatgc   1680
ttattaatga tggattaaca gtatcaagga gtcgttgagc ctctttgata tagtccttag   1740
actgttgtaa ggactgattc atgctggata tctgacttga tatatcaact ttatctgtaa   1800
agactggagg accgatagca atgccttcag aattataatt tactgacccc agatatttcc   1860
ctaagctgat aatcacatta ccgagtacgg ctgtaggaca ggtggtgttg tcaatcatca   1920
gcagagtttg ttctcctgat tgtgagattg ccctgcctgt tgtttgacac tgacatgtaa   1980
cacttatgca attggcaaac agaaccccgt tagatagtgc aaatctggga acatgtgatg   2040
aaacaaccag ctctcgagga cacttctcag tcgatcccgt taaacattct ctcatgttgt   2100
tggtcatagg tgtggcataa tcttggttgc agatcacgct cctctttgta attaggcaaa   2160
atccaatctc tatatttgat attaatgtat tccttaccaa tatgaaattt gggacaatac   2220
tgatccattc tgaattatca ttgttgaagc tcactggtaa caactcttgg atataggcct   2280
gttgaatttc agtcagaata ggaaaataaa ccctgacaat tatatagtag ctacttagat   2340
caacatagat gatttgacct gttatgctgt cactttctag aagatcatca aagtcttctg   2400
tagcgtaacc caatgttctt agcagtgttt cataatttcc accgaatgcc tgagatatag   2460
cctgtatagt cattgaatta gaaactgggt cttgaaggtt gggcccaaat acgaatagca   2520
aatcagagag gtactttgat aatgccagat ctagtgagag ttctgtctgt ttgcagctta   2580
tcttgtcaat tgtcggtact aaattagtat taatgtaatc ctgtagagca gtcagcacat   2640
agactgtctt ttctgcagtc tcttgaagtt taacgacagc ttcattagtt gattcaatgc   2700
tgcttttgag tttgttgatg ttgtcagcat tcttcattgc ctcatatagt gctacacctg   2760
cagtgatttg agctgcggtt gcaatcccaa tagcaactcc tgccattata actccggcta   2820
atctcacatc accgacaagg tcatgagtgt tgtttttgta gatctctaac gctcccttta   2880
taggtgttaa gataccgttt aatcgtgttt tataattttc catgacactc cctgtgcact   2940
gagacatgtt cgacacattc ggaatcattt ttataacaat gtcttttgtg agaggattgc   3000
ttttaatctt gtattttctt gttactcctt tgacaagtcc aattttactc aatttctcat   3060
aatgtagaat cccaacacta cactccgaga tcatcaaaat caatattaaa agattacaat   3120
aacatctctt gtcaagtata actaccatta cgatacaaac ttaacggata tcgcgataat   3180
gaaataattt atgattattt ctcgctttca atttaacaca accctcaaga acctttgtat   3240
ttattttcac tttttaagta tagaataaag aagctctaat taattaacga gcagatagtc   3300
tcgttctcgc cctgcctgat gactaattaa ttaacccggg tttttattag ctaattagca   3360
```

-continued

```
atatagattc aatatgataa ttactctaag ttggtaaact aaaaccagct attttccgta   3420

aatgtaatta tattttttatt gttcttatag gtatttttgt aaaaatcatt ttcttatatc   3480

tattatataa tattttttta tcatatttat tatctatcca atacctactg ggtattatga   3540

aaggaaaaac tattctacat tcaggacacg tattttcagt atctgtattt ctggtagtat   3600

ctgcccaacg tcttatacat gataggcaaa aaatatgttt acaacttggg agaattccaa   3660

aatactgttc ggaaatatgt tttttgttta tttcttctat gcatatgcca cactttttac   3720

tggtacttct tttaaacaca atcaaagaat ctctatctac taaacaagtt ttcttgtgag   3780

aaactcgttg gttaatatcg gtagggtgta gtatatatag accacagata tcacattgat   3840

ctccgtgtat atacttacat tttttaccat aatagcatct accaagttct ataaacgggc   3900

atagagtgtt ttcacaggat actattttta attcatcgtt accgaataac gcattataga   3960

aattaatcat tttgtatata tcgtttgtaa aatcatcccc tatccactca ataacataac   4020

gtatcatatt ttgtttgaga taaaatcctg ttataataag tttcttacct ttaccataga   4080

ctttaacaat agcattatct actgacttat tattgtaaat gtctaataat gctttagaag   4140

tagaaagacg caaccatcta gaaaagtatt tattccgcat tttacataat ttactacaat   4200

taacgtaacc gttattcttc attattataa cctttatatc tctatacttg atcgaatcaa   4260

aagatccgtc tatacattca ataacataat catcttgtga taaatctgat actgaatatt   4320

ttccgtgaat gttatttatg tttgatgagt cgtcctcctt cattggttta tattgttgga   4380

aaatgatcaa aaccgtgcag ctacgctgtt atatattact aatccaacaa tatatttctt   4440

ccgttgtaaa gtcttctaga gctaatattt ttactttatg aatatcgtct ctagttttat   4500

ttcttatata cttaacgtat ttatttttcg taatataaga tataacattt tgattattag   4560

aataatataa cactatttgt agatatatat catcatcatg ataggcatat cttgtagcta   4620

tatgatacat tagaaaagca tcgaatatct catcggaaga gcgcatgtct atacaaacta   4680

tgtctccttt agatttctca taccaaaata tattatcgtt ttctgcatac gaattacatt   4740

tataaactat ttcacagttg tttcttcttt tattcttgta aagggtcacc caattcgccc   4800

tatagtgagt cgtattacaa ttcactggcc gtcgttttac                         4840
```

<210> SEQ ID NO 26
<211> LENGTH: 546
<212> TYPE: PRT
<213> ORGANISM: Artificial Sequence
<220> FEATURE:
<223> OTHER INFORMATION: Description of Artificial Sequence: Synthetic
      plasmid pSL-6851-29

<400> SEQUENCE: 26

```
Met Val Val Ile Leu Asp Lys Arg Cys Tyr Cys Asn Leu Leu Ile Leu
  1               5                  10                  15

Ile Leu Met Ile Ser Glu Cys Ser Val Gly Ile Leu His Tyr Glu Lys
             20                  25                  30

Leu Ser Lys Ile Gly Leu Val Lys Gly Val Thr Arg Lys Tyr Lys Ile
         35                  40                  45

Lys Ser Asn Pro Leu Thr Lys Asp Ile Val Ile Lys Met Ile Pro Asn
     50                  55                  60

Val Ser Asn Met Ser Gln Cys Thr Gly Ser Val Met Glu Asn Tyr Lys
 65                  70                  75                  80

Thr Arg Leu Asn Gly Ile Leu Thr Pro Ile Lys Gly Ala Leu Glu Ile
                 85                  90                  95
```

-continued

```
Tyr Lys Asn Asn Thr His Asp Leu Val Gly Asp Val Arg Leu Ala Gly
            100                 105                 110

Val Ile Met Ala Gly Val Ala Ile Gly Ile Ala Thr Ala Ala Gln Ile
        115                 120                 125

Thr Ala Gly Val Ala Leu Tyr Glu Ala Met Lys Asn Ala Asp Asn Ile
    130                 135                 140

Asn Lys Leu Lys Ser Ser Ile Glu Ser Thr Asn Glu Ala Val Val Lys
145                 150                 155                 160

Leu Gln Glu Thr Ala Glu Lys Thr Val Tyr Val Leu Thr Ala Leu Gln
                165                 170                 175

Asp Tyr Ile Asn Thr Asn Leu Val Pro Thr Ile Asp Lys Ile Ser Cys
            180                 185                 190

Lys Gln Thr Glu Leu Ser Leu Asp Leu Ala Leu Ser Lys Tyr Leu Ser
        195                 200                 205

Asp Leu Leu Phe Val Phe Gly Pro Asn Leu Gln Asp Pro Val Ser Asn
    210                 215                 220

Ser Met Thr Ile Gln Ala Ile Ser Gln Ala Phe Gly Gly Asn Tyr Glu
225                 230                 235                 240

Thr Leu Leu Arg Thr Leu Gly Tyr Ala Thr Glu Asp Phe Asp Asp Leu
                245                 250                 255

Leu Glu Ser Asp Ser Ile Thr Gly Gln Ile Ile Tyr Val Asp Leu Ser
            260                 265                 270

Ser Tyr Tyr Ile Ile Val Arg Val Tyr Phe Pro Ile Leu Thr Glu Ile
        275                 280                 285

Gln Gln Ala Tyr Ile Gln Glu Leu Leu Pro Val Ser Phe Asn Asn Asp
    290                 295                 300

Asn Ser Glu Trp Ile Ser Ile Val Pro Asn Phe Ile Leu Val Arg Asn
305                 310                 315                 320

Thr Leu Ile Ser Asn Ile Glu Ile Gly Phe Cys Leu Ile Thr Lys Arg
                325                 330                 335

Ser Val Ile Cys Asn Gln Asp Tyr Ala Thr Pro Met Thr Asn Asn Met
            340                 345                 350

Arg Glu Cys Leu Thr Gly Ser Thr Glu Lys Cys Pro Arg Glu Leu Val
        355                 360                 365

Val Ser Ser His Val Pro Arg Phe Ala Leu Ser Asn Gly Val Leu Phe
    370                 375                 380

Ala Asn Cys Ile Ser Val Thr Cys Gln Cys Gln Thr Thr Gly Arg Ala
385                 390                 395                 400

Ile Ser Gln Ser Gly Glu Gln Thr Leu Leu Met Ile Asp Asn Thr Thr
                405                 410                 415

Cys Pro Thr Ala Val Leu Gly Asn Val Ile Ile Ser Leu Gly Lys Tyr
            420                 425                 430

Leu Gly Ser Val Asn Tyr Asn Ser Glu Gly Ile Ala Ile Gly Pro Pro
        435                 440                 445

Val Phe Thr Asp Lys Val Asp Ile Ser Ser Gln Ile Ser Ser Met Asn
    450                 455                 460

Gln Ser Leu Gln Gln Ser Lys Asp Tyr Ile Lys Glu Ala Gln Arg Leu
465                 470                 475                 480

Leu Asp Thr Val Asn Pro Ser Leu Ile Ser Met Leu Ser Met Ile Ile
                485                 490                 495

Leu Tyr Val Leu Ser Ile Ala Ser Leu Cys Ile Gly Leu Ile Thr Phe
            500                 505                 510
```

-continued

```
Ile Ser Phe Ile Ile Val Glu Lys Lys Arg Asn Thr Tyr Ser Arg Leu
        515                 520                 525

Glu Asp Arg Arg Val Arg Pro Thr Ser Ser Gly Asp Leu Tyr Tyr Ile
    530                 535                 540

Gly Thr
545


<210> SEQ ID NO 27
<211> LENGTH: 3911
<212> TYPE: DNA
<213> ORGANISM: Artificial Sequence
<220> FEATURE:
<221> NAME/KEY: CDS
<222> LOCATION: (1800)..(3437)
<220> FEATURE:
<223> OTHER INFORMATION: Description of Artificial Sequence: Synthetic
      plasmid pSL-6851-29

<400> SEQUENCE: 27

ggaaacagct atgaccatga ttacgaattg cggccgcaat tctgaatgtt aaatgttata     60

ctttggatga agctataaat atgcattgga aaaataatcc atttaaagaa aggattcaaa    120

tactacaaaa cctaagcgat aatatgttaa ctaagcttat tcttaacgac gctttaaata    180

tacacaaata aacataattt ttgtataacc taacaaataa ctaaaacata aaaataataa    240

aaggaaatgt aatatcgtaa ttattttact caggaatggg gttaaatatt tatatcacgt    300

gtatatctat actgttatcg tatactcttt acaattacta ttacgaatat gcaagagata    360

ataagattac gtatttaaga gaatcttgtc atgataattg ggtacgacat agtgataaat    420

gctatttcgc atcgttacat aaagtcagtt ggaaagatgg atttgacaga tgtaacttaa    480

taggtgcaaa aatgttaaat aacagcattc tatcggaaga taggatacca gttatattat    540

acaaaaatca ctggttggat aaaacagatt ctgcaatatt cgtaaaagat gaagattact    600

gcgaatttgt aaactatgac aataaaaagc catttatctc aacgacatcg tgtaattctt    660

ccatgtttta tgtatgtgtt tcagatatta tgagattact ataaactttt tgtatactta    720

tattccgtaa actatattaa tcatgaagaa aatgaaaaag tatagaagct gttcacgagc    780

ggttgttgaa aacaacaaaa ttatacattc aagatggctt acatatacgt ctgtgaggct    840

atcatggata atgacaatgc atctctaaat aggtttttgg acaatggatt cgaccctaac    900

acggaatatg gtactctaca atctcctctt gaaatggctg taatgttcaa gaataccgag    960

gctataaaaa tcttgatgag gtatggagct aaacctgtag ttactgaatg cacaacttct   1020

tgtctgcatg atgcggtgtt gagagacgac tacaaaatag tgaaagatct gttgaagaat   1080

aactatgtaa acaatgttct ttacagcgga ggctttactc ctttgtgttt ggcagcttac   1140

cttaacaaag ttaatttggt taaacttcta ttggctcatt cggcggatgt agatatttca   1200

aacacggatc ggttaactcc tctacatata gccgtatcaa ataaaaattt aacaatggtt   1260

aaacttctat tgaacaaagg tgctgatact gacttgctgg ataacatggg acgtactcct   1320

ttaatgatcg ctgtacaatc tggaaatatt gaaatatgta gcacactact taaaaaaaat   1380

aaaatgtcca gaactgggaa aaattgatct tgccagctgt aattcatggt agaaaagaag   1440

tgctcaggct acttttcaac aaaggagcag atgtaaacta catctttgaa agaaatggaa   1500

aatcatatac tgttttggaa ttgattaaag aaagttactc tgagacacaa aagaggtagc   1560

tgaagtggta ctctcaaagg tacgtgacta attagctata aaaaggatcc gggttaatta   1620

attagtcatc aggcagggcg agaacgagac tatctgctcg ttaattaatt agagcttctt   1680
```

-continued

```
tattctatac ttaaaaagtg aaaataaata caaaggttct tgagggttgt gttaaattga   1740

aagcgagaaa taatcataaa ttatttcatt atcgcgatat ccgttaagtt tgtatcgta    1799

atg gta gtt ata ctt gac aag aga tgt tat tgt aat ctt tta ata ttg     1847
Met Val Val Ile Leu Asp Lys Arg Cys Tyr Cys Asn Leu Leu Ile Leu
  1               5                  10                  15

att ttg atg atc tcg gag tgt agt gtt ggg att cta cat tat gag aaa     1895
Ile Leu Met Ile Ser Glu Cys Ser Val Gly Ile Leu His Tyr Glu Lys
             20                  25                  30

ttg agt aaa att gga ctt gtc aaa gga gta aca aga aaa tac aag att     1943
Leu Ser Lys Ile Gly Leu Val Lys Gly Val Thr Arg Lys Tyr Lys Ile
         35                  40                  45

aaa agc aat cct ctc aca aaa gac att gtt ata aaa atg att ccg aat     1991
Lys Ser Asn Pro Leu Thr Lys Asp Ile Val Ile Lys Met Ile Pro Asn
     50                  55                  60

gtg tcg aac atg tct cag tgc aca ggg agt gtc atg gaa aat tat aaa     2039
Val Ser Asn Met Ser Gln Cys Thr Gly Ser Val Met Glu Asn Tyr Lys
 65                  70                  75                  80

aca cga tta aac ggt atc tta aca cct ata aag gga gcg tta gag atc     2087
Thr Arg Leu Asn Gly Ile Leu Thr Pro Ile Lys Gly Ala Leu Glu Ile
                 85                  90                  95

tac aaa aac aac act cat gac ctt gtc ggt gat gtg aga tta gcc gga     2135
Tyr Lys Asn Asn Thr His Asp Leu Val Gly Asp Val Arg Leu Ala Gly
            100                 105                 110

gtt ata atg gca gga gtt gct att ggg att gca acc gca gct caa atc     2183
Val Ile Met Ala Gly Val Ala Ile Gly Ile Ala Thr Ala Ala Gln Ile
        115                 120                 125

act gca ggt gta gca cta tat gag gca atg aag aat gct gac aac atc     2231
Thr Ala Gly Val Ala Leu Tyr Glu Ala Met Lys Asn Ala Asp Asn Ile
    130                 135                 140

aac aaa ctc aaa agc agc att gaa tca act aat gaa gct gtc gtt aaa     2279
Asn Lys Leu Lys Ser Ser Ile Glu Ser Thr Asn Glu Ala Val Val Lys
145                 150                 155                 160

ctt caa gag act gca gaa aag aca gtc tat gtg ctg act gct cta cag     2327
Leu Gln Glu Thr Ala Glu Lys Thr Val Tyr Val Leu Thr Ala Leu Gln
                165                 170                 175

gat tac att aat act aat tta gta ccg aca att gac aag ata agc tgc     2375
Asp Tyr Ile Asn Thr Asn Leu Val Pro Thr Ile Asp Lys Ile Ser Cys
            180                 185                 190

aaa cag aca gaa ctc tca cta gat ctg gca tta tca aag tac ctc tct     2423
Lys Gln Thr Glu Leu Ser Leu Asp Leu Ala Leu Ser Lys Tyr Leu Ser
        195                 200                 205

gat ttg cta ttc gta ttt ggg ccc aac ctt caa gac cca gtt tct aat     2471
Asp Leu Leu Phe Val Phe Gly Pro Asn Leu Gln Asp Pro Val Ser Asn
    210                 215                 220

tca atg act ata cag gct ata tct cag gca ttc ggt gga aat tat gaa     2519
Ser Met Thr Ile Gln Ala Ile Ser Gln Ala Phe Gly Gly Asn Tyr Glu
225                 230                 235                 240

aca ctg cta aga aca ttg ggt tac gct aca gaa gac ttt gat gat ctt     2567
Thr Leu Leu Arg Thr Leu Gly Tyr Ala Thr Glu Asp Phe Asp Asp Leu
                245                 250                 255

cta gaa agt gac agc ata aca ggt caa atc atc tat gtt gat cta agt     2615
Leu Glu Ser Asp Ser Ile Thr Gly Gln Ile Ile Tyr Val Asp Leu Ser
            260                 265                 270

agc tac tat ata att gtc agg gtt tat ttt cct att ctg act gaa att     2663
Ser Tyr Tyr Ile Ile Val Arg Val Tyr Phe Pro Ile Leu Thr Glu Ile
        275                 280                 285

caa cag gcc tat atc caa gag ttg tta cca gtg agc ttc aac aat gat     2711
Gln Gln Ala Tyr Ile Gln Glu Leu Leu Pro Val Ser Phe Asn Asn Asp
    290                 295                 300
```

-continued

```
aat tca gaa tgg atc agt att gtc cca aat ttc ata ttg gta agg aat     2759
Asn Ser Glu Trp Ile Ser Ile Val Pro Asn Phe Ile Leu Val Arg Asn
305                 310                 315                 320

aca tta ata tca aat ata gag att gga ttt tgc cta att aca aag agg     2807
Thr Leu Ile Ser Asn Ile Glu Ile Gly Phe Cys Leu Ile Thr Lys Arg
                325                 330                 335

agc gtg atc tgc aac caa gat tat gcc aca cct atg acc aac aac atg     2855
Ser Val Ile Cys Asn Gln Asp Tyr Ala Thr Pro Met Thr Asn Asn Met
            340                 345                 350

aga gaa tgt tta acg gga tcg act gag aag tgt cct cga gag ctg gtt     2903
Arg Glu Cys Leu Thr Gly Ser Thr Glu Lys Cys Pro Arg Glu Leu Val
        355                 360                 365

gtt tca tca cat gtt ccc aga ttt gca cta tct aac ggg gtt ctg ttt     2951
Val Ser Ser His Val Pro Arg Phe Ala Leu Ser Asn Gly Val Leu Phe
    370                 375                 380

gcc aat tgc ata agt gtt aca tgt cag tgt caa aca aca ggc agg gca     2999
Ala Asn Cys Ile Ser Val Thr Cys Gln Cys Gln Thr Thr Gly Arg Ala
385                 390                 395                 400

atc tca caa tca gga gaa caa act ctg ctg atg att gac aac acc acc     3047
Ile Ser Gln Ser Gly Glu Gln Thr Leu Leu Met Ile Asp Asn Thr Thr
                405                 410                 415

tgt cct aca gcc gta ctc ggt aat gtg att atc agc tta ggg aaa tat     3095
Cys Pro Thr Ala Val Leu Gly Asn Val Ile Ile Ser Leu Gly Lys Tyr
            420                 425                 430

ctg ggg tca gta aat tat aat tct gaa ggc att gct atc ggt cct cca     3143
Leu Gly Ser Val Asn Tyr Asn Ser Glu Gly Ile Ala Ile Gly Pro Pro
        435                 440                 445

gtc ttt aca gat aaa gtt gat ata tca agt cag ata tcc agc atg aat     3191
Val Phe Thr Asp Lys Val Asp Ile Ser Ser Gln Ile Ser Ser Met Asn
    450                 455                 460

cag tcc tta caa cag tct aag gac tat atc aaa gag gct caa cga ctc     3239
Gln Ser Leu Gln Gln Ser Lys Asp Tyr Ile Lys Glu Ala Gln Arg Leu
465                 470                 475                 480

ctt gat act gtt aat cca tca tta ata agc atg ttg tct atg atc ata     3287
Leu Asp Thr Val Asn Pro Ser Leu Ile Ser Met Leu Ser Met Ile Ile
                485                 490                 495

ctg tat gta tta tcg atc gca tcg ttg tgt ata ggg ttg att aca ttt     3335
Leu Tyr Val Leu Ser Ile Ala Ser Leu Cys Ile Gly Leu Ile Thr Phe
            500                 505                 510

atc agt ttt atc att gtt gag aaa aag aga aac acc tac agc aga tta     3383
Ile Ser Phe Ile Ile Val Glu Lys Lys Arg Asn Thr Tyr Ser Arg Leu
        515                 520                 525

gag gat agg aga gtc aga cct aca agc agt ggg gat ctc tac tac att     3431
Glu Asp Arg Arg Val Arg Pro Thr Ser Ser Gly Asp Leu Tyr Tyr Ile
    530                 535                 540

ggg aca tagcccgggt ttttatgact agttaatcac ggccgcttat aaagatctaa     3487
Gly Thr
545

aatgcataat ttctaaataa tgaaaaaaag tacatcatga gcaacgcgtt agtatatttt   3547

acaatggaga ttaacgctct ataccgttct atgtttattg attcagatga tgttttagaa   3607

aagaaagtta ttgaatatga aaactttaat gaagatgaag atgacgacga tgattattgt   3667

tgtaaatctg ttttagatga agaagatgac gcgctaaagt atactatggt tacaaagtat   3727

aagtctatac tactaatggc gacttgtgca agaaggtata gtatagtgaa aatgttgtta   3787

gattatgatt atgaaaaacc aaataaatca gatccatatc taaaggtatc tcctttgcac   3847

ataatttcat ctattcctag tttagaatac ctgcagccaa gcttggcact ggccgtcgtt   3907
```

-continued ttac 3911

<210> SEQ ID NO 28
<211> LENGTH: 3911
<212> TYPE: DNA
<213> ORGANISM: Artificial Sequence
<220> FEATURE:
<223> OTHER INFORMATION: Description of Artificial Sequence: Synthetic
plasmid pSL-6851-29

<400> SEQUENCE: 28
gtaaaacgac ggccagtgcc aagcttggct gcaggtattc taaactagga atagatgaaa 60
ttatgtgcaa aggagatacc tttagatatg gatctgattt atttggtttt tcataatcat 120
aatctaacaa cattttcact atactatacc ttcttgcaca agtcgccatt agtagtatag 180
acttatactt tgtaaccata gtatacttta gcgcgtcatc ttcttcatct aaaacagatt 240
tacaacaata atcatcgtcg tcatcttcat cttcattaaa gttttcatat tcaataactt 300
tcttttctaa aacatcatct gaatcaataa acatagaacg gtatagagcg ttaatctcca 360
ttgtaaaata tactaacgcg ttgctcatga tgtacttttt ttcattattt agaaattatg 420
cattttagat ctttataagc ggccgtgatt aactagtcat aaaaacccgg gctatgtccc 480
aatgtagtag agatccccac tgcttgtagg tctgactctc ctatcctcta atctgctgta 540
ggtgtttctc tttttctcaa caatgataaa actgataaat gtaatcaacc ctatacacaa 600
cgatgcgatc gataatacat acagtatgat catagacaac atgcttatta atgatggatt 660
aacagtatca aggagtcgtt gagcctcttt gatatagtcc ttagactgtt gtaaggactg 720
attcatgctg gatatctgac ttgatatatc aactttatct gtaaagactg gaggaccgat 780
agcaatgcct tcagaattat aatttactga ccccagatat ttccctaagc tgataatcac 840
attaccgagt acggctgtag gacaggtggt gttgtcaatc atcagcagag tttgttctcc 900
tgattgtgag attgccctgc ctgttgtttg acactgacat gtaacactta tgcaattggc 960
aaacagaacc ccgttagata gtgcaaatct gggaacatgt gatgaaacaa ccagctctcg 1020
aggacacttc tcagtcgatc ccgttaaaca ttctctcatg ttgttggtca taggtgtggc 1080
ataatcttgg ttgcagatca cgctcctctt tgtaattagg caaaatccaa tctctatatt 1140
tgatattaat gtattcctta ccaatatgaa atttgggaca atactgatcc attctgaatt 1200
atcattgttg aagctcactg gtaacaactc ttggatatag gcctgttgaa tttcagtcag 1260
aataggaaaa taaaccctga caattatata gtagctactt agatcaacat agatgatttg 1320
acctgttatg ctgtcacttt ctagaagatc atcaaagtct tctgtagcgt aacccaatgt 1380
tcttagcagt gtttcataat ttccaccgaa tgcctgagat atagcctgta tagtcattga 1440
attagaaact gggtcttgaa ggttgggccc aaatacgaat agcaaatcag agaggtactt 1500
tgataatgcc agatctagtg agagttctgt ctgtttgcag cttatcttgt caattgtcgg 1560
tactaaatta gtattaatgt aatcctgtag agcagtcagc acatagactg tcttttctgc 1620
agtctcttga agtttaacga cagcttcatt agttgattca atgctgcttt tgagtttgtt 1680
gatgttgtca gcattcttca ttgcctcata tagtgctaca cctgcagtga tttgagctgc 1740
ggttgcaatc ccaatagcaa ctcctgccat tataactccg gctaatctca catcaccgac 1800
aaggtcatga gtgttgtttt tgtagatctc taacgctccc tttataggtg ttaagatacc 1860
gtttaatcgt gttttataat tttccatgac actccctgtg cactgagaca tgttcgacac 1920
attcggaatc atttttataa caatgtcttt tgtgagagga ttgcttttaa tcttgtattt 1980

-continued

```
tcttgttact cctttgacaa gtccaatttt actcaatttc tcataatgta gaatcccaac   2040

actacactcc gagatcatca aaatcaatat taaaagatta caataacatc tcttgtcaag   2100

tataactacc attacgatac aaacttaacg gatatcgcga taatgaaata atttatgatt   2160

atttctcgct ttcaatttaa cacaaccctc aagaaccttt gtatttattt tcacttttta   2220

agtatagaat aaagaagctc taattaatta acgagcagat agtctcgttc tcgccctgcc   2280

tgatgactaa ttaattaacc cggatccttt ttatagctaa ttagtcacgt acctttgaga   2340

gtaccacttc agctacctct tttgtgtctc agagtaactt tctttaatca attccaaaac   2400

agtatatgat tttccatttc tttcaaagat gtagtttaca tctgctcctt tgttgaaaag   2460

tagcctgagc acttcttttc taccatgaat tacagctggc aagatcaatt tttcccagtt   2520

ctggacattt tatttttttt aagtagtgtg ctacatattt caatatttcc agattgtaca   2580

gcgatcatta aaggagtacg tcccatgtta tccagcaagt cagtatcagc acctttgttc   2640

aatagaagtt taaccattgt taaattttta tttgatacgg ctatatgtag aggagttaac   2700

cgatccgtgt ttgaaatatc tacatccgcc gaatgagcca atagaagttt aaccaaatta   2760

actttgttaa ggtaagctgc caaacacaaa ggagtaaagc ctccgctgta aagaacattg   2820

tttacatagt tattcttcaa cagatctttc actattttgt agtcgtctct caacaccgca   2880

tcatgcagac aagaagttgt gcattcagta actacaggtt tagctccata cctcatcaag   2940

atttttatag cctcggtatt cttgaacatt acagccattt caagaggaga ttgtagagta   3000

ccatattccg tgttagggtc gaatccattg tccaaaaacc tatttagaga tgcattgtca   3060

ttatccatga tagcctcaca gacgtatatg taagccatct tgaatgtata attttgttgt   3120

tttcaacaac cgctcgtgaa cagcttctat actttttcat tttcttcatg attaatatag   3180

tttacggaat ataagtatac aaaaagttta tagtaatctc ataatatctg aaacacatac   3240

ataaaacatg gaagaattac acgatgtcgt tgagataaat ggctttttat tgtcatagtt   3300

tacaaattcg cagtaatctt catcttttac gaatattgca gaatctgttt tatccaacca   3360

gtgatttttg tataaatataa ctggtatcct atcttccgat agaatgctgt tatttaacat   3420

ttttgcacct attaagttac atctgtcaaa tccatctttc caactgactt tatgtaacga   3480

tgcgaaatag catttatcac tatgtcgtac ccaattatca tgacaagatt ctcttaaata   3540

cgtaatctta ttatctcttg catattcgta atagtaattg taaagagtat acgataacag   3600

tatagatata cacgtgatat aaatatttaa ccccattcct gagtaaaata attacgatat   3660

tacatttcct tttattattt ttatgtttta gttatttgtt aggttataca aaaattatgt   3720

ttatttgtgt atatttaaag cgtcgttaag aataagctta gttaacatat tatcgcttag   3780

gttttgtagt atttgaatcc tttctttaaa tggattattt ttccaatgca tatttatagc   3840

ttcatccaaa gtataacatt taacattcag aattgcggcc gcaattcgta atcatggtca   3900

tagctgtttc c                                                        3911
```

```
<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

gcacttgatg tgattaga                                                    18
```

-continued

```
<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30

gatttgctat tcgtatttgg gcccaacctt                                      30


<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31

aaggttgggc ccaaatacga atagcaaatc                                      30
```

NIPAH VIRUS VACCINES

CROSS-REFERENCE TO RELATED APPLICATIONS

This application claims priority from U.S. Provisional Application Ser. No. 60/674,583, filed Apr. 25, 2005.

INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to recombinant vaccines against Nipah virus and the administration of such vaccines.

BACKGROUND OF THE INVENTION

Nipah virus is a member of the Paramyxoviridae family and is related to the Hendra virus (formerly called equine morbillivirus). The Nipah virus was initially isolated in 1999 upon examining samples from an outbreak of encephalitis and respiratory illness among adult men in Malaysia and Singapore (see, e.g., Chua et al., Lancet. Oct. 9, 1999; 354 (9186):1257-9 and Paton et al., Lancet. Oct. 9, 1999; 354 (9186):1253-6). The host for Nipah virus is still unknown, but flying foxes (bats of the *Pteropus* genus) are suspected to be the natural host.

Because of changes in ecological conditions, flying foxes are increasingly coming into contact with humans and domesticated animals. Therefore, it is conceivable that the viruses in flying foxes may infect domesticated animals and humans, which could result in a more virulent, possibly fatal, disease. Nipah virus caused a relatively mild disease in pigs in Malaysia and Singapore and the virus was transmitted to humans, cats and dogs through close contact with infected pigs.

Infectious with Nipah virus in humans has been associated with an encephalitis characterized by fever and dowsiness and more serious central nervous system disease, such as coma, seizures and inability to maintain breathing (see, e.g., Lee et al., Ann Neurol. September 1999; 46(3):428-32). Illness with Nipah virus begins with 3-14 days of fever and headache, followed by drowsiness and disorientation characterized by mental confusion. These signs and symptoms can progress to coma within 24-48 hours. Some patients have had a respiratory illness during the early part of their infections. Serious nervous disease with Nipah virus encephalitis has been marked by some sequelae, such as persistent convulsions and personality changes. During the Nipah virus disease outbreak in 1998-1999, about 40% of the patients with serious nervous disease who entered hospitals died from the illness (see, e.g., Lam & Chua, Clin Infect Dis. May 1, 2002; 34 Suppl 2:S48-51).

Accordingly, a goal of animal health is the betterment of human health by preventing disease transmission between animals and/or humans.

Nipah virus infection can be prevented by avoiding animals that are known to be infected and using appropriate personal protective equipment devices when it is necessary to come into contact with potentially infected animals. The drug ribavirin has been shown to be effective against the Nipah virus in vitro, however, controlled drug investigations have not been performed and the clinical usefulness is uncertain.

If an efficient program to prevent or treat Nipah virus infection is to be developed, it will be necessary to define the viral antigens which are important in inducing protective responses and to formulate potential immunoprophylactic treatments. The attachment (G) and fusion (F) glycoproteins of Nipah virus have been implicated as viral antigens (see, e.g., Bossart et al., J Virol. November 2002; 76(22): 11186-98 and Guillaume et al., J Virol. January 2004; 78(2):834-40). The Nipah virus glycoproteins (G and F) when expressed as vaccinia virus recombinants have induced an immune response in hamsters which protected against a lethal challenge by Nipah virus (see, e.g., Guillaume et al., J Virol. January 2004; 78(2):834-40). However, it was observed that in both active and passive immunization, the antibody response to Nipah virus was strongly stimulated, suggesting that the efficacy of the immunization is related to the capability of the vector to replicate.

Accordingly, there is a need in the art for an efficacious and reliable Nipah virus vaccine where heterologous proteins are expressed with limited or no productive replication.

Citation or identification of any document in this application is not an admission that such document is available as prior art to the present invention.

SUMMARY OF THE INVENTION

The invention is based, in part, on the development of an efficacious recombinant vaccine that immunizes pigs against Nipah virus with an attenuated canarypox or attenuated fowlpox vector encoding a Nipah virus glycoprotein so there can be expression of the heterologous proteins with limited or no productive replication.

The invention may comprise an avipox expression vector encompassing a polynucleotide that encodes a Nipah virus glycoprotein. In one embodiment, the Nipah virus glycoprotein may be the attachment (G) protein. Advantageously, the polynucleotide may comprise the nucleotide base sequence of nucleotide 8943 to nucleotide 10751 of SEQ ID NO: 1 or the polynucleotide encodes the peptide of SEQ ID NO: 8. In another embodiment, the Nipah virus glycoprotein may be the fusion (F) protein. Advantageously, the polynucleotide may comprise the nucleotide base sequence of nucleotide 6654 to nucleotide 8294 of SEQ ID NO: 1 or the polynucleotide encodes the peptide of SEQ ID NO: 7. In yet another embodiment, the Nipah virus glycoprotein may be the attachment (G) protein and the fusion (F) protein. Advantageously, the polynucleotide may comprise the nucleotide base sequence of nucleotide 6654 to nucleotide 8294 and the nucleotide base sequence of nucleotide 8943 to nucleotide 10751 of SEQ ID NO: 1 or the polynucleotide encodes the peptide of SEQ ID NO: 7 and SEQ ID NO: 8.

The avipox expression vector may be an attenuated avipox expression vector. In one embodiment, the avipox expression vector may be a canarypox vector. Advantageously, the canarypox vector may be ALVAC. In another embodiment, the avipox expression vector may be a fowlpox vector. Advantageously, the fowlpox vector may be TROVAC.

The invention encompasses a formulation for delivery and expression of a Nipah virus glycoprotein, wherein the formulation may comprise any one of the vectors described above and a pharmaceutically or veterinarily acceptable carrier, vehicle or excipient. In one embodiment, the carrier, vehicle or excipient may facililate infection and/or improves preservation of the vector. The invention also encompasses method of delivering a Nipah virus glycoprotein to an animal, comprising administering the above formulation of paragraph to an animal. Advantageously, the animal is a pig.

The invention also encompasses a method of eliciting an immune response in an animal that may comprise administering a composition that may comprise any one of the vectors described above in an effective amount for eliciting an immune response. The invention also relates to a method of eliciting an immune response in an animal that may comprise administering a composition that may comprise a cell, wherein the cell may comprise any one of the vectors described above in an effective amount for eliciting an immune response. Advantageously, the animal is a pig.

The invention further encompasses a method of inducing an immunological or protective response in an animal that may comprise administering a composition that may comprise any one of the vectors described above in an effective amount for eliciting an immune response. The invention further relates to a method of inducing an immunological or protective response in an animal that may comprise administering a composition that may comprise a cell, wherein the cell may comprise any one of the vectors described above in an effective amount for eliciting an immune response. Advantageously, the animal is a pig.

The invention also provides for a kit for performing any of the above described methods comprising the any of the above described compositions and optionally, instructions for performing the method.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 illustrates Nipah virus nucleotide (FIG. 1A) and amino acid (FIG. 1B) sequences. See, e.g., GenBank Accession No. NC_002728, Chua et al., Science. May 26, 2000; 288(5470):1432-5; Harcourt et al., Virology. Aug. 15, 2001; 287(1):192-201; Chan et al., J Gen Virol. September 2001; 82(Pt 9):2151-5 and Chua et al., Microbes Infect. February 2002; 4(2):145-51, the disclosures of which are incorporated by reference in their entireties.

FIG. 2 illustrates the construction of the plasmid pSL-6802-1-4. FIG. 2D is the nucleotide sequence of the left and right arms and the expression cassette with translation of the Nipah virus G gene.

FIG. 3 illustrates the construction of the plasmid pSL-6802-2-5. FIG. 3C is the nucleotide sequence of the left and right arms and the expression cassette with translation of the Nipah virus G gene.

FIG. 4 illustrates the construction of the plasmid pSL-6839-1. FIG. 4D is the nucleotide sequence of left and right arms and the expression cassette with translation of the Nipah virus F gene.

FIG. 5 illustrates the construction of the plasmid pSL-6851-29. FIG. 5A illustrates the PCR oligonucleotides fro the amplification of the Nipah F gene (11456.5L and 11457.5L are disclosed as SEQ ID NOS 30 and 31, respectively in order of appearance). FIG. 5C is the nucleotide sequence of the left and right arms and the expression cassette with translation of the Nipah virus F gene.

FIG. 7 illustrates a Nipah F immunoblot.

DETAILED DESCRIPTION

Figures 2A, 2B:
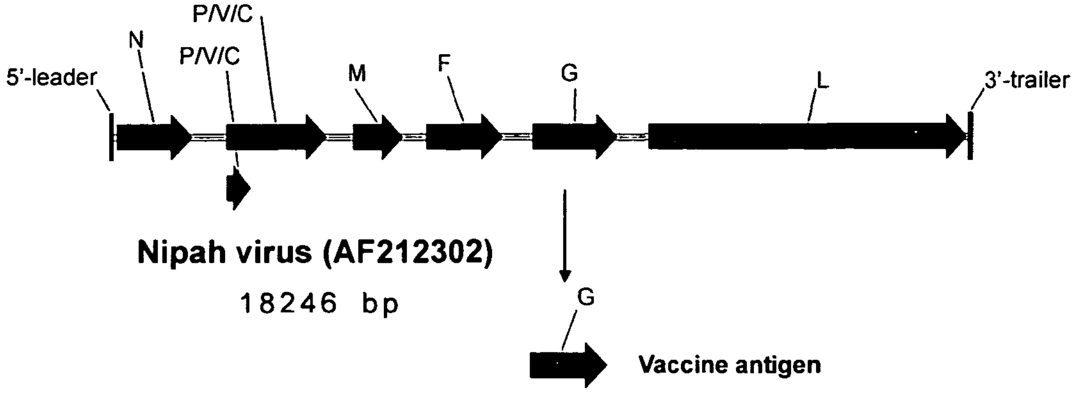
FIG. 2A is a map of the Nipah virus coding regions.
FIG. 2B illustrates the PCR oligonucleotides for the amplification of the Nipah G gene.

The invention is based, in part, on the development of an efficacious recombinant vaccine against Nipah virus. Therefore, the invention encompasses, in part, a recombinant vaccine against Nipah virus.

In an embodiment of the invention, a Nipah virus gene is encoded into an expression vector. In an advantageous embodiment, the Nipah virus gene encodes a glycoprotein. In a particularly advantageous embodiment, the Nipah virus gene encodes the attachment (G) glycoprotein. In another particularly advantageous embodiment, the Nipah virus gene encodes the fusion (F) glycoprotein.

In an advantageous embodiment, the expression vector is a viral vector. In a particularly advantageous embodiment, the viral vector is an avipox vector. In a more advantageous embodiment, the avipox vector is a canarypox vector or a fowlpox vector. More advantageously, the avipox vector is an attenuated avipox vector. In a particularly advantageous embodiment, the attenuated avipox vector is an attenuated canarypox or an attenuated fowlpox vector. Advantageously, the attenuated canarypox vector is ALVAC and the attenuated fowlpox vector is TROVAC.

In another embodiment, the Nipah virus protein is any Nipah virus protein with a known protein sequence, or a fragment thereof. In an advantageous embodiment, the Nipah virus protein is a glycoprotein. In a particularly advantageous embodiment, the Nipah virus protein is the attachment (G) glycoprotein, advantageously with the sequence of SEQ ID NO: 8. In another particularly advantageous embodiment, the Nipah virus protein is the fusion (F) glycoprotein, advantageously with the sequence of SEQ ID NO: 7.

In a particularly advantageous embodiment of the invention, the recombinant constructs are the ALVAC construct expressing Nipah G designated as vCP2199, the ALVAC construct expressing Nipah F designated as vCP2208, the TROVAC construct expressing Nipah G designated as vFP2200 and the TROVAC construct expressing Nipah F designated as vFP2207.

In another embodiment of the invention, the Nipah virus protein includes, but is not limited to, nucleocapsid protein (advantageously SEQ ID NO.: 2), phosphoprotein (advantageously SEQ ID NO: 3), V protein (advantageously SEQ ID NO: 4), C protein (advantageously SEQ ID NO: 5), matrix protein (advantageously SEQ ID NO: 6) or polymerase (advantageously SEQ ID NO: 9).

The terms “protein”, “peptide”, “polypeptide” and “polypeptide fragment” are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

In another embodiment, the Nipah virus gene is any Nipah virus gene with a known nucleotide sequence. In an advantageous embodiment, the Nipah virus gene encodes a glycoprotein. In a particularly advantageous embodiment, the Nipah virus gene encodes the attachment (G) glycoprotein, advantageously nucleotides 8943 to 10751 of SEQ ID NO: 1. In another particularly advantageous embodiment, the Nipah virus gene encodes the fusion (F) glycoprotein, advantageously nucleotides 6654 to 8294 of SEQ ID NO: 1.

In another embodiment of the invention, the Nipah virus gene may encode a nucleocapsid protein (advantageously nucleotides 113 to 1711 of SEQ ID NO: 1), phosphoprotein (advantageously nucleotides 2406 to 4535 of SEQ ID NO: 1), V protein (advantageously nucleotides 2406 to 3775 of SEQ ID NO: 1), C protein (advantageously nucleotides 2428 to 2928 of SEQ ID NO: 1), matrix protein (advantageously nucleotides 5108 to 6166 of SEQ ID NO: 1) or polymerase (advantageously nucleotides 11259 to 18213 of SEQ ID NO: 1).

A “polynucleotide” is a polymeric form of nucleotides of any length, which contain deoxyribonucleotides, ribonucleotides, and analogs in any combination. Polynucleotides may have three-dimensional structure, and may perform any function, known or unknown. The term “polynucleotide” includes double-, single-stranded, and triple-helical molecules. Unless otherwise specified or required, any embodiment of the invention described herein that is a polynucleotide encompasses both the double stranded form and each of two complementary forms known or predicted to make up the double stranded form of either the DNA, RNA or hybrid molecule.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An “isolated” polynucleotide or polypeptide is one that is substantially free of the materials with which it is associated in its native environment. By substantially free, is meant at least 50%, advantageously at least 70%, more advantageously at least 80%, and even more advantageously at least 90% free of these materials.

The invention further comprises a complementary strand to a Nipah virus polynucleotide, advantageously to a Nipah virus glycoprotein polynucleotide.

The complementary strand can be polymeric and of any length, and can contain deoxyribonucleotides, ribonucleotides, and analogs in any combination.

Hybridization reactions can be performed under conditions of different “stringency.” Conditions that increase stringency of a hybridization reaction are well known. See for examples, “Molecular Cloning: A Laboratory Manual”, second edition (Sambrook et al. 1989). Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2 or more washing steps; wash incubation times of 1, 2, or 15 minutes; and wash solutions of 6×SSC, 1×SSC, 0.1×SSC, or deionized water.

The invention further encompasses polynucleotides encoding functionally equivalent variants and derivatives of Nipah virus polypeptides and functionally equivalent fragments thereof which may enhance, decrease or not significantly affect properties of the polypeptides encoded thereby. These functionally equivalent variants, derivatives, and fragments display the ability to retain the activity of a Nipah virus polypeptide, advantageously a Nipah virus glycoprotein. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993;Nature Genetics 3: 266-272; Karlin & Altschul, 1993; Proc. Natl. Acad. Sci. USA 90: 5873-5877; all of which are incorporated by reference herein).

In general, comparison of amino acid sequences is accomplished by aligning an amino acid sequence of a polypeptide of a known structure with the amino acid sequence of a the polypeptide of unknown structure. Amino acids in the sequences are then compared and groups of amino acids that are homologous are grouped together. This method detects conserved regions of the polypeptides and accounts for amino acid insertions and deletions. Homology between amino acid sequences can be determined by using commercially available algorithms (see also the description of homology above). In addition to those otherwise mentioned herein, mention is made too of the programs BLAST, gapped BLAST, BLASTN, BLASTP, and PSI-BLAST, provided by the National Center for Biotechnology Information. These programs are widely used in the art for this purpose and can align homologous regions of two amino acid sequences.

In all search programs in the suite the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Alternatively or additionally, the term "homology" or "identity", for instance, with respect to a nucleotide or amino acid sequence, can indicate a quantitative measure of homology between two sequences. The percent sequence homology can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}=8$; $N_{dif}=2$).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur &. Lipman, Proc Natl Acad Sci USA 1983; 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

And, without undue experimentation, the skilled artisan can consult with many other programs or references for determining percent homology.

The invention further encompasses a Nipah virus protein, advantageously a Nipah virus glycoprotein, contained in a vector molecule or an expression vector and operably linked to an enhancer and/or a promoter element if necessary. In an advantageous embodiment, the promoter is a cytomegalovirus (CMV) promoter. In another embodiment, the enhancers and/or promoters include various cell or tissue specific promoters, various viral promoters and enhancers and various Nipah virus DNA sequences isogenically specific for each animal species.

A "vector" refers to a recombinant DNA or RNA plasmid or virus that comprises a heterologous polynucleotide to be delivered to a target cell, either in vitro or in vivo. The he terologous polynucleotide may comprise a sequence of interest for purposes of therapy, and may optionally be in the form of an expression cassette. As used herein, a vector need not be capable of replication in the ultimate target cell or subject. The term includes cloning vectors for translation of a polynucleotide encoding sequence. Also included are viral vectors.

The term "recombinant" means a polynucleotide of genomic cDNA, semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide, may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, enhancer, ribosome binding sites, polyadenylation sites, transcription terminator, additional transcription units under control of the same or a different promoter, sequences that permit cloning, expression, homologous recombination, and transformation of a host cell, and any such construct as may be desirable to provide embodiments of this invention.

Elements for the expression of a Nipah virus protein, advantageously a Nipah virus glycoprotein, are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses and a transcription terminator for poxviruses. When the polynucleotide encodes a polyprotein fragment, e.g. a Nipah virus protein, advantageously, in the vector, an ATG is placed at 5' of the reading frame and a stop codon is placed at 3'. Other elements for controlling expression may be present, such as enhancer sequences, stabilizing sequences and signal sequences permitting the secretion of the protein.

Methods for making and/or administering a vector or recombinants or plasmid for expression of gene products of genes of the invention either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450 and 6; 312,683; U.S. patent application Ser. No. 920,197, filed Oct. 16, 1986; WO 90/01543; WO91/11525; WO 94/16716; WO 96/39491; WO 98/33510; EP 265785; EP 0 370 573; Andreansky et al., Proc. Natl. Acad. Sci. USA 1996; 93:11313-11318; Ballay et al., EMBO J. 1993; 4:3861-65; Felgner et al., J. Biol. Chem. 1994; 269:2550-2561; Frolov et al., Proc. Natl. Acad. Sci. USA 1996; 93:11371-11377; Graham, Tibtech 1990; 8:85-87; Grunhaus et al., Sem. Virol. 1992; 3:237-52; Ju et al., Diabetologia 1998; 41:736-739; Kitson et al., J. Virol. 1991; 65:3068-3075; McClements et al., Proc. Natl. Acad. Sci. USA 1996; 93:11414-11420; Moss, Proc. Natl. Acad. Sci. USA 1996; 93:11341-11348; Paoletti, Proc. Natl. Acad. Sci. USA 1996; 93:11349-11353; Pennock et al., Mol. Cell. Biol. 1984; 4:399-406; Richardson (Ed), Methods in Molecular Biology 1995; 39, "Baculovirus Expression Protocols," Humana Press Inc.; Smith et al. (1983) Mol. Cell. Biol. 1983; 3:2156-2165; Robertson et al., Proc. Natl. Acad. Sci. USA 1996; 93:11334-11340; Robinson et al., Sem. Immunol. 1997; 9:271; and Roizman, Proc. Natl. Acad. Sci. USA 1996; 93:11307-11312. Thus, the vector in the invention can be any suitable recombinant virus or virus vector, such as a poxvirus (e.g., vaccinia virus, avipox virus, canarypox virus, fowlpox virus, raccoonpox virus, swinepox virus, etc.), adenovirus (e.g., canine adenovirus), herpesvirus, baculovirus, retrovirus, etc. (as in documents incorporated herein by reference); or the vector can be a plasmid. The herein cited and incorporated herein by reference documents, in addition to providing examples of vectors useful in the practice of the invention, can also provide sources for non-Nipah virus proteins or fragments thereof, e.g., non-Nipah virus proteins or fragments thereof, cytokines, etc. to be expressed by vector or vectors in, or included in, the compositions of the invention.

The cytokine or cytokines can be in protein form in the immunogenic or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector therefor.

The cytokine(s) can be chosen from: interleukin 18 (IL-18), interleukin 12 (IL-12), interleukin 15 (IL-15), MIP-1$\alpha$ (macrophage inflammatory protein 1$\alpha$; Marshall E. et al., Br. J. Cancer, 1997, 75 (12), 1715-1720), GM-CSF (Granulocyte-Macrophage Colony-Stimulating Factor. Preferably, use is made of cytokines of the species to be vaccinated; that is, advantageously, the cytokine is matched to the target or host species, and, note for example, porcine GM-CSF (S. Inumaru et al. Immunol. Cell Biol. 1995, 73(5), 474-476),canine GM-CSF (example 8 of WO00/77043), feline GM-CSF (example 9 of WO00/77043).

WO00/77210 provides the nucleotide sequence and the amino acid sequence corresponding to equine GM-CSF, the in vitro GM-CSF production and the construction of vectors (e.g., plasmids and viral vectors) permitting in vivo equine GM-CSF expression The present invention also relates to preparations comprising vectors, such as expression vectors, e.g., therapeutic compositions. The preparations can comprise, consist essentially of, or consist of one or more vectors, e.g., expression vectors, such as in vivo expression vectors, comprising, consisting essentially or consisting of (and advantageously expressing) one or more of Nipah virus polynucleotides and, advantageously, the vector contains and expresses a polynucleotide that includes, consists essentially of, or consists of a coding region encoding a Nipah virus protein, advantageously a Nipah virus glycoprotein, in a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of a Nipah virus glycoprotein, or a fragment thereof.

According to another embodiment, the vector or vectors in the preparation comprise, or consist essentially of, or consist of polynucleotide(s) encoding one or more proteins or fragment(s) thereof of a Nipah virus protein, advantageously a Nipah virus glycoprotein. The inventive preparation advantageously comprises, consists essentially of, or consists of, at least two vectors comprising, consisting essentially of, or consisting of, and advantageously also expressing, advantageously in vivo under appropriate conditions or suitable conditions or in a suitable host cell, polynucleotides from different Nipah virus isolates encoding the same proteins and/or for different proteins, but advantageously for the same proteins. As to preparations containing one or more vectors containing, consisting essentially of or consisting of polynucleotides encoding, and advantageously expressing, advantageously in vivo, a Nipah virus protein, advantageously a Nipah virus glycoprotein, or an epitope thereof, it is advantageous that the expression products be from two, three or more different Nipah virus isolates, advantageously strains. The invention is also directed at mixtures of vectors that contain, consist essentially of, or consist of coding for, and express, different Nipah virus proteins.

In an advantageous embodiment, the vector is a viral vector, advantageously an avipox vector containing Nipah virus gene, advantageously a Nipah virus glycoprotein gene. In a particularly advantageous embodiment, the avipox vector is a canary pox vector, advantageously, an attenuated canarypox vector such as ALVAC. Attenuated canarypox viruses are described in U.S. Pat. No. 5,756,103 (ALVAC) and WO01/05934. In another particularly advantageous embodiment, the avipox vector is a fowlpox vector, advantageously an attenuated fowlpox vector such as TROVAC. Reference is also made to U.S. Pat. No. 5,766,599 which pertains to the atenuated fowlpox strain TROVAC.

In one particular embodiment the viral vector is a poxvirus, e.g. a vaccinia virus or an attenuated vaccinia virus, (for instance, MVA, a modified Ankara strain obtained after more than 570 passages of the Ankara vaccine strain on chicken embryo fibroblasts; see Stickl & Hochstein-Mintzel, Munch. Med. Wschr., 1971, 113, 1149-1153; Sutter et al., Proc. Natl. Acad. Sci. U.S.A., 1992, 89, 10847-10851; available as ATCC VR-1508; or NYVAC, see U.S. Pat. No. 5,494,807, for instance, Examples 1 to 6 and et seq of U.S. Pat. No. 5,494,807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO96/40241), an avipox virus or an attenuated avipox virus (e.g., canarypox, fowlpox, dovepox, pigeonpox, quailpox, ALVAC or TROVAC; see, e.g., U.S. Pat. No. 5,505,941, 5,494,807), swinepox, raccoonpox, camelpox, or myxomatosis virus.

According to another embodiment of the invention, the poxvirus vector is a canarypox virus or a fowlpox virus vector, advantageously an attenuated canarypox virus or fowlpox virus. In this regard, is made to the canarypox available from the ATCC under access number VR-111. Attenuated canarypox viruses are described in U.S. Pat. No. 5,756,103 (ALVAC) and WO01/05934. Numerous fowlpox virus vaccination strains are also available, e.g. the DIFTOSEC CT strain marketed by MERIAL and the NOBILIS VARIOLE vaccine marketed by INTERVET; and, reference is also made to U.S. Pat. No. 5,766,599 which pertains to the atenuated fowlpox strain TROVAC.

For information on the method to generate recombinants thereof and how to administer recombinants thereof, the skilled artisan can refer documents cited herein and to WO90/12882, e.g., as to vaccinia virus mention is made of U.S. Pat. Nos. 4,769,330, 4,722,848, 4,603,112, 5,110,587, 5,494,807, and 5,762,938 inter alia; as to fowlpox, mention is made of U.S. Pat. Nos. 5,174,993, 5,505,941 and U.S. Pat. No. 5,766,599 inter alia; as to canarypox mentionis made of U.S. Pat. No. 5,756,103 inter alia; as to swinepox mention is made of U.S. Pat. No. 5,382,425 inter alia; and, as to raccoonpox, mention is made of WO00/03030 inter alia.

When the expression vector is a vaccinia virus, insertion site or sites for the polynucleotide or polynucleotides to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, advantageously the insertion site or sites are ORF(s) C3, C5 and/or C6; see also documents cited herein, especially those pertaining to canarypox virus. In the case of fowlpox, advantageously the insertion site or sites are ORFs F7 and/or F8; see also documents cited herein, especially those pertaining to fowlpox virus. The insertion site or sites for MVA virus area advantageously as in various publications, including Carroll M. W. et al., Vaccine, 1997, 15 (4), 387-394; Stittelaar K. J. et al., J. Virol., 2000, 74 (9), 4236-4243; Sutter G. et al., 1994, Vaccine, 12 (11), 1032-1040; and, in this regard it is also noted that the complete MVA genome is described in Antoine G., Virology, 1998, 244, 365-396, which enables the skilled artisan to use other insertion sites or other promoters.

Advantageously, the polynucleotide to be expressed is inserted under the control of a specific poxvirus promoter, e.g., the vaccinia promoter 7.5 kDa (Cochran et al., J. Virology, 1985, 54, 30-35), the vaccinia promoter 13L (Riviere et al., J. Virology, 1992, 66, 3424-3434), the vaccinia promoter HA (Shida, Virology, 1986, 150, 451-457), the cowpox promoter ATI (Funahashi et al., J. Gen. Virol., 1988, 69, 35-47), the vaccinia promoter H6 (Taylor J. et al., Vaccine, 1988, 6, 504-508; Guo P. et al. J. Virol., 1989, 63, 4189-4198; Perkus M. et al., J. Virol., 1989, 63, 3829-3836), inter alia.

Advantageously, for the vaccination of mammals the expression vector is a canarypox or a fowlpox. In this way, there can be expression of the heterologous proteins with limited or no productive replication.

According to one embodiment of the invention, the expression vector is a viral vector, in particular an in vivo expression vector. In an advantageous embodiment, the expression vector is an adenovirus vector, such as a human adenovirus (HAV) or a canine adenovirus (CAV). Advantageously, the adenovirus is a human Ad5 vector, an E1-deleted and/or disrupted adenovirus, an E3-deleted and/or disrupted adenovirus or an E1- and E3-deleted and/or disrupted adenovirus. Optionally, E4 may be deleted and/or disrupted from any of the adenoviruses described above. For example, the human AdS vectors described in Yarosh et al. and Lutze-Wallace et al. can be used to express a Nipah virus glycoprotein gene according to the methods of the invention (see, e.g., Yarosh et al., Vaccine. September 1996; 14(13):1257-64 and Lutze-Wallace et al., Biologicals. December 1995; 23(4):271-7).

In one embodiment the viral vector is a human adenovirus, in particular a serotype 5 adenovirus, rendered incompetent for replication by a deletion in the E1 region of the viral genome. The deleted adenovirus is propagated in E1-expressing 293 cells or PER cells, in particular PER.C6 (F. Falloux et al Human Gene Therapy 1998, 9, 1909-1917). The human adenovirus can be deleted in the E3 region eventually in combination with a deletion in the E1 region (see, e.g. J. Shriver et al. Nature, 2002, 415, 331-335, F. Graham et al Methods in Molecular Biology Vol. 7: Gene Transfer and Expression Protocols Edited by E. Murray, The Human Press Inc, 1991, p 109-128; Y. Ilan et al Proc. Natl. Acad. Sci. 1997, 94, 2587-2592; S. Tripathy et al Proc. Natl. Acad. Sci. 1994, 91, 11557-11561; B. Tapnell Adv. Drug Deliv. Rev. 1993, 12, 185-199; X. Danthinne et al Gene Thrapy 2000, 7, 1707-1714; K. Berkner Bio Techniques 1988, 6, 616-629; K. Berkner et al Nucl. Acid Res. 1983, 11, 6003-6020; C. Chavier et al J. Virol. 1996, 70, 4805-4810). The insertion sites can be the E1 and/or E3 loci eventually after a partial or complete deletion of the E1 and/or E3 regions. Advantageously, when the expression vector is an adenovirus, the polynucleotide to be expressed is inserted under the control of a promoter functional in eukaryotic cells, such as a strong promoter, preferably a cytomegalovirus immediate-early gene promoter (CMV-IE promoter). The CMV-IE promoter is advantageously of murine or human origin. The promoter of the elongation factor 1 α can also be used. In one particular embodiment a promoter regulated by hypoxia, e.g. the promoter HRE described in K. Boast et al Human Gene Therapy 1999, 13, 2197-2208), can be used. A muscle specific promoter can also be used (X. Li et al Nat. Biotechnol. 1999, 17, 241-245). Strong promoters are also discussed herein in relation to plasmid vectors. A poly(A) sequence and terminator sequence can be inserted downstream the polynucleotide to be expressed, e.g. a bovine growth hormone gene or a rabbit β-globin gene polyadenylation signal.

In another embodiment the viral vector is a canine adenovirus, in particular a CAV-2 (see, e.g. L. Fischer et al. Vaccine, 2002, 20, 3485-3497; U.S. Pat. No. 5,529,780; U.S. Pat. No. 5,688,920; PCT Application No. WO95/14102). For CAV, the insertion sites can be in the E3 region and /or in the region located between the E4 region and the right ITR region (see U.S. Pat. No. 6,090,393; U.S. Pat. No. 6,156,567). In one embodiment the insert is under the control of a promoter, such as a cytomegalovirus immediate-early gene promoter (CMV-IE promoter) or a promoter already described for a human adenovirus vector. A poly(A) sequence and terminator sequence can be inserted downstream the polynucleotide to be expressed, e.g. a bovine growth hormone gene or a rabbit β-globin gene polyadenylation signal.

In another particular embodiment the viral vector is a herpesvirus such as a canine herpesvirus (CHV) or a feline herpesvirus (FHV). For CHV, the insertion sites may be in particular in the thymidine kinase gene, in the ORF3, or in the UL43 ORF (see U.S. Pat. No. 6,159,477). In one embodiment the polynucleotide to be expressed is inserted under the control of a promoter functional in eukaryotic cells, advantageously a CMV-IE promoter (murine or human). In one particular embodiment a promoter regulated by hypoxia, e.g. the promoter HRE described in K. Boast et al Human Gene Therapy 1999, 13, 2197-2208), can be used. A poly(A) sequence and terminator sequence can be inserted downstream the polynucleotide to be expressed, e.g. bovine growth hormone or a rabbit β-globin gene polyadenylation signal.

According to a yet further embodiment of the invention, the expression vector is a plasmid vector or a DNA plasmid vector, in particular an in vivo expression vector. In a specific, non-limiting example, the pVR1020 or 1012 plasmid (VICAL Inc.; Luke C. et al., Journal of Infectious Diseases, 1997, 175, 91-97; Hartikka J. et al., Human Gene Therapy, 1996, 7, 1205-1217) can be utilized as a vector for the insertion of a polynucleotide sequence. The pVR1020 plasmid is derived from pVR1012 and contains the human tPA signal sequence.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide encoding a Nipah virus protein, advantageously a Nipah virus glycoprotein, variant, analog or fragment, operably linked to a promoter or under the control of a promoter or dependent upon a promoter. In general, it is advantageous to employ a strong promoter functional in eukaryotic cells. The preferred strong promoter is the immediate early cytomegalovirus promoter (CMV-IE) of human or murine origin, or optionally having another origin such as the rat or guinea pig. The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart M. et al., Cell, 1985, 41, 521-530) or murine CMV-IE.

In more general terms, the promoter has either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa M. et al., Vaccine, 2000, 18, 2337-2344), or the actin promoter (Miyazaki J. et al., Gene, 1989, 79, 269-277).

Functional sub fragments of these promoters, i.e., portions of these promoters that maintain an adequate promoting activity, are included within the present invention, e.g. truncated CMV-IE promoters according to PCT Application No. WO98/00166 or U.S. Pat. No. 6,156,567 can be used in the practice of the invention. A promoter in the practice of the invention consequently includes derivatives and sub fragments of a full-length promoter that maintain an adequate promoting activity and hence function as a promoter, preferably promoting activity substantially similar to that of the actual or full-length promoter from which the derivative or sub fragment is derived, e.g., akin to the activity of the truncated CMV-IE promoters of U.S. Pat. No. 6,156,567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub fragments.

Advantageously, the plasmids comprise or consist essentially of other expression control elements. It is particularly advantageous to incorporate stabilizing sequence(s), e.g., intron sequence(s), preferably the first intron of the hCMV-IE (PCT Application No. WO89/01036), the intron II of the rabbit β-globin gene (van Ooyen et al., Science, 1979, 206, 337-344).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

According to another embodiment of the invention, the expression vectors are expression vectors used for the in vitro expression of proteins in an appropriate cell system. Protein production can take place by the transfection of mammalian cells by plasmids, by replication or expression without productive replication of viral vectors on mammal cells or avian cells, or by *Baculovirus* replication (see, e.g., U.S. Pat. No. 4,745,051; Vialard J. et al., J. Virol., 1990 64 (1), 37-50; Verne A., Virology, 1988, 167, 56-71), e.g. *Autographa californica* Nuclear Polyhedrosis Virus AcNPV, on insect cells (e.g. Sf9 *Spodoptera frugiperda* cells, ATCC CRL 1711; see also U.S. Pat. Nos. 6,228,846, 6,103,526). Mammalian cells which can be used are advantageously hamster cells (e.g. CHO or BHK-21) or monkey cells (e.g. COS or VERO). The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods.

It is understood to one of skill in the art that conditions for culturing a host cell varies according to the particular gene and that routine experimentation is necessary at times to determine the optimal conditions for culturing a Nipah virus protein, advantageously a Nipah virus glycoprotein, depending on the host cell. A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

In an advantageous embodiment, the invention provides for the administration of a therapeutically effective amount of a formulation for the delivery and expression of a Nipah virus protein, advantageously a Nipah virus glycoprotein, in a target cell. Determination of the therapeutically effective amount is routine experimentation for one of ordinary skill in the art. In one embodiment, the formulation comprises an expression vector comprising a polynucleotide that expresses a Nipah virus protein, advantageously a Nipah virus glycoprotein, and a pharmaceutically or veterinarily acceptable carrier, vehicle or excipient. In an advantageous embodiment, the pharmaceutically or veterinarily acceptable carrier, vehicle or excipient facilitates transfection and/or improves preservation of the vector or protein.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

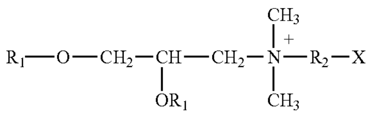

in which $R_1$ is a saturated or unsaturated straight-chain aliphatic radical having 12 to 18 carbon atoms, $R_2$ is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr J. P., 1994, Bioconjugate Chemistry, 5, 382-389), to form DMRIE-DOPE.

Advantageously, the plasmid mixture with the adjuvant is formed extemporaneously and advantageously contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is advantageously about 95: about 5 to about 5:about 95, more advantageously about 1: about 1, e.g., 1:1.

The DMRIE or DMRIE-DOPE adjuvant:plasmid weight ratio can be between about 50: about 1 and about 1: about 10, such as about 10: about 1 and about 1 about 5, and advantageously about 1: about 1 and about 1: about 2, e.g., 1:1 and 1:2.

In a specific embodiment, the pharmaceutical composition is directly administered in vivo, and the encoded product is expressed by the vector in the host. The methods of in vivo delivery a vector encoding Nipah virus protein, advantageously a Nipah virus glycoprotein (see, e.g., U.S. Pat. No. 6,423,693; patent publications EP 1052286, EP 1205551, U.S. patent publication 20040057941, WO 9905300 and Draghia-Akli et al., Mol Ther. December 2002; 6(6):830-6; the disclosures of which are incorporated by reference in their entireties) can be modified to deliver a Nipah virus protein, advantageously a Nipah virus glycoprotein, of the present invention. The in vivo delivery of a vector encoding a Nipah virus protein, advantageously a Nipah virus glycoprotein, described herein can be accomplished by one of ordinary skill in the art given the teachings of the above-mentioned references.

Advantageously, the pharmaceutical and/or therapeutic compositions and/or formulations according to the invention comprise or consist essentially of or consist of an effective quantity to elicit a therapeutic response of one or more expression vectors and/or polypeptides as discussed herein; and, an effective quantity can be determined from this disclosure, including the documents incorporated herein, and the knowledge in the art, without undue experimentation.

The immunogenic compositions and vaccines according to the invention may comprise or consist essentially of one or more adjuvants. Particularly suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one ore more non-methylated CpG units (Klinman D. M. et al., Proc. Natl. Acad. Sci., USA, 1996, 93, 2879-2883; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, (5) cytokines, (6) aluminum hydroxide or aluminum phosphate or (7) other adjuvants discussed in any document cited and incorporated by referenc into the instant application, or (8) any combinations or mixtures thereof.

The oil in water emulsion (3), which is especially appropriate for viral vectors, can be based on:

- light liquid paraffin oil (European pharmacopoeia type),
- isoprenoid oil such as squalane, squalene,
- oil resulting from the oligomerization of alkenes, e.g. isobutene or decene,
- esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as:

esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, polyoxypropylene-polyoxyethylene copolymer blocks, such as Pluronic, e.g., L121.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether. Reference is also made to J. Fields et al.,

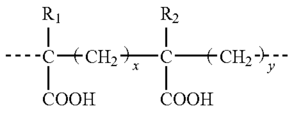

Nature 186: 778-780, Jun. 4, 1960.

With regard to structure, the acrylic or methacrylic acid polymers and EMA are preferably formed by basic units having the following formula:

in which:

$R_1$ and $R_2$, which can be the same or different, represent H or $CH_3$ x=0 or 1, preferably x=1 y=1 or 2, with x+y=2.

For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final vaccine composition can range between 0.01 and 1.5% w/v, advantageously 0.05 to 1% w/v and preferably 0.1 to 0.4% w/v.

One skilled in the art can determine the effective plasmid dose to be used for each immunization or vaccination protocol and species from this disclosure and the knowledge in the art.

In an advantageous embodiment, the pharmaceutical and/or therapeutic compositions and/or formulations according to the invention are administered by injection, such as, but not limited to, intramuscular (IM), intradermal (ID) or subcutaneous (SC) injection.

Also in connection with such a therapeutic composition, from the disclosure herein and the knowledge in the art, the skilled artisan can determine the number of administrations, the administration route, and the doses to be used for each injection protocol, without any undue experimentation.

In an advantageous embodiment, the recombinant vaccine can be administered to a pig or infected or transfected into cells in an amount of about at least $10^3$ pfu; more preferably about $10^4$ pfu to about $10^{10}$ pfu, e.g., about $10^5$ pfu to about $10^9$ pfu, for instance about $10^6$ pfu to about $10^8$ pfu, per dose, for example, per 2 ml dose. In a particularly advantageous embodiment, the dose is about $10^8$ pfu per dose.

The method includes at least one administration to an animal of an efficient amount of the therapeutic composition according to the invention. The animal may be male, female, pregnant female and newborn. This administration may be notably done by intramuscular (IM), intradermal (ID) or subcutaneous (SC) injection or via intranasal or oral administration. In an advantageous embodiment, the therapeutic composition according to the invention can be administered by a syringe or a needleless apparatus (like, for example Pigjet, Biojector or Vitajet (Bioject, Oreg., USA)). Another approach to administer plasmid is to use electroporation see, e.g. S. Tollefsen et al. Vaccine, 2002, 20, 3370-3378; S. Tollefsen et al. Scand. J. Immunol., 2003, 57, 229-238; S. Babiuk et al., Vaccine, 2002, 20, 3399-3408; PCT Application No. WO99/01158.

The invention relates to the use of the pharmaceutical compositions for vaccinating in animals against Nipah virus infection. The invention relates to the use of the pharmaceutical compositions for vaccinating in animals against Hendra virus infection. In a particular embodiment, the pharmaceutical compositions comprising Nipah F and Nipah G according to the present invention are used for vaccinating in animals against infections caused by Nipah or Hendra viruses. In an advantageous embodiment, the animal is a pig. In other advantageous embodiments, the animal is a cat, dog, horse or human.

The invention also provides for a method for preventing Nipah virus transmission between a first animal and a second animal comprising immunizing or eliciting an immune response in a first animal using any of the methods described herein to prevent disease transmission to the second animal. The invention also provides for a method for preventing Hendra virus transmission from an infected animal to another animal comprising immunizing or eliciting an immune response in a first animal using any of the methods described herein to prevent disease transmission to the second animal. In a particular embodiment, the pharmaceutical compositions comprising Nipah F and Nipah G according to the present invention are used for vaccinating said first animals against infections caused by Nipah or Hendra viruses. In an advantageous embodiment, wherein the first animal is a pig. The second animal is a cat a dog, or a horse, advantageously a human.

The invention also provides for a kit for performing any of the above described methods comprising the any of the above described compositions and optionally, instructions for performing the method.

The invention will now be further described by way of the following non-limiting examples.

EXAMPLES

Example 1

Constructs

Construction of the plasmid pSL-6802-1-4. pSL-6802-1-4 comprises the flanking sequences of the C5 locus, H6 vaccinia promoter and G Nipah virus gene to generate VCP2199. The Nipah virus was isolated from human CSF. The Nipah G gene was PCR amplified and inserted into plasmid pTM1, generating pTM1 Nipah G. The purpose was to construct a pC5 H6p Nipah G donor plasmid for generation of an ALVAC canarypox virus recombinant expressing Nipah G. The plasmid name was pC5 H6p Nipah G, pSL-6802-1-4. The plasmid backbone was pCXL-148-2, pC5 H6p comprising the H6 vaccinia promoter, the left and the right arms corresponding to the C5 locus of insertion. The plasmid pCXL-148-2 is derived from the plasmid pNVQH6C5LSP-1 8 by a single base mutation from T to C in the C5 right arm. The plasmid pNVQH6C5LSP-18 is described in S. Loosmore et al US2005/0031641.

Figure 2C:
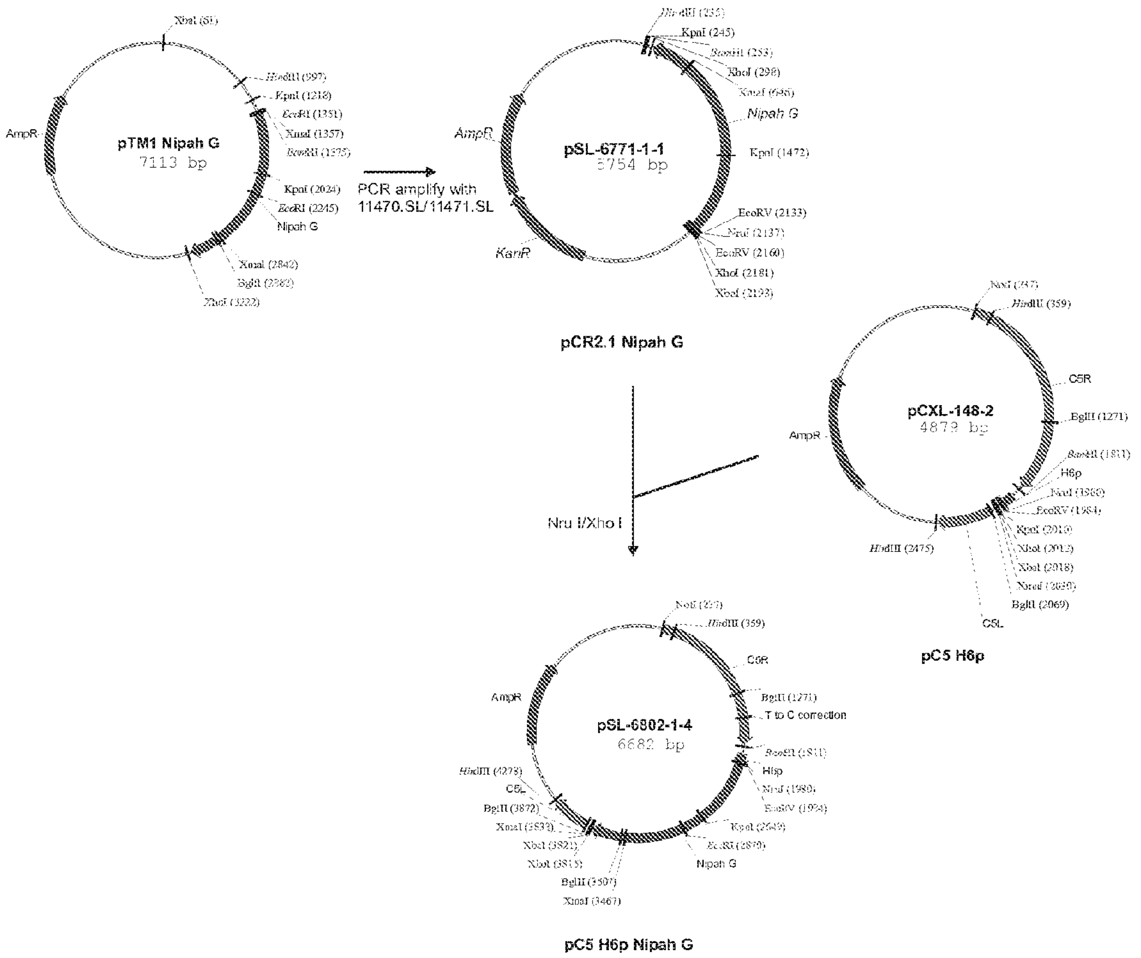
FIG. 2C illustrates the construction of pSL-6802-1-4.

The Nipah G gene was PCR amplified using pTM1 Nipah G as template and primers 11470.SL and 11471.SL (FIG. 2B). The ~1.8 kb PCR fragment was cloned into pCR2.1, generating clone pSL-6771-1-1 (pCR2.1 H6p Nipah G), which was confirmed by sequence analysis (FIG. 2C). The ~1.8 kb Nru I-Xho I H6p Nipah G fragment from pSL-6771-1-1 was cloned into pCXL-148-2 (pC5 H6p), generating pSL-6802-1-4 (pC5 H6p Nipah G), which was confirmed by sequence analysis (FIGS. 2C AND 2D).

Construction of the plasmid pSL-6802-2-5. pSL-6802-2-5 comprises the flanking sequences of the F8 locus, H6 vaccinia promoter and G Nipah virus gene to generate VFP2200. The Nipah virus was isolated from human CSF. The Nipah G gene was PCR amplified and inserted into plasmid pTM1, generating pTM1 Nipah G. The purpose was to construct a pF8 H6p Nipah G donor plasmid for generation of a fowlpox recombinant expressing Nipah G. The plasmid name was pF8 H6p Nipah G, pSL-6802-2-5. The plasmid backbone was pSL-6427-2-1, pF8 H6p comprising the H6 promoter, the left and the right arms of the F8 locus of insertion. The plasmid pSL-6427-2-1 is derived from the plasmid pSL-5440-5-1 by a single base mutation from C to T in the F8 left arm. The plasmid pSL-5440-5-1 is described in S. Loosmore et al US2005/0031641.

Figures 3A, 3B:
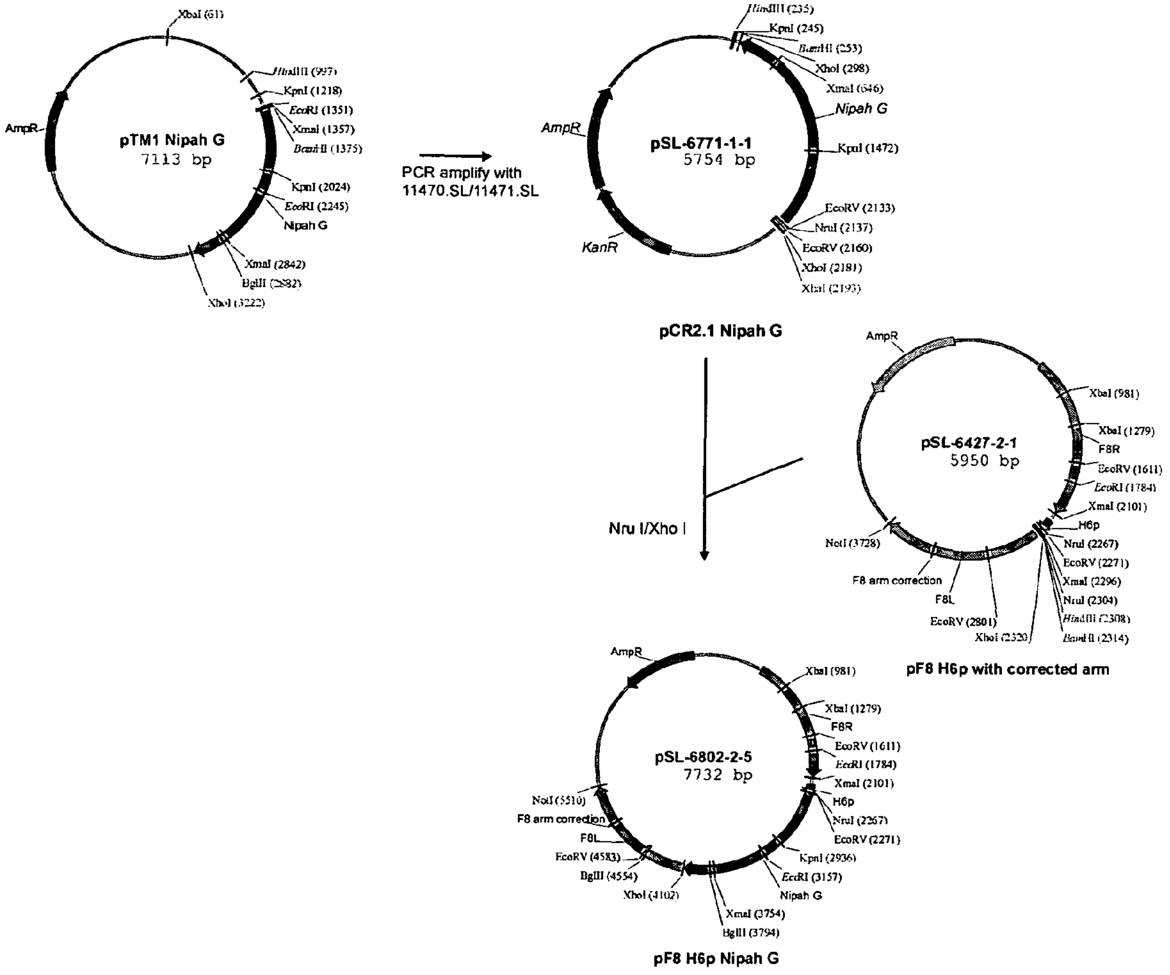
FIG. 3A illustrates the PCR oligonucleotides for the amplification of the Nipah G gene.
FIG. 3B illustrates the construction of pSL-6802-2-5.

The Nipah G gene was PCR amplified using pTM1 Nipah G as template and primers 11470.SL and 11471.SL (FIG. 3A). The ~1.8 kb PCR fragment was cloned into pCR2.1, generating clone pSL-6771-1-1 (pCR2.1 H6p Nipah G), which was confirmed by sequence analysis (FIG. 3 B). The ~1.8 kb Nru I-Xho I H6p Nipah G fragment from pSL-6771-1-1 was cloned into pSL-6427-2-1 (pF8 H6p), generating pSL-6802-2-5 (pF8 H6p Nipah G), which was confirmed by sequence analysis (FIGS. 3B AND 3C).

Construction of the plasmidpSL-6839-1. pSL-6839-1 comprises the flanking sequences of the F8 locus, H6 vaccinia promoter and F Nipah virus gene to generate VFP2207. The Nipah virus was isolated from human CSF. The Nipah F gene was PCR amplified and inserted into plasmid pTM1, generating pTM1 Nipah F. The purpose was to construct a pF8 H6p Nipah F donor plasmid for generation of a fowlpox recombinant expressing Nipah F. The plasmid name: pF8 H6p Nipah F, pSL-6839-1. The plasmid backbone was pSL-6427-2-1, pF8 H6p comprising the H6 vaccinia promoter, the left and the right arms of the F8 locus of insertion.

Figures 4A, 4B:
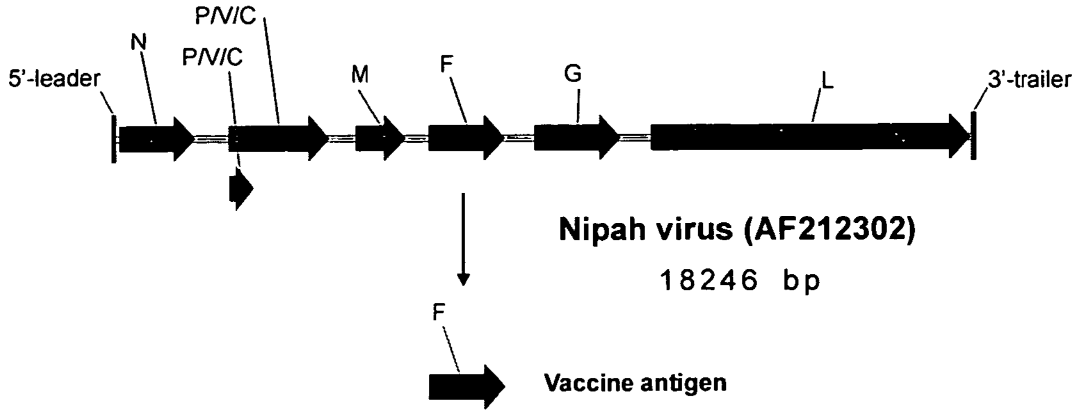
FIG. 4A is a map of the Nipah virus and vaccine antigen.
FIG. 4B illustrates the PCR oligonucleotides for the amplification of the Nipah F gene (11456.5L and 11457.5L are disclosed as SEQ ID NOS 30 and 31, respectively in order of appearance).
Figure 4C:
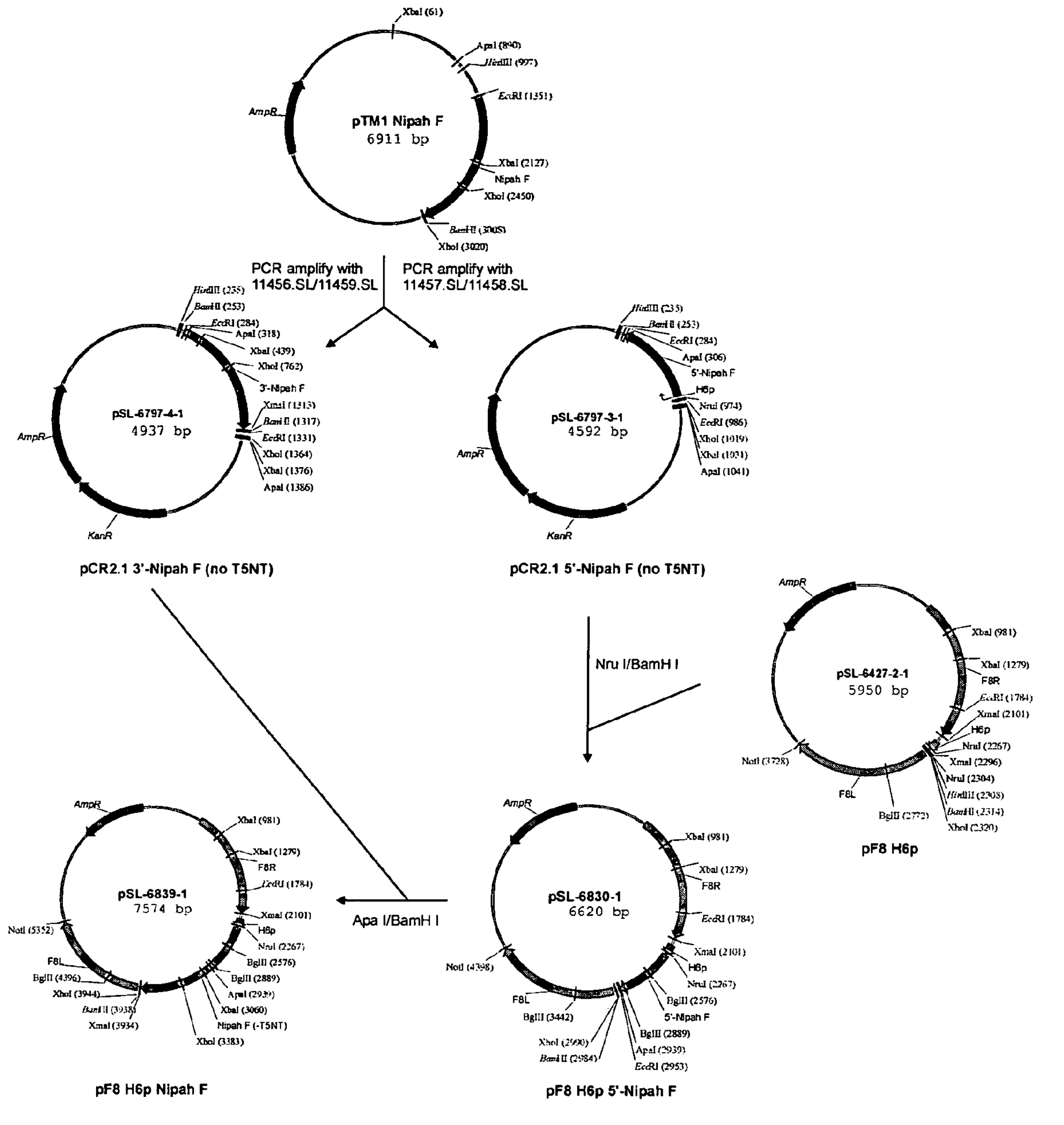
FIG. 4C illustrates the construction of pSL-6839-1.

There was an internal T5NT sequence in Nipah F that was removed by site-directed mutagenesis. A fragment encoding the 3'-end of the H6 promoter and the 5'-end of the Nipah Fgene was PCR amplified using primers 11457.SL and 11458.SL. In the amplified fragment the T5NT sequence was removed and an Apa I site was introduced for cloning purposes (FIG. 4B). The fragment was cloned into pCR2.1, generating pSL-6797-3-1 (pCR2.1 H6p 5'-Nipah F, no T5NT), which was confirmed by sequence analysis (FIG. 4C). The 3'-Nipah F fragment was PCR amplified using primers 11456.SL and 11459.SL. In the amplified fragment the T5NT sequence was removed and an Apa I site was introduced for cloning purposes (FIG. 4B). The fragment was cloned into pCR2.1, generating pSL-6797-4-1 (pCR2.1 3'-Nipah F, no TSNT), which was confirmed by sequence analysis (FIGS. 4C). The ~0.7kb Nru I-BamH I H6p 5'-Nipah F fragment from pSL-6797-3-1 was inserted into pSL-6427-2-1 (pF8 H6p), generating pSL-6830-1 (pF8 H6p 5'-Nipah F). The ~1.0 kb Apa I-BamH I 3'-Nipah F fragment from pSL-6797-4-1 was inserted between Apa I and Bam H I of pSL-6830-1, generating pSL-6839-1 (pF8 H6p Nipah F), which was confirmed by sequence analysis (FIGS. 4C and 4D).

Construction of the plasmid pSL-6851-29. pSL-6851-29 comprises the flanking sequences of the C5 locus, H6 vaccinia promoter and F Nipah virus gene to generate VCP2208. The Nipah virus was isolated from human CSF. The Nipah F gene was PCR amplified and inserted into plasmid pTM1, generating pTM1 Nipah F. The purpose was to construct a pC5 H6p Nipah F donor plasmid to generate an ALVAC canarypoxvirus recombinant expressing Nipah F. The plasmid name was pSL-6851-29, pC5 H6p Nipah F. The plasmid backbone was pCXL-148-2, pC5 H6p comprising the H6 vaccinia promoter, the left arm and the right arm of the C5 locus of insertion.

Figure 5B:
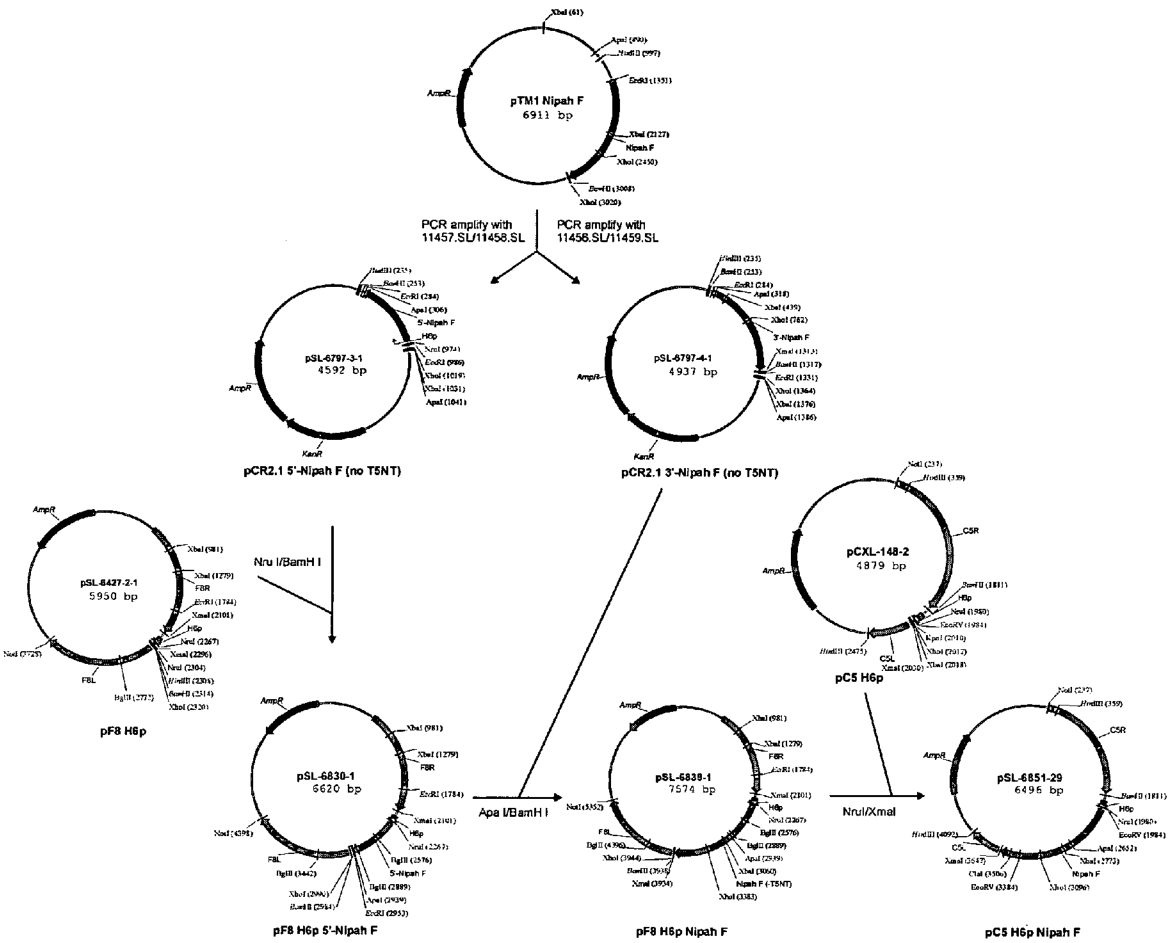
FIG. 5B is a plasmid diagram of pSL-6851-29.

There was an internal T5NT sequence in Nipah F that was removed by site-directed mutagenesis. A fragment encoding the 3'-end of the H6 promoter and the 5'-end of the Nipah F gene was PCR amplified using primers 11457.SL and 11458.SL. In the amplified fragment the TSNT sequence was remove and an Apa I site was introduced for cloning purposes (FIG. 5A). The fragment was cloned into pCR2.1, generating pSL-6797-3-1 (pCR2.1 H6p 5'-Nipah F, no T5NT), which was confirmed by sequence analysis (FIG. 5B). The 3'-Nipah F fragment was PCR amplified using primers 11456.SL and 11459.SL. In the amplified fragment the TSNT sequence was removed and an Apa I site was introduced for cloning purposes (FIG. 5A). The fragment was cloned into pCR2.1, generating pSL-6797-4-1 (pCR2.1 3'-Nipah F, no TSNT), which was confirmed by sequence analysis (FIG. 5B). The ~0.7 kb Nru I-BamH I H6p 5'-Nipah F fragment from pSL-6797-3-1 was inserted into pSL-6427-2-1 (pF8 H6p), generating pSL-6830-1 (pF8 H6p 5'-Nipah F). The ~1.0 kb Apa I-BamH I 3'-Nipah F fragment from pSL-6797-4-1 was inserted between Apa I and Bam H I of pSL-6830-1, generating pSL-6839-1 (pF8 H6p Nipah F), which was confirmed by sequence analysis. The 1.7kb Nru I-Xma I H6p Nipah F fragment from pSL-6839-1 was inserted into pCXL-148-2 (pC5 H6p) to generate pSL-6851-29 (pC5 H6p Nipah F), which was confirmed by sequence analysis (FIGS. 5B and 5C).

Construction of the Fowlpox-recombinant expressing Nipah F, vFP2207. The gene was Nipah F. The donor plasmid was pSL-6839-1. The insertion site was the F8 locus of Fowl pox. The promoters was the vaccinia virus H6 promoter. The cells for in vitro recombination were primary chicken embryo fibroblast cells (1° CEF) grown in 10% FBS, DMEM.

The in vitro recombination was performed by transfection of 1° CEF cells with Not I-linearized donor plasmid pSL-6839-1 (20 ug). The transfected cells were subsequently infected with Fowlpox as rescue virus at MOI of 10. After 48 h, the transfected-infected cells were harvested, sonicated and used for recombinant virus screening. Recombinant plaques were screened based on the plaque lift hybridization method using a Nipah F specific probe, which was labeled with horseradish peroxidase. After four sequential rounds of plaque purification, the recombinant designated as vFP2207 was generated and confirmed by hybridization as 100% positive for the insert and 100% negative for the F8 ORF.

Construction of the Canarypox recombinant expressing Nipah G, vCP2199. The gene was Nipah G. The donor plasmid was pSL-6802-1-4. The insertion site was C5. The promoter was the H6 promoter. The cells for in vitro recombination were primary chicken embryo fibroblast cells (1° CEF) grown in 10% FBS, DMEM.

The in vitro recombination was performed by transfection of 1° CEF cells with Not I-linearized donor plasmid pSL-6802-1-4 (15 ug) The transfected cells were subsequently infected with ALVAC as rescue virus at MOI of 10 After 24 h, the transfected-infected cells were harvested, sonicated and used for recombinant virus screening. Recombinant plaques were screened based on the plaque lift hybridization method using Nipah G-specific probe which was labeled with horse radish peroxidase After five sequential rounds of plaque purification, the recombinant designated as vCP2199 was generated and confirmed by hybridization as 100% positive for the Nipah G insert and 100% negative for the C5 ORF.

Construction of the Fowlpox recombinant expressing, Nipah G, vFP2200. The genes was Nipah G. The donor plasmid was pSL6802-2-5. The insertion site was F8. The promoter was the H6 promoter. The cells for in vitro recombination were primary chicken embryo fibroblast cells (1° CEF) grown in 10% FBS, DMEM.

The in vitro recombination was performed by transfection of 1° CEF cells with Not I-linearized donor plasmid pSL6802-2-5 (15 ug). The transfected cells were subsequently infected with fowlpox as rescue virus at MOI of 8. After 48 h, the transfected-infected cells were harvested, sonicated and used for recombinant virus screening. Recombinant plaques were screened based on the plaque lift hybridization method using Nipah G-specific probe which was labeled with horse radish peroxidase. After four sequential rounds of plaque purification, the recombinant designated as vFP2200-was generated They were confirmed by hybridization as 100% positive for the Nipah G insert and 100% negative for the F8 ORF.

Construction of the Canarypox recombinant expressing Nipah F, vCP2208. The gene was Nipah F. The donor plasmid was pSL6851.29 (pC5 H6p Nipha F). The insertion site was C5. The promoter was the vaccinia H6 promoter. Cells for in vitro recombination were primary chicken embryo fibroblast cells (1° CEF) grown in 10% FBS, DMEM.

The in vitro recombination was performed by transfection of 1° CEF cells with Not I-linearized donor plasmid pSL6851.29 (10 ug). The transfected cells were subsequently infected with the ALVAC as rescue virus at MOI of 10. After 24 h, the transfected-infected cells were harvested, sonicated and used for recombinant virus screening. Recombinant plaques were screened based on the plaque lift hybridization method using a Nipah F-specific probe which was labeled with horse radish peroxidase. After four sequential rounds of plaque purification, the recombinant designated as vCP2208 was generated and confirmed by hybridization as 100% positive for the Nipah F insert and 100% negative for the C5 ORF.

Example 2

Expression

Figure 6:
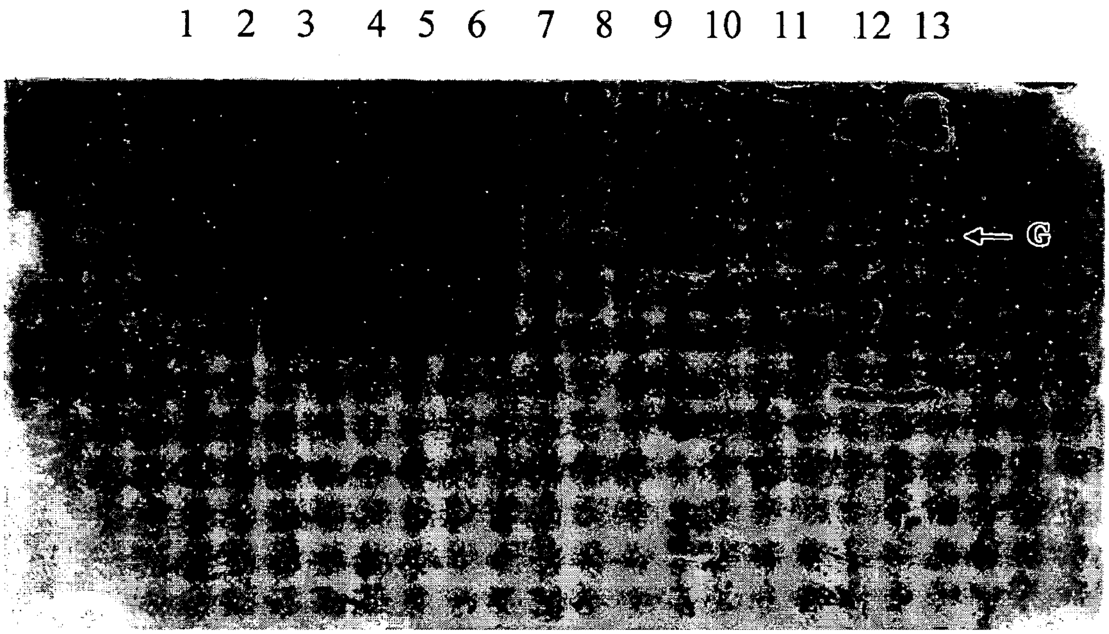
FIG. 6 illustrates a Nipah G western blot. Lane 1 was the ALVAC supt, lane 2 was the vCP2199 supt (ALVAC Nipah G), lane 3 was the vCP2199 supt (ALVAC Nipah G), lane 4 was the fowlpox supt, lane 5 was the vFP2200 supt (fowlpox Nipah G), lane 6 was the vFP2200 supt (fowlpox Nipah G), lane 7 was the markers (177.6, 113.9, 81.2, 60.7, 47.4, 36.1, 25.3, 19.0, 14.7, 6.1 kDa, lane 8 was the ALVAC pellet, lane 9 was vCP2199 pellet, lane 10 was the vCP2199 pellet, lane 11 was the fowlpox pellet, lane 12 was the vFP2200 pellet and lane 13 was the vFP2200 pellet.

Western blot of Fowlpox Nipah G, vFP2200 (FIG. 6). Primary CEF cells were infected with vCP2199 (ALVAC C5 H6p Nipah G) and vFP2200 (Fowlpox F8 H6p Nipah G) at MOI of 10 and incubated at 37° C. for 24 hrs. The cells and culture supernatant were then harvested. Sample proteins were separated on a 10% SDS-PAGE gel, transferred to Immobilon nylon membrane. The guinea pig antiserum and chemiluminescence system were used. Nipah G was expressed in cell pellets for vCP2199 and vFP2200. It did not show up in supernatant.

Figure 7A:
FIG. 7A was blotted with guinea pig antiserum.
Figure 7B:
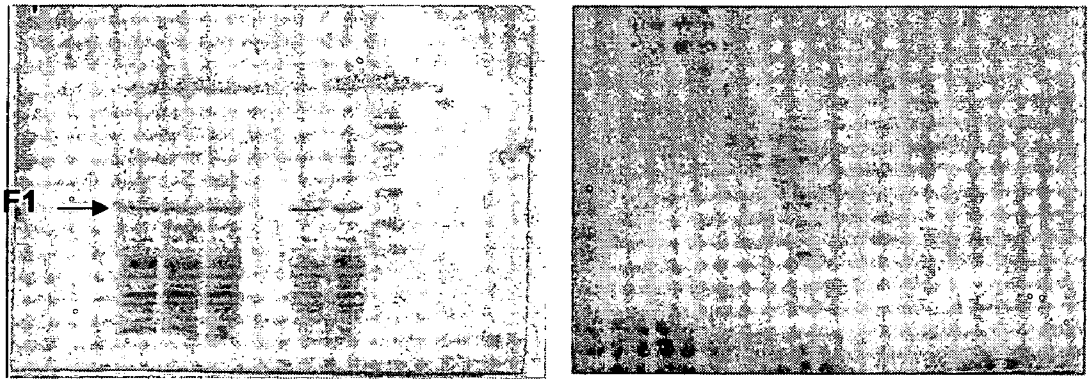
FIG. 7B was blotted with porcine antiserum. Gel #1 was the Nipah F recombinants (pellets only). Lane 1 was a space, lane 2 was Fowlpox, lane 3 was vFP2207, lane 4 was vFP2207, lane 5 was a space, lane 6 was ALVAC, lane 7 was cvCP2208, lane 8 was marker 170, 130, 100, 72, 55, 40, 33, 24 kDa and lanes 9 and 10 were spaces. Gel #2 was the Nipah F recombinants (supemant only). Lane 1 was a space, lane 2 was Fowlpox, lane 3 was vFP2207, lane 4 was vFP2207, lane 5 was Marker 170, 130, 100, 72, 55, 40, 33, 24 kDa, lane 6 was a space, lane 7 was ALVAC, lane 8 was a space, lane 9 was vCP2208 and lane 10 was a space.

Western blot of ALVAC Nipah F, vCP2208 (FIGS. 7A and 7B). Primary CEF cells were infected with vCP2208. (ALVAC C5 H6p Nipah F) s at MOI of 10 and incubated for 24 hours. The supernatant was harvested and clarified. The cells were harvested and suspended in water to lyse. Lysate and supernatant were separated by 10% SDS-PAGE. The protein was transferred to nylon membrane and blocked with Western blocking buffer. Using guinea pig antiserum and chemiluminescence developing system it was shown expressions of F protein from vCP2208 (ALVAC C5 H6p Nipah F). Using porcine antiserum and horseradish peroxidase system it was shown also expression of the F protein from vCP2208 but with a lower intensity.

Western blot of ALVAC Nipah G, vCP2199 (FIG. 6). Primary CEF cells were infected with vCP2199 (ALVAC C5 H6p Nipah G) and vFP2200 (Fowlpox F8 H6p Nipah G) at MOI of 10 and incubated at 37° C. for 24 hrs. The cells and culture supernatant were then harvested. Sample proteins were separated on a 10% SDS-PAGE gel, transferred to Immobilon nylon membrane. The guinea pig antiserum and chemiluminescence system were used. Nipah G was expressed in cell pellets for vCP2199 and vFP2200. It did not show up in supernatant.

Western blot of Fowlpox Nipah F, vFP2207 (FIGS. 7A and 7B). Primary CEF cells were infected with vFP2207 (Fowlpox F8 H6p Nipah F) at MOI of 10 and incubated for 24 hours. The supernatant was harvested and clarified. The cells were harvested and suspended in water to lyse. Lysate and supernatant were separated by 10% SDS-PAGE. The protein was transferred to nylon membrane and blocked with Western blocking buffer. Using guinea pig antiserum and chemiluminescence developing system shown expressions of F protein from vFP2207 (Fowlpox F8 H6p Nipah F). Using porcine antiserum and horseradish peroxidase system it was shown also expression of the F protein from vFP2207 but with a lower intensity.

Example 3

Serology and Protection

Sixteen pigs were allocated randomly into four groups. Group F animals were immunized with $10^8$ pfu/dose of VCP2208 expressing Nipah virus F protein. Group G animals were immunized with $10^8$ pfu/dose of VCP2199 expressing Nipah virus G protein. Group G+F animals were immunized with a mixture containing $10^8$ pfu/dose of VCP2199 and $10^8$ pfu/dose of VCP 2208 expressing respectively Nipah virus G and F proteins. Group challenge animals were unvaccinated control animals.

The pigs were injected by intramuscular route on Day 0 and Day 14. The pigs were challenged by intranasal inoculation of $2.5\times10^5$ pfu of Nipah virus on Day 28. Seven days post challenge the presence of virus is identified by RT-PCR or virus isolation in various organs and in nasal swabs. Blood samples are collected on D0, D7, D14, D21, D28, D29, D30, D31, D32, D34, and D35 after the first injection and antibody titers are measured by IgG indirect ELISA or seroneutralisation assay. The neutralizing antibodies were determined in microtiter plaque reduction neutralization assay (mPRNT) as previously described (H. Weingartl et al. Can. J. Vet. Rrs. 2003, 67, 128-132), using Vero V-76 cells and 1% carboxymethylcellulose overlay. Wells with 90% plaque reduction were considered positive for presence of Nipah virus neutralizing antibodies. ELISA and neutralizing titers (NT) data are presented in Table 1. The combined Nipah F/G induced the highest neutralizing titer prior to challenge, followed closely by G vaccine. The F vaccine induced lower neutralizing antibodies.

Virus Plaque Assay: Virus plaque assay was performed in 12-well plates (Costar, Corning, N.Y.) with either Vero 76 or PT-K75 confluent monolayers. Virus inoculum (400 µl/well) was incubated on cells for 1 h at 33° C., 5% CO2, and then replaced with 2 ml of 2% carboxymethyl-cellulose, sodium salt, medium viscosity/DMEM (Sigma Chemical, St. Louis, Mo.)/2% FBS overlay, and incubated at 33° C., 5% $CO_2$. The cells were fixed after 5 days with 4% formaldehyde and stained with 0.5% of crystal violet/80% methanol/PBS. Real time RT-PCR was performed on serum/plasma and PMBC samples only, according to V.

Guillaume et al J. Virol. Method. 2004, 120, 229-237, using a SmartCycler (Cepheid), Quantitech kit (Qiagen), and primers and probe (Applied Biosystems International) located within the N gene. Forward primer GCA CTT GAT GTG ATT AGA (SEQ ID NO: 29) and reverse primer GGC AGT GTC GGG AGC TGT AA (SEQ ID NO: 12), located within the N gene, yielding a 395 by amplicon. The real time RT-PCR was standardized using Nipah virus N gene cloned in to the pSHAME2a plasmid with sensitivity of 300 copies/reaction in 100 µl sample. Samples becoming positive at 35 cycles were considered negative.

Nipah virus was isolated at very low titer in trigeminal ganglion of pig #33 (one plaque), #35 (one plaque) and #36. In control animals Nipah virus could be reisolated from a number of tissues up to 10e3 pfu/ml: pig #39 positive in turbinates, trachea, olfactory bulbs, trigeminal ganglion, bronchiolar lymph node and submandibular lymph nodes (LN); pig #40 positive in turbinates, trachea, olfactory bulb, meninges, trigeminal ganglion, bronchiolar LN, submandibular LN and brain. The RT-PCR results are provided in Tables 2 and 3. The FIGS. are threshold cycle numbers. No RNA is detected in immunized pigs plasma, serum or the PBMC of the pigs immunized with F/G vaccine.

These results show a clear protection with recombinant expressing either Nipah virus F or G proteins and a full protection with the combination of Nipah virus F+G proteins.

Example 4

Cross-Neutralization

Eighteen pigs were allocated randomly into four groups. Group F of 4 animals were immunized with $10^8$ pfu/dose of vCP2208 expressing Nipah virus F protein. Group G of 4 animals were immunized with $10^8$ pfu/dose of vCP2199 expressing Nipah virus G protein. Group G+F of 4 animals were immunized with a mixture containing $10^8$ pfu/dose of vCP2199 and $10^8$ pfu/dose of vCP 2208 expressing respectively Nipah virus G and F proteins. As unvaccinated control group, 6 animals were naturally infected with with Nipah viruses and carried up to 28 days post infection (dpi). This group was named "long term infection".

The pigs of groups F, G and G+F were injected by intramuscular route on Day 0 and Day 14. Blood samples are collected on D27 after the vaccination (dpv or day post vaccination) and antibody titers are measured by seroneutralisation assay. The neutralizing antibodies were determined in microtiter plaque reduction neutralization assay (mPRNT) as previously described (H. Weingartl et al. Can. J. Vet. Rrs. 2003, 67, 128-132), using Vero V-76 cells seeded in 96 well plate at $1.2 \times 10^5$ cells/cm$^2$ (40,000 cells per well) incubated in 5% $CO_2$ 37° C., with DMEM medium supplemented with 10% FBS.

100 µL of serial two-fold sera dilutions (1/10-1/1280) was incubated for 1 hour 5% $CO_2$ 37° C. with 100 µL of either Hendra or Nipah virus adjusted to contain 1000 PFU per 100 µL. All the dilutions were made in DMEM.

After incubation 100 µL of the above mixture was transferred onto V76 cells monolayer. The plate with inoculum was incubated for 1 hour at 5% $CO_2$ 37° C.

After 1 hour inoculum was removed and replaced with 100 µL of 2% carboxymethylcellulose solution in DMEM supplemented with 2% FBS. The plates were incubated at 5% $CO_2$ 37° C. for 72 hours.

Back titration for the Nipah virus gave the result that the working dilution was 500 PFU/well, and for Hendra virus: 625 PFU/well.

Note: Sera from the pigs vaccinated with F protein were diluted two-fold from 1/50 to 1/2400.

Wells with 90% plaque reduction were considered positive for presence of Nipah virus neutralizing antibodies or for presence of Hendra virus neutralizing antibodies. Neutralizing titers data are presented in Table 4. The combined Nipah F/G induced a synergistic effect for the production of antibodies against the Hendra virus, which are not produced during a natural infection with Nipah viruses (see results of long term infection group). The G vaccine or the F vaccine alone induced no or lower neutralizing antibodies against Hendra viruses than the F+G vaccine. There is not correlation between the levels of antibody titer against Nipah viruses and those against Hendra viruses.

TABLE 1

ELISA and NT Data (dpv = days post vaccination, dpi = days post infection)

| ELISA | | N4 F | | | | N4 G | | | | N4 Challenge | | | | N4 G + F | | | |
|---|---|---|---|---|---|---|---|---|---|---|---|---|---|---|---|---|---|
| Data | Pig# | 31 | 32 | 33 | 34 | 35 | 36 | 37 | 38 | 39 | 40 | 41 | 42 | 43 | 44 | 45 | 46 |
| pre vac | | 0 | 0 | 0 | 0 | 0 | 0 | 0 | 0 | | | | | 0 | 0 | 0 | 0 |
| 7 dpv | | 0 | 0 | 0 | 0 | | | | | | | | | 0 | 0 | 0 | 0 |
| 14 dpv | Boost | 0 | 0 | 0 | 0 | 0 | 0 | 0 | 0 | | | | | 100 | 0 | 0 | 100 |
| 21 dpv | | 0 | 0 | 0 | 0 | 1600 | 3200 | 3200 | 1600 | | | | | 1600 | 6400 | 1600 | 6400 |
| | Pre chal | 0 | 0 | 0 | 0 | 1600 | 3200 | 3200 | 3200 | 0 | 100? | 0 | 0 | 800 | 3200 | 800 | 3200 |
| | 1 dpi | 0 | 100 | | | 400 | | | | 100 | 0 | | | 800 | 800 | | |
| | 2 dpi | | | 100 | 0 | | | 1600 | 800 | | | 0 | 100 | | | 400 | 800 |
| | 3 dpi | 0 | 0 | | | 800 | 800 | | | 0 | 0 | | | 800 | 1600 | | |
| | 4 dpi | | | 0 | 0 | | | 1600 | 3200 | | | 0 | 0 | | | 200 | 800 |
| | 5 dpi | | | | | | | | | | | | | | | | |
| | 6 dpi | 0 | 0 | | | 400 | 400 | | | 100 | 100 | | | | 1600 | | 800 |

TABLE 1-continued

ELISA and NT Data (dpv = days post vaccination, dpi = days post infection)

| | | | | | | | | | | | | | | | | | |
|---|---|---|---|---|---|---|---|---|---|---|---|---|---|---|---|---|---|
| | 7 dpi | | | 0 | 0 | | | 1600 | 800 | | | 200 | 400 | 800 | | 200 | |
| | 8 dpi | | | | | | | | | | | | | | | | |

| NT | | N4 F | | | | N4 G | | | | N4 Challenge | | | | N4 G + F | | | |
|---|---|---|---|---|---|---|---|---|---|---|---|---|---|---|---|---|---|
| Data | Pig# | 31 | 32 | 33 | 34 | 35 | 36 | 37 | 38 | 39 | 40 | 41 | 42 | 43 | 44 | 45 | 46 |
| pre vac | | <20 | <20 | <20 | <20 | <20 | <20 | <20 | <20 | | | | | <20 | <20 | <20 | <20 |
| 7 dpv | | <20 | <20 | <20 | 20 | x | x | x | x | | | | | 20 | 20 | <20 | <20 |
| 14 dpv | Boost | x | x | x | x | 40 | 30 | 40 | <20 | | | | | 40 | 20 | 40 | 40 |
| 21 dpv | | 80 | <160 | 80 | <320 | 1280 | <320 | 1280 | 1280 | | | | | 1280 | 1280 | 320 | 640 |
| | Pre chal | 80 | 80 | 80 | 160 | 640 | 1280 | 640 | 320 | <20 | <20 | <20 | <20 | 1280 | 2560 | 640 | 1280 |
| | 1 dpi | 80 | 80 | | | 640 | 640 | | | <20 | <20 | | | 640 | 2560 | | |
| | 2 dpi | | | 160 | 160 | | | <640 | 160 | | | <20 | <20 | | | 640 | 1280 |
| | 3 dpi | 80 | 80 | | | 320 | 640 | | | <20 | <20 | | | 320 | 640 | | |
| | 4 dpi | | | 80 | 160 | | | 640 | 320 | | | <20 | <20 | | | 320 | 640 |
| | 5 dpi | | | | | | | | | | | | | | | | |
| | 6 dpi | 20 | 40 | | | 320 | 1280 | | | <20 | <20 | | | | 1280 | | 320 |
| | 7 dpi | | | 20 | 80 | | | 640 | 640 | | | <20 | <20 | 1280 | | 1280 | |
| | 8 dpi | | | | | | | | | | | | | | | | |

TABLE 2

Real time RT-PCR in tissues (CSF = cerebrospinal fluid, LN = lymph node)

| sample | 31 | 32 | 33<br>F | 34 | 35 | 36 | 37<br>G | 38 | 39<br>RT | 40<br>RT | 41<br>RT<br>challenge | 42<br>RT | 43 | 44 | 45<br>F + G | 46 |
|---|---|---|---|---|---|---|---|---|---|---|---|---|---|---|---|---|
| hind brain | — | — | — | — | — | — | — | — | 28 | 24 | 24.3 | — | — | — | — | — |
| | | | | | | | | | 31 | 24.8 | 24.8 | | | | | |
| CSF | — | — | — | — | — | — | — | — | nd | 0 | 29.3 | 30.5 | — | — | — | — |
| | | | | | | | | | | | 29.6 | 28.9 | | | | |
| olfactory bulb | — | — | — | — | — | — | — | — | 25 | 18 | 23.5 | nd | — | — | — | — |
| | /32 | | | | 30 | | | | | 19 | 23.8 | | | | | |
| trigeminal ganglion | — | — | 28.5 | 30 | 32 | — | — | — | 26 | 18 | 25.1 | 18.8 | — | — | — | — |
| | | | | | | | | | | 19 | 25 | 23.8 | | | | |
| turbinate | — | — | — | — | — | — | — | — | 19 | 18 | 27.6 | 25.6 | — | — | — | — |
| | | | | | | | | | 20 | | 30.8 | 29 | | | | |
| trachea | — | — | — | 29 | — | — | 31 | 31 | 18 | 19 | 29 | 0- | — | — | — | — |
| | | | | | | | | | 19.7 | | 28.2 | | | | | |
| lung | — | — | — | — | — | — | — | — | 0 | — | — | — | — | — | — | — |
| submandibular LN | — | — | — | — | — | — | — | — | 23 | 23 | —? | — | — | — | — | — |
| | | | | | | | | | 21.5 | | nd | | | | | |
| | | | | | | | | | | | saliv? | | | | | |
| bronchiolar LN | — | — | — | — | — | — | — | — | 22.5 | 24 | — | — | — | — | — | |
| | | | | | | | | | 21.7 | | | | | | | |
| spleen | — | — | — | — | — | — | — | — | 0 | — | — | — | — | — | — | — |

TABLE 3

Real time RT-PCR, pharyngeal swabs

| | sample | | | | | | | | | | | | | | | |
|---|---|---|---|---|---|---|---|---|---|---|---|---|---|---|---|---|
| | 31 | 32 | 33<br>F | 34 | 35 | 36 | 37<br>G | 38 | 39<br>RT | 40<br>RT | 41<br>RT<br>challenge | 42<br>RT | 43 | 44 | 45<br>F + G | 46 |
| pharyngeal swab 1 dpi | — | — | | | — | — | | | — | — | | | — | — | | |
| pharyngeal swab 2 dpi | | | — | — | | | — | — | | | — | — | | | — | — |
| pharyngeal swab 3 dpi | — | 28<br>27.5 | | | — | — | | | 31.3<br>31.8 | 29.4<br>27.7 | | | — | — | | |
| pharyngeal swab 4 dpi | | | — | — | | | — | — | | | — | — | | | — | — |

TABLE 3-continued

Real time RT-PCR, pharyngeal swabs

| | sample | | | | | | | | | | | | | | | |
|---|---|---|---|---|---|---|---|---|---|---|---|---|---|---|---|---|
| | 31 | 32 | 33 | 34 | 35 | 36 | 37 | 38 | 39 RT | 40 RT | 41 RT | 42 RT | 43 | 44 | 45 | 46 |
| | F | | | | G | | | | challenge | | | | F + G | | | |
| pharyngeal swab 6 dpi | — | — | | | — | — | | | 25.3 27.3 | 28.5 28.3 | | | — | | — | |
| pharyngeal swab 7 dpi | | | — | — | | | — | — | | | 27.3 24.8 | 24.6 25.8 | | — | | — |
| | 31 | 32 | 33 | 34 | 35 | 36 | 37 | 38 | 39 | 40 | 41 | 42 | 43 | 44 | 45 | 46 |

TABLE 4

Neutralization titers

| Groups | Long term infection | | | | | | F vaccinated | | | | | G vaccinated | | | | G + F vaccinated | | |
|---|---|---|---|---|---|---|---|---|---|---|---|---|---|---|---|---|---|---|
| dpi | 23 | 11 | 29 | 27 | 24 | 28 | 0 | 0 | 0 | 0 | 0 | 0 | 0 | 0 | 0 | 0 | 0 | 0 |
| dpv | — | — | — | — | — | — | 27 | 27 | 27 | 27 | 27 | 27 | 27 | 27 | 27 | 27 | 27 | 27 |
| Nipah virus titration | 320 | 320 | 640 | 640 | 640 | 1280 | 200 | 200 | 200 | 400 | 640 | 1280 | 2560 | 1280 | 1280 | 1280 | 640 | 1280 |
| Hendra virus titration | 0 | 0 | 0 | 0 | 0 | 0 | 0 | 0 | 20 | 0 | 0 | 20 | 0 | 0 | 80 | 80 | 80 | 80 |

The invention is further described by the following numbered paragraphs:

1. An avipox expression vector comprising a polynucleotide that encodes a Nipah virus glycoprotein.

2. The avipox expression vector of paragraph 1 wherein the Nipah virus glycoprotein is the attachment (G) protein.

3. The avipox expression vector of paragraph 1 wherein the Nipah virus glycoprotein is the fusion (F) protein.

4. The avipox expression vector of paragraph 1 wherein the Nipah virus glycoprotein is the attachment (G) protein and the fusion (F) protein.

5. The avipox expression vector of paragraph 2 wherein the polynucleotide comprises the nucleotide base sequence of nucleotide 8943 to nucleotide 10751 of SEQ ID NO: 1.

6. The avipox expression vector of paragraph 3 wherein the polynucleotide comprises the nucleotide base sequence of nucleotide 6654 to nucleotide 8294 of SEQ ID NO: 1.

7. The avipox expression vector of paragraph 4 wherein the polynucleotide encodes the peptide of SEQ ID NO: 8.

8. The avipox expression vector of paragraph 2 wherein the polynucleotide encodes the peptide of SEQ ID NO: 7.

9. The avipox expression vector of paragraph 3 wherein the polynucleotide encodes the peptide of SEQ ID NO: 7 and the peptide of SEQ ID NO: 8.

10. The avipox expression vector of paragraph 5 wherein the polynucleotide comprises the nucleotide base sequence of nucleotide 6654 to nucleotide 10751 of SEQ ID NO: 1.

11. The avipox expression vector of paragraphs 1 to 10 wherein the avipox expression vector is an attenuated avipox expression vector.

12. The avipox expression vector of paragraphs 1 to 11 wherein the avipox expression vector is a canarypox vector.

13. The canarypox vector of paragraph 12 wherein the canarypox vector is ALVAC.

14. The avipox expression vector of paragraphs 1 to 11 wherein the avipox expression vector is a fowlpox vector.

15. The fowlpox vector of paragraph 14 wherein the fowlpox vector is TROVAC.

16. An expression vector wherein the expression vector is vCP2199.

17. An expression vector wherein the expression vector is vCP2208.

18. An expression vector wherein the expression vector is vFP2200.

19. An expression vector wherein the expression vector is vVP2207.

20. A formulation for delivery and expression of a Nipah virus glycoprotein, wherein the formulation comprises the vector of any one of paragraphs 1 to 19 and a pharmaceutically or veterinarily acceptable carrier, vehicle or excipient.

21. The formulation of paragraph 20, wherein the carrier, vehicle or excipient facilitates transfection and/or improves preservation of the vector.

22. A method of delivering a Nipah virus glycoprotein to an animal, comprising administering the formulation of paragraph 21 or 22 to the animal.

23. The method of paragraph 22 wherein the animal is a pig.

24. A method of eliciting an immune response in an animal comprising administering a composition comprising the vector of any one of paragraphs 1 to 19 in an effective amount for eliciting an immune response.

25. A method of eliciting an immune response in an animal comprising administering a composition comprising a cell, wherein the cell comprises the vector of any one of paragraphs 1 to 19 in an effective amount for eliciting an immune response.

26. A method of inducing an immunological or protective response in an animal comprising administering a composition comprising the vector of any one of paragraphs 1 to 19 in an effective amount for eliciting an immune response.

27. A method of inducing an immunological or protective response in an animal comprising administering a composition comprising a cell, wherein the cell comprises the vector of any one of paragraphs 1 to 19 in an effective amount for eliciting an immune response.

28. The method of any one of paragraphs 24 to 27 wherein the animal is a pig.

29. A method for preventing Nipah virus transmission between a first animal and a second animal comprising the method of any one of paragraphs 24 to 27 wherein the animal of any one of paragraphs 24 to 27 is the first animal.

30. The method of paragraph 29 wherein the first animal is a pig.

31. The method of paragraph 29 or 30 wherein the second animal is a human.

32. The method of paragraph 29 or 30 wherein the second animal is a cat or a dog.

33. A kit for performing the method of any one of paragraphs 22 to 32 comprising the vectors of any one of paragraphs 1 to 19 or the formulations of any one of paragraphs 20 or 21 and instructions for performing the method.

Having thus described in detail advantageous embodiments of the present invention, it is to be understood that the invention defined by the above paragraphs is not to be limited to particular details set forth in the above description as many apparent variations thereof are possible without departing from the spirit or scope of the present invention.

What is claimed is:

1. An expression vector comprising a polynucleotide having the sequence as set forth in SEQ ID NO:27 or SEQ ID NO:28.

2. An expression vector comprising a polynucleotide having the sequence as set forth in SEQ ID NO:24 or SEQ ID NO:25.

* * * * *